United States Patent
Renner et al.

(10) Patent No.: US 8,574,564 B2
(45) Date of Patent: Nov. 5, 2013

(54) IMMUNOSTIMULATORY NUCLEIC ACID PACKAGED PARTICLES FOR THE TREATMENT OF HYPERSENSITIVITY

(75) Inventors: Wolfgang A. Renner, Kilchberg (CH); Martin F. Bachmann, Seuzach (CH); Indulis Cielens, Riga (LV); Conrad Johannes Coester, Neuhof (DE); Klaus Dietmeier, Zürich (CH); Sebastian Fuchs, Munich (DE); Vania Manolova, Zürich (CH); Patrik Maurer, Winterthur (CH); Paul Pumpens, Riga (LV); Regina Renhofa, Riga (LV); Alain Tissot, Zürich (CH); Yu Zou, Birmensdorf (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 267 days.

(21) Appl. No.: 12/576,086

(22) Filed: Oct. 8, 2009

(65) Prior Publication Data

US 2010/0303846 A1    Dec. 2, 2010

Related U.S. Application Data

(63) Continuation of application No. 11/638,664, filed on Dec. 14, 2006, now abandoned.

(60) Provisional application No. 60/750,042, filed on Dec. 14, 2005, provisional application No. 60/812,592, filed on Jun. 12, 2006.

(51) Int. Cl.
*A01N 63/00* (2006.01)
*A61K 48/00* (2006.01)

(52) U.S. Cl.
USPC .......................................... 424/93.2; 514/44

(58) Field of Classification Search
USPC ........................................... 514/44; 424/93.2
See application file for complete search history.

(56) References Cited

U.S. PATENT DOCUMENTS

| | | | |
|---|---|---|---|
| 5,057,540 A | 10/1991 | Kensil et al. |
| 5,071,651 A | 12/1991 | Sabara et al. |
| 5,374,426 A | 12/1994 | Sabara et al. |
| 5,698,424 A | 12/1997 | Mastico et al. |
| 5,871,747 A | 2/1999 | Gengoux-Sedlik et al. |
| 5,935,821 A | 8/1999 | Chatterjee et al. |
| 5,962,636 A | 10/1999 | Bachmaier et al. |
| 6,159,728 A | 12/2000 | Stockley et al. |
| 6,194,388 B1 | 2/2001 | Krieg et al. |
| 6,207,646 B1 | 3/2001 | Krieg et al. |
| 6,239,116 B1 | 5/2001 | Krieg et al. |
| 6,326,200 B1 | 12/2001 | Valmori et al. |
| 6,339,068 B1 | 1/2002 | Krieg et al. |
| 6,406,705 B1 | 6/2002 | Davis et al. |
| 6,429,199 B1 | 8/2002 | Krieg et al. |
| 6,653,292 B1 | 11/2003 | Krieg et al. |
| 6,719,978 B2 | 4/2004 | Schiller et al. |
| 6,727,230 B1 | 4/2004 | Hutcherson et al. |
| 6,949,520 B1 | 9/2005 | Hartmann et al. |
| 6,977,245 B2 | 12/2005 | Klinman et al. |
| 7,094,409 B2 | 8/2006 | Bachmann et al. |
| 7,115,266 B2 | 10/2006 | Bachmann |
| 7,128,911 B2 | 10/2006 | Bachmann et al. |
| 7,585,847 B2 | 9/2009 | Bratzler et al. |
| 8,202,688 B2 | 6/2012 | Davis et al. |
| 2001/0044416 A1 | 11/2001 | McCluskie et al. |
| 2002/0081295 A1 | 6/2002 | Schiller et al. |
| 2003/0050268 A1 | 3/2003 | Krieg et al. |
| 2003/0091593 A1 | 5/2003 | Bachmann et al. |
| 2003/0091599 A1 | 5/2003 | Davis et al. |
| 2003/0099668 A1 | 5/2003 | Bachmann et al. |
| 2003/0219459 A1 | 11/2003 | Bachmann et al. |
| 2003/0224010 A1 | 12/2003 | Davis et al. |
| 2004/0005338 A1* | 1/2004 | Bachmann et al. ........ 424/204.1 |
| 2004/0030118 A1 | 2/2004 | Wagner et al. |
| 2004/0234512 A1 | 11/2004 | Wagner et al. |
| 2004/0235777 A1 | 11/2004 | Wagner et al. |
| 2004/0235778 A1 | 11/2004 | Wagner et al. |
| 2005/0043529 A1 | 2/2005 | Davis et al. |
| 2007/0184068 A1 | 8/2007 | Renner et al. |

FOREIGN PATENT DOCUMENTS

| | | |
|---|---|---|
| DE | 2 034 118 | 1/1972 |
| DE | 10 2004 041 340 A1 | 2/2006 |
| EP | 0 468 520 A2 | 1/1992 |
| EP | 0 772 619 B1 | 5/1997 |
| EP | 0 855 184 A1 | 7/1998 |
| GB | 2 220 211 A | 1/1990 |
| JP | 2001-151698 A | 6/2001 |
| WO | WO 94/15878 A1 | 12/1990 |
| WO | WO 92/11291 A1 | 7/1992 |

(Continued)

OTHER PUBLICATIONS

U.S. Appl. No. 08/593,554, Carson et al.
Barnes, W. M., "PCR amplification of up to 35-kb DNA with high fidelity and high yield from lambda bacteriophage templates.", *Proc Natl Acad Sci U S A* 91(6):2216-20, National Academy of Sciences, USA (1994).
Bousarghin, I., "Positively charged sequences of human papillomavirus type 16 capsid proteins are sufficient to mediate gene transfer into target cells via the heparan sulfate receptor.", *J Gen Virol* 84(Pt 1):157-64, Society for General Microbiology, UK (2003).

(Continued)

*Primary Examiner* — Marcia S Noble
*Assistant Examiner* — Magdalene Sgagias
(74) *Attorney, Agent, or Firm* — Fanelli Haag & Kilger PLLC

(57) ABSTRACT

The application is related to compositions and methods for the treatment of hypersensitivity, wherein the compositions comprise a particle packaged with immunostimulatory nucleic acids. The compositions of the invention are particularly useful in the treatment of atopic eczema, asthma and IgE-mediated allergy (type I allergy), especially pollen allergy and house dust allergy.

20 Claims, 6 Drawing Sheets

(56) References Cited

FOREIGN PATENT DOCUMENTS

Figure 1:
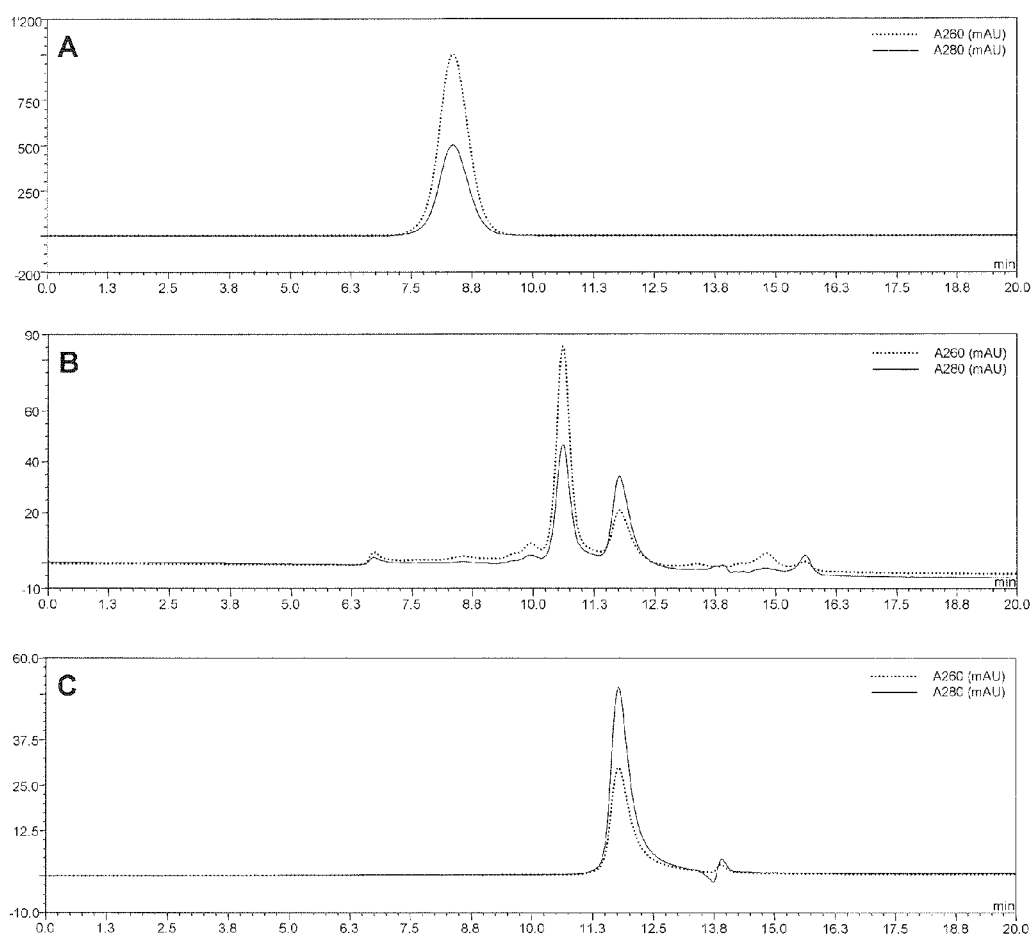

| WO | WO 92/13081 A1 | 8/1992 |
|---|---|---|
| WO | WO 94/02499 | 2/1994 |
| WO | WO 94/02499 A1 | 2/1994 |
| WO | WO 95/26204 A1 | 10/1995 |
| WO | WO 96/02555 A1 | 2/1996 |
| WO | WO 96/30523 A2 | 10/1996 |
| WO | WO 96/40162 A1 | 12/1996 |
| WO | WO 97/26883 A1 | 7/1997 |
| WO | WO 97/28259 A1 | 8/1997 |
| WO | WO 98/15631 A1 | 4/1998 |
| WO | WO 98/16247 A1 | 4/1998 |
| WO | WO 98/18810 A1 | 5/1998 |
| WO | WO 98/33517 A1 | 8/1998 |
| WO | WO 98/37919 A1 | 9/1998 |
| WO | WO 98/49195 A1 | 11/1998 |
| WO | WO 98/50071 A1 | 11/1998 |
| WO | WO 98/52581 A1 | 11/1998 |
| WO | WO 98/55495 A1 | 12/1998 |
| WO | WO 98/55495 A2 | 12/1998 |
| WO | WO 99/11275 A2 | 3/1999 |
| WO | WO 99/28478 A1 | 6/1999 |
| WO | WO 99/29723 A1 | 6/1999 |
| WO | WO 99/51259 A2 | 10/1999 |
| WO | WO 99/57289 A2 | 11/1999 |
| WO | WO 99/58118 A2 | 11/1999 |
| WO | WO 00/00462 A1 | 1/2000 |
| WO | WO 00/06588 A1 | 2/2000 |
| WO | WO 00/14217 A2 | 3/2000 |
| WO | WO 00/23955 A1 | 4/2000 |
| WO | WO 00/32227 A2 | 6/2000 |
| WO | WO 00/37610 A2 | 6/2000 |
| WO | WO 00/39304 A2 | 6/2000 |
| WO | WO 00/39304 A2 | 7/2000 |
| WO | WO 00/46365 A1 | 8/2000 |
| WO | WO 00/50006 A2 | 8/2000 |
| WO | WO 00/50461 A1 | 8/2000 |
| WO | WO 00/54803 A2 | 9/2000 |
| WO | WO 00/62800 A2 | 10/2000 |
| WO | WO 01/00232 A2 | 1/2001 |
| WO | WO 01/12223 A2 | 2/2001 |
| WO | WO 01/16320 A1 | 3/2001 |
| WO | WO 01/22972 A2 | 4/2001 |
| WO | WO 01/22990 A2 | 4/2001 |
| WO | WO 01/26681 A2 | 4/2001 |
| WO | WO 01/35991 A2 | 5/2001 |
| WO | WO 01/38358 A2 | 5/2001 |
| WO | WO 01/54720 A1 | 8/2001 |
| WO | WO 01/56603 A1 | 8/2001 |
| WO | WO 01/58478 A1 | 8/2001 |
| WO | WO 01/62275 A1 | 8/2001 |
| WO | WO 01/85208 A2 | 11/2001 |
| WO | WO 02/10416 A1 | 2/2002 |
| WO | WO 02/053141 A2 | 7/2002 |
| WO | WO 02/056905 A2 | 7/2002 |
| WO | WO 02/056907 A2 | 7/2002 |
| WO | WO 03/024480 A2 | 3/2003 |
| WO | WO 03/024481 A2 | 3/2003 |
| WO | WO 03/030656 A2 | 4/2003 |
| WO | WO 03/031466 A2 | 4/2003 |
| WO | WO 03/039225 A2 | 5/2003 |
| WO | WO 03/040164 A2 | 5/2003 |
| WO | WO 03/040308 A2 | 5/2003 |
| WO | WO 03/045431 A2 | 6/2003 |
| WO | WO 03/059386 A2 | 7/2003 |
| WO | WO 2004/000351 A1 | 12/2003 |
| WO | WO 2004/007538 A2 | 1/2004 |
| WO | WO 2004/009124 A2 | 1/2004 |
| WO | WO 2004/071493 A1 | 8/2004 |
| WO | WO 2005/014110 A1 | 2/2005 |
| WO | WO 2005/042018 A2 | 5/2005 |

OTHER PUBLICATIONS

Chien, Y. W., Nasal Drug Delivery and Delivery Systems. In: Novel Drug Delivery Systems; Second Edition, Marcel Dekker Inc., USA (1992).

Cooper, C. L., "Safety and immunogenicity of CPG 7909 injection as an adjuvant to Fluarix influenza vaccine.", *Vaccine* 22(23-24):3136-43, Elsevier, The Netherlands (2004).

Del Prete, G., "Human Th1 and Th2 lymphocytes: their role in the pathophysiology of atopy.", *Allergy* 47(5):450-5, Munksgaard, Denmark (1992).

Fanucchi, M. V., "Immunostimulatory oligonucleotides attenuate airways remodeling in allergic monkeys.", *Am J Respir Crit Care Med* 170(11):1153-7, American Thoracic Society, USA (2004).

Gauvreau, G. M., "Immunostimulatory sequences regulate interferon-inducible genes but not allergic airway responses.", *Am J Respir Crit Care Med* 174(1):15-20, American Thoracic Society, USA (2006).

Hallsworth, M. P., "Selective enhancement of GM-CSF, TNF-alpha, IL-1 beta and Il-8 production by monocytes and macrophages of asthmatic subjects.", *Eur Respir J* 7(6):1096-102, ERS Journals Ltd, UK (1994).

Holt, P.G., "Supression of IgE responses following inhalation of antigen", *Immunol Today* 8:14-18, Elsevier Science Publishers V.V., The Netherlands (1987).

Hsu, C.-H., "Inhibition of specific IgE response in vivo by allergen-gene transfer." *Int Immunol* 8(9):1045-11, Oxford University Press, UK (1996).

Kanzler, H., "Therapeutic targeting of innate immunity with Toll-like receptor agonists and antagonists.", *Nat Med* 13(5):552-9, Nature Publishing Group. UK (2007).

Kimura, Y., "Binding of oligoguanylate to scavenger receptors is required for oligonucleotides to augment NK cell activity and induce IFN.", *J Biochem*, 116(5) 991-4, Oxford University Press, UK (1994).

Kline, J. N., "Immune Redirection by CpG Oligonucleotides: Conversion of a Th2 Response to a Th1 Response in a Murine Model of Asthma", *Journal of Investigative Medicine*, 45 (3): 282A, American Federation for Medical Research, USA (1997).

Komazin-Meredith, G., "The positively charged surface of herpes simplex virus UL42 mediates DNA binding.", *J Biol Chem* 283(10):6154-61, The American Society for Biochemistry and Molecular Biology Inc., USA (2008).

Krieg, A. M., "A role for endogenous retroviral sequences in the regulation of lymphocyte activation.", *J Immunol* 143(8):2448-51, The American Association of Immunologists, USA (1989).

Krieg, A. M., "B Cell Activation Induced by Oligodeoxynucleotides (ODN) or DNA Containing Un-Methylated CpG Motifs", ACR Poster Session on Oct. 27, 1994, also published in "Arthritis and Rheumatism", 37(9), Suppl,t S379, Lippincott, Philadelphia, US (1994).

Krieg, A. M., "Immune Stimulation by CpG DNA", *Antisense & Nucleic Acid Drug Development* 9:429-31, Mary Ann Libert Inc., USA (1999).

Kuby, J., "IgE-Mediated (Type 1) Hypersensitivity. In: Immunology", *Immunology*: 358-359, W.H. Freeman and Company, USA (1992).

Kuramoto, E., "Changes of host cell infiltration into Meth A fibrosarcoma tumor during the course of regression induced by injections of a BCG nucleic acid fraction.", *Int J Immunopharmacol* 14(5):773-82, Pergamon Press Ltd., UK (1992).

Leong, D. L. Y., "Antigenic Competition Between Endotoxic Adjuvant and a Protein Antigen.", *Infect Immun* 3(2):308-317, American Society for Microbiology, USA (1971).

Li, X.-M., "Mucosal IFN-gamma gene transfer inhibits pulmonary allergic responses in mice.", *J Immunol* 157(8):3216-9, The American Association of Immunologists, USA (1996).

Livingston, P. O., "Serological response of melanoma patients receiving melanoma cell vaccines. I. Autologous cultured melanoma cells.", *Int J Cancer* 30(4):413-22, John Wiley & Sons, USA (1982).

McPeck, M., "Aerosol delivery during continuous nebulization.", *Chest* 111(5): 1200-5, The American College of Chest Physicians, USA (1997).

Mobley, J. L., "Cytokine networks in allergic lung inflammation: an opportunity for drug intervention.", *Expert Opin Investig Drugs* 6(1):1-6, Ashley Publications Ltd.. UK (1997).

(56) References Cited

OTHER PUBLICATIONS

Nyce, J. W., "Respirable antisense oligonucleotides as novel therapeutic agents for asthma and other pulmonary diseases.", *Expert Opin Investig Drugs* 6(9):1149-56, Ashley Publications Ltd., UK (1997).
Nyce, J. W., "DNA antisense therapy for asthma in an animal model.", *Nature* 385(6618):721-5, Nature Publishing Group, USA (1997).
Pisetsky, D.S., "Stimulation of Murine Lymphocyte Proliferation by a Phosphorothioate Oligonucleotide with antisense activity for herpes simplex Virus", *Life Sciences* 54:101-107, Pergamon Press, USA (1993).
Raz, E., "Intradermal gene immunization: the possible role of DNA uptake in the induction of cellular immunity to viruses.", *Proc Natl Acad Sci USA* 91(20):9519-23, Proceeding of the National Academy of Sciences of the United States of America, USA (1994).
Tokanuga, T., "Synthetic oligonucleotides with particular base sequences from the cDNA encoding proteins of *Mycobacterium bovis* Bcg induce interferons and activate natural killer cells.", *Microbiol Immunol* 36(1):55-66, Wiley, UK, (1992).
Uhlmann, E., "Antisense Oligonucleotides: A New Therapeutic Principle", *Chemical Reviews* 90(4):544-584, American Chemical Society, USA (1990).
Vogel, F. R., "A compendium of vaccine adjuvants and excipients.", *Pharm Biotechnol* 6:141-228, Elsevier, The Netherlands (1995).
Yamamoto, S., "In vitro augmentation of natural killer cell activity and production of interferon-alpha/beta and -gamma with deoxyribonucleic acid fraction from *Mycobacterium bovis* BCG.", *Jpn J Cancer Res* 79(7):866-73, Blackwell Publishing, UK, (1988).
Abou-Jawdah, Y., et al., Immunodiagnosis of Prune dwarf virus using antiserum produced to its recombinant coat protein, *J. Virol. Methods* 121:31-38, Elsevier (Oct. 2004).
Addo, M.R., et al., "Comprehensive Epitope Analysis of Human Immunodeficiency Virus Type 1 (HIV-1)-Specific T-cell Responses Directed Against the Entire Expressed HIV-1 Genome Demonstrate Broadly Directed Responses, but no Correlation to Viral Load," *J. Virol.* 77:2081-2092, American Society for Microbiology (2003).
Adhin, M.R., et al., Nucleotide Sequence from the ssRNA Bacteriophage JP34 Resolves the Discrepancy between Serological and Biophysical Classification, *Virology* 170:238-242, Academic Press (1989).
Aggarwal N., et al., Biodegradable Alginate Microspheres as a Delivery System for Naked DNA, *Can. J. Vet. Res.* 63:148-152, Canadian Veterinary Medical Association (1999).
Allison, A.C., "Adjuvants and Immune Enhancement," *Int. J. Technol. Assess. Health Care* 10:107-120, Cambridge University Press (1994).
Andersson, M., et al., "Various Methods for Testing Nasal Responses in Vivo: a Critical Review," *Acta Otolaryngol.* 115:705-713, Scandinavian University Press (1995).
Aral, C., and Akbuga J., "Preparation and in vitro transfection efficency of chitosan microspheres containing plasmid DNA.poly(L-lysine) complexes," *J. Pharm. Pharm. Sci.* 6:321-326, The Society of Pharmacy & Pharmaceutical Sciences (2003).
Aukunuru J.V., at al., "Nanoparticle formulation enhances the delivery and activity of a vascular endothelial growth factor antisense oligonucleotide in human retinal pigment epithelial cells," *J. Pharm. Pharrnacoi.* 55:1199.-1206, The Authors (2003).
Avgoustakis, K., "Pegylated Poly(lactide) and Poly(Lactide-Co-Glycolide) Nanoparticles: Preparation, Properties and Possible Applications in Drug Delivery," *Curr Drug Deliv.* 1:321-333, Bentham Science Publishers Ltd, (Oct. 2004).
Aynié, I., et al., "Spongelike Alginate Nanoparticles as a New Potential System for the Delivery of Antisense Oligonucleotides," *Antisense Nuc. Acid Drug Dev.* 9:301-312, Mary Ann Liebert Inc. (1999).
Azami, S., et al., "Optimization of a two-step desolvation method for preparing gelatin nanoparticles and cell uptake studies in 143B osteosarcoma cancer cells," *J. Pharm. Pharm. Sci.* 9:124-132, The Society of Pharmacy & Pharmaceutical Sciences (Mar. 2006).
Ballas, Z.K., et al., "Induction of NK activity in Murine and Human cells by CpG Motifs in Oligodecynucleotides and Bacterial DNA," *J. Immunol.* 157:1840-1845, The American Association of Immunologists (1996).
Bangham, A.D., et al., "Diffusion of Univalent Ions across the Lamellae of Swollen Phospholipids," *J. Mol. Biol.* 13238-252, Academic Press (1965).
Bartholomé, E.J., et al., "IFN-β Interferes with the Differentiation of Dendritic Cells from Peripheral Blood Mononuclear Cells: Selective Inhibition of CD40-Dependent Interleukin-12 Secretion," *J. Interferon Cytokine Res.* 19:471-478, Mary Ann Liebert Inc. (1999).
Beaucage, S. L., and Caruthers, M. H., "Deoxynucleoside Phosphoramidites—A New Class of Key Intermediates for Deoxypolynucleotide Synthesis," *Tetrahedron Lett.* 22:1859-1862, Pergamon Press Ltd. (1981).
Blackwell, S.E., and Krieg, A.M., "CpG-A-Induced Monocyte IFN-γ-Inducible Protein-10 Production is Regulated by Plasmacytoid Dendritic Cell-Derived IFN-$\alpha^1$," *J. immunol.* 170:4061-4068, The American Association of Immunologists Inc. (2003).
Boeckle, S., et al., "Purification of polyethylenimine polyplexes highlights the role of free polycations in gene transfer," *J. Gene Med.* 6:1102-1111, Wiley & Sons Ltd. (Oct. 2004).
Bousquet, J., et al., "Allergic Rhitinis and its Impact on Asthma," Aria Workshop Group; WHO, *J. Allergy Clin. Immunol.* 108S147-S134, The American Academy of Allergy, Asthma, and Immunology and ARIA (2001).
Bousquet, Y., et al., "Molecular Mechanisms of the Adsorption of a Model Protein (Human Serum Albumin) on Poly(Methylidene Malonate 2.1.2) Nanoparticles," *Pharm. Res.* 16:141-147, Plenum Publishing Corporation (1999).
Branda, R.F., et al., "Amplification of antibody production by phosohorothioate oligodeoxynucleotides," *J. Lab. Clin. Med.* 128:329-338, Mosby-Year Book Inc. (1996).
Breton, P., et al., "Physico-chemical characterization, preparation and performance of poly (methylidene malonate 2. 1.2) nanoparticles," *Biomaterials* 19:271-231, Elsevier Science (1998).
Brown, W.L., et al., "RNA Bacteriophage Capsid-Mediated Drug Delivery and Epitope Presentation," *Intervirology* 45:371-380, S. Karger AG (2002).
Buonaguro, L., et al., "High efficient production of $Pr55^{g3g}$ virus-like particles expressing multiple HIV-1 epitopes, including a gp120 protein derived from an Ugandan HIV-1 isolate of subtype A," *Antiviral Res.* 49:35-47, Elsevier Science (2001).
Cella, M., et al., "Maturation, Activation, and Protection of Dendritic Cells Induced by Double-stranded RNA," *J. Exp. Med.* 189821-829, The Rockefeller University Press (1999).
Cella, M., et al., "Plasmacytoid monocytes migrate to inflamed lymph nodes and produce large amounts of type I interferon," *Nat. Med.* 5:919-923, Nature America Inc. (1999).
Childhood Asthma Management Program Research Group, "Long-Term Effects of Budesonide or Nedocromil in Children with Asthma," *N. Engl. J. Med.* 343:1054-1063, Massachusetts Medical Society (2000).
Choi, Y.G., and Rao A.L.N., "Packaging of Tobacco Mosaic Virus Subgenomic RNAs by Brome Mosaic Virus Coat Protein Exhibits RNA Controlled Polymorphism," *Virology* 275:249-257, Academic Press (2000).
Choi, Y.G., et al., "tRNA elements mediate the assembly of an icosahedral RNA virus," *Proc. Natl. Acad. Sci. USA* 99:655-660, National Academy of Sciences (2002).
Clark, B., et al., "Immunity against both polyomavirus VP1 and a transgene product induced following intranasal delivery of VP1 pseudocapsid-DNA complexes," *J. Gen. Virol.* 82:2791-2797, SGM (2001).
Coester, C. J., et al., "Gelatin nanoparticles by two step desolvation—a new preparation method, surface modifications and cell uptake," *J. Microencapsulation* 17:187-193, Taylor & Francis Ltd. (2000).
Coester, C., et al., "Development of a New Carrier System for Oligonucleotides and Plasmids Based on Gelatin Nanoparticles," *New Drugs* 1:14-17, ICMENS (2003).

(56) References Cited

OTHER PUBLICATIONS

Cohen, S., et al., "The pharmacokinetics of, and humoral responses to, antigen delivered by microencapsulated liposomes," *Proc. Natl. Acad. Sci. USA* 88:10440-10444, National Academy of Sciences (1991).
Cooper, C.L., et al., "Safety and immunogenicity of CPG 7909 injection as an adjuvant to Fluarix influenza vaccine," *Vaccine* 22:3136-3143, Elsevier Ltd. (Aug. 2004).
Dalpke, A.H., et al., "Phosphodiester CpG oligonucleotides as adjuvants: polyguanosine runs enhance cellular uptake and improve immunostimulative activity of phosphodiester CpG oligonucleotides in vitro and in vivo," *Immunology* 106:102-112, Blackwell Science Ltd. (2002).
DeClercq, E., "Interferon Induction by Polynucleotides, Modified Polynucleotides, and Polycarboxylates," *Methods Enzymol* 78: 227-236, Academic Press (1981).
Diwan, M., et al., "Biodegradable Nanoparticle Mediated Antigen Delivery to Human Cord Blood Derived Dendritic Cells for Induction of Primary T Cell Responses," *J. Drug Target.* 11:495-507, Taylor & Francis Ltd. (2003).
Eason, J.E., et aL, "Effects of Substituting Granulin or a Granulin-Polyhedrin Chimera for Polyhedrin on Virion Occlusion and Polyhedral Morphology in *Autographa californica* Multinucleocapsid Nuclear Polyhedrosis Virus," *J. Virol.* 72:6237-6243, American Society for Microbiology (1998).
Emile, C., et al., "Encapsulation of Oligonucleotides in Stealth Me.PEG-PLA$_{50}$ Nanoparticles by Complexation with Structured Oligopeptides," *Drug Deliv.* 3:187-195, Taylor & Francis (1996).
Fattal, E., et al., "Biodegradable polyalkylcyanoacrylate nanoparticles for the delivery of oligonucleotides," *J. Control. Release* 53:137-143, Elsevier Science (1998).
Fehr, T., et al., "T cell-independent type I antibody responses against B cell epitopes expressed repetitively on recombinant virus particles," *Proc. Natl. Acad. Sci. USA* 95:9477-9481, National Academy of Sciences (1998).
Fernández-Fernández, M.R., et al., "Identification of immunogenic Hot Spots within Plum Pox Potyvirus Capsid Protein for Efficient Antigen Presentation," *J. Virol.* 76:12646-12653, American Society for Microbiology (2002).
Fitchen, J., et al., "Plant virus expressing hybrid coat protein with added murine epitope elicits autoantibody response," *Vaccine* 13:1051-1057, Elsevier Science (1995).
Fukasawa, M., et al., "Liposome oligomannose—coated with neoglycolipid, a new candidate for a safe adjuvant for induction of CD8$^+$ cytotoxic T lymphocytes," *FEBS Lett.* 441:353-356, Federation of European Biochemical Societies (1998).
Gavett, S,H., et al., "Interleukin 12 Inhibits Antigen-induced Airway Hyperresponsiveness, Inflammation, and Th2 Cytokine Expression in Mice," *J. Exp. Med.* 182:1527-1536, The Rockefeller University Press (1995).
Gerber, S., et al., "Human Papiliornavirus Virus-Like Particles Are Efficient Oral Immunogens when Coadministered with *Escherichia coli* Heat-Labile Enterotoxin Mutant R192G or CpG DNA," *J. Virol.* 75:4752-4760, American Society for Microbiology (2001).
Gilbert, S.C., et al., "A protein particle vaccine containing multiple malaria epitopes" *Nat. Biotechnol.* 15:1280-1284, Nature America Publishing(1997).
Goeckeritz, B.E., et al., "Multivalent cross-linking of membrane lg sensitizes murine B cells to a broader spectrum of CpG-containing oligodeoxynucleotide motifs, Including their methylated counterparts, for stimulation of proliferation and lg secretion," *Int. Immunol.* 11:1693-1700, Oxford University Press(1999).
Golmohammadi, R., et al., "The crystal structure of bacteriophage Qβ at 3.5 A revolution," *Structure* 4:543-554, Cell Press(1996).
Gursel, I., et al., "Sterically Stabilized Cationic Liposomes Improve the Uptake and Immunostimulatory Activity of CpG Oligonucleotides," *J. Immunol.* 167:3324-3328, The American Association of Immunologists Inc. (2001).

Guschlbauer, W., et al., "Four-Stranded Nucleic Acid Structures 25 Years Later: From Guanosine Gels to Telomer DNA.," *J. Biomol. Struct. Dyn.* 8:491-511, Adenine Press (1990).
Halperin, S.A., et al., "A phase I study of the safety and immunogenicity of recombinant hepatitis B surface antigen co-administered with an immunostimulatory phosphorothioate oligonucleotide adjuvant," *Vaccine* 21:2461-2467, Elsevier Science Ltd. (2003).
Halpern, M.D., et al., "Bacterial DNA Induces Murine Interferon-γ Production by Stimulation of Interleukin-12 and Tumor Necrosis Factor-α," *Cell Immunol.* 167:72-78, Academic Press Inc. (1996).
Hartmann, G., et al., "CpG DNA: A potent signal for growth, activation, and maturation of human dendritic cells," *Proc. Natl. Acad. Sci. USA* 96:9305-9310, National Academy of Sciences (1999).
Hawley, A.E., et al., "Preparation of Biodegradable, Surface Engineered PLGA Nanospheres with Enhanced Lymphatic Drainage and Lymph Node Uptake," *Pharm. Res.* 14:657-661, Plenum Publishing Corporation (1997).
Heath, A.W., Cytokines arid the Rational Choice of Immunological Adjuvants, *Cancer Biother.* 9:1-6, Mary Ann Liebert, Inc., Publishers (1994).
Hessel, E.M., et al., "Imrnunostimuiatory oligonucleotides block allergic airway inflammation by inhibiting Th2 cell activation and IgE-mediated cytokine induction," *J. Exp. Med.* 202:1563-1573, The Rockefeller University Press (Dec. 2005).
Hsu, C.H., et al., "Irnmunoprophylaxis of allergen-induced immunoglobulin E synthesis and airway hyperresponsiveness in vivo by genetic immunization," *Nat. Med.* 2:540-544, Nature Publishing Company (1996).
Iho, S., et al., "Oligodeoxynucleotides Containing Palindrome Sequences with Internal 5'-CpG-3' Act Directly on Human NK and Activated T Cells to Induce IFN-γ Production In Vitro," *J. Immunol.* 163:3642-3652, The American Association of Immunologists (1999).
Ioannou, X.P., et al., "CpG-containing oligodeoxynucleotides, in combination with conventional adjuvants, enhance the magnitude and change the bias of the immune responses to a herpesvirus glycoprotein," *Vaccine* 21:127-137, Elsevier Science (2002).
Irache, J.M., et al., "Albumin Canoparticles for the Intravitreal Delivery of Anticytomegaloviral Drugs," *Mini Rev. Med. Chem.* 5:293-305, Bentham Science Publishers Ltd. (2005).
Jain, S., et al., "Synthesis of Protein-Loaded Hydrogel Particles in an Aqueous Two-Phase System for Coincident Antigen and CpG Oligonucleotide Delivery to Antigen-Presenting Cells," *Biomacromolecules* 6:2590-2600, American Chemical Society (Sep.-Oct. 2005).
Janeway, C., and Travers, P., "The Immune System in Health and Disease," in *Immuno-Biology, Third Edition*, Current Biology Ltd., New York, NY, 13 pages(1997).
Jegerlehner, A., et alL, "A molecular assembly system that renders antigens of choice highly repetitive for induction of protective B cell responses," *Vaccine* 20:3104-3112, Elsevier Science (2002).
Jiang, A., et al., "A Genetically Engineered Spleen Necrosis Virus-Derived Retroviral Vactor That Displays the HIV Type 1 Glycoprotein 120 Envelope Peptide," *Hum. Gene Ther.* 10:2627-2636, Mary Ann Liebert Inc. (1999).
Jiang, B., et al., "Heterotypic protection from rotavirus infection in mice vaccinated with virus-like particles." *Vaccine* 17:1005-1013, Elsevier Science (1999 ).
Jiang, X. J., et al., "Norwalk Virus Genome Cloning and Characterization." *Science* 250:1580-1583, American Association for the Advancement of Science (1990).
Joelson, T., et al., "Presentation of a foreign peptide on the surface of tomato bushy stunt virus," *J. Gen. Virol.* 78:1213-1217, SGM (1997).
Johansson, S.G.O., et al., "Revised nomenclature for allergy for global use: Report of the Nomenclature Review Committee of the World Allergy Organization," *J. Allergy Clin. Immunol.* 113:832-835, American Academy of Allergy, Asthma and Immunology (May 2004).
Johansson, S.G.O., et al., "A revised nomenclature for allergy. An EAACI position statement from the EAACI nomenclature task force," *Allergy* 56:813-824, Munksgaard (2001).

(56) References Cited

OTHER PUBLICATIONS

Johnson, J.E., and Speir, J.A., "Quasi-equivalent Viruses: A Paradigm for Protein Assemblies," *J. Mol. Biol.* 269:666-675, Academic Press Limited (1997).

Johnson, J.M., et al., "Interaction with Capsid Protein Alters RNA Structure and the Pathway for In Vitro Assembly of Cowpea Chlorotic Mottle Virus," *J. Mol. Biol.* 335:455-464, Elsevier Ltd. (Jan. 2004).

Johnson, K.N., et al., "Heterologous RNA Encapsidated in Pariacoto Virus-Like Particles Forms a Dodecahedral Cage Similar to Genomic RNA in Wild-Type Virions," *J. Virol.* 78:11371-11378, American Society for Microbiology (Oct. 2004).

Juniper, E.F., et al., "Modification of the asthma quality of life questionnaire (standardised) for patients 12 years and older," *Health Qual. Life Outcomes* 3:1-6, BioMed. Central Ltd. (Sep. 2005).

Kaisho, T., and Akira, S., "Toll-like receptors as adjuvant receptors," *Biochim. Biophys. Acta* 1589:1-13, Elsevier Science (2002).

Kakizawa, Y., etal., "Block copolymer-coated calcium phosphate nanoparticles sensing intracellular environment for oligodeoxynucleotide and siRNA delivery," *J. Control Release* 97:345-356, Elsevier (2004).

Kastelein, R.A., et al.,"Effect of the sequences from the ribosome-binding site on the yield of protein from the cloned gene for phage MS2 coat protein," *Gene* 23:245-254 (1983).

Kerkmann, M., et al., "Activation with CpG-A and CpG-B Oligonucleotides Reveals Two Distinct Regulatory Pathways of Type I IFN Synthesis in Human Plasmacytoid Dendritic Cells," *J. Immunol.* 170:4465-4474, The American Association of Immunologists Inc (2003).

Kline, J.N., et al., "Cutting Edge: Modulation of Airway Inflammation by CpG Oligodeoxynucleotides in a Murine Model of Asthma," *J. Immunol.* 160:2555-2559, The American Association of Immunologists (1998).

Kline, J.N., & el., "Treatment of established asthma in a murine model using CpG oligodeoxynucleotides," *Am J. Physiol. Lung Cell Mol. Physiol.* 283:L170-L179, American Physiological Society (2002).

Klinman, D.M., "Immunotherapeutic uses of CpG oligodeoxynuoleotides," *Nat. Rev. Immunol.* 4:249-258, Nature Publishing Group (Apr. 2004).

Klinman, D.M., et al., "Immunotherapeutic Applications of CpG-containing Oligodeoxynucleotides," *Drug News Perspect.* 13:289-296, Prous Science (2000).

Klinman, D.M., et al., "CpG motifs present in bacteria DNA rapidly induce lymphocytes to secrete interleukin 6, interleukin 12, and interferon γ," *Proc. Natl. Acad. Sci. USA* 93:2879-2883, Academy of Sciences (1996).

Klinman, D.M., et al., "CpG oligonucleotides improve the protective immune response induced by the anthrax vaccination of rhesus macaques," *Vaccine* 22:2881-2886, Elsevier Ltd. (Jul. 2004).

Kozlovska, T.M., et al., "RNA phage Qγ Coat Protein as a Carrier for Foreign Epitopes," *Intervirology* 39:9-15, S. Karger AG Basel (1996).

Krieg, A.M., "CpG Motifs in Bacterial DNA and Their Immune Effects," *Annu. Rev. Immunol.* 20:709-760, Annual Reviews (2002).

Krieg, A.M., "Mechanisms and applications of immune stimulatory CpG oligodeoxynucleotides" *Biochim. Biophys. Acta* 1489:107-116, Elsevier Science (1999).

Krieg, A.M., and Davis, H.L., "Enhancing vaccines with immune stimulatory CpG DNA," *Curr. Opin. Mol. Ther.* 3:15-24, PharmaPress Ltd. (2001).

Krieg, A.M., et al., "CpG motifs in bacterial DNA trigger direct B-cell activation," *Nature* 374:546-549, Nature Publishing Group (1995).

Krieg, A.M., et al., "Oligodeoxynucleotide Modifications Determine the Magnitude of B Cell Stimulation by CpG Motifs," *Antisense Nuc. Acid Drug Dev.* 6:133-139, Mary Ann Liebert Inc. (1996).

Krug, A., et al., "CpG Oligonucleotides Induce a Monocyte-Derived Dendritic Cell-Like Phenotype That Preferentially Activates CD8 T Cells," *J. Immunol.* 170:3468-3477, The American Association of Immunologists Inc. (2003).

Krug, A., et al., "Identification of CpG oligonucleotide sequences with high induction of IFN-α/β in plasmacytoid dendritic cells," *Eur. J. Immunol.* 31:2154-2163, Wiley-VCH Verlag (2001).

Kumar, M.N. V.R., "Nano and Microparticles as Controlled Drug Delivery Devices," *J. Pharm. Pharm. Sci.* 3:234-258; The Society of Pharmacy & Pharmaceutical Sciences (2000).

Kuramoto, E., et al., "Oligonucleotide sequences required for natural killer cell activation," *Jpn. J. Cancer Res.* 83:1128-1131, Japanese Cancer Association (1992).

Lechner, F., et al., "Virus-Like Particles as a Modular System for Novel Vaccines," *Intervirology* 45:212-217, S. Karger AG (2002).

Lee, S.W., et al., "Effects of a Hexameric Deoxyriboguanosine Run Conjugation into CpG Oligodeoxynucleotides on Their Immunostimulatory Potentials," *J. Immunol.* 165:3631-3639, The American Association of Immunologists (2000).

Leib H., et al., "Adjuvant/carrier activity of inactivated tick-borne encephalitis virus," *Vaccine* 16:340-345, Elsevier Science (1998).

Lemarchand, C., et al., "Polysaccharide-decorated nanoparticles," *Eur. J. Pharm. Biopharm.* 58:327-341, Elsevier B.V. (Sep. 2004).

Leong, K.W., et al., "DNA-polycation nanospheres as non-viral gene delivery vehicles," *J. Control. Release* 53:183-193, Elsevier (1998).

Levy, H.B., "Induction of Interferon In Vivo and In Vitro by Polynucleotides and Derivatives, and Preparation of Derivatives," *Methods Enzymol.* 78:242-251, Academic Press (1981).

Li, Y,, et al., "Nanoparticles bearing polyethyleneglycol-coupled transferrin as gene carriers: preparation and in vitro evaluation," *Int. J. Pharm.* 259:93-101, Elsevier Science B.V. (2003).

Liljas, L., et al., "Crystal Structure of Bacteriophage fr Capsids at 3.5 Å Resolution," *J. Mol. Biol.* 244:279-290, Academic Press Limited (1994).

Liu, H.M., et al., "Immunostimulatory CpG Oligodeoxynucleotides Enhance the Immune Response to Vaccine Strategies Involving Granulocyte-Macrophage Colony-Stimulating Factor," *Blood* 92:3730-3736, The American Society of Hematology(1998).

Ludewig, B., et al., "In vivo antigen loading and activation of dendritic cells via a liposomal peptide vaccine mediates protective antiviral and anti-tumour immunity," *Vaccine* 19:23-32, Elsevier Science Ltd. (2000).

Luo, L., et al., "Induction of V3-Specific Cytotoxic T Lymphocyte Responses by HIV *gag* Particles Carrying Multiple Immunodominant V3 Epitopes of gp120," *Virology* 240:316-325, Academic Press (1998 ).

Mahon, B.P., et al., "The Rational Design of Vaccine Adjuvants for Mucosal and Neonatal Immunization," *Curr. Med. Chem.* 8:1057-1076, Bentham Science Publishers (2001).

Malm, L.R., et al., "Guidelines for nasal provocations with aspects on nasal patency, airflow, and airflow resistance" *Rhinoiogy* 38:1-6, International Rhinologic Society (2000).

Mao, H.Q., et al, "Chitosan-DNA nanoparticles as gene carriers: synthesis, characterization and transfection efficiency," *J. Control. Release* 70:399-421, Elsevier Science (2001).

Martin, S.J., et al., "Immunization of human HIV-seronegative volunteers with recombinant p17/p24:Ty virus-like particles elicits HIV-1 p24-specific cellular and humoral immune responses," *AIDS* 7:1315-1323, Current Science Ltd. (1993).

Marusic, C., et al., "Chimeric Plant Virus Particles as Immunogens for Inducing Murine and Human Immune Responses Against Human Immunodeficiency Virus Type 1," *J. Virol.* 75:8434-8439, American Society for Microbiology (2001).

Matsui, S.M., et al., "The Isolation and Characterization of a Norwalk Virus-specific cDNA," *J. Clin. Invest.* 87:1456 1461, The American Society for Clinical Investigation, Inc. (1991).

Mayer, G., et al., "Oligonucleotide-protamine-albumin nanoparticles: Protamine sulfate causes drastic size reduction," *J. Control. Release* 106:181-187, Elsevier (Aug. 2005).

Moss, R.B., et al., "In vitro immune function after vaccination with an inactivated, gp120-depleted antigen with immunostimulatory oligodeoxynucleotides," *Vaccine* 18:1081-1087, Elsevier Science (2000).

(56) References Cited

OTHER PUBLICATIONS

Natilla, A., et al., "Cucumber mosaic virus as carrier of a hepatitis C virus-derived epitope," *Arch. Virol.* 149:137-154, Springer Verlag (Jan. 2004).

Ni, CZ., et al., "Crystal structure of the coat protein from the GA bacteriophage: Model of the unassembled dimer," *Protein Sci.* 5:2485-2493, Cold Spring Harbor Laboratory Press (1996).

Notka, F., et al., "Accelerated clearance of SHIV in rhesus monkeys by virus-like particle vaccines is dependent on induction of neutralizing antibodies," *Vaccine* 18:291-301, Elsevier Science (2000)

Oxenius, A., et al., "CpG-Containing Oligonucleotides Are Efficient Adjuvants for Induction of Protective Antiviral Immune Responses with T-cell Peptide Vaccines," *J. Virol.* 73:4120-4126, American Society for Macrobiology (1999).

Pallas, V., et al., "In vitro for RNA binding properties of the coat protein of prunus necrotic ringspot ilarvirus and their comparison to related and unrelated viruses," *Arch. Virol.* 144:797-803, Springer-Verlag (1998).

Pamujula, S., et al. "Oral delivery of spray dried PLGA/amifostine nanoparticles," *J. Pharm. Pharmacol.* 56:1119-1125, The Authors (Sep. 2004).

Pelisek, J., et al., "Optimized lipopolyplex formulations for gene transfer to human colon carcinoma cells under in vitro conditions," *J. Gene Med.* 8:186-197, John Wiley & Sons Ltd. (Feb. 2006).

Pestka, S., "Interferon Standards and General Abbreviations," *Methods Enzymol.* 119:14-23, Academic Press New York (1986).

Pisetsky, D.S., and Reich, C.F., "Stimulation of Murine Lymphocyte Proliferation by a Phosphorothioate Oligonucleotide with Antisense Activity for Herpes Simplex Virus," *Life Sci.* 54:101-107, Pergamon Press (1994).

Priano, C. et al., "A Complete Plasmid-Based Complementation System for RNA Coliphage Qβ: Three Proteins of Bacteriophages Qβ (Group III) and SP (Group IV) can be Interchanged," *J. Mol. Biol.* 249:283-297, Academic Press Limited (1995).

Pushko, P., et al., "Analysis of RNA phage fr coat protein assembly by insertion, deletion and substitution mutagenesis," *Prot. Eng.* 6:883-891, Oxford University Press (1993).

Putney, S.D., et al., "Enhanced Anti-Tumor Effects with Microencapsulated c-*myc* Antisense Oligonucleotide," *Antisense Nuc. Acid Drug Dev.* 9:451-458, Mary Ann Liebert Inc. (1999).

Qu, F., and Morris, T.J., "Encapsidation of Turnip Crinkle Virus is Defined by a Specific Packaging Signal and RNA Size," *J. Virol.* 71:1428-1435, American Society for Microbiology (1997).

Raz, E., "Introduction: gene vaccination, current concepts and future directions," *Springer Semin. Immunopathol.* 19:131-137, Springer-Verlag (1997).

Raz, E., et al., "Preferential induction of a Th1 immune response and inhibition of specific IgE antibody formation by plasmid DNA immunization," *Proc. Natl. Acad. Sci. USA* 93:5141-5145, National Academy of Sciences (1996).

Roy, K., et aL, "Oral gene delivery with chitosan—DNA nanoparticles generates immunologic protection in a murine model of peanut allergy," *Nat. Med.* 5:387-391, Nature America Inc. (1999).

Ruzicka, T. et al., "A Short-Term Trial of Tacrolimus ointment for atopic Dermatitis," *N. Engl. J. Med.* 337:816-821, Massachusetts Medical Society (1997).

Sasnauskas, K., et al., "Yeast Cells Allow High-Level Expression and Formation of Polyomavirus-Like Particles," *Biol. Chem.* 380:381-286, Walter de Gruyter (1999).

Sato, Y., et al., "Immunostimulatory DNA Sequences Necessary for Effective Intradermal Gene Immunization," *Science* 273:352-354, American Association for the Advancement of Science (1996).

Schwarz, K., "Role of Toll-like receptors in costimulating cytotoxic T cell in responses," *Eur. J. Immunol.* 33:1465-1470, Wiley-VCH Verlag (2003).

Scott, M.T., et al., "Adjuvant Activity of Saponin: Antigen Localization Studies," *Int. Arch. Allergy Appl. Immunol.* 77:409-412, S. Karger Ag Basel (1985).

Semple, S.C., et al., "Lipid-Based Formulations of Antisense Oligonucleotides for Systemic Delivery Applications," *Methods Enzymol.* 313:322-341, Academic Press (2000).

Serre, K., et al., "Efficient Presentation of Multivalent Antigens Targeted to Various Cell Surface Molecules of Dendritic Cells and Surface Ig of Antigen-Specific B Cells," *J. Immunol.* 161:6059-6067, The American Association of Immunologists (1996).

Siegal, F.P., et al., "The Nature of the Principal Type 1 Interferon-Producing Cells in Human Blood," *Science* 284:1835-1837, American Association for the Advancement of Science (1999).

Storni, T., et al., "Critical Role for Activation of Antigen-Presenting Cells in Priming of Cytotoxic T Cell Responses After Vaccination with Virus-Like Particles," *J. Immunol.* 168:2880-2886, The American Association of Immunologists (2002).

Tars, K., et al., "The Crystal Structure of Bacteriophage GA and a Comparison of Bacteriophages Belonging to the Major Groups of *Escherichia coli* Leviviruses," *J. Mol. Biol.* 271:759-773, Academic Press Limited (1997).

Tondelli, L., et al., "Core-shell nanospheres for oligonucleotide delivery. .V: Adsorption/release behavior of 'stealth' nanospheres," *J. Biomater. Sci. Polymer. Edn.* 14:1209-1227, (2003).

Torrence, P.F., "Preparation of a Synthetic Polynucleotide Interferon Inducer," *Methods Enzymol.* 78:326-331, Academic Press Inc. (1981).

Truong-Le, V.L. et al., "Controlled Gene Delivery by DNA-Gelatin Nanospheres," *Hum. Gene Ther.* 9:1709-1717, Mary Ann Liebert Inc. (1998).

Twomey, T., et al., "Structure and immunogenicity of experimental foot-and-mouth disease and poliomyelitis vaccines," *Vaccine* 13:1603-1610, Elsevier Science Ltd. (1995).

Uhlmann, E., and Vollmer, J., "Recent advances in the development of immunostirnulatory oligonucleotides," *Curr. Opin. Drug Discov. Dev.* 6:204-217, Current Drugs (2003).

Ulrich, R., et al., "Core particles of hepatitis B virus as carrier for foreign epitopes," *Virus Res.* 50:141-182, Academic Press (1998).

Van Ojik, H., et al., "Phase I/II with CpG 7909 as adjuvant to vaccination with MAGE-3 protein in patients with MAGE-3 positive tumors," *Annals of Oncology. Abstract Book of the 27th ESMO Congress, Nice, France, Supplement* 5:157-158 (2002).

Verthelyi, D., et al., "CpG oiigodeoxynucleotides improve the response to hepatitis B immunization in healthy and SIV-infected rhesus macaques," *AIDS* 18:1003-1008, Lippincott Williams & Wilkins (Apr. 2004).

Verthelyi, D., et al., "Human Peripheral Blood Cells Differentially Recognize and Respond to Two Distinct CPG Motifs," *J. Immunol.* 166:2372-2377, The American Association of Immunologists (2001).

Vogel, V., et al., "Oligonucleotide-protamine-albumin nanoparticles: preparation, physical properties, and intracellular distribution," *J Control. Release* 103:99-11, Elsevier (Mar. 2005).

Vollmer, J., et al., "Characterization of three CpG oligodeoxynucleotide classes with distinct immunostimulatory activities," *Eur. J. Immunol.* 43:251-262, Wiley-VCH Verlag (Jan. 2004).

Vrtala, S., et al., "Immunization with Purified Natural and Recombinant Allergens Induces Mouse IgG1 Antibodies That Recognize Similar Epitopes as Human IgE and Inhibit the Human IgE-Allergen Interaction and Allergen-Induced Basophil Degranulation," *J. Immunol.* 160:6137-6144, The American Association of Immunologists (1998).

Wagner, E., et al., "Targeting of Polyplexes: Toward Synthetic Virus Vector Systems," *Adv. Genet.* 53:333-354, Elsevier Inc. (2005).

Walker, G.F., et al, "Toward Synthetic Viruses: Endosomal pH-Triggered Deshielding of Targeted Polyplexes Greatly Enhances Gene Transfer in Vitro and in Vivo," *Mol. Ther.* 11:418-425, The American Society of Gene Therapy (Mar. 2005).

Warnes, A., et al., "Expression of the measles virus nucleoprotein gene in *Escherichia coli* and assembly of nucleocapsid-like structures," *Gene* 160:173-178, The American Society of Gene Therapy (1995).

Wartlick. H., et al., "Tumour cell delivery of antisense oligonucleotides by human serum albumin nanoparticles," *J. Control. Release* 96:483-495. Elsevier (May 2004).

(56) References Cited

OTHER PUBLICATIONS

Weiner, G., "Declaration in support of U.S. Appl. No. 09/286,098," 1-9 (2000).
Weiner, G.J. et al., "Immunostimulatory oligodeoxynucleotides containing the CpG motif are effective as immune adjuvants in tumor antigen immunization," *Poc. Natl. Acad. Sci. USA* 94:10833-10837, National Academy of Sciences (1997).
Westwood, A., et al , "Immunological responses after immunisation of mice with microparticles containing antigen and single stranded RNA (polyuridylic acid)," *Vaccine* 24:1736-1743, Elsevier (Mar. 2006).
Weyermann, J., et al., "Comparison of antisense oligonucleotide drug delivery systems," *J. Control. Release* 100:411-423, Elsevier (Dec. 2004)..
Xu, W., et al., "Intranasal delivery of chitosan-DNA vaccine generates mucosal SIgA and anti-CVB3 protection," *Vaccine* 22:3603-3612, Elsevier (Sep. 2004).
Yamamoto, S., at al,, "Unique Palindromic Dequences in SYnthetic Oligonucleotides are Required to Induce IFN [correction of INF] and Augment IFN-Mediated [correction of INF] Natural Killer Activity," *J. Immunol.* 148:4072-4076, American Association of Immunologists (1992).
Yamamoto, S., et al., "The discovery of immunostimulatory DNA sequence," *Springer Semin. Immunopathol.* 22:11-19, Springer Verlag (2000).
Yamamoto, T., et al., "Ability of Oligonucleotides with Certain Palindromes to Induce Interferon Production and Augment Natural Killer Cell Activity is Associated with Their Base Length," *Antisense Res. Dev.* 4:119-22, Mary Ann Liebert Inc. (1994).
Yamamoto, T., et al., "Synthetic Oligonucleotides with Certain Palindromes Stimulate Interferon Production of Human Peripheral Blood Lymphocytes in vitro," *Jpn. J. Cancer Res.* 85:775-779, (1994).
Yu, D., et al., "Potent CpG oligonucleotides containing phosphodiester linkages: in vitro and in vivo immunostimulatory properties," *Biochem. Biophys. Res. Commun.* 297:83-90, Academic Press (2002).
Zhu, S.G., et al., "Poly(L-lysine)-modified silica nanoparticles for the delivery of antisense oligonucleotides," *Biotechnol. Appl. Biochem.* 39:179-187, Portland Press Ltd. (Apr. 2004).
Zillies, J., and Coester, C., "Evaluating gelatin based nanoparticles as a carrier system for double stranded oligonucleotides," *J. Pharm. Pharm. Sci.* 7:17-21, The Society of Pharmacy & Pharmaceutical Sciences (Feb. 2004).
Zlotnick, A., et al., "Mechanism of Capsid Assembly for an Icosahedral Plant Virus," *Virology* 277:450-456, Academic Press (2000).
Zobel, H.P., et al., "Cationic Polyhexylcyanoacrylate Nanopanicles as Carriers for Antisense Oligonucleotides," *Antisense Nuc. Acid Drug Dev.* 7:483-493, Mary Ann Liebert Inc. (1997).
Zwiorek, K., et al., "Gelatin nanoparticles as a new and simple gene delivery system," *J. Pharm. Pharm. Sci.* 7:22-28, The Society of Pharmacy & Pharmaceutical Sciences (Feb. 2004).
Dialog File 351, Accession No. 437404, English language abstract for DE 2 034 118 (document AS1 on accompanying PTO/SB/08A), Jan. 13, 1972.
Dialog File 351, Accession No. 437404, English language abstract for DE 10 2004 041 340 (document AW8 on accompanying PTO/SB/08A), Feb. 23, 2006.
Bachmann, M.F. and Zinkernagel, R.M., "The influence of virus structure on antibody responses and virus serotype formation," *Immunol. Today* 17:553-558, Elsevier Science Publishers (1996).
Chackerian, B., et al., "Induction of autoantibodies to mouse CCR5 with recombinant papillomavirus particles," *Proc. Natl. Acad. Sci. USA* 96:2373-2378, National Academy of Sciences (1999).
Klovins, J., et al., "Nucleotide sequence of a ssRNA phage from *Acinetobacter*: kinship to coliphages," *J. Gen. Virol.* 83:1523-1533, Society for General Microbiology (Jun. 2002).

Kozlovska, T.M., et al., "Recombinant RNA phage Qβ capsid particles synthesized and self-assembled in *Escherichia coli*," *Gene* 137:133-137, Elsevier Science Publishers (1993).
Kratz, P.A., et al., "Native display of complete foreign protein domains on the surface of hepatitis B virus capsids," *Proc. Natl. Acad. Sci. USA* 96:1915-1920 (1999).
Li, Y., et al., "Vaccination Against Angiogenesis-Associated Antigens: A Novel Cancer Immunotherapy Strategy," *Curr. Mol. Med.* 3:773-779, Bentham Science Publishers Ltd. (Dec. 2003).
Neirynck, S., et al., "A universal influenza A vaccine based on the extracellular domain of the M2 protein," *Nat. Med.* 5:1157-1163, Nature Publishing Company (1999).
Nieland, J.D., et al., "Chimeric Papillomavirus Virus-like Particles Induce a Murine Self-Antigen-Specific Protective and Therapeutic Antitumor Immune Response," *J. Cell. Biochem.* 73:145-152, Wiley-Liss Inc. (1999).
Slepushkin, V.A., et al., "Protection of mice against influenza A virus challenge by vaccination with baculovirus-expressed M2 protein," *Vaccine* 13:1399-1402, Elsevier Science Ltd. (1995).
Vasiljeva, I., et al., "Mosaic Qβ coats as a new presentation model," *FEBS Lett.* 431:7-11, Elsevier Science B.V. (1998).
Witte, L., et al., "Monoclonal antibodies targeting the VEGF receptor-2 (Flk1/KDR) as an anti-angiogenic therapeutic strategy," *Cancer Metastasis Rev.* 17:155-161, Kluwer Academic Publishers (1998).
Allison (1994) Int J Technol Assess Health Care 10(1):107-20—Adjuvants and Immune Enhancement.
Azuma (1992) Vaccine 10(14):1000-6—Synthetic immunoadjuvants: application to non-specific host stimulation and potentiation of vaccine immunogenicity.
Bird (1987) TIG 3(12):342-347—CpG islands as gene markers in the vertebrate nucleus.
Branda et al. (1993) Biochem Pharmacol 45(10):2037-43—Immune Stimulation by an Antisense Oligomer Complementary to the rev Gene of HIV-1.
Buonaguro et al. (Jan. 2001) Antiviral Res 49(1):35-47 High efficient production of Pr55$^{gag}$ virus-like particles expressing multiple HIV-1 epitopes, including a gp120 protein derived from an Ugandan HIV-I isolate of subtype A.
Cella et al. (1999) Nat Med 5(8):919-23—Plasmacytoid monocytes migrate to inflamed lymph nodes and produce large amounts of type I interferon.
Cella et al. (1999) J Exp Med 189(5):821-9—Maturation, Activation, and Protection of Dendritic Cells Induced by Double-stranded RNA.
Choi and Rao (Sep. 2000) Virology 275(2):249-57—Packaging of Tobacco Mosaic Virus Subgenomic RNAs by Brome Mosaic Virus Coat Protein Exhibits RNA Controlled Polymorphism.
Choi et al. (Jan. 2002) Proc Natl Acad Sci U S A 99(2):655-60—tRNA elements mediate the assembly of an icosahedral RNA virus.
Clark et al. (Nov. 2001) J Gen Virol 82(Pt 11):2791-7—Immunity against both polyomavirus VP1 and a transgene product induced following intranasal delivery of VP1 pseudocapsid-DNA complexes.
Dalpke et al. (May 2002) Immunology 106(1):102-12—Phosphodiester CpG oligonucleotides as adjuvants: polyguanosine runs enhance cellular uptake and improve immunostimulative activity of phosphodiester CpG oligonucleotides in vitro and in vivo.
Francois et al. (1988) Clin Immunol Immunopathol 48(3):297-306—Examination of the Inhibitory and Stimulatory Effects of IFN-α, -β, and -γ on Human B-cell Proliferation Induced by Various B-cell Mitogens.
Gilkeson et al. (1989) J Immunol. 142(5):1482-6—Induction of Anti-double Stranded DNA Antibodies in Normal Mice by Immunization with Bacterial DNA.
Holt (1994) Lancet 344(8920):456-8—A potential vaccine strategy for asthma and allied atopic diseases during early childhood
Kataoka et al. (1992) Jpn J Cancer Res 83(3):244-7—Antitumor Activity Synthetic Oligonucleotides with Sequences from cDNA Encoding Proteins of *Mycobacterium bovis* BCG.
Kerkmann (May 2003) J Immunol 170(9):4465-74—Activation with CpG-A and CpG-B Oligonucleotides Reveals Two Distinct Regulatory Pathways of Type I IFN Synthesisin Human Plasmacytoid Dendritic Cells.

(56) References Cited

OTHER PUBLICATIONS

Kline et al. (1996) J. Invest Med 44(7):380A—Cpg Motif Oligonucleotides are Effective in Prevention of Eosinophilic Inflammation in a Murine Model of Asthma.
Kline et al. (1998) J Immunol 160(6):2555-9—Modulation of Airway Inflammation by CpG Oligodeoxynucleotides in a Murine Model of Asthma.
Kline et al. (Feb. 2002) Am J Physiol Lung Cell Mol Physiol 283(1):L170-9—Treatment of established asthma in a murine model using CpG oligodeoxynucleotides.
Klinman (Apr. 2004) Nat Rev Immunol 4(4):249-58—Immunotherapeutic uses of CpG Oligodeoxynucleotides.
Kuramoto et al. (1992) Cancer Immunol Immunother 34(5):283-8—Induction of T-cell-mediated immunity against MethA fibrosarcoma by intratumoral injections of a bacillus Calmette-Guérin nucleic acid fraction.
Lee et al. (Oct. 2000) J Immunol 165(7):3631-9—Effects of a Hexameric Deoxyriboguanosine Run Conjugation into CpG Oligodeoxynucleotides on Their Immunostimulatory Potentials.
Lotz et al. (1987) J Rheumatol 14(1):42-5—Effects of Recombinant Human Interferons on Rheumatoid Arthritis B Lymphocytes Activated by Epstein-Barr Virus.
McIntyre et al. (1993) Antisense Res Dev 3(4):309-22—A Sense Phosphorothioate Oligonucleotide Directed to the Initiation Codon of Transcription Factor $Nf_{-K}$ B P65 Causes Sequence-Specific Immune Stimulation.
Merritt and Johnson (1965) J Immunol 94( ):416-22 Studies on the Adjuvant Action of Bacterial Endotoxins on Antibody Formation. Vi. Enhancement of Antibody Formation by Nucleic Acids.
Messina et al. (1991) J Immunol 147(6):1759-64—Stimulation of In Vitro Murine Lymphocyte Proliferation by Bacterial DNA.
Messina et al. (1993) Cell Immunol 147(1):148-57—The influence of DNA Structure on the in Vitro Stimulation of Murine Lymphocytes by Natural and Synthetic Polynucleotide Antigens.
Mojcik et al. (1993) Clin Immunol Immunopathol 67(2):130-6—Administration of a Phosphorothioate Oligonucleotide Antisense to Murine Endogenous Retroviral MCF Env Causes Immune Effects in Vivo in a Sequence-Specific Manner.
Nohria and Rubin (1994) Biotherapy 7(3-4):261-9—Cytokines as potential vaccine adjuvants.
Pisetsky et al. (1993) Mol Biol Rep 18(3):217-21—Stimulation of in vitro proliferation of murine lymphocytes by synthetic oligodeoxynucleotides.
Saiki et al. (1988) Vaccine 6(3):238-44—Induction of tumoricidal macrophages and production of cytokines by synthetic muramyl dipeptide analogues.
Takauji et al. (Nov. 2002) J Leukoc Biol 72(5):1011-9—CpG-DNA-induced IFN-α production involves p38 MAPK-dependent STAT1 phosphorylation in human plasmacytoid dendritic cell precursors.
Yamamoto et al. (1992) J Immunol 148(12):4072-6—Unique Palindromic Sequences in Synthetic Oligonucleotides Are Required to Induce IFN [Correction of INF] and Augment IFN-Mediated [Correction of INF] Natural Killer Activity.
Brazolot Millan, C., et al., "CpG DNA can induce strong Th1 humoral and cell-mediated immune responses against hepatitis B surface antigen in young mice," *Proc.Natl. Acad. Sci. USA* 95:15553-15558, National Academy of Sciences, US (1998).
Chackerian, B., et al., "Conjugation of a self-antigen to papillomavirus-like particles allows for efficient induction of protective autoantibodies," *J Clin. Invest.* 108:415-423, The American Society for Clinical Investigation, US (Aug. 2001).
Chu, R.S., et al.,"CpG oligodeoxynucleotides act as adjuvants that switch on T helper 1 (Th1) Immunity," *J. Exp. Med.* 186:1623-1631, The Rockefeller University Press, US (1997).
Davis, H.L., et al. "CpG DNA is a potent enhancer of specific immunity in mice immunized with recombinant hepatitis B surface antigen," *J. Immunol.* 160:870-876, The American Assoc. of Immunologists, US (1998).
Goldmann, C., et al., "Molecular cloning and expression of major structural protein VP1 of the human polyomavirus JC virus: formation of virus-like particles useful for immunological and therapeutic studies," *J. Virol.* 73:4465-4469, American Society for Microbiology, US (1999).
Goldmann, C., et al., "Packaging of small molecules into VP1-virus-like particles of the human polyomavirus JC virus," *J. Virol. Methods* 90:85-90, Elsevier Science B.V., Netherlands (Oct. 2000).
Hill, A.V.S., et al., "DNA-based vaccines for malaria: a heterologous prime-boost immunisation strategy," (Proceedings of a conference titled "Development and clinical progress of DNA vaccines," held at the Paul-Ehrlich-Institut, Langen, Germany, Oct. 6-8, 1999) *Dev. Biol.* (Basel) 104:171-179, Karger, Switzerland (Aug. 2000).
Horner, A.A., et al, "Immunostimulatory DNA is a potent mucosal adjuvant," *Cell.Immunol.* 190:77-82, Academic Press, US (1998).
Kalams, S.A. and Walker, B.D., "The critical need for CD4 help in maintaining effective cytotoxic T lymphocyte responses," *J Exp. Med.* 188:2199-2204, The Rockefeller University Press, US (1998).
Klenerman, P. and Zinkernagel, R.M., "Original antigenic sin impairs cytotoxic T lymphocyte responses to viruses bearing variant epitopes," *Nature* 394:482-485, Macmillan Publishers Ltd., UK (1998).
Klinman, D.M., et al., "CpG motifs as immune adjuvants," *Vaccine* 17:19-25, Elsevier Science Ltd., Netherlands (1999).
Krieg, A.M., "Direct immunologic activities of CpG DNA and implications for gene therapy," *J. Gene Med.* 1:56-63, John Wiley & Sons, Ltd., UK (1999).
Krieg, A.M., et al., "The role of CpG dinucleotides in DNA vaccines," *Trends Microbiol.* 6:23-27, Elsevier Science Ltd., Netherlands (1998).
Lenz, P., et al., "Papillomavirus-like particles induce acute activation of dendritic cells," *J. Immunol.* 166:5346-5355, The American Assoc. of Immunologists, US (May, 2001).
McCluskie, M.J. and Davis, H.L., "Cutting edge: CpG DNA is a potent enhancer of systemic and mucosal immune responses against hepatitis B surface antigen with intranasal administration to mice," *J. Immunol.* 161:4463-4466, The American Assoc. of Immunologists, US (1998).
McCluskie, M.J. and Davis, H.L., "Novel strategies using DNA for the induction of mucosal immunity," *Crit. Rev. in Immunol.* 19:303-329, Begell House, Inc., US (1999).
Roman, M., et al., "Immunostimulatory DNA sequences function as T helper-1-promoting adjuvants," *Nat. Med.* 3:849-854, Nature Publishing Group, UK (1997).
Scott, D., et al., "Immunogenicity of biotinylated hapten-avidin complexes," *Mol. Immunol.* 21:1055-1060, Pergamon Press Ltd., US (1984).
Sedlik, C., et al., "Recombinant parvovirus-like particles as an antigen carrier: a novel nonreplicative exogenous antigen to elicit protective antiviral cytotoxic T cells," *Proc. Natl. Acad. Sci. USA* 94:7503-7508, National Academy of Sciences, US (1997).
Stacey, K.J. and Blackwell, J.M., "Immunostimulatory Dna as an adjuvant in vaccination against *Leishmania major*," *Infect. Immun.* 67:3719-3726, American Society for Microbiology, US (1999).
Wagner, R., et al., "Construction, expression, and immunogenicity of chimeric HIV-1 virus-like particles," *Virology* 220:128-140, Academic Press, Inc., US (1996).
Patent Abstract of Japan, English language Abstract of Japanese Patent Publication No. 2001-151698 A, published Jun. 5, 2001.
Storni, T., et al., "Nonmethylated , CG Motifs Packaged into Virus-Like Particles Induce Protective Cytotoxic T Cell Responses in the Absence of Systemic Side Effects," *J. Immunol.* 172(3):1777-1785, American Association of Immunologists, Inc., United States (2004).
Co-pending U.S. Appl. 13/038,272, inventors Bachmann, M.F., et al., filed Mar. 1, 2011 (Not Published).
Co-pending U.S. Appl. No. 13/294,006, inventors Bachmann, M.F., et al., filed Nov. 10, 2011 (Not Published).
U.S. Appl. No. 60/156,147, filed Sep. 27, 1999.
U.S. Appl. No. 60/156,147, filed Jul. 10, 2002, Hartmann et al.
Albert, M.L., "Dendritic cells acquire antigen from apoptotic cells and induce class 1-restricted CTLs.", *Nature* 392(6671):86-9 Macmillan Publishers Ltd, UK (1998).
Bachmann, M.F., "Dendritic cells process exogenous viral proteins and virus-like particles for class 1 presentation to CD8+ cytotoxic T

(56) References Cited

OTHER PUBLICATIONS lymphocytes." *Eur J Immunol* 26(11):2595-600, VCH Verlagsgesellschaft mbH, Germany (1996).

Banchereau, "J., Dendritic cells and the control of immunity.", *Nature* 392(6673):245-52, Macmillan Publishers Ltd, UK (1998).

Cella, M., "Origin, maturation and antigen presenting function of dendritic cells.", *Curr Opin Immunol* 9(1):10-6, Current Biology, UK (1997).

Gluckman, "J.C., In vitro generation of human dendritic cells and cell therapy.", *Cytokines Cell Mol Ther* 3(3):187-96, Martin Dunitz Ltd, UK (1997).

Klimek, L., "Assessment of clinical efficacy of CYT003-QbG10 in patients with allergic rhinoconjunctivitis: a phase IIb study.", *Clin Exp Allergy* 41(9):1305-12, Wiley, USA (2011).

Klinman, D.M., "Therapeutic applications of CpG-containing oligodeoxynucleotides.", *Antisense Nucleic Acid Drug Dev* 8(2):181-4, Mary Ann Liebert Inc., USA (1998).

Krieg, A.M., "Mechanisms and applications of immune stimulatory CpG oligodeoxynucleotides.", *Biochim Biophys Acta* 1489(1):107-16, Elsevier Science B.V., The Netherlands (1999).

Kündig, T.M., "Duration of TCR stimulation determines costimulatory requirement of T cells.", *Immunity* 5(1):41-52, Cell Press, Elsevier, USA (1996).

Lim, F., "The RNA-binding site of bacteriophage Qbeta coat protein.", *J Biol Chem* 271(50):31839-45, The American Society for Biochemistry and Molecular Biology Inc., USA (1996).

Ridge, J.P., "A conditioned dendritic cell can be a temporal bridge between a CD4+ T-helper and T-killer cell.", *Nature* 393(6684):474-8, Macmillan Publishers Ltd, UK (1998).

Senti, G., "Use of A-type CpG oligodeoxynucleotides as an adjuvant in allergen-specific immunotherapy in humans: a phase I/IIa clinical trial.", *Clin Exp Allergy* 39(4):562-70, Wiley, USA (2009).

Steinman, R.M., "Dendritic cells and immune-based therapies.", *Exp Hematol* 24(8):859-62, International Society for Experimental Hermatology, (1996).

Weigle, W.O., "Analysis of autoimmunity through experimental models of thyroiditis and allergic encephalomyelitis.", *Adv Immunol* 30:159-273. Academic Press Inc., USA (1980).

Yamamoto, T., "Lipofection of synthetic oligodeoxyribonucleotide having a palindromic sequence of AACGTT to murine splenocytes enhances interferon production and natural killer activity.", *Microbiol Immunol* 38(10):831-6, Wiley, USA (1994).

* cited by examiner

SEQUENCE LISTING

```
<160> NUMBER OF SEQ ID NOS: 80

<210> SEQ ID NO 1
<211> LENGTH: 185
<212> TYPE: PRT
<213> ORGANISM: Hepatitis B virus

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60
```

```
Leu Met Thr Leu Ala Thr Trp Val Gly Asn Asn Leu Glu Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Asn Ala Pro Ile Leu Ser Thr Leu Pro
130                 135                 140

Glu Thr Thr Val Val Arg Arg Arg Gly Arg Ser Pro Arg Arg
145                 150                 155                 160

Arg Thr Pro Ser Pro Arg Arg Arg Arg Ser Gln Ser Pro Arg Arg
                165                 170                 175

Arg Ser Gln Ser Arg Glu Ser Gln Cys
                180                 185

<210> SEQ ID NO 2
<211> LENGTH: 188
<212> TYPE: PRT
<213> ORGANISM: Hepatitis B virus

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Gly Gly
 65                  70                  75                  80

Lys Gly Gly Ser Arg Asp Leu Val Val Ser Tyr Val Asn Thr Asn Val
                 85                  90                  95

Gly Leu Lys Phe Arg Gln Leu Leu Trp Phe His Ile Ser Cys Leu Thr
            100                 105                 110

Phe Gly Arg Glu Thr Val Leu Glu Tyr Leu Val Ser Phe Gly Val Trp
        115                 120                 125

Ile Arg Thr Pro Pro Ala Tyr Arg Pro Pro Asn Ala Pro Ile Leu Ser
130                 135                 140

Thr Leu Pro Glu Thr Thr Val Val Arg Arg Arg Asp Arg Gly Arg Ser
145                 150                 155                 160

Pro Arg Arg Arg Thr Pro Ser Pro Arg Arg Arg Arg Ser Gln Ser Pro
                165                 170                 175

Arg Arg Arg Arg Ser Gln Ser Arg Glu Ser Gln Cys
                180                 185

<210> SEQ ID NO 3
<211> LENGTH: 132
<212> TYPE: PRT
<213> ORGANISM: Bacteriophage Qbeta

<400> SEQUENCE: 3

Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
```

```
                    20                  25                  30
Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
        50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
        130

<210> SEQ ID NO 4
<211> LENGTH: 329
<212> TYPE: PRT
<213> ORGANISM: Bacteriophage Qbeta

<400> SEQUENCE: 4

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr Trp Thr Leu Leu Ile Ala Gly Gly Gly Ser Gly
    130                 135                 140

Ser Lys Pro Asp Pro Val Ile Pro Asp Pro Pro Ile Asp Pro Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
            180                 185                 190

Val Glu Leu Gln Pro Arg Glu Phe Asp Val Ala Leu Lys Asp Leu Leu
        195                 200                 205

Gly Asn Thr Lys Trp Arg Asp Trp Asp Ser Arg Leu Ser Tyr Thr Thr
    210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
```

```
                        260                 265                 270
Lys Ser Ile Asn Ala Tyr Cys Ser Leu Ser Asp Ile Ala Ala Tyr His
            275                 280                 285

Ala Asp Gly Val Ile Val Gly Phe Trp Arg Asp Pro Ser Ser Gly Gly
        290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
                325

<210> SEQ ID NO 5
<211> LENGTH: 129
<212> TYPE: PRT
<213> ORGANISM: Bacteriophage R17

<400> SEQUENCE: 5

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Met Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr

<210> SEQ ID NO 6
<211> LENGTH: 130
<212> TYPE: PRT
<213> ORGANISM: Bacteriophage fr

<400> SEQUENCE: 6

Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Asn Asn Arg Lys Tyr Thr Val Lys Val Glu
    50                  55                  60

Val Pro Lys Val Ala Thr Gln Val Gln Gly Gly Val Glu Leu Pro Val
65                  70                  75                  80

Ala Ala Trp Arg Ser Tyr Met Asn Met Glu Leu Thr Ile Pro Val Phe
                85                  90                  95

Ala Thr Asn Asp Asp Cys Ala Leu Ile Val Lys Ala Leu Gln Gly Thr
            100                 105                 110

Phe Lys Thr Gly Asn Pro Ile Ala Thr Ala Ile Ala Ala Asn Ser Gly
        115                 120                 125
```

-continued

```
Ile Tyr
    130

<210> SEQ ID NO 7
<211> LENGTH: 130
<212> TYPE: PRT
<213> ORGANISM: Bacteriophage GA

<400> SEQUENCE: 7

Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
            20                  25                  30

Leu Ser Asn Asn Ser Arg Ser Gln Ala Tyr Arg Val Thr Ala Ser Tyr
        35                  40                  45

Arg Ala Ser Gly Ala Asp Lys Arg Lys Tyr Ala Ile Lys Leu Glu Val
    50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
    130

<210> SEQ ID NO 8
<211> LENGTH: 132
<212> TYPE: PRT
<213> ORGANISM: Bacteriophage SP

<400> SEQUENCE: 8

Met Ala Lys Leu Asn Gln Val Thr Leu Ser Lys Ile Gly Lys Asn Gly
1               5                   10                  15

Asp Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Phe Lys
    50                  55                  60

Val Gln Ile Lys Leu Gln Asn Pro Thr Ala Cys Thr Arg Asp Ala Cys
65                  70                  75                  80

Asp Pro Ser Val Thr Arg Ser Ala Phe Ala Asp Val Thr Leu Ser Phe
                85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
        115                 120                 125

Asn Pro Ala Tyr
    130

<210> SEQ ID NO 9
<211> LENGTH: 329
<212> TYPE: PRT
<213> ORGANISM: Bacteriophage SP

<400> SEQUENCE: 9
```

Ala Lys Leu Asn Gln Val Thr Leu Ser Lys Ile Gly Lys Asn Gly Asp
1               5                   10                  15

Gln Thr Leu Thr Leu Thr Pro Arg Gly Val Asn Pro Thr Asn Gly Val
            20                  25                  30

Ala Ser Leu Ser Glu Ala Gly Ala Val Pro Ala Leu Glu Lys Arg Val
            35                  40                  45

Thr Val Ser Val Ala Gln Pro Ser Arg Asn Arg Lys Asn Phe Lys Val
50                  55                  60

Gln Ile Lys Leu Gln Asn Pro Thr Ala Cys Thr Arg Asp Ala Cys Asp
65                  70                  75                  80

Pro Ser Val Thr Arg Ser Ala Phe Ala Asp Val Thr Leu Ser Phe Thr
            85                  90                  95

Ser Tyr Ser Thr Asp Glu Glu Arg Ala Leu Ile Arg Thr Glu Leu Ala
            100                 105                 110

Ala Leu Leu Ala Asp Pro Leu Ile Val Asp Ala Ile Asp Asn Leu Asn
            115                 120                 125

Pro Ala Tyr Trp Ala Ala Leu Leu Val Ala Ser Ser Gly Gly Gly Asp
            130                 135                 140

Asn Pro Ser Asp Pro Asp Val Pro Val Val Pro Asp Val Lys Pro Pro
145                 150                 155                 160

Asp Gly Thr Gly Arg Tyr Lys Cys Pro Phe Ala Cys Tyr Arg Leu Gly
            165                 170                 175

Ser Ile Tyr Glu Val Gly Lys Glu Gly Ser Pro Asp Ile Tyr Glu Arg
            180                 185                 190

Gly Asp Glu Val Ser Val Thr Phe Asp Tyr Ala Leu Glu Asp Phe Leu
            195                 200                 205

Gly Asn Thr Asn Trp Arg Asn Trp Asp Gln Arg Leu Ser Asp Tyr Asp
            210                 215                 220

Ile Ala Asn Arg Arg Arg Cys Arg Gly Asn Gly Tyr Ile Asp Leu Asp
225                 230                 235                 240

Ala Thr Ala Met Gln Ser Asp Asp Phe Val Leu Ser Gly Arg Tyr Gly
            245                 250                 255

Val Arg Lys Val Lys Phe Pro Gly Ala Phe Gly Ser Ile Lys Tyr Leu
            260                 265                 270

Leu Asn Ile Gln Gly Asp Ala Trp Leu Asp Leu Ser Glu Val Thr Ala
            275                 280                 285

Tyr Arg Ser Tyr Gly Met Val Ile Gly Phe Trp Thr Asp Ser Lys Ser
            290                 295                 300

Pro Gln Leu Pro Thr Asp Phe Thr Gln Phe Asn Ser Ala Asn Cys Pro
305                 310                 315                 320

Val Gln Thr Val Ile Ile Pro Ser
            325

<210> SEQ ID NO 10
<211> LENGTH: 130
<212> TYPE: PRT
<213> ORGANISM: Bacteriophage MS2

<400> SEQUENCE: 10

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
            35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 11
<211> LENGTH: 133
<212> TYPE: PRT
<213> ORGANISM: Bacteriophage M11

<400> SEQUENCE: 11

Met Ala Lys Leu Gln Ala Ile Thr Leu Ser Gly Ile Gly Lys Lys Gly
1               5                   10                  15

Asp Val Thr Leu Asp Leu Asn Pro Arg Gly Val Asn Pro Thr Asn Gly
            20                  25                  30

Val Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ser Asp Val Thr Phe Ser
                85                  90                  95

Phe Thr Gln Tyr Ser Thr Val Glu Glu Arg Ala Leu Val Arg Thr Glu
            100                 105                 110

Leu Gln Ala Leu Leu Ala Asp Pro Met Leu Val Asn Ala Ile Asp Asn
        115                 120                 125

Leu Asn Pro Ala Tyr
    130

<210> SEQ ID NO 12
<211> LENGTH: 133
<212> TYPE: PRT
<213> ORGANISM: Bacteriophage MX1

<400> SEQUENCE: 12

Met Ala Lys Leu Gln Ala Ile Thr Leu Ser Gly Ile Gly Lys Asn Gly
1               5                   10                  15

Asp Val Thr Leu Asn Leu Asn Pro Arg Gly Val Asn Pro Thr Asn Gly
            20                  25                  30

Val Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ala Asp Val Thr Phe Ser
                85                  90                  95

-continued

Phe Thr Gln Tyr Ser Thr Asp Glu Glu Arg Ala Leu Val Arg Thr Glu
            100                 105                 110

Leu Lys Ala Leu Leu Ala Asp Pro Met Leu Ile Asp Ala Ile Asp Asn
        115                 120                 125

Leu Asn Pro Ala Tyr
        130

<210> SEQ ID NO 13
<211> LENGTH: 330
<212> TYPE: PRT
<213> ORGANISM: Bacteriophage NL95

<400> SEQUENCE: 13

Met Ala Lys Leu Asn Lys Val Thr Leu Thr Gly Ile Gly Lys Ala Gly
1               5                   10                  15

Asn Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Tyr Lys
    50                  55                  60

Val Gln Ile Lys Leu Gln Asn Pro Thr Ala Cys Thr Lys Asp Ala Cys
65                  70                  75                  80

Asp Pro Ser Val Thr Arg Ser Gly Ser Arg Asp Val Thr Leu Ser Phe
                85                  90                  95

Thr Ser Tyr Ser Thr Glu Arg Glu Arg Ala Leu Ile Arg Thr Glu Leu
            100                 105                 110

Ala Ala Leu Leu Lys Asp Asp Leu Ile Val Asp Ala Ile Asp Asn Leu
        115                 120                 125

Asn Pro Ala Tyr Trp Ala Ala Leu Leu Ala Ala Ser Pro Gly Gly Gly
    130                 135                 140

Asn Asn Pro Tyr Pro Gly Val Pro Asp Ser Pro Asn Val Lys Pro Pro
145                 150                 155                 160

Gly Gly Thr Gly Thr Tyr Arg Cys Pro Phe Ala Cys Tyr Arg Arg Gly
                165                 170                 175

Glu Leu Ile Thr Glu Ala Lys Asp Gly Ala Cys Ala Leu Tyr Ala Cys
            180                 185                 190

Gly Ser Glu Ala Leu Val Glu Phe Glu Tyr Ala Leu Glu Asp Phe Leu
        195                 200                 205

Gly Asn Glu Phe Trp Arg Asn Trp Asp Gly Arg Leu Ser Lys Tyr Asp
    210                 215                 220

Ile Glu Thr His Arg Arg Cys Arg Gly Asn Gly Tyr Val Asp Leu Asp
225                 230                 235                 240

Ala Ser Val Met Gln Ser Asp Glu Tyr Val Leu Ser Gly Ala Tyr Asp
                245                 250                 255

Val Val Lys Met Gln Pro Pro Gly Thr Phe Asp Ser Pro Arg Tyr Tyr
            260                 265                 270

Leu His Leu Met Asp Gly Ile Tyr Val Asp Leu Ala Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Arg Phe Asn Arg His Asn Cys Pro
305                 310                 315                 320

Val Gln Thr Val Ile Val Ile Pro Ser Leu
                325                 330

```
<210> SEQ ID NO 14
<211> LENGTH: 129
<212> TYPE: PRT
<213> ORGANISM: Bacteriophage f2

<400> SEQUENCE: 14
```

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Leu Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr

```
<210> SEQ ID NO 15
<211> LENGTH: 128
<212> TYPE: PRT
<213> ORGANISM: Bacteriophage PP7

<400> SEQUENCE: 15
```

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125

```
<210> SEQ ID NO 16
<211> LENGTH: 132
<212> TYPE: PRT
<213> ORGANISM: Bacteriophage Qbeta

<400> SEQUENCE: 16
```

Ala Lys Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
            115                 120                 125

Asn Pro Ala Tyr
            130

<210> SEQ ID NO 17
<211> LENGTH: 132
<212> TYPE: PRT
<213> ORGANISM: Bacteriophage Qbeta

<400> SEQUENCE: 17

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
            115                 120                 125

Asn Pro Ala Tyr
            130

<210> SEQ ID NO 18
<211> LENGTH: 132
<212> TYPE: PRT
<213> ORGANISM: Bacteriophage Qbeta

<400> SEQUENCE: 18

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe

```
                     85                   90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 19
<211> LENGTH: 132
<212> TYPE: PRT
<213> ORGANISM: Bacteriophage Qbeta

<400> SEQUENCE: 19

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 20
<211> LENGTH: 132
<212> TYPE: PRT
<213> ORGANISM: Bacteriophage Qbeta

<400> SEQUENCE: 20

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130
```

<210> SEQ ID NO 21
<211> LENGTH: 131
<212> TYPE: PRT
<213> ORGANISM: Bacteriophage AP205

<400> SEQUENCE: 21

Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 22
<211> LENGTH: 131
<212> TYPE: PRT
<213> ORGANISM: Bacteriophage AP205

<400> SEQUENCE: 22

Met Ala Asn Lys Thr Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 23
<211> LENGTH: 131
<212> TYPE: PRT
<213> ORGANISM: Bacteriophage AP205

<400> SEQUENCE: 23

Met Ala Asn Lys Pro Met Gln Pro Ile Thr Ser Thr Ala Asp Lys Ile

```
            1               5                  10                 15
Val Trp Ser Asp Pro Thr Arg Leu Ser Thr Thr Phe Ser Ala Ser Leu
                20                  25                  30

Leu Arg Gln Arg Val Lys Val Gly Ile Ala Glu Leu Asn Asn Val Ser
            35                  40                  45

Gly Gln Tyr Val Ser Val Tyr Lys Arg Pro Ala Pro Lys Pro Glu Gly
        50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
            115                 120                 125

Thr Thr Ala
        130

<210> SEQ ID NO 24
<211> LENGTH: 5
<212> TYPE: PRT
<213> ORGANISM: artificial sequence
<220> FEATURE:
<223> OTHER INFORMATION: paptide

<400> SEQUENCE: 24

Gly Gly Lys Gly Gly
1               5

<210> SEQ ID NO 25
<211> LENGTH: 26
<212> TYPE: DNA
<213> ORGANISM: artificial sequence
<220> FEATURE:
<223> OTHER INFORMATION: CpG

<400> SEQUENCE: 25
ggggggggga cgatcgtcgg gggggg                                      26

<210> SEQ ID NO 26
<211> LENGTH: 28
<212> TYPE: DNA
<213> ORGANISM: artificial sequence
<220> FEATURE:
<223> OTHER INFORMATION: CpG

<400> SEQUENCE: 26
gggggggggg acgatcgtcg gggggggg                                    28

<210> SEQ ID NO 27
<211> LENGTH: 30
<212> TYPE: DNA
<213> ORGANISM: artificial sequence
<220> FEATURE:
<223> OTHER INFORMATION: CpC oligonucleotide

<400> SEQUENCE: 27
gggggggggg gacgatcgtc gggggggggg                                  30

<210> SEQ ID NO 28
<211> LENGTH: 10
<212> TYPE: DNA
<213> ORGANISM: artificial sequence
```

-continued

```
<220> FEATURE:
<223> OTHER INFORMATION: CpG

<400> SEQUENCE: 28
gacgatcgtc                                                                          10

<210> SEQ ID NO 29
<211> LENGTH: 19
<212> TYPE: DNA
<213> ORGANISM: artificial sequence
<220> FEATURE:
<223> OTHER INFORMATION: CpG

<400> SEQUENCE: 29
ggggacgatc gtcggggggg                                                               19

<210> SEQ ID NO 30
<211> LENGTH: 20
<212> TYPE: DNA
<213> ORGANISM: artificial sequence
<220> FEATURE:
<223> OTHER INFORMATION: CpG

<400> SEQUENCE: 30
gggggacgat cgtcggggggg                                                              20

<210> SEQ ID NO 31
<211> LENGTH: 21
<212> TYPE: DNA
<213> ORGANISM: artificial sequence
<220> FEATURE:
<223> OTHER INFORMATION: CpG

<400> SEQUENCE: 31
ggggggacga tcgtcggggg g                                                             21

<210> SEQ ID NO 32
<211> LENGTH: 22
<212> TYPE: DNA
<213> ORGANISM: artificial sequence
<220> FEATURE:
<223> OTHER INFORMATION: CpG

<400> SEQUENCE: 32
gggggggacg atcgtcgggg gg                                                            22

<210> SEQ ID NO 33
<211> LENGTH: 24
<212> TYPE: DNA
<213> ORGANISM: artificial sequence
<220> FEATURE:
<223> OTHER INFORMATION: CpG

<400> SEQUENCE: 33 gggggggggac gatcgtcggg gggg                                                         24

<210> SEQ ID NO 34
<211> LENGTH: 30
<212> TYPE: DNA
<213> ORGANISM: artificial sequence
<220> FEATURE:
<223> OTHER INFORMATION: CpG

<400> SEQUENCE: 34 gggggggcgac gacgatcgtc gtcggggggg                                                   30
```

```
<210> SEQ ID NO 35
<211> LENGTH: 6
<212> TYPE: DNA
<213> ORGANISM: artificial sequence
<220> FEATURE:
<223> OTHER INFORMATION: palindrome

<400> SEQUENCE: 35 gacgtc                                                                     6

<210> SEQ ID NO 36
<211> LENGTH: 6
<212> TYPE: DNA
<213> ORGANISM: artificial sequence
<220> FEATURE:
<223> OTHER INFORMATION: palindrome

<400> SEQUENCE: 36 aacgtt                                                                     6

<210> SEQ ID NO 37
<211> LENGTH: 6
<212> TYPE: DNA
<213> ORGANISM: artificial sequence
<220> FEATURE:
<223> OTHER INFORMATION: palindrome

<400> SEQUENCE: 37 aacgtt                                                                     6

<210> SEQ ID NO 38
<211> LENGTH: 6
<212> TYPE: DNA
<213> ORGANISM: artificial sequence
<220> FEATURE:
<223> OTHER INFORMATION: palindrome

<400> SEQUENCE: 38 atcgat                                                                     6

<210> SEQ ID NO 39
<211> LENGTH: 6
<212> TYPE: DNA
<213> ORGANISM: artificial sequence
<220> FEATURE:
<223> OTHER INFORMATION: palindrome

<400> SEQUENCE: 39 cgatcg                                                                     6

<210> SEQ ID NO 40
<211> LENGTH: 6
<212> TYPE: DNA
<213> ORGANISM: artificial sequence
<220> FEATURE:
<223> OTHER INFORMATION: palindrome

<400> SEQUENCE: 40 cgtacg                                                                     6

<210> SEQ ID NO 41
<211> LENGTH: 6
<212> TYPE: DNA
<213> ORGANISM: artificial sequence
<220> FEATURE:
<223> OTHER INFORMATION: palindrome

<400> SEQUENCE: 41
```

```
cgcgcg                                                              6

<210> SEQ ID NO 42
<211> LENGTH: 6
<212> TYPE: DNA
<213> ORGANISM: artificial sequence
<220> FEATURE:
<223> OTHER INFORMATION: palindrome

<400> SEQUENCE: 42 gcgcgc                                                              6

<210> SEQ ID NO 43
<211> LENGTH: 6
<212> TYPE: DNA
<213> ORGANISM: artificial sequence
<220> FEATURE:
<223> OTHER INFORMATION: palindrome

<400> SEQUENCE: 43 tcgcga                                                              6

<210> SEQ ID NO 44
<211> LENGTH: 8
<212> TYPE: DNA
<213> ORGANISM: artificial sequence
<220> FEATURE:
<223> OTHER INFORMATION: palindrome

<400> SEQUENCE: 44 acgatcgt                                                            8

<210> SEQ ID NO 45
<211> LENGTH: 12
<212> TYPE: DNA
<213> ORGANISM: artificial sequence
<220> FEATURE:
<223> OTHER INFORMATION: palindrome

<400> SEQUENCE: 45
cgacgatcgt cg                                                      12

<210> SEQ ID NO 46
<211> LENGTH: 18
<212> TYPE: DNA
<213> ORGANISM: artificial sequence
<220> FEATURE:
<223> OTHER INFORMATION: palindrome

<400> SEQUENCE: 46
cgacgacgat cgtcgtcg                                                18

<210> SEQ ID NO 47
<211> LENGTH: 18
<212> TYPE: DNA
<213> ORGANISM: artificial sequence
<220> FEATURE:
<223> OTHER INFORMATION: palindrome

<400> SEQUENCE: 47
cgacgacgat cgtcgtcg                                                18

<210> SEQ ID NO 48
<211> LENGTH: 6
<212> TYPE: DNA
<213> ORGANISM: artificial sequence
```

```
<220> FEATURE:
<223> OTHER INFORMATION: palindrome

<400> SEQUENCE: 48 aacgtt                                                                  6

<210> SEQ ID NO 49
<211> LENGTH: 8
<212> TYPE: DNA
<213> ORGANISM: artificial sequence
<220> FEATURE:
<223> OTHER INFORMATION: palindrome

<400> SEQUENCE: 49 caacgttg                                                                8

<210> SEQ ID NO 50
<211> LENGTH: 10
<212> TYPE: DNA
<213> ORGANISM: artificial sequence
<220> FEATURE:
<223> OTHER INFORMATION: palindrome

<400> SEQUENCE: 50
acaacgttgt                                                             10

<210> SEQ ID NO 51
<211> LENGTH: 12
<212> TYPE: DNA
<213> ORGANISM: artificial sequence
<220> FEATURE:
<223> OTHER INFORMATION: palindrome

<400> SEQUENCE: 51
aacaacgttg tt                                                          12

<210> SEQ ID NO 52
<211> LENGTH: 14
<212> TYPE: DNA
<213> ORGANISM: artificial sequence
<220> FEATURE:
<223> OTHER INFORMATION: palindrome

<400> SEQUENCE: 52
caacaacgtt gttg                                                        14

<210> SEQ ID NO 53
<211> LENGTH: 12
<212> TYPE: DNA
<213> ORGANISM: artificial sequence
<220> FEATURE:
<223> OTHER INFORMATION: palindrome

<400> SEQUENCE: 53
cggcgcgcgc cg                                                          12

<210> SEQ ID NO 54
<211> LENGTH: 12
<212> TYPE: DNA
<213> ORGANISM: artificial sequence
<220> FEATURE:
<223> OTHER INFORMATION: palindrome

<400> SEQUENCE: 54
cgacggccgt cg                                                          12
```

```
<210> SEQ ID NO 55
<211> LENGTH: 12
<212> TYPE: DNA
<213> ORGANISM: artificial sequence
<220> FEATURE:
<223> OTHER INFORMATION: palindrome

<400> SEQUENCE: 55
ccggcgcgcc gg                                                            12

<210> SEQ ID NO 56
<211> LENGTH: 6
<212> TYPE: DNA
<213> ORGANISM: artificial sequence
<220> FEATURE:
<223> OTHER INFORMATION: palindrome

<400> SEQUENCE: 56 cgcgcg                                                                    6

<210> SEQ ID NO 57
<211> LENGTH: 12
<212> TYPE: DNA
<213> ORGANISM: artificial sequence
<220> FEATURE:
<223> OTHER INFORMATION: palindrome

<400> SEQUENCE: 57
cggcgcgcgc cg                                                            12

<210> SEQ ID NO 58
<211> LENGTH: 10
<212> TYPE: DNA
<213> ORGANISM: artificial sequence
<220> FEATURE:
<223> OTHER INFORMATION: palindrome

<400> SEQUENCE: 58
ggcgcgcgcc                                                               10

<210> SEQ ID NO 59
<211> LENGTH: 6
<212> TYPE: DNA
<213> ORGANISM: artificial sequence
<220> FEATURE:
<223> OTHER INFORMATION: palindrome

<400> SEQUENCE: 59 cggccg                                                                    6

<210> SEQ ID NO 60
<211> LENGTH: 12
<212> TYPE: DNA
<213> ORGANISM: artificial sequence
<220> FEATURE:
<223> OTHER INFORMATION: palindrome

<400> SEQUENCE: 60
cggcggccgc cg                                                            12

<210> SEQ ID NO 61
<211> LENGTH: 11
<212> TYPE: DNA
<213> ORGANISM: artificial sequence
<220> FEATURE:
<223> OTHER INFORMATION: C-type CpG

<400> SEQUENCE: 61
```

```
tcgtcgtttt a                                                             11

<210> SEQ ID NO 62
<211> LENGTH: 13
<212> TYPE: DNA
<213> ORGANISM: artificial sequence
<220> FEATURE:
<223> OTHER INFORMATION: C-type CpG

<400> SEQUENCE: 62
cggcgccgtg ccg                                                           13

<210> SEQ ID NO 63
<211> LENGTH: 13
<212> TYPE: DNA
<213> ORGANISM: artificial sequence
<220> FEATURE:
<223> OTHER INFORMATION: C-type CpG

<400> SEQUENCE: 63
cggcgtcgtg ccg                                                           13

<210> SEQ ID NO 64
<211> LENGTH: 24
<212> TYPE: DNA
<213> ORGANISM: artificial sequence
<220> FEATURE:
<223> OTHER INFORMATION: C-type CpG

<400> SEQUENCE: 64
tcgtcgtttt acggcgccgt gccg                                               24

<210> SEQ ID NO 65
<211> LENGTH: 24
<212> TYPE: DNA
<213> ORGANISM: artificial sequence
<220> FEATURE:
<223> OTHER INFORMATION: C-type CpG

<400> SEQUENCE: 65
tcgtcgtttt acggcgtcgt gccg                                               24

<210> SEQ ID NO 66
<211> LENGTH: 22
<212> TYPE: DNA
<213> ORGANISM: artificial sequence
<220> FEATURE:
<223> OTHER INFORMATION: C-type CpG

<400> SEQUENCE: 66
tcgtcgtttt cggcgcgcgc cg                                                 22

<210> SEQ ID NO 67
<211> LENGTH: 22
<212> TYPE: DNA
<213> ORGANISM: artificial sequence
<220> FEATURE:
<223> OTHER INFORMATION: C-type CpG

<400> SEQUENCE: 67
tcgtcgtttt cgacggccgt cg                                                 22

<210> SEQ ID NO 68
<211> LENGTH: 22
<212> TYPE: DNA
<213> ORGANISM: artificial sequence
```

```
<220> FEATURE:
<223> OTHER INFORMATION: C-type CpG

<400> SEQUENCE: 68
tcgtcgtttt ccggcgcgcc gg                                    22

<210> SEQ ID NO 69
<211> LENGTH: 22
<212> TYPE: DNA
<213> ORGANISM: artificial sequence
<220> FEATURE:
<223> OTHER INFORMATION: C-type CpG

<400> SEQUENCE: 69
tcgtcgtttt cggcgcgcgt cg                                    22

<210> SEQ ID NO 70
<211> LENGTH: 22
<212> TYPE: DNA
<213> ORGANISM: artificial sequence
<220> FEATURE:
<223> OTHER INFORMATION: C-type CpG

<400> SEQUENCE: 70
tcggcgcgcg ccgtcgtcgt tt                                    22

<210> SEQ ID NO 71
<211> LENGTH: 22
<212> TYPE: DNA
<213> ORGANISM: artificial sequence
<220> FEATURE:
<223> OTHER INFORMATION: C-type CpG

<400> SEQUENCE: 71
ttggcgcgcg ccgtcgtcgt tt                                    22

<210> SEQ ID NO 72
<211> LENGTH: 22
<212> TYPE: DNA
<213> ORGANISM: artificial sequence
<220> FEATURE:
<223> OTHER INFORMATION: C-type CpG

<400> SEQUENCE: 72
tcgtcgtttt cgtcggccgc cg                                    22

<210> SEQ ID NO 73
<211> LENGTH: 22
<212> TYPE: DNA
<213> ORGANISM: artificial sequence
<220> FEATURE:
<223> OTHER INFORMATION: C-type CpG

<400> SEQUENCE: 73
tcgtcgtttt cggcttttgc cg                                    22

<210> SEQ ID NO 74
<211> LENGTH: 22
<212> TYPE: DNA
<213> ORGANISM: artificial sequence
<220> FEATURE:
<223> OTHER INFORMATION: C-type CpG

<400> SEQUENCE: 74
tcgtcgtttt cggcgttttt tt                                    22
```

```
<210> SEQ ID NO 75
<211> LENGTH: 22
<212> TYPE: DNA
<213> ORGANISM: artificial sequence
<220> FEATURE:
<223> OTHER INFORMATION: C-type CpG

<400> SEQUENCE: 75
tcgtcgtttt cggcggccgc cg                                      22

<210> SEQ ID NO 76
<211> LENGTH: 23
<212> TYPE: DNA
<213> ORGANISM: artificial sequence
<220> FEATURE:
<223> OTHER INFORMATION: CpG 2006-PS

<400> SEQUENCE: 76
tcgtcgtttt gtcgttttgt cgt                                     23

<210> SEQ ID NO 77
<211> LENGTH: 20
<212> TYPE: DNA
<213> ORGANISM: artificial sequence
<220> FEATURE:
<223> OTHER INFORMATION: CpG 2216

<400> SEQUENCE: 77
gggggacgat cgtcgggggg                                         20

<210> SEQ ID NO 78
<211> LENGTH: 20
<212> TYPE: DNA
<213> ORGANISM: artificial sequence
<220> FEATURE:
<223> OTHER INFORMATION: CpG D19

<400> SEQUENCE: 78
ggtgcatcga tgcagggggg                                         20

<210> SEQ ID NO 79
<211> LENGTH: 60
<212> TYPE: DNA
<213> ORGANISM: artificial sequence
<220> FEATURE:
<223> OTHER INFORMATION: CpG G102x

<400> SEQUENCE: 79
gggggggggg gacgatcgtc gggggggggg gggggggggg gacgatcgtc gggggggggg    60

<210> SEQ ID NO 80
<211> LENGTH: 21
<212> TYPE: DNA
<213> ORGANISM: artificial sequence
<220> FEATURE:
<223> OTHER INFORMATION: CpG 1668-CpG

<400> SEQUENCE: 80
tccatgacgt tcctgaataa t                                       21
```

IMMUNOSTIMULATORY NUCLEIC ACID PACKAGED PARTICLES FOR THE TREATMENT OF HYPERSENSITIVITY

CROSS REFERENCE TO RELATED APPLICATIONS

This application is a continuation of U.S. application Ser. No. 11/638,664, filed Dec. 14, 2006, and which claims the benefit of U.S. Provisional Application No. 60/750,042, filed Dec. 14, 2005, and U.S. Provisional Application No. 60/812,592, filed Jun. 12, 2006, the disclosures of each of which are entirely incorporated herein by reference in their entireties.

FIELD OF THE INVENTION

This invention relates to the field of immunology and the treatment of hypersensitivity by immunologically active compositions. The compositions of the invention comprise particles, preferably virus-like particles, nanoparticles, microparticles or liposomes which are packaged with an immunostimulatory nucleic acid. The compositions of the invention are useful in the treatment of hypersensitivity, preferably allergy, including diseases such as atopic eczema, asthma and IgE-mediated allergy (type-I allergy), especially pollen allergy (hay fever). The invention therefore also provides methods for the treatment of these diseases.

SUMMARY OF THE INVENTION

In a first aspect, the invention provides a composition for use as a medicament, the composition comprising, essentially consisting of, or consisting of a particle and an immunostimulatory nucleic acid (ISS-NA), wherein said particle is packaged with said ISS-NA.

It was surprisingly found that the inventive compositions are useful in the prophylactic and therapeutic treatment of hypersensitivity, preferably allergy. In a further aspect the invention thus provides a composition for use in a method of treating hypersensitivity, preferably allergy in an animal, the composition comprising a particle and immunostimulatory nucleic acid (ISS-NA), wherein said particle is packaged with said ISS-NA. In a specific aspect the invention provides a composition for use in a method of treating hypersensitivity, preferably allergy in an animal, the composition comprising a virus-like particle and an unmethylated CpG-containing oligonucleotide, wherein said virus-like particle is packaged with said unmethylated CpG-containing oligonucleotide. In a preferred embodiment said hypersensitivity is an allergy, preferably IgE-mediated asthma, atopic eczema or IgE-mediated allergy (type I allergy). In a further preferred embodiment said particle is selected from a nanoparticle, a microparticle and a liposome. In a further preferred embodiment said particle is a VLP, preferably a VLP of an RNA-bacteriophage, again preferably a VLP of bacteriophage Qβ. In a further preferred embodiment said unmethylated CpG-containing oligonucleotide exclusively consists of phosphodiester bound nucleotides, most preferably of G10 (SEQ ID NO:27).

In a further aspect the invention provides a process of producing a composition for use in a method of treating hypersensitivity in an animal, said composition comprising (a) a virus-like particle; and (b) an unmethylated CpG-containing oligonucleotide; wherein said virus-like particle (a) is packaged with said unmethylated CpG-containing oligonucleotide (b), said process comprising the steps of (i) incubating said VLP (a) with said unmethylated CpG-containing oligonucleotide (b); (ii) adding RNase; and (iii) purifying said composition.

In a further aspect, the invention provides a process of producing a composition for use in a method of treating hypersensitivity in an animal, said composition comprising (a) a virus-like particle; and (b) an unmethylated CpG-containing oligonucleotide; wherein said virus-like particle (a) is packaged with said unmethylated CpG-containing oligonucleotide (b), said process comprises the steps of (i) incubating said VLP with RNase; (ii) adding said unmethylated CpG-containing oligonucleotide; and (iii) purifying the composition.

In a further aspect the invention provides a process of producing a composition for use in a method of treating hypersensitivity in an animal, said composition comprising (a) a virus-like particle; and (b) an unmethylated CpG-containing oligonucleotide; wherein said virus-like particle (a) is packaged with said unmethylated CpG-containing oligonucleotide (b) said process comprising the steps of (i) disassembling said VLP; (ii) adding said unmethylated CpG-containing oligonucleotide; and (iii) reassembling said VLP.

In a further aspect the invention provides a process of producing a composition for use in a method of treating hypersensitivity in an animal, said composition comprising (a) a virus-like particle; and (b) an unmethylated CpG-containing oligonucleotide; wherein said virus-like particle (a) is packaged with said unmethylated CpG-containing oligonucleotide (b) said process comprises the steps of (i) incubating said VLP with solutions comprising metal ions capable of hydrolyzing the nucleic acids of said VLP; (ii) adding said unmethylated CpG-containing oligonucleotide; and (iii) purifying said composition, wherein preferably said metal ions of step (i) are selected from the group consisting of (a) zinc (Zn) ions; (b) copper (Cu) ions; (c) iron (Fe) ions; (d) any mixtures of at least one ion of (a), (b) and/or (c). In a preferred embodiment, said VLP is produced in a bacterial expression system.

In a further aspect the invention provides a process of producing a composition for use in a method of treating hypersensitivity in an animal, said composition comprising (a) a virus-like particle; and (b) an unmethylated CpG-containing oligonucleotide; wherein said virus-like particle (a) is packaged with said unmethylated CpG-containing oligonucleotide (b) said process comprises the steps of (i) incubating said VLP under alkaline conditions, preferably in the presence of NaOH, most preferably in the presence of about 25 mM NaOH; (ii) adding said unmethylated CpG-containing oligonucleotide; and (iii) purifying said composition.

In a further aspect the invention provides a process of producing a composition for use in a method of treating hypersensitivity in an animal, said composition comprising (a) a virus-like particle; and (b) an unmethylated CpG-containing oligonucleotide; wherein said virus-like particle (a) is packaged with said unmethylated CpG-containing oligonucleotide (b), said process comprising the steps of (i) incubating said VLP with a solution capable of destabilizing said VLP, wherein preferably said VLP is a VLP of bacteriophage Qβ; (ii) purifying the coat protein from said solution; and (iii) reassembling said coat protein to a VLP in the presence of unmethylated CpG-containing oligonucleotide and an oxidizing agent.

In a further aspect the invention provides compositions for use as a medicament, wherein said compositions are obtainable by a process comprising the steps of (i) incubating a VLP with unmethylated CpG-containing oligonucleotides; (ii) adding RNase; and (iii) purifying said composition.

In a further aspect the invention provides compositions for use as a medicament, wherein said compositions are obtainable by a process comprising the steps of (i) incubating a VLP with RNase; (ii) adding unmethylated CpG-containing oligonucleotides; and (iii) purifying the composition.

In a further aspect the invention provides compositions for use as a medicament, wherein said compositions are obtainable by a process comprising the steps of (i) disassembling a VLP; (ii) adding unmethylated CpG-containing oligonucleotides; and (iii) reassembling said VLP.

In a further aspect the invention provides compositions for use as a medicament, wherein said compositions are obtainable by a process comprising the steps of (i) incubating a VLP with solutions comprising metal ions capable of hydrolyzing the nucleic acids of said VLP; (ii) adding unmethylated CpG-containing oligonucleotides; and (iii) purifying said composition.

In a further aspect the invention provides compositions for use in a method of treating allergy in an animal, wherein said compositions are obtainable by a process comprising the steps of (i) incubating a VLP with unmethylated CpG-containing oligonucleotides; (ii) adding RNase; and (iii) purifying said composition.

In a further aspect the invention provides compositions for use in a method of treating allergy in an animal, wherein said compositions are obtainable by a process comprising the steps of (i) incubating a VLP with RNase; (ii) adding unmethylated CpG-containing oligonucleotides; and (iii) purifying the composition.

In a further aspect the invention provides compositions for use in a method of treating allergy in an animal, wherein said compositions are obtainable by a process comprising the steps of (i) disassembling a VLP; (ii) adding unmethylated CpG-containing oligonucleotides; and (iii) reassembling said VLP.

In a further aspect the invention provides compositions for use in a method of treating allergy in an animal, wherein said compositions are obtainable by a process comprising the steps of (i) incubating a VLP with solutions comprising metal ions capable of hydrolyzing the nucleic acids of said VLP; (ii) adding unmethylated CpG-containing oligonucleotides; and (iii) purifying said composition.

In a further aspect the invention provides pharmaceutical compositions comprising a composition of the invention.

In a further aspect the invention provides a method of treating hypersensitivity, preferably allergy in an animal, said method comprising introducing into said animal a composition of the invention.

A further aspect of the invention is the use of a composition of the invention or of a pharmaceutical composition of the invention for the manufacture of a pharmaceutical for the treatment of hypersensitivity in an animal, wherein preferably said hypersensitivity is an allergy, wherein further preferably said allergy is selected from the group consisting of: (a) IgE-mediated asthma, (b) atopic eczema; and (c) IgE-mediated allergy (type I allergy), preferably pollen allergy (hay fever) or house dust allergy.

DETAILED DESCRIPTION OF THE FIGURES

FIG. 1: Characterization of purified Qβ coat protein by analytical size exclusion chromatography. (A) sample of purified Qβ VLP. The observed peak (ratio A260/A280=2) is dominated by the RNA core of the VLP, because the absorption coefficient of RNA at 260 nm is approx. 100 fold higher than the absorption coefficient of the coat protein. (B) sample of the supernatant of the disassembly reaction. Released coat protein is indicated by the presence of the protein-like peak at approx. 12 min. Furthermore several species of non-precipitated RNA molecules are present in the range 6.8 to 11 min. (C) sample of purified Qβ coat protein. Analysis was performed in PBS on column TSK G5000PW×1 (Tosoh Bioscience).

Figure 2:
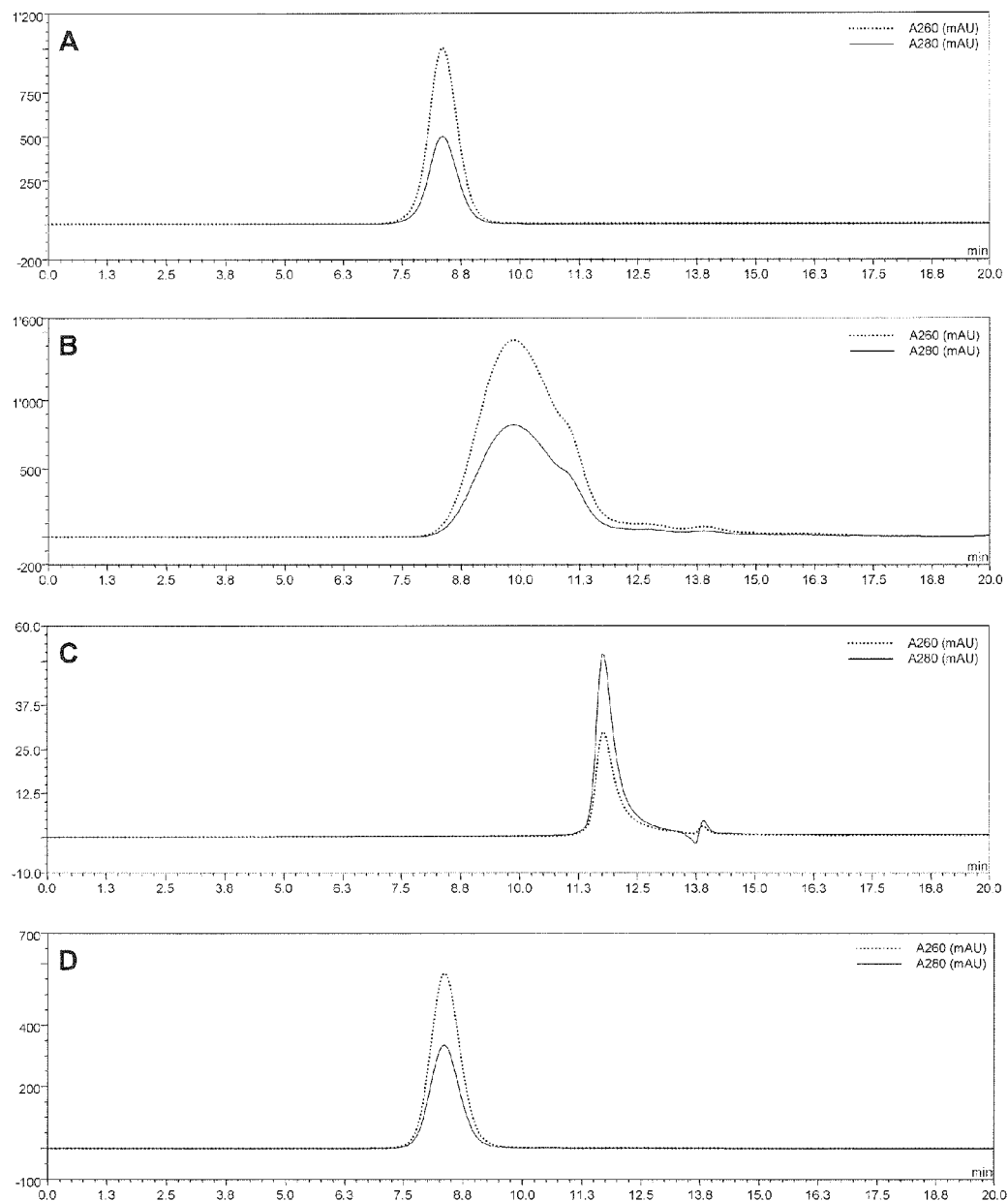

FIG. 2: Analytical size exclusion chromatography of (A) native Qβ VLP, (D) QβG10 VLP and the packaging components (B) oligo nucleotide G10 and (C) Qβ coat protein. The observed peak for QβG10 VLP (D) (ratio A260/A280=1.74) is dominated by the G10 core of the VLP, because the absorption coefficient of G10 at 260 nm is approx. 130 fold higher than the absorption coefficient of the coat protein. Analysis was performed in PBS on column TSK G5000PW×1 (Tosoh Bioscience).

Figure 3:
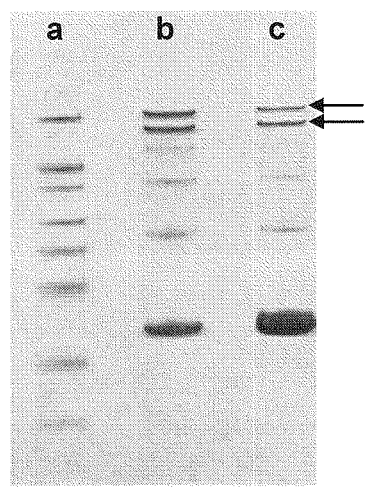

FIG. 3: Non-reducing SDS-PAGE analysis of native Qβ VLP and in vitro assembled QβG10. The position of the coat protein pentamers and hexamers is indicated ((a) molecular weight marker, (b) Qβ VLP, (c) QβG10).

Figure 4:
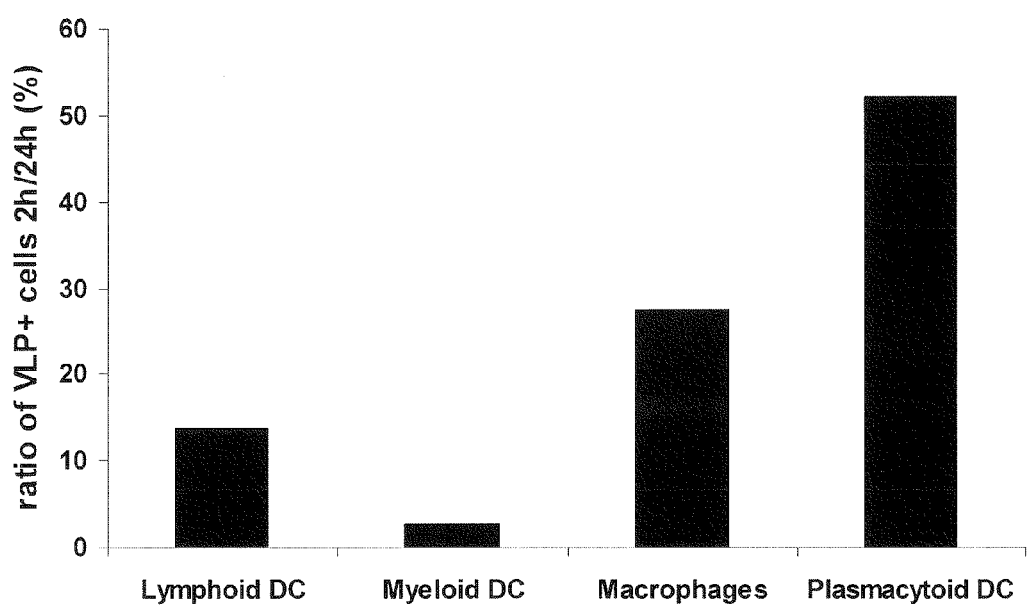

FIG. 4: Ratio of the number of VLP+ cells at 2 h over the number of VLP+ cells at 24 h in the myeloid-DC, lymphoid-DC, Macrophage, pDC and B-cell populations after subcutaneous injection in the footpad, as a measure of DC-mediated or free draining of VLP to the Lymphnode. Anti-CD11c, -CD11b, -B220 and -CD19 antibodies were used to identify myeloid- and lymphoid-DC, Macrophages, pDCs and B cells by FACS analysis.

Figure 5:
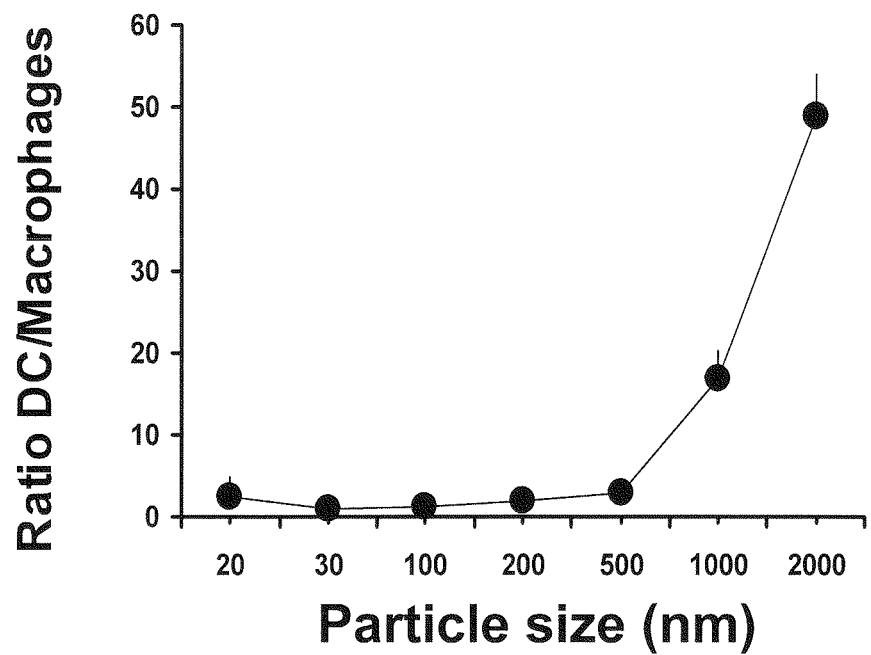
Figure 5:
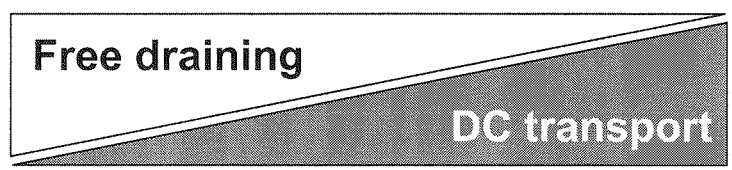

FIG. 5: Ratio between percentages of particle-positive DC and macrophages. Mice were injected with nanoparticles of different size. 48 h later cells were analyzed by FACS.

Figure 6:
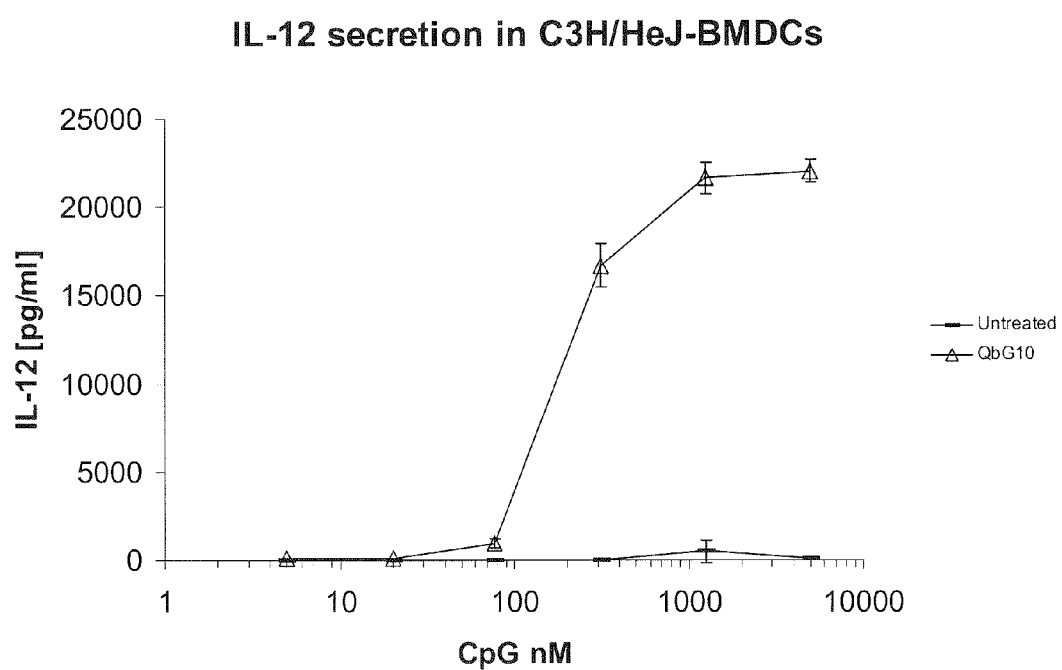

FIG. 6: Activation of BMDCs by QβG10. BMDCs were activated by QβG10 and hence secreted IL-12 in a dose dependent manner (dose is given as equivalent of G10 oligonucleotide packaged in the Qβ VLPs) while untreated control cells did not secrete any IL-12.

DETAILED DESCRIPTION OF THE INVENTION

Unless defined otherwise, all technical and scientific terms used herein have the same meanings as commonly understood by one of ordinary skill in the art to which this invention belongs.

"hypersensitivity": In the context of the invention the term "hypersensitivity" is to be understood as suggested in Johansson et al. 2001, Allergy 56:813-824 as any objectively reproducible symptom or signs, initiated by exposure to a defined stimulus at a dose tolerated by normal subjects. Hypersensitivity reactions are reproducible in the sense that there is reasonable evidence from history, examination, or investigation of a link between the symptoms and the environmental factors to which the patients attribute their symptoms. The term hypersensitivity encompasses non-allergic hypersensitivity and allergic hypersensitivity (allergy). Non-allergic hypersensitivity is any hypersensitivity which does not comprise an involvement of the immune system or at least where no involvement of the immune system can be detected, wherein allergic hypersensitivity always comprises an involvement of the cellular or humoral immune system. Hypersensitivity preferably refers to allergic and non-allergic forms of a disease selected from the group consisting of: (a) asthma, (b) rhinitis, (c) conjunctivitis, (d) rhinoconjuctivitis, (e) dermatitis, (e) urticaria, (e) food hypersensitivity, (e) drug hypersensitivity, (e) insect sting or bite hypersensitivity, and (e) anaphylaxis. In particular, hypersensitivity also includes any type of allergy.

Further preferably, hypersensitivity refers to allergic forms of a disease selected from the group consisting of: (a) asthma, (b) rhinitis, (c) conjunctivitis, (d) rhinoconjuctivitis, (e) dermatitis, (e) urticaria, (e) food hypersensitivity, (e) drug hypersensitivity, (e) insect sting or bite hypersensitivity, and (e) anaphylaxis. In particular, hypersensitivity also includes any type of allergy.

"allergy": In the context of the application the term "allergy" stands for "allergic hypersensitivity" and is to be understood as suggested by Johansson et al. 2001, Allergy 56:813-824 and Johannson et al. 2004, J. Allergy Clin. Immunol. 113(5) 832-835. Unless otherwise indicated, the application follows the nomenclature for allergy as set forth therein. Allergy or allergic hypersensitivity is a hypersensitivity reaction initiated by immunologic mechanisms in response to a substance (allergen), often in a genetically predisposed individual (atopy). Allergy can be antibody- or cell-mediated. In most patients, the antibody typically responsible for an allergic reaction belongs to the IgE isotype (see "antibodies") and these patients may be said to suffer from IgE-mediated allergy (type-I allergy). It must be noted that not all IgE-mediated allergic reactions occur in atopic subjects. In non IgE-mediated allergy, the antibody may belong to the IgG isotype. Thus, within the meaning of the application, "allergy" refers to both, IgE-mediated allergy (type-I allergy) and non IgE-mediated allergy. IgE-mediated allergy is preferably addressed by the invention. Therefore, in the context of the invention allergy preferably refers to IgE-mediated allergy. Allergies are classified according to the source of the antigen evoking the hypersensitive reaction. In one embodiment allergy is selected from (a) food allergy, (b) drug allergy, (c) house dust allergy, (d) insect venom or bite allergy, and (e) pollen allergy. Alternatively, allergies are classified based on the major symptoms of the hypersensitive reaction. Thus, in another embodiment allergy refers to any allergic form of a disease selected from the group of (a) asthma, (b) rhinitis, (c) conjunctivitis, (d) rhinoconjunctivitis, (e) dermatitis, (f) urticaria and (g) anaphylaxis.

"type-I allergy": the terms "type-I allergy" and "IgE-mediated allergy" are used interchangeably and relate to IgE-mediated hypersensitivities to allergens. Preferred embodiments of the invention relate to IgE-mediated allergy selected from the group consisting of (a) pollen allergy (hay fever); (b) house dust allergy; (c) food allergy; (d) drug allergy; (e) insect venom or bite allergy, preferably bee venom allergy; and (f) animal allergy, preferably cat allergy.

"hay fever": typical form of an IgE-mediated allergy (type-I allergy) against pollen which may comprise rhinitis, conjunctivitis and/or asthma, wherein asthma preferably occurs in chronic forms of hay fever.

"atopy", "atopic diseases": Atopy is a personal or familial tendency to produce IgE antibodies in response to low doses of allergens, usually proteins, and to develop typical symptoms such as asthma, rhinoconjunctivitis, or eczema/dermatitis. The first manifestations of atopy in a child are often allergic symptoms, such as diarrhea, wheezing, and skin rashes, and only later can the responsible IgE antibody be detected. Allergic symptoms in a typical atopic individual may be referred to as atopic. In one embodiment of the invention hypersensitivity is an atopic disease, preferably an atopic disease selected from the group consisting of (a) atopic asthma, (b) atopic eczema, (c) atopic IgE-mediated allergy, preferably pollen allergy (hay fever), house dust allergy or house dust mite allergy. In one embodiment the application relates to IgE-mediated allergy in general, irrespective of whether or not said IgE-mediated allergy is regarded as atopic or non atopic allergy. However, specifically preferred embodiments of the invention relate to atopic allergy, preferably to IgE-mediated atopic allergy.

"rhinitis": The term "rhinitis" relates to hypersensitivity symptoms from the nose, for example, itching, sneezing, increased secretion, and blockage. Rhinitis relates to non-allergic as well as allergic, i.e. immunologically mediated, rhinitis. Preferred embodiments of the invention relate to allergic rhinitis, preferably to IgE-mediated and non IgE-mediated forms of allergic rhinitis. Specifically preferred embodiments relate to IgE-mediated allergic rhinitis.

"conjunctivitis": The term conjunctivitis relates to irritations of the eye which can be of allergic as well as non-allergic origin, wherein allergic conjunctivitis encompasses IgE-mediated and non IgE-mediated allergic conjunctivitis. Allergic conjunctivitis, especially IgE mediated allergic conjunctivitis is commonly accompanied by allergic rhinitis, so this disorder is appropriately termed allergic rhinoconjunctivitis. Besides IgE-mediated conjunctivitis, contact allergic conjunctivitis involving TH1 mechanisms occurs. Non-allergic conjunctivitis also often accompanies non-allergic rhinitis. Preferred embodiments of the invention relate to allergic conjunctivitis, including IgE-mediated and non IgE-mediated forms of allergic conjunctivitis. Specifically preferred embodiments relate to IgE-mediated allergic conjunctivitis. Further preferred embodiments relate to IgE-mediated allergic rhinoconjunctivitis.

"asthma": Asthma or asthma bronchiale is a chronic respiratory disease due to inflammation of the air passages in the lungs and affects the sensitivity of the nerve endings in the airways so they become easily irritated. In an attack, the lining of the passages swell causing the airways to narrow and reducing the flow of air in and out of the lungs. Asthma can occur in a intermittent form (2 attacks per week or less during daytime, 2 attacks per month or less at night), in persistent form (permanent attacks during daytime, frequent attacks at night) and in any intermediate form. Within the meaning of the application the term asthma relates to non-allergic as well as to allergic asthma. Preferred embodiments of the invention relate to allergic asthma, including IgE-mediated and non IgE-mediated forms of asthma. Specifically preferred embodiments relate to IgE-mediated allergic asthma, most preferably to atopic asthma.

"atopic asthma": IgE-mediated form of asthma in patients with a genetic predisposition which often occurs in conjunction with atopic eczema and IgE-mediated allergies, for example pollen allergy (hay fever), house dust or dust mite.

"dermatitis": The term "dermatitis" relates to local inflammation of the skin and encompasses, besides other forms, "eczema" and "contact dermatitis" (see definitions below). Preferred embodiments of the invention relate to dermatitis, preferably to eczema and contact dermatitis.

"eczema": The term "eczema" relates to the atopic eczema/dermatitis syndrome (AEDS), describing an aggregation of several skin diseases with certain clinical characteristics in common involving a genetically determined skin barrier defect. This genetically determined target organ sensitivity constitutes the basis for eczema. In children and young adults of the atopic constitution, the underlying inflammation is dominated by an IgE-antibody associated reaction (atopic eczema). In chronic cases, the inflammation seems to be less influenced by IgE antibody, and the dominating cells in biopsies are lymphocytes. Eczema relates to non-allergic eczema and allergic eczema. Preferred embodiments of the invention relate to eczema, preferably allergic eczema including atopic (IgE-mediated) eczema and non atopic forms of eczema. Most preferably, the invention relates to atopic (IgE-mediated) eczema.

"contact dermatitis": The term "contact dermatitis" relates to local inflammatory reaction in the skin caused by close contact with low molecular weight chemicals or irritants. Contact dermatitis can be of allergic as well as non-allergic nature. Allergic contact dermatitis is mediated by immunological mechanisms, predominantly TH1 lymphocytes. Typical allergens acting as haptens and causing allergic contact dermatitis are nickel, chromium ions, fragrances, preservatives, and urushiol, from the poison ivy plant. Exposure can occur through oral uptake, so-called systemic allergic contact dermatitis. A subgroup of contact dermatitis, protein contact dermatitis, is an IgE-associated reaction caused by absorption of proteins through damaged skin. Preferred embodiments of the invention relate to contact dermatitis, preferably allergic contact dermatitis. Further preferred embodiments relate to protein contact dermatitis.

"urticaria": The term "urticaria" relates to a non inflammatory reaction in the skin caused by an irritant or allergen and includes non-allergic urticaria as well as allergic urticaria. Allergic urticaria is mediated by immunological mechanisms, which commonly is IgE-mediated but can also be immune complex-associated. Urticaria can also develop locally after topical contact with the allergen, as occurs on the hands of a person with latex allergy wearing latex gloves or in a person with dog allergy licked by a dog. Preferred embodiments of the invention relate to urticaria, preferably allergic urticaria, most preferably IgE-mediated allergic urticaria.

"food hypersensitivity": The term "food hypersensitivity" relates to adverse reaction to food, which can be of non-allergic as well as allergic nature. Allergic food hypersensitivities can be IgE-mediated and are referred to as food allergies. Severe, generalized allergic reactions to food can be classified as anaphylaxis (see below). Preferred embodiments of the invention relate to food allergy, preferably to IgE-mediated food allergy.

"drug hypersensitivity": The term "drug hypersensitivity" relates to hypersensitive reactions of the body towards drugs which can be of non-allergic as well as of allergic nature. When immunologic mechanisms have been shown, either antibody or cell mediated, the reactions are referred to as drug allergy. Drug allergies can be mediated by IgE. Preferred embodiments of the invention relate to drug hypersensitivity, preferably to drug allergy, most preferably to IgE-mediated drug allergy.

"insect sting hypersensitivity" or "insect bite hypersensitivity": these terms relate to hypersensitive reactions towards insect venom and saliva which can be of non-allergic as well as allergic nature. Insect sting hypersensitivity or insect bite hypersensitivity mediated by an immunologic mechanism is referred to as venom or saliva allergy, as in bee venom allergy. The large quantity of venom allergen in a sting is comparable with years of inhaled pollen allergen. This high-dose sensitization probably explains why there is no need for a genetic predisposition for developing such an allergy. Preferred embodiments of the invention relate to venom allergy, preferably to IgE-mediated venom allergy, most preferably to IgE mediated bee venom allergy.

"anaphylaxis": The term "anaphylaxis" refers to a severe, life-threatening, generalized or systemic hypersensitive reaction. The reaction usually develops gradually, most often starting with itching of the gums/throat, the palms, or the soles, and local urticaria; developing to a multiple organ reaction often dominated by severe asthma; and culminating in hypotension and shock. Hypotension and severe bronchospasm do not have to be present for a reaction to be classified as anaphylaxis. Anaphylaxis can be of non-allergic as well as of allergic nature. Allergic anaphylaxis involves an immunologic mechanism like an IgG immune complex, complement related, or immune cell-mediated mechanism. Anaphylaxis preferably relates to an anaphylactic reaction mediated by IgE antibodies (IgE-mediated anaphylaxis), most preferably to peanut-induced food anaphylaxis or bee venom-induced anaphylaxis.

"allergen": The term "allergen" refers to a substance causing allergy. Preferred allergens are allergens disclosed in Shough, H. et al., REMINGTON'S PHARMACEUTICAL SCIENCES, 19th edition, (Chap. 82), Mack Publishing Company, Mack Publishing Group, Easton, Pa. (1995), the entire contents of which is hereby incorporated by reference. Allergens serve as antigens in vertebrate animals. The term "allergen", as used herein, also refers to "allergen extracts" and "allergenic epitopes." Very preferred allergens are selected from the group consisting of: pollens (e.g. grass, ragweed, birch and mountain cedar); house dust and dust mites; mammalian epidermal allergens and animal danders; mold and fungus; insect bodies and insect venom; feathers; food; and drugs (e.g. penicillin).

"allergen extracts"/"provocation test solutions": Allergen extracts are components of provocation test solutions to be used for conjunctival, nasal and bronchial challenges. Such allergen extracts are commercially available and methods for producing such extracts are well-known. Preferred are single allergen provocation solutions comprising a single allergen extract which is prepared from a source selected from the group consisting of (i) tree species or a grass species, most preferably selected from the group consisting of alder, ash, birch, hazel, orchard grass, velvet grass, rye grass, timothy grass, Kentucky blue grass, Meadow fescue, Bermuda grass, ragweed, rye and wheat; (ii) epithelia of different animal species, preferably epithelia from an animal species selected from the group consisting of cat, dog and horse; (iii) moulds, preferably moulds selected from the group consisting of aspergillus, candida, alternaria, and saccharomyces; and (iv) mite species, preferably mite species selected from the group consisting of *Dermatophagoides farinae*, *Dermatophagoides pteronyssinus* and *Acarus siro*. Allergen extracts comprising allergen mixtures can also be used in provocation test solutions. Preferred are allergen mixtures of different grasses, preferably of orchard grass, velvet grass, rye grass, timothy grass, Kentucky blue grass and/or Meadow fescue. Further preferred are allergen mixtures of grasses, cereals, different trees and/or animal hair. Provocation solutions are usually prepared in physiological saline and can be preserved by addition of 0.4% phenol.

"antibody": As used herein, the term "antibody" refers to molecules belonging to the class of immunoglobulins which are capable of binding an epitope or antigenic determinant.

"antigen": As used herein, the term "antigen" refers to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. Antigens as used herein may also be mixtures of several individual antigens. However "antigen" does not encompass any of the components of the compositions of the invention. In particular, the term "antigen" does not refer to the particle nor to the ISS-NA of the invention. The term "antigen" also does not refer to any component forming the particle of the invention, such as, for example capsid protein.

"epitope": As used herein, the term "epitope" refers to continuous or discontinuous portions of a polypeptide having antigenic or immunogenic activity in an animal, preferably a mammal, and most preferably in a human. An epitope is recognized by an antibody or a T cell through its T cell receptor in the context of an MHC molecule.

"immune response": As used herein, the term "immune response" refers to a humoral immune response and/or cellular immune response leading to the activation or proliferation of B- and/or T-lymphocytes and/or antigen presenting cells and/or other cells of the innate immune system, such as pDC. Alternatively, the immune response may also result in an altered function of effector cells, such as mast cells.

"inducing an immune response": A substance, preferably an ISS-NA is capable of inducing an immune response when upon exposure of a cell or an organism to said substance, preferably to an effective amount of said substance, an immune response is detectable in said cell or animal which does not occur in the untreated control.

"stimulating production of IFN-alpha": The production of IFN-alpha by a cell, preferably by a dendritic cell, after exposure to a specific substance is a strong indication of an immunostimulatory effect of said substance. Therefore, ISS-NA which are capable of inducing the production of IFN-alpha are preferred in the context of the invention. IFN-alpha production by a cell can be determined by various methods generally known in the art, preferably by a method selected from (a) ELISA, most preferably by ELISA essentially as described in Example 14; (b) flow cytometry analysis using fluorochrom-conjugated antibodies, preferably as described in Example 14; and (c) cytopathicity inhibition bioassays. A typical cytopathicity inhibition bioassay is based on bovine MDBK cells infected with vesicular stomatitis virus, as previously described in Pestka, S. (1986) "Interferon Standards and General Abbreviations", in Methods in Enzymology, Academic Press, New York 119, 14-23. In the context of the application a substance, preferably an immunostimulatory nucleic acid, is regarded as being "capable of stimulating IFN-alpha production", when the production of IFN-alpha by a cell as detected by any one of the above described methods, preferably by ELISA, most preferably as described in Example 14, is significantly increased upon exposure of said cell to said substance as compared to a control cell, wherein typically and preferably, said IFN-alpha production is increased by a factor of at least about 2, more preferably by a factor of about 3 or more.

"enhancing an immune response": A substance which enhances an immune response, refers to a substance, preferably to an ISS-NA, which is capable of intensifying or modulating the immune response of a cell or an animal upon exposure of said cell or said animal to said substance, as compared to a suitable control. This observation can relate to any parameter known in the art to be indicative for an immune response, preferably to the formation of cytokines and to cytotoxicity. For example, the lytic activity of cytotoxic T cells can be measured, e.g. using a $^{51}$Cr release assay, with and without the substance, preferably the ISS-NA. The amount of the substance at which the CTL lytic activity is enhanced as compared to the CTL lytic activity without the substance is said to be an amount sufficient to enhance the immune response. In a preferred embodiment, the immune response is enhanced by a factor of at least about 2, more preferably by a factor of about 3 or more. The amount or type of cytokines secreted may also be altered. Alternatively, the amount of antibodies induced or their subclasses may be altered.

"Immunostimulatory nucleic acid (ISS-NA)": As used herein, the term immunostimulatory nucleic acid refers to a nucleic acid capable of inducing and/or enhancing an immune response. ISS-NA, as used herein, comprise ribonucleic acids and in particular desoxyribonucleic acids, wherein both, ribonucleic acids and desoxyribonucleic acids may be either double stranded or single stranded. Preferred ISS-NA are desoxyribonucleic acids, wherein further preferably said desoxyribonucleic acids are single stranded. Preferably, ISS-NA contain at least one CpG motif comprising an unmethylated C. Very preferred ISS-NA comprise at least one CpG motif, wherein said at least one CpG motif comprises or preferably consist of at least one, preferably one, CG dinucleotide, wherein the C is unmethylated. Preferably, but not necessarily, said CG dinucleotide is part of a palindromic sequence. ISS-NA not containing CpG motifs as described above encompass, by way of example, nucleic acids lacking CG dinucleotides, as well as nucleic acids containing CG dinucleotides with a methylated C. The term "immunostimulatory nucleic acid" as used herein also refers to nucleic acids that contain modified bases, preferably 4-bromo-cytosine. Specifically preferred in the context of the invention are ISS-NA which are capable of stimulating IFN-alpha production in dendritic cells.

"oligonucleotide": As used herein, the term "oligonucleotide" refers to a nucleic acid sequence comprising 2 or more nucleotides, preferably at least about 6 nucleotides to about 100,000 nucleotides, more preferably about 6 to about 2000 nucleotides, and still more preferably about 6 to about 300 nucleotides, even more preferably about 20 to about 300 nucleotides, and even more preferably about 20 to about 100 nucleotides, and most preferably 20 to 40 nucleotides. Very preferably oligonucleotides comprise about 30 nucleotides, more preferably oligonucleotides comprise exactly 30 nucleotides, and most preferably oligonucleotides consist of exactly 30 nucleotides. The term oligonucleotide also refers to a nucleic acid comprising more than 100 to about 2000 nucleotides, preferably more than 100 to about 1000 nucleotides, and more preferably more than 100 to about 500 nucleotides.

Oligonucleotides are polyribonucleotides or polydeoxyribonucleotides and are preferably selected from (a) unmodified RNA or DNA, and (b) modified RNA or DNA. The modification may comprise the backbone or nucleotide analogues. Oligonucleotides are preferably selected from the group consisting of (a) single- and double-stranded DNA, (b) DNA that is a mixture of single- and double-stranded regions, (c) single- and double-stranded RNA, (d) RNA that is mixture of single- and double-stranded regions, and (e) hybrid molecules comprising DNA and RNA that are single-stranded or, more preferably, double-stranded or a mixture of single- and double-stranded regions. In a further embodiment oligonucleotides are triple-stranded regions and higher-ordered structures comprising RNA or DNA or both RNA and DNA. In further embodiments oligonucleotide are synthetic, genomic or recombinant. Preferred oligonucleotides are selected from the group consisting of λ-DNA, cosmid DNA, artificial bacterial chromosome, yeast artificial chromosome and filamentous bacteriophage, preferably M13. In one embodiment oligonucleotide refers to (a) DNA or RNA containing at least one modified nucleotide or at least one nucleotide analogue, or (b) to DNA or RNA with backbones modified for stability or for other reasons. Preferred nucleotide modifications/analogs are selected from the group consisting of (a) peptide nucleic acid, (b) inosin, (c) tritylated bases, (d) phosphorothioates, (e) alkylphosphorothioates, (f) 5-nitroindole desoxyribofuranosyl, (g) 5-methyldesoxycytosine, and (h) 5,6-dihydro-5,6-dihydroxydesoxythymidine. Phosphothioated nucleotides are protected against degradation in a cell or an organism and are therefore preferred nucleotide modifications. Further preferred are chemically, enzymatically or metabolically modified forms of polynucleotides as typically found in nature, as well as the chemical forms of DNA and RNA characteristic of viruses and cells. Other nucleotide analogs or modifications will be evident to those skilled in the art. However, unmodified oligonucleotides consisting exclusively of phosphodiester bound nucleotides, typically are more active as ISS-NA than modified nucleotides and are therefore generally preferred in the context of the invention. Most preferred are oligonucleotides consisting exclusively of phosphodiester bound deoxynucleotides. Further preferred are oligonucleotides capable of stimulating IFN-alpha production in cells, preferably in dendritic cells. Very preferred oligonucleotides capable of stimulating IFN-alpha production in cells are selected from A-type CpGs and C-type CpGs.

"CpG motif": As used herein, the term "CpG motif" refers to a pattern of nucleotides that includes an unmethylated central CpG, i.e. the unmethylated CpG dinucleotide, in which the C is unmethylated, surrounded by at least one base, preferably one or two nucleotides, flanking (on the 3' and the 5' side of) the central CpG. Typically and preferably, the CpG motif as used herein, comprises or alternatively consists of the unmethylated CpG dinucleotide and two nucleotides on its 5' and 3' ends. Without being bound by theory, the bases flanking the CpG confer a significant part of the activity to the CpG oligonucleotide.

"CpG"/"unmethylated CpG-containing oligonucleotide": As used herein, the term "unmethylated CpG-containing oligonucleotide" or "CpG" refers to an oligonucleotide, preferably to an oligodesoxynucleotide, containing at least one CpG motif. Thus, a CpG contains at least one unmethylated cytosine, guanine dinucleotide. Preferred CpGs stimulate/activate, e.g. have a mitogenic effect on, or induce or increase cytokine expression by, a vertebrate bone marrow derived cell. For example, CpGs can be useful in activating B cells, NK cells and antigen-presenting cells, such as dendritic cells, monocytes and macrophages. Preferably, CpG relates to an oligodesoxynucleotide, preferably to a single stranded oligodesoxynucleotide, containing an unmethylated cytosine followed 3' by a guanosine, wherein said unmethylated cytosine and said guanosine are linked by a phosphate bond, wherein preferably said phosphate bound is a phosphodiester bound or a phosphothioate bound, and wherein further preferably said phosphate bond is a phosphodiester bound. CpGs can include nucleotide analogs such as analogs containing phosphorothioester bonds and can be double-stranded or single-stranded. Generally, double-stranded molecules are more stable in vivo, while single-stranded molecules have increased immune activity. Preferably, as used herein, a CpG is an oligonucleotide that is at least about ten nucleotides in length and comprises at least one CpG motif, wherein further preferably said CpG is 10 to 60, more preferably 15 to 50, still more preferably 20 to 40, still more preferably about 30, and most preferably exactly 30 nucleotides in length. A CpG may consist of methylated and/or unmethylated nucleotides, wherein said at least one CpG motif comprises at least one CG dinucleotide wherein the C is unmethylated. The CpG may also comprise methylated and unmethylated sequence stretches, wherein said at least one CpG motif comprises at least one CG dinucleotide wherein the C is unmethylated. Very preferred CpGs consist exclusively of unmethylated nucleotides. Very preferably, CpG relates to a single stranded oligodesoxynucleotide containing an unmethylated cytosine followed 3' by a guanosine, wherein said unmethylated cytosine and said guanosine are linked by a phosphodiester bound. Still more preferably, CpG relates to a single stranded oligodesoxynucleotide containing an unmethylated cytosine followed 3' by a guanosine, wherein said unmethylated cytosine and said guanosine are linked by a phosphodiester bound, and wherein said CpG consist exclusively of unmethylated nucleotides. Most preferably, CpG relates to a single stranded oligodesoxynucleotide of about 30 nucleotides in length, containing an unmethylated cytosine followed 3' by a guanosine, wherein said unmethylated cytosine and said guanosine are linked by a phosphodiester bound, and wherein said CpG consist exclusively of unmethylated nucleotides. The CpGs can include nucleotide analogs such as analogs containing phosphorothioester bonds and can be double-stranded or single-stranded. Generally, phosphodiester CpGs are A-type CpGs as indicated below, while phosphothioester stabilized CpGs are B-type CpGs or C-type CpGs. Preferred CpG oligonucleotides in the context of the invention are A-type CpGs and C-type CpG, most preferred are A-type CpGs.

"A-type CpG": As used herein, the term "A-type CpG" or "D-type CpG" refers to an oligodesoxynucleotide (ODN) comprising at least one CpG motif. A-type CpGs preferentially stimulate activation of T cells and the maturation of dendritic cells and are capable of stimulating IFN-alpha production. In A-type CpGs, the nucleotides of the at least one CpG motif are linked by at least one phosphodiester bond. A-type CpGs comprise at least one phosphodiester bond CpG motif which may be flanked at its 5' end and/or, preferably and, at its 3' end by phosphorothioate bound nucleotides. Preferably, the CpG motif, and hereby preferably the CG dinucleotide and its immediate flanking regions comprising at least one, preferably two nucleotides, are composed of phosphodiester nucleotides. Preferred A-type CpGs exclusively consist of phosphodiester (PO) bond nucleotides. Further preferred A-type CpGs do not comprise phosphothioate bounds. Typically and preferably, the term "A-type CpG" or "D-type CpG" as used within this specification, refers to an oligodesoxynucleotide (ODN) comprising at least one CpG motif and having poly G motifs at the 5' and/or 3' ends. Typically and preferably, the poly G motif comprises or alternatively consists of at least one, preferably at least three, at least 4, 5, 6, 7, 8, 9, 10, 11, 12, 13, 14, or 15 Gs (guanosines), most preferably by at least 10 Gs. In some embodiments, the 5' and/or 3' ends, typically and preferably at least one G of the poly G motifs at the 5' and/or 3' ends, preferably at least two, three or four, even more preferably all Gs of the poly G motif, are phosphorothioate modified. However, in a very preferred embodiment, all Gs of the poly G motif are linked by phosphodiester bonds. Preferably, the A-type CpG of the invention comprises or alternatively consists of a palindromic sequence. Typically and preferably, the CpG motif is part of said palindromic sequence. Typically and preferably, all nucleotides, but at least the CpG motif of the palindromic sequence, are composed of phosphodiester nucleotides. Typically and preferably, the palindromic sequence is SEQ ID NO:28. Very preferred A-type CpGs are 16 to 30 nucleotides in length, consist exclusively of phosphodiester bound nucleotides, comprise a palindromic sequence, preferably the palindromic sequence of SEQ ID NO:28, and are flanked at their 5' and at their 3' end by a poly G motif consisting of 3 to 10 Gs.

"B-type CpG": As used herein, the term "B-type CpG" (K-type) relates to a CpG oligonucleotide which predominantly or preferably exclusively consists of modified nucleotides, preferably phosphorothioate modified nucleotides. B-type CpGs stimulate preferentially B-cell and to some extent NK-cell activation and cytokine production.

"C-type CpG": As used herein, the term "C-type CpG" relates to a CpG oligonucleotide which like a B-type oligonucleotide predominantly or preferably exclusively consists of modified nucleotides, preferably phosphorothioate modified nucleotides. Examples of C-type CpGs have been described in WO2005/042018A2 and in Vollmer et al. 2004, Eur. J. Immunol. 43:351-262 which are incorporated herein by reference. Specific reference is made to SEQ IDs NO: 1 to 69 of WO2005/042018A2. C-type CpGs combine effects of A-type and B-type CpGs and stimulate B-cell or NK-cell activation and IFN-alpha production, preferably IFN-alpha production in dendritic cells. C-type CpCs which are capable of stimulating IFN-alpha production, preferably in dendritic cells, are generally preferred in the context of the invention. In contrast to A-type CpGs, C-type CpGs do not typically comprise poly-G stretches. C-type CpGs preferably comprise or alternatively consist of palindromic sequences comprising CpG motifs, preferably palindromic sequences as depicted in SEQ ID NOs:53 to 60. Further preferred C-type CpGs comprise a sequence selected from the group consisting of (a) TCGTCGTTTTA (SEQ ID NO:61), (b) CGGCGCCGTGCCG (SEQ ID NO:62) and (c) CGGCGTCGTGCCG (SEQ ID NO:63), wherein the 5' end of said C-type CpG preferably consists of SEQ ID NO:61 and/or wherein the 3' end of said C-type CpG preferably consists of a nucleotide sequence selected from SEQ ID NO:62 and SEQ ID NO:63, most preferably the 3' end of said C-type CpG consists of SEQ ID NO:63. Further preferred C-type CpGs are selected from the group consisting of (a) TCGTCGTTTTACGGCGCCGTGCCG (SEQ ID NO:64) and (b) TCGTCGTTTTACGGCGTCGTGCCG (SEQ ID NO:65), wherein preferably all nucleic acids of said C-type CpGs are phosphorothioate bound. Further preferred C-type CpGs are selected from the group consisting of (a) TCpGTCGTTTTACGGCGCCGTGCCG (SEQ ID NO:64); (b) TCGTCGTTTTACpGGCpGCCpGTGCCG (SEQ ID NO:64); (c) TCGTCGTTT TACpGGCGCCpGTGCCG (SEQ ID NO:64); (d) TCGTCpGTTTTACpGGCGCCpGTGCCG (SEQ ID NO:64); wherein p indicates phosphodiester bounds while all other nucleotides are phosphorothioate bound. C-type CpGs selected from the group consisting of (a) TCGTCGTTTCGGCGCGCGCCG (SEQ ID NO:66); (b) TCGTCGTTTTCGACGGCCGTCG (SEQ ID NO:67); (c) TCGTCGTTTTCCGGCGCGCCGG (SEQ ID NO:68); (d) TCGTCGTTTTCGGCGCGCGTCG (SEQ ID NO:69); (e) TCGGCGCGCGCCGTCGTCGTTT (SEQ ID NO:70); (f) TTGGCGCGCGCCGTCGTCGTTT (SEQ ID NO:71); (g) TCGTCGTTTTCGTCGGCCGCCG (SEQ ID NO:72); (h) TCGTCGTTTTCGGCTTTTGCCG (SEQ ID NO:73); (i) TCGTCGTTTTCGGCGTTTTTTT (SEQ ID NO:74); and (j) TCGTCGTTTTCGGCGGCCGCCG (SEQ ID NO:75) are potent inducers of IFN-alpha production (Vollmer et al. 2004, Eur. J. Immunol. 43:351-262, p. 253, see Table 1 therein) and are thus specifically preferred immunostimulatory nucleic acids in the context of the invention.

"palindromic sequence": A palindromic sequences is a nucleotide sequence which, when existing in the form of a double stranded nucleic acid with regular base pairing (A/T; C/G), would consist of two single strands with identical sequence in 5'-3' direction. An immunostimulatory nucleic acids of the invention preferably comprises a palindromic sequence, preferably a palindromic sequence consisting of at least 6, preferably of at least 7, 8, 9 or 10, most preferably of exactly 10 nucleotides, wherein most preferably said palindromic sequence preferably comprises a CpG motif. Palindromic sequences of immunostimulatory nucleic acids useful in the context of the invention are, for example, described in Yamamoto et al. 1992, J. Immunol. 148(12):4072-4076 and Kuramoto et al. 1992, Jpn. J. Cancer Res. 83:1128-1131. Preferred palindromic sequences comprise a CpG motif and are selected from the group consisting of (a) GACGTC (SEQ ID NO:35), (b) AGCGCT (SEQ ID NO:36), (c) AACGTT (SEQ ID NO:37), (d) ATCGAT (SEQ ID NO:38); (e) CGATCG (SEQ ID NO:39); (f) CGTACG (SEQ ID NO:40); (g) CGCGCG (SEQ ID NO:41); (h) GCGCGC (SEQ ID NO:42); (i) TCGCGA (SEQ ID NO:43); (j) ACGATCGT (SEQ ID NO:44); (k) CGACGATCGTCG (SEQ ID NO:45); (l) CGACGACGATCGTCGTCG (SEQ ID NO:46); (m) GACGATCGTC (SEQ ID NO:28), (n) CGACGACGATCGTCGTCG (SEQ ID NO:47); (o) AACGTT (SEQ ID NO:48); (p) CAACGTTG (SEQ ID NO:49); (q) ACAACGTTGT (SEQ ID NO:50); (r) AACAACGTTGTT (SEQ ID NO:51); (s) CAACAACGTTGTTG (SEQ ID NO:52); (t) CGGCGCGCGCCG (SEQ ID NO:53); (u) CGACGGCCGTCG (SEQ ID NO:54); (v) CCGGCGCGCCGG (SEQ ID NO:55); (w) CGCGCG (SEQ ID NO:56), (x) CGGCGCGCGCCG (SEQ ID NO:57); (y) GGCGCGCGCC (SEQ ID NO:58); (z) CGGCCG (SEQ ID NO:59); and (aa) CGGCGGCCGCCG (SEQ ID NO:60). A-type CpGs preferably comprise a palindromic sequence selected from palindromic sequences (a) to (s), while C-type CpGs preferably comprise a palindromic sequence selected from palindromic sequences (t) to (aa).

"packaged": The term "packaged" as used herein refers to the state of an ISS-NA, in particular an unmethylated CpG-containing oligonucleotide, in relation to the particle, in particular the VLP. The term "packaged" as used herein refers to covalent binding, preferably by chemically coupling. More preferably, the term "packaged" refers to non-covalent binding, preferably to ionic interactions, hydrophobic interactions, or hydrogen bonds. Covalent bonds are preferably selected from the group consisting of ester, ether, phosphoester, amide, peptide, imide, carbon-sulfur bonds, and carbon-phosphorus bonds. Very preferably, the term "packaged" as used herein refers to the enclosement, or partial enclosement, of said ISS-NA within the particle. For example, the unmethylated CpG-containing oligonucleotide can be enclosed by the VLP without the existence of an actual binding, neither covalently nor non-covalently, or with a non-covalent binding.

Typically and preferably, a particle packaged with ISS-NA protects said ISS-NA from degradation, preferably from DNAse or RNAse hydrolysis. Therefore, in the preferred meaning, the term "packaged" indicates that the ISS-NA, preferably the unmethylated CpG-containing oligonucleotide, in a packaged state is not accessible to DNAse or RNAse hydrolysis. More preferably, the term "packaged" indicates that the ISS-NA, preferably the unmethylated CpG-containing oligonucleotide, is not accessible to DNAse hydrolysis, wherein further preferably the DNAse is DNAseI or Benzonase. Still more preferably, the term "packaged" indicates that the unmethylated CpG-containing oligonucleotide is not accessible to Benzonase hydrolysis.

The accessibility of the ISS-NA, in particular the of the unmethyated CpG-containing oligonucleotide for DNAse (e.g. DNaseI or Benzonase) is preferably assayed as described in Examples 11-17 of WO2003/024481A2 (see p. 111 therein). In a preferred meaning, a VLP is regarded as being packaged with an unmethylated CpG-containing oligonucleotide, when after treatment with Benzonase (190 U Benzonase/mg capsid protein in a buffer comprising 2 mM $MgCl_2$, pH 7.2, 20-25° C., 18 h) at least 90%, preferably at least 95%, most preferably at least 98% of said unmethylated CpG-containing oligonucleotide can be recovered from said VLP (e.g. in an ethidiumbromide stained gel). It is apparent for the artisan that such assays require appropriate controls and may need to be adapted to the specific combination of VLP and unmethylated CpG-containing oligonucleotide. In a more preferred meaning, a VLP of an RNA bacteriophage is regarded as being packaged with an unmethylated CpG-containing oligonucleotide, when after treatment with Benzonase (190 U Benzonase/mg capsid protein in a buffer comprising 2 mM $MgCl_2$, pH 7.2, 20-25° C., 18 h) at least 90%, preferably at least 95%, most preferably at least 98% of said unmethylated CpG-containing oligonucleotide can be recovered from said VLP of an RNA bacteriophage. In a very preferred meaning, a VLP of a RNA bacteriophage is regarded as being packaged with G10 (SEQ ID NO:27) oligonucleotide, when after treatment with Benzonase (190 U Benzonase/mg capsid protein in a buffer comprising 2 mM $MgCl_2$, pH 7.2, 20-25° C., 18 h) at least 90%, preferably at least 95%, most preferably at least 98% of said unmethylated CpG-containing oligonucleotide can be recovered from said VLP of an RNA bacteriophage. In more specific meaning, a VLP of a RNA bacteriophage Qβ, AP205, GA or fr is regarded as being packaged with G10 (SEQ ID NO:27) oligonucleotide, when after treatment with Benzonase (190 U Benzonase/mg capsid protein in a buffer comprising 2 mM $MgCl_2$, pH 7.2, 20-25° C., 18 h) at least 90%, preferably at least 95%, most preferably at least 98% of said unmethylated CpG-containing oligonucleotide can be recovered from said VLP of an RNA bacteriophage. In a very specific meaning, a VLP of a RNA bacteriophage Qβ is regarded as being packaged with G10 (SEQ ID NO:27) oligonucleotide, when after treatment with Benzonase (190 U Benzonase/mg capsid protein in a buffer comprising 2 mM $MgCl_2$, pH 7.2, 20-25° C., 18 h) at least 90%, preferably at least 95%, most preferably at least 98% of said unmethylated CpG-containing oligonucleotide can be recovered from said VLP of RNA bacteriophage Qβ.

Alternatively, the packaging state of an ISS-NA in a particle, in particular of ISS-NA which do not constitute a substrate for DNAse or RNAse hydrolysis, can be assessed by size exclusion chromatography or SDS-PAGE and subsequent spectroscopic analysis as described in Example 4. A further possibility to verify the packaging state of a particle packaged with an ISS-NA is dialysis or tangential flow filtration of the particle, for example under conditions as described in Example 1, wherein non-packaged nucleic acids are removed while packaged nucleic aids remain associated with said particle.

In the very preferred meaning, and wherein the particle is a virus particle or a virus-like particle of a bacteriophage, preferably of an RNA-bacteriophage, further preferably of an RNA bacteriophage Qβ, and most preferably of a virus-like particle of a RNA-bacteriophage Qβ, and wherein said ISS-NA is a unmethylated CpG-containing oligonucleotide, preferably a A-type CpG, further preferably the SEQ ID NO:27, the term "packaged" indicates that the particle packaged with said ISS-NA elutes at the same retention time as the virus-like particle of said bacteriophage, preferably of said RNA-bacteriophage, further preferably of said RNA bacteriophage Qβ obtained by recombinant expression of the coat protein in *E. coli*, preferably wherein said retention time is determined by size exclusion chromatography, preferably as described in Example 4 of the present application, and comprises said ISS-NA as determined preferably as described in Example 4 of the present application.

In preferred embodiments, the ISS-NA, preferably the unmethylated CpG-containing oligonucleotide, is packaged inside the particle, preferably VLP capsids, most preferably in a non-covalent manner. Protocols for the preparation of VLPs packaged with unmethylated CpG-containing oligonucleotide are provided in the prior art, e.g. in WO2003/024481A2 (see Examples 2, 3, 7, 8, 10, 11, 12, 13, 14, 15, 16, and 17 therein, in particular Examples 14-17 therein) and WO2004/000351A1. The disclosure of both publications is incorporated to this application by reference. Further Protocols for the preparation of VLPs packaged with unmethylated CpG-containing oligonucleotide are provided Examples 1, 3 5 and 6 of the present application.

It is to be understood that under the assay conditions specified above, especially those of Examples 11-17 of WO2003/024481A2, some synthetic particles which are packaged with said ISS-NA may release a certain limited amount of ISS-NA, wherein said release typically follows a bi- or more phasic kinetic, wherein said kinetic may comprise a fast initial burst release phase and at least one slow release phase. For example, a certain percentage of the ISS-NA packaged in a synthetic particle may be released in a burst release phase, when incubated at 37° C. or 30° C. in physiological buffers, in vitro. In this case the burst release phase is followed by at least one slow release phase. In some cases the second release phase will be flat, meaning that no or very limited amounts of ISS-NA are released from the synthetic particle in that phase. The two or more phases are identified by examination of the release kinetic of ISS-NA from the synthetic particle. Typically, an initial burst release phase will be complete in a few hours but may last up to 24 hours, while the slow release phase may last from 2-3 days up to 6 days or longer. In some cases, the slow release phase may be nearly flat, with no or very little ISS-NA released after the burst release phase. Alternatively, there may be no initial burst phase, but rather one or more slow release phases. As the burst release phase may be concomitant to nuclease or serum exposure in an assay to assess packaging, protection from degradation by nucleases or serum assessed in this assay may not be complete. In the instance of an initial burst release phase of oligonucleotide under the conditions used in the assays to test protection, protection is assessed during the time span of the assay corresponding to the slow release phase. Thus, the term "packaged" as related to particles being synthetic particles but not being virus particles or virus-like particles also encompasses compositions comprising, essentially consisting of, or consisting of synthetic particles and ISS-NA's, in which such release of ISS-NA by said synthetic particle takes place, provided that at least 30%, preferably at least 40%, more preferably at least 50%, still more preferably at least 60%, even more preferably at least 70%, and most preferably at least 80% of the ISS-NA packaged in said synthetic particle is remaining associated with said synthetic particle at the end of the assay.

"particle": Particles of the invention have a diameter of 10 to 10000 nm, preferably of 20 to 1000 nm, more preferably 20 to 500 nm, still more preferably 20 to 300 nm, still more preferably 20 to 200 nm, and most preferably 20 to 100 nm, wherein these particles can preferably be packaged with an ISS-NA. Particles of the invention are preferably selected from the group consisting of synthetic particles and VLPs. Very preferred particles of the invention are VLPs, most preferably VLPs of RNA phages.

"size of a particle": The size of a spherical or nearly spherical particle is determined as the medium diameter of a population of particles; the size of an elliptic, longitudinal or irregular formed particle refers to the arithmetic medium of the longest axis in a population of particles. Typically and preferably, the size of a particle, preferably of a nanoparticle or a microparticle, most preferably of a nanoparticle, is determined dynamic light scattering (DLS) technology (Example 13).

"synthetic particles": As used herein, "synthetic particle" refers to particles which are formed by chemical or physical processes, preferably by polymerization of monomers, precipitation of polymers, assembly of macromolecules brought together, for example by aggregation or heat denaturation, chemical cross-linking of said assembled macromolecules. Preferred synthetic particles are selected from liposomes, microparticles, and nanoparticles. Further preferred synthetic particles are selected from liposomes, microparticles, nanoparticles, and virosomes. Very preferred synthetic particles are nanoparticles. The term "synthetic particles" does not refer to particles formed by assembly of viral proteins. Particles formed from viral coat proteins are specifically referred to as virus particles or virus-like particles. Viroids, retrotransposon particles, and all particles formed from genetically encoded viral proteins are also understood as virus particles or virus-like particles.

"liposomes": As used herein, the term "liposome" refers to phospholipid vesicles comprising one or more, preferably one, two, or three phospholipid bilayer membranes. Liposomes vary in charge and in size depending on the method of preparation and the lipids used. The liposome of the present invention may be neutral, cationic, anionic, stealth, or cationic stealth. Preferably, the liposome of the invention is a cationic liposome. The liposome may have a diameter between 100 and 800 nm, preferably between 100 and 400 nm, more preferably between 100 and 300 nm, even more preferably between 100 and 200 nm, most preferably less than 200 nm. The term "liposome", as used herein, shall also encompass modified liposomes, preferably modified liposomes, wherein the surface of the liposomes may be specifically modified to optimize binding to DC, for example, via specific sugar moieties (Fukasawa et al., (1998), FEBS, 441, 353-356) or antibodies (Serre et al. (1998), J. Immunol., 161, 6059-6067).

"lipopolyplex": Lipopolyplex particles are liposomes comprising or, preferably, essentially consisting of, most preferably consisting of a cationic lipid, a polycation and ISS-NA or DNA, whereby it is thought that the cationic lipid forms an additional protective layer surrounding the complex of ISS-NA or DNA with the polycation (Pelisek J. et al. J Gene Med 2006; 8:186-197).

"microparticle": As used herein, "microparticle" refers to synthetic particles of controlled dimension in the order of micrometers (i.e. >1 μm, and <1000 μm). Preferred microparticles have a size of 1 to 10 μm, preferably 1 to 5 μm, more preferably 1 to 2 μm.

"nanoparticle": As used herein, "nanoparticle" refers to synthetic particles of controlled dimension in the order of nanometers, wherein preferably ISS-NA can be entrapped, encapsulated, non-covalently bound, covalently attached or dissolved in said nanoparticles. The size of a nanoparticle is preferably less than 1000, 900, 800, 700, 600, 500, 400, 300, 200, 100 or 50 nm, wherein further preferably said nanoparticle is not smaller than about 10, 15, 20, 30, 40, or 50 nm. Preferably the nanoparticle is not smaller than 50 nm. Thus, nanoparticles of the invention are preferably 10 to 500 nm, more preferably 20 to 400 nm, still more preferably 40 to 300 nm, still more preferably 50 to 200 nm and most preferably 50 to 100 nm in size. Preferred in the context of the invention are nanoparticles of 100 to 300 nm in size, more preferred are nanoparticles of 100 to 200 nm in size. Very preferred are nanoparticles of 50 to 200 nm in size. The term nanoparticle encompasses particles of spherical, elliptic, longitudinal or irregular structure, preferably comprising or consisting of at least one a polymer. Nanoparticle also encompasses nanocapsules, and poliplex particles. Nanocapsules are nanoparticles comprising a reservoir, e.g. oily reservoir, wherein said reservoir is surrounded by a polymer wall (Maria J. Alonso, in Microparticulate systems for the delivery of proteins and vaccines, Eds. S. Cohen and Howard Bernstein, Marcel Dekker, New York 1996, p 206). A nanoparticle of a certain material, e.g. a polyester nanoparticle, refers to a nanoparticle comprising or preferably essentially consisting, most preferably consisting of said material. In the context of the invention this formulation does not exclude the presence of the ISS-NA in the nanoparticle.

Polymers suitable for the production of nanoparticles, including nanocapsules, refer to: biodegradable polyesters (e.g. poly-lactic acid, poly-(lactic glycolic acid) copolymer (referred to as PLA and PLGA), poly-e-caprolactone (referred to as PECL)), poly-(alkylcyanoacrylates) (referred to as PACA), chitosan, alginate, cross-linked human serum albumin, human serum albumin, gelatin, Schizofyllan, dextran. Nanoparticles may also be prepared from non-biodegradable materials such as polystyrene, colloidal gold, silica, or metal clusters. In addition, hydrophilic components such as e.g. PEG, polysaccharides (Lemarchand C. et al. (Eur J Pharm Biopharm. 2004 September; 58:327-41), dextran, chitosan, polylysine, lecithine and the like may also be incorporated as copolymer or as coating reagent on the surface of the nanoparticle. Complexation agent such as polylysine (PLL), poly(ethylene imine) (PEI), protamine, spermine or positively charged structured oligopeptides may be incorporated into nanoparticles together with nucleic acids, bound to the surface of nanoparticles for incorporation of nucleic acids, covalently attached to reactive groups on the nanoparticle, or incorporated during the polymerization process into the nanoparticle. Alternative complexation agents include metal salts such as Zinc acetate.

"polyplex": Polyplex particles are nanoparticles formed by the direct interaction of a cationic polymer, also called polycation, such polylysine (PLL), poly(ethylene imine) (PEI) or the like with a nucleic acid, preferably an ISS-NA. A Polyplex may also be formed by the direct interaction of PEG-PLL, or, for example, of a branched PEI with said nucleic acid, preferably said ISS-NA.

"Complexation agent": a complexation agent is an agent which non-covalently binds to an ISS-Na and neutralizes or at least partially reduces the effective charge of the resulting complex. Examples of complexation agents are polylysine (PLL), spermine, protamine, polyethyleneimine (PEI), branched PEI, lysine-rich structured oligopeptides, cationic lipids such as DOTAP and the like, and metal cations as provided by their salts such as zinc acetate, magnesium, calcium chloride, or the like. More complex polymers, such as poly(ethylene)glycol-polylysine (PEG-PLL) copolymers may also be used as complexation agent.

"biodegradable": A material, preferably a particle, most preferably a microparticle or nanoparticle, is referred to as biodegradable when it is degradable or erodable under normal mammalian physiological conditions. Degradation of the particle may occur, for example, by dissolving of the particle, by enzymatic degradation, preferably by hydrolysis or oxidation, or by destabilisation of the particle by any other chemical or physical process. Normal mammalian physiological conditions can be recreated in the test-tube by incubating samples in serum at 37° C. Microparticles or nanoparticles are considered biodegradable, if they are degraded upon incubation for 72 hours at 37° C. in human serum from healthy volunteers. In the context of this definition, "degraded" means that the microparticle or nanoparticle loses at least 5%, preferably at least 10%, more preferably at least 20%, still more preferably at least 50% of its mass and/or average polymer length. Most preferably, the particle is completely degraded under these conditions. Conversely, a microparticle or nanoparticle is referred to as non-biodegradable, if it does not loses at least 5% of its mass and/or average polymer length upon incubation in human serum for 72 hours at 37° C. Very preferred are particles which are biodegradable at low pH, preferably at a pH which is found in the endosomes of immune cells, more preferably at ph of 4.5 to 6, most preferably at pH of about 5.

"coat protein": As used herein, the term "coat protein(s)" refers to the protein(s) of a bacteriophage or a RNA bacteriophage capable of being incorporated within the capsid assembly of the bacteriophage or the RNA bacteriophage. However, when referring to the specific gene product of the coat protein gene of RNA bacteriophages the term "CP" is used. For example, the specific gene product of the coat protein gene of RNA bacteriophage Qβ is referred to as "Qβ CP", whereas the "coat proteins" of bacteriophage Qβ comprise the "Qβ CP" as well as the A1 protein. The capsid of Bacteriophage Qβ is composed mainly of the Qβ CP, with a minor content of the A1 protein. Likewise, the VLP Qβ coat protein contains mainly Qβ CP, with a minor content of A1 protein.

"recombinant VLP": The term "recombinant VLP", as used herein, refers to a VLP that is obtained by a process which comprises at least one step of recombinant DNA technology. The term "VLP recombinantly produced", as used herein, refers to a VLP that is obtained by a process which comprises at least one step of recombinant DNA technology. Thus, the terms "recombinant VLP" and "VLP recombinantly produced" are interchangeably used herein and should have the identical meaning.

"virus particle": The term "virus particle" as used herein refers to the morphological form of a virus. In some virus types it comprises a genome surrounded by a protein capsid; others have additional structures (e.g., envelopes, tails, etc.).

"virus-like particle (VLP)", as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. Preferably a virus-like particle in accordance with the invention is non-replicative and/or non-infectious since it lacks all or part of the viral genome or genome function. In one embodiment, a virus-like particle is a virus particle, in which the viral genome has been physically or chemically inactivated, removed by disassembly and reassembly, or by assembly of purified proteins into a VLP. Typically and more preferably a virus-like particle lacks all or part of the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, preferably RNA bacteriophage. The terms "viral capsid" or "capsid", refer to a macromolecular assembly composed of viral protein subunits. Typically, there are 60, 120, 180, 240, 300, 360 and more than 360 viral protein subunits. Typically and preferably, the interactions of these subunits lead to the formation of viral capsid or viral-capsid like structure with an inherent repetitive organization, wherein said structure is, typically, spherical or tubular. For example, the capsids of RNA bacteriophages or HBcAgs have a spherical form of icosahedral symmetry. The term "capsid-like structure" as used herein, refers to a macromolecular assembly composed of viral protein subunits resembling the capsid morphology in the above defined sense but deviating from the typical symmetrical assembly while maintaining a sufficient degree of order and repetitiveness. The invention encompasses VLPs, preferably non-natural VLPs, comprising a icosahedral symmetry. One common feature of virus particle and virus-like particle is its highly ordered and repetitive arrangement of its subunits.

"virus-like particle of a RNA bacteriophage": As used herein, the term "virus-like particle of a RNA bacteriophage" refers to a virus-like particle comprising, or preferably consisting essentially of or consisting of coat proteins, mutants or fragments thereof, of a RNA bacteriophage. In addition, virus-like particle of a RNA bacteriophage resembling the structure of a RNA bacteriophage, being non replicative and/or non-infectious, and lacking at least the gene or genes encoding for the replication machinery of the RNA bacteriophage, and typically also lacking the gene or genes encoding the protein or proteins responsible for viral attachment to or entry into the host. This definition should, however, also encompass virus-like particles of RNA bacteriophages, in which the aforementioned gene or genes are still present but inactive, and, therefore, also leading to non-replicative and/or non-infectious virus-like particles of a RNA bacteriophage. Preferred VLPs derived from RNA bacteriophages exhibit icosahedral symmetry and consist of 180 subunits. Within this present disclosure the term "subunit" and "monomer" are interexchangeably and equivalently used within this context. Preferred methods to render a virus-like particle of a RNA bacteriophage non replicative and/or non-infectious is by physical, chemical inactivation, such as UV irradiation, formaldehyde treatment, typically and preferably by genetic manipulation. Alternatively, individual proteins may be isolated from whole virions and assembled into VLPs in vitro.

"synthetic VLP": Particles formed from non-naturally occurring proteins or peptides which spontaneously assemble intracellularly or in vitro are referred to as synthetic VLPs. Examples for synthetic VLPs are provided in WO04071493A1 which is incorporated herein by reference. Synthetic VLPs also encompasses particles which require nucleic acids or metal ions for assembly. Preferred synthetic particles have a defined size of 10 to 1000 nm, preferably 10 to 300 nm, more preferably 10 to 150 nm, and most preferably 15 to 100 nm. Other preferred synthetic VLPs may exist in two or more defined conformations, e.g. 15 nm and 25 nm.

"virosome": As used herein, the term virosome relates to a reconstituted virus envelope, preferably to a reconstituted influenza virus envelope, more preferably to a reconstituted envelope of influenza A virus, most preferably to a reconstituted envelope of influenza A/Singapore virus. Virosomes are known in the art as drug carrier systems. A virosome comprises a lipid membrane, wherein said lipid membrane typically and preferably comprises a unilamellar lipid bilayer. In a preferred meaning the term virosome relates to a reconstituted influenza virus envelope, preferably to a reconstituted influenza A virus envelope, most preferably to a reconstituted influenza A/Singapore virus envelope, wherein said reconstituted influenza virus envelope, preferably said reconstituted influenza A virus envelope, most preferably said reconstituted influenza A/Singapore virus envelope comprises lipid membrane, wherein said lipid membrane comprises influenza glycoproteins, wherein preferably said influenza glycoproteins are selected from hemagglutinin HA and neuraminidase NA. Typically and preferably virosomes attach to target cells via HA. Very preferred virosomes comprise a lipid membrane, preferably a lipid bilayer, wherein said lipid membrane or said lipid bilayer comprise or preferably predominantly consist of cationic lipids. Virosomes comprising cationic lipids in their lipid membrane are particularly suited for the delivery of ISS-NA, especially of oligonucleotides. Further preferred are specific virosomes, which attach to a target cell by an antibody or a fragment thereof which is comprised in the lipid membrane. Thus, in a further preferred meaning, the term virosome relates to a specific virosomes comprising a lipid membrane, wherein said lipid membrane comprises specific antibodies or fragments thereof, preferably Fab fragments or Fab' fragments, wherein preferably the specificity of said antibodies or fragments thereof allows to direct the virosome to a specific target cell. Typically and preferably, a virosome is taken up by the target cell by receptor-mediated endocytosis.

"effective amount": As used herein, the term "effective amount" refers to an amount necessary or sufficient to realize a desired biologic effect. An effective amount of the composition, preferably the pharmaceutical composition, would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount". The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

"treatment": As used herein, the terms "treatment", "treat", "treated" or "treating" refer to prophylaxis and/or therapy. When used with respect to an atopic disease, for example, the term refers to a therapeutic treatment which reduces the symptom score of the treated patient as assessed by a standard method commonly used to assess the severity of the symptoms of the disease the patient is suffering from. The term can also refer to a prophylactic treatment of an atopic disease which, for example, prevents or ameliorates the symptoms a patient typically develops upon exposure to a challenging agent as compared to an untreated patient.

"pharmaceutically acceptable carrier": The compositions of the invention can be combined, optionally, with a pharmaceutically-acceptable carrier. The term "pharmaceutically-acceptable carrier" as used herein means one or more compatible solid or liquid fillers, diluents or encapsulating substances which are suitable for administration into a human or other animal. The term "carrier" denotes an organic or inorganic ingredient, natural or synthetic, with which the active ingredient is combined to facilitate the application.

"pharmaceutical composition": As used herein, the term "pharmaceutical composition" refers to a formulation which contains the composition of the invention and which is in a form that is capable of being administered to an animal. Typically and preferably, the pharmaceutical composition comprises a conventional saline or buffered aqueous solution medium in which the composition of the present invention is suspended or dissolved. In this form, the composition of the present invention can be used conveniently to prevent, ameliorate, or otherwise treat a condition. Upon introduction into a host, the pharmaceutical composition is able to provoke an immune response including, but not limited to, the production of antibodies and/or cytokines and/or the activation of cytotoxic T cells, antigen presenting cells, helper T cells, dendritic cells and/or other cellular responses. Preferred pharmaceutical compositions induce a cytokine milieu, typically and preferably the formation of IFN-alpha, which is reducing allergic and/or asthmatic symptoms. Optionally, the pharmaceutical composition additionally includes an adjuvant which can be present in either a minor or major proportion relative to the composition of the present invention.

"adjuvant": The term "adjuvant" as used herein refers to non-specific stimulators of the immune response or substances that allow generation of a depot in the host which when combined with the composition of the invention provides for an even more enhanced and/or prolonged immune response, preferably cytokine production. A variety of adjuvants is known in the art and useful in the invention. Preferred adjuvants are selected from the group consisting of incomplete Freund's adjuvant, aluminum containing adjuvants, modified muramyldipeptide, surface active substances such as lysolecithin, pluronic polyols, polyanions, peptides, oil emulsions, keyhole limpet hemocyanins, dinitrophenol, BCG (bacille Calmette Guerin) *Corynebacterium parvum*, ligands of toll-like receptors (TLR) which include but are not limited to peptidoglycans, lipopolysaccharides and their derivatives, poly I:C, immunostimulatory oligonucleotides, imidazoquinolines such as resiquimod and imiquimod, flagellins, monophosphoryl lipid immunomodulator, AdjuVax 100a, QS-21, QS-18, GPI-0100, CRL1005, MF-59, OM-174, OM-197, OM-294, Virosomal adjuvant technology and any mixture thereof. A very preferred adjuvant for the purpose of the invention is aluminium containing adjuvant, preferably an aluminium containing mineral gel, most preferably alhydrogel. In a very preferred embodiment said adjuvant is alhydrogel. The term adjuvant also encompasses a mixture of any of the substances listed above. Particles of the invention, preferably VLPs, have been generally described as an adjuvant. However, the term "adjuvant", as used within the context of this application, refers to an adjuvant not being the particle of the invention, in particular not the VLP used for the inventive compositions. In each case, the term adjuvant refers to an adjuvant used in addition to said particle.

"polypeptide": As used herein the term "polypeptide" refers to a polymer composed of amino acid residues, generally natural amino acid residues, linked together through peptide bonds. Although a polypeptide may not necessarily be limited in size, the term polypeptide is often used in conjunction with peptide of a size of about ten to about 50 amino acids.

"protein": As used herein, the term protein refers to a polypeptide of a size of above 20, more preferably of above 50 amino acid residues. Proteins generally have a defined three dimensional structure although they do not necessarily need to, and are often referred to as folded, in contrast to peptides and polypeptides which often do not possess a defined three-dimensional structure, but rather can adopt a large number of different conformations, and are referred to as unfolded.

"sequence identity": The amino acid sequence identity of polypeptides can be determined conventionally using known computer programs such as the Bestfit program. When using Bestfit or any other sequence alignment program, preferably using Bestfit, to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, polypeptides or a fragment thereof disclosed in this invention.

"Sequence homology": The homology of nucleotide sequences is preferably determined by the program blastn which is an implementation of the BLAST algorithm, most preferably using the default settings of the software.

"fragment of a protein", in particular fragment of a recombinant protein or recombinant coat protein, as used herein, is defined as a polypeptide, which is of at least 70%, preferably at least 80%, more preferably at least 90%, even more preferably at least 95% the length of the wild-type recombinant protein, or coat protein, respectively and which preferably retains the capability of forming VLP. Preferably the fragment is obtained by at least one internal deletion, at least one truncation or at least one combination thereof. The term "fragment of a recombinant protein" or "fragment of a coat protein" shall further encompass polypeptide, which has at least 80%, preferably 90%, even more preferably 95% amino acid sequence identity with the "fragment of a recombinant protein" or "fragment of a coat protein", respectively, as defined above and which is preferably capable of assembling into a virus-like particle.

The term "mutant coat protein" refers to a polypeptide having an amino acid sequence derived from the wild type recombinant protein, or coat protein, respectively, wherein the amino acid sequence is at least 80%, preferably at least 85%, 90%, 95%, 97%, or 99% identical to the wild type sequence and preferably retains the ability to assemble into a VLP.

"animal": As used herein, the term "animal" refers to any animal, preferably to any animal comprising an immune system, including non-vertebrates, preferably arachnids and insects, and vertebrates. Typically and preferably, animal relates to vertebrates, more preferably to mammals, most preferably to humans. Thus, animal includes, for example, humans, sheep, horses, cattle, pigs, dogs, cats, rats, mice, birds, reptiles, fish, insects and arachnids.

"one", "a/an": When the terms "one," "a," or "an" are used in this disclosure, they mean "at least one" or "one or more," unless otherwise indicated.

"about": within the meaning of the present application the expression about shall have the meaning of +/−10%. For example about 100 shall mean 90 to 110.

As previously disclosed, VLPs packaged with unmethylated CpG-containing oligonucleotides can enhance B and T cell responses. It was also previously observed, that application of a CpG-containing oligonucleotide together with an allergen ameliorated allergic response. It was now surprisingly found that no covalent linkage, coupling or mixing of allergen with the particle of the invention, preferably the VLP, is required to achieve an effect in the treatment of hypersensitivity, preferably allergy. Even more surprisingly, it was found that no administration or co-administration of a specific antigen or allergen is required in the treatment of hypersensitivity, preferably allergy, using the compositions of the invention. Furthermore, said effect is not limited to VLPs packaged with unmethylated CpG-containing oligonucleotides but can be generalized to particles of the invention packaged with immunostimulatory nucleic acids (ISS-NA).

Applicants have discovered that hypersensitivities may be cured by treatment with particles packaged with ISS-NA. Applicants have also shown that particles of appropriate size diffuse readily to draining lymph nodes after intradermal or subcutaneous injection, where they are taken up mainly by dendritic cells (DC) and macrophages. Various DCs, including plasmacytoid dendritic cells (pDC), monocyte derived and leucophil dendritic cells or macrophages are activated upon uptake of particles, preferably VLPs, packaged with unmethylated CpG-containing oligonucleotide via the Toll-9 receptor. Applicants have also discovered that polystyrene nanoparticles with sizes of 50 to 200 nm also readily diffuse to the draining lymph node, while larger particles (>500 nm) remain at the site of injection during the same time span after subcutaneous injection. PLGA nanoparticles have been shown to be phagocytosed by dendritic cells (DCs) (Diwan et al. J Drug Target. 2003; 11:495-507). Moreover murine DCs pulsed with PLGA nanoparticles having co-incorporated an unmethylated CpG-containing oligodesoxynucleotide and an antigen have been shown to enhance antigen specific T-cell activation in an in vitro T-cell stimulation assay, as compared to DCs pulsed with PLGA nanoparticles incorporating only antigen. Therefore, nanoparticles incorporating an ISS-NA like an unmethylated CpG-containing oligodesoxynucleotide are able to stimulate dendritic cells upon uptake, and these dendritic cells thereafter activated T-cells. In human dendritic cells, Toll-like receptor 9 expression is limited to a small subset, the so called plasmacytoid dendritic cells. We show herein that Qβ virus-like particles, which have a size of about 30 nm, are taken up by human plasmacytoid dendritic cells, and therefore can deliver ISS-NA to these cells. Interestingly, mast cells also express TLR-9. A recent report has shown the role of CpG-containing oligonucleotide in preventing Th2-cell activation upon allergen challenge (Hessel et al. (2005) J. exp. Med. 11:1563-73.). Therefore, uptake of particles such as nanoparticles or VLPs packaged with ISS-NA, such as unmethylated CpG-containing oligonucleotide, by plasmacytoid dendritic cells or antigen presenting cells such as classical dendritic cells may lead to inhibition of the activation of Th2 cells and thereby inhibit the allergen induced response. The same report involved mast cells in the suppressive action of unmethylated CpG-containing oligonucleotide on the allergic response. Mast cells are active in phagocytosis, and it is possible that particles of the invention, preferably nanoparticles or VLPs, wherein said nanoparticles or VLPs, preferably said VLPs, are packaged with ISS-NA, preferably with unmethylated CpG-containing oligonucleotide, mediate their effect in part via inhibiting mast cells, providing for another alternative or complementary possible mechanism of action of the VLP or nanoparticle packaged with unmethylated CpG-containing oligonucleotide. However, the mode of action of the compositions of the invention is not limited to this mechanism.

Based on the aforementioned findings, the invention provides compositions, pharmaceutical compositions and methods for the treatment or prevention of hypersensitivity, preferably allergy in an animal. In particular, the invention provides a composition for use in a method of treating hypersensitivity in an animal, the composition comprising a particle and an ISS-NA, wherein said particle is packaged with said ISS-NA. The invention provides methods and compositions which are especially useful for treating and/or preventing hypersensitivity, preferably allergy, more preferably atopic eczema, atopic asthma and type I allergies like, for example, pollen allergy (hay fever).

In this context, the term particle refers to any structure which, with respect to its chemical an physical characteristics, can be packaged with ISS-NA, wherein preferably said particle is capable of protecting said ISS-NA from degradation in the body of said animal and/or wherein said particle is capable of specifically delivering and releasing said ISS-NA to immune cells. Thus, to be effective, the particle of the invention preferably is able to (i) package an ISS-NA and (ii) to deliver said ISS-NA to immune cells in the body. The particle of the invention is therefore to be understood in a very broad sense.

In a preferred embodiment said particle is selected from the group consisting of synthetic particle, virus particle and VLP.

The particles of the invention can be biodegradable or non biodegradable. Biodegradable particles are generally preferred to prevent accumulation of said particle in the body of said animal and to avoid toxicity effects which might be associated with such accumulation. Therefore, in a preferred embodiment said particle, preferably said synthetic particle, most preferably said nanoparticle, comprises or, preferably, essentially consists of, most preferably consists of a biodegradable material. In a further preferred embodiment said particle, preferably said synthetic particle, most preferably said nanoparticle, is biodegradable. In a very preferred embodiment said synthetic particle packaged with said ISS-NA is biodegradable. In a further preferred embodiment said particle, preferably said synthetic particle, releases said ISS-NA, preferably inside the target cell, most preferably in the endosome of the target cell. In a further preferred embodiment said particle, preferably said synthetic particle is degraded in the endosomal compartment of the target cell containing proteases and exhibiting a low pH, preferably about pH 5.

In one embodiment of the invention said particle is a synthetic particle, preferably a synthetic particle selected from the group consisting of liposome, microparticle and nanoparticle, wherein more preferably said synthetic particle is liposome or a nanoparticle, and even more preferably a nanoparticle. In a further embodiment of the invention said particle is a synthetic particle, preferably a synthetic particle selected from the group consisting of liposome, microparticle, nanoparticle and virosome. Synthetic particles of the invention comprise or preferably essentially consist of, most preferably consist of non-biodegradable materials, of biodegradable materials or of a mixture of both, wherein said biodegradable materials may be organic or inorganic, or a combination of both.

In a preferred embodiment said synthetic particle is a microparticle or a nanoparticle, preferably a nanoparticle, wherein said synthetic particle comprises or preferably essentially consists of, most preferably consists of a material selected from the group consisting of: (a) polyesters, preferably selected from PLA, poly(glycolic acid) and PECL, (b) copolymers of polyesters, preferably PLGA, (c) block copolymers of polyester and PEG, (d) polyorthoesters, (e) poly(anhydrides), (f) poly(sebacic acid), (g) polyanhydrides based on sebacic acid monomers incorporating amino acids, (h) polyanhydride esters, (i) polyphosphazene, preferably polyphosphazene containing hydrolysis-sensitive ester groups (Andrianov A K and Payne L G, in Microparticulate systems for the delivery of proteins and vaccines, Eds. S. Cohen and Howard Bernstein, Marcel Dekker, New York 1996, p 127-147), (j) polyamide, (k) macromolecules and modified macromolecules of biological origins, preferably selected from proteins (e.g. gelatin, human serum albumin) and (l) polysaccharides (e.g. dextran, chitosan, alginate, Schyzofyllan), (m) methacrylate-based materials, preferably selected from poly(methyl methacrylate) and copolymers, preferably PEG-methacrylate or PEG-dimethacrylate, (n) methyl methacrylate based materials, preferably selected from PEG based comonomers and ionic comonomers, (o) poly(methylidene malonate 2.1.2) as described by Bousquet Y et al. Biomaterials. 1998 January-February; 19:271-8 and Breton P et al. Pharm Res. 1999; 16:141-7, (p) colloidal gold, (q) polystyrene, (r) polyethylene, (s) polypropylene, (t) latex, (u) ferromagnetic or paramagnetic materials, (v) dextran, (w) hydroxyapatite, and (x) a mixture of any of the materials listed above.

In a preferred embodiment said synthetic particle is a microparticle or a nanoparticle, preferably a nanoparticle, wherein said synthetic particle comprise or preferably essentially consist of, most preferably consist of a non-biodegradable material selected from the group consisting of: (a) colloidal gold, (b) polystyrene, (c) polyethylene, (d) polypropylene, (e) latex, (f) ferromagnetic or paramagnetic materials, (g) dextran and (h) hydroxyapatite.

In a more preferred embodiment said synthetic particle, preferably said nanoparticle, comprises or preferably essentially consists of, most preferably consists of a biodegradable material selected from the group consisting of: (a) polyesters, preferably selected from PLA, poly(glycolic acid) and PECL, (b) copolymers of polyesters, preferably PLGA, (c) block copolymers of polyester and PEG, (d) polyorthoesters, (e) poly(anhydrides), (f) poly(sebacic acid), (g) polyanhydrides based on sebacic acid monomers incorporating amino acids, (h) polyanhydride esters, (i) polyphosphazene, preferably polyphosphazene containing hydrolysis-sensitive ester groups (Andrianov A. K. and Payne L G, in Microparticulate systems for the delivery of proteins and vaccines, Eds. S. Cohen and Howard Bernstein, Marcel Dekker, New York 1996, p. 127-147), (j) polyamide, and (k) macromolecules and modified macromolecules of biological origins, preferably selected from proteins (e.g. gelatin, human serum albumin) and polysaccharides (e.g. dextran, chitosan, alginate, Schyzofyllan).

In a still more preferred embodiment said biodegradable material is selected from (a) polyesters, preferably selected from PLA, poly(glycolic acid) and PECL, (b) copolymers of polyesters, preferably PLGA, (c) block copolymers of polyester and PEG, (d) polyorthoesters, (e) poly(anhydrides), (f) poly(sebacic acid), (g) polyanhydrides based on sebacic acid monomers incorporating amino acids, (h) polyanhydride esters, (i) polyphosphazene, preferably polyphosphazene containing hydrolysis-sensitive ester groups (Andrianov A K and Payne L G, in Microparticulate systems for the delivery of proteins and vaccines, Eds. S. Cohen and Howard Bernstein, Marcel Dekker, New York 1996, p. 127-147), and (j) polyamide.

In a still more preferred embodiment said biodegradable material is selected from (a) polyesters, preferably polyesters selected from PLA, poly(glycolic acid) and PECL, and (b) copolymers of polyesters, preferably PLGA. In a very preferred embodiment said biodegradable material is PLA or PLGA, most preferably PLA.

In a further preferred embodiment said particles, preferably said synthetic particles, most preferably said nanoparticles comprise or preferably essentially consist of at least one, preferably exactly three, more preferably exactly two, most preferably exactly one biodegradable polymer(s), wherein preferably said polymer is degraded into biocompatible non-toxic monomers, wherein still more preferably said biodegradable polymer is a polyester (see Maria J. Alonso et al., in Microparticulate systems for the delivery of proteins and vaccines, Eds. S. Cohen and Howard Bernstein, Marcel Dekker, New York 1996, p 203-242).

Nanoparticles may be formed by chemical or physical processes such as polymerization or condensation of monomers, for example in nanodroplets of an emulsion, precipitation of polymers, coacervation of macromolecules, assembly of macromolecules brought together, for example, by the process of emulsification, by ionic interactions, aggregation, heat denaturation or chemical cross-linking of said assembled macromolecules. Nanoparticles may also have a composite structure involving two or more layers with different properties, such as core-shell particles with a hydrophobic core layer of a polymer and a hydrophilic outer shell layer of another polymer, such as poly(ethylene)glycol (PEG). Other examples of core-shell nanoparticles include nanoparticles where a charged polymer, such as polylysine, is adsorbed to the surface of the nanoparticle. Alternatively, more complex nanoparticles may be produced, where co-monomers carrying a cationic moiety and co-monomers carrying a PEG moiety are included in the polymerization process and preferentially locate to the nanoparticle surface during the polymerization process. Thus, in a preferred embodiment said nanoparticle comprises an outer shell layer, wherein preferably said outer shell layer comprises or alternatively essentially consists of PEG. In a very preferred embodiment said nanoparticle comprises a core and a shell layer, wherein said core comprises or alternatively essentially consists of polyester and wherein said shell layer comprises or alternatively essentially consists of PEG. In a further preferred embodiment said nanoparticle comprises a core and a shell layer, wherein said core comprises or alternatively essentially consists of polyalkylcyanoacrylat and wherein preferably said shell layer comprises or alternatively essentially consists of PEG.

In a further preferred embodiment said nanoparticle is a core-shell nanoparticle, wherein preferably the shell layer of said core-shell nanoparticle is packages with said ISS-NA. Preferably, said shell layer of said core-shell nanoparticle is positively charged. Further preferably said shell layer of said core-shell particle comprises or alternatively essentially consists of a polymer, wherein preferably said polymer is selected from polylysine, cethyltrimethylammonium bromide (CTAB) and polyethyleneimine. Alternatively, said ISS-NA may preferentially associate with the core layer, for example of a CaP-PEG-PAA nanoparticle.

In a further preferred embodiment said nanoparticle is a polyplex. A polyplex nanoparticle is formed by the direct association of a complexation agent such as PEI, PLL or PEG-PLL with an ISS-NA, forming a so called polyplex (Boeckle S. et al. J Gene Med 2004; 6:1102-1111; Wagner E. et al. Adv Genet. 2005; 53:333-54; Walker G. et al. Mol Ther. 2005; 11:418-25).

The size of nanoparticles can be determined with known methods such as scanning- and transmission-electron microscopy, or photon correlation spectroscopy or dynamic light scattering, as reviewed in Alonso M. J. (in Microparticulate systems for the delivery of proteins and vaccines, Eds. S. Cohen and Howard Bernstein, Marcel Dekker, New York 1996, p 203-242). Surface properties such as surface charge, and in particular the zeta-potential, can be measured by determining the velocities of nanoparticles in an electrical field using methods such as electrophoretic mobility measurement. Laser Doppler anemometry or Electrophoretic light scattering may also be used. Alternatively, the sonic response to an alternating electric field (electronic sonic amplitude effect) may be used as well. The measurements can be performed with commercially available devices. The zeta potential is informative to predict the aggregation behaviour of a nanoparticle, or its ability to adsorb charged components on its surface, and thus helps optimizing the properties of nanoparticles.

In a preferred embodiment said nanoparticle comprises or alternatively essentially consists of polyesters, preferably of aliphatic polyesters. Aliphatic polyesters are degraded by random hydrolytic cleavage, into physiologically occurring metabolites. These materials have been used for resorbable sutures, and a polyester microsphere formulation for parenteral injection of Leuprolide acetate, a Gonadotropin Releasing Hormone analog, is a marketed product. Several polymers can be used in the preparation of the nanoparticles of the invention and have been described: poly(lactic acid) (PLA), poly(glycolic acid) (PGA), or Copolymers of PLAA and PGA, poly(-lactic-co-glycolic acid) named PLGA, are particularly suited. The racemic, amorphous form is preferred. These polymers are commercially available, and their synthesis is well known in the art. Their synthesis is described, for example, by Avgoustakis K (Curr Drug Deliv. 2004; 1:321-33). The properties of polyester microsphere, and PLGA in particular, as well as methods to produce them have been reviewed and described for example by Kissel T and Koneberg R (in Microparticulate systems for the delivery of proteins and vaccines, Eds. S. Cohen and Howard Bernstein, Marcel Dekker, New York 1996, p. 51-87). These methods include spray drying methods, water-in-oil-in-water emulsion solvent evaporation methods and phase separation methods. In a preferred embodiment said nanoparticle comprises or alternatively essentially consists of PLGA, wherein preferably the molar ratio of the monomers constituting PLGA is 50% mol LA and 50% mol GA. Increasing the proportion of either of the monomer leads to slower degradation of the polymer. For example, a polymer with a ratio of LA to GA of 85:15 has a rate of degradation about two-and a half time slower than with a ratio of 50:50. Thus, the properties of PLGA polymer can be manipulated by changing the proportion of the monomers.

Preparation of nanoparticles and in particular of nanoparticles made from polyester materials has been reviewed for example by Alonso M J, (in Microparticulate systems for the delivery of proteins and vaccines, Eds. S. Cohen and Howard Bernstein, Marcel Dekker, New York 1996, p 203-242) or Avgoustakis K (Curr Drug Deliv. 2004; 1:321-33). Methods for producing polyester nanoparticles are also described therein, and include methods collectively referred to as polymer precipitation methods. In these methods, the polymer dissolved in an organic solvent is emulsified in water containing a stabilizer. The organic solvent diffuses from the organic phase into the aqueous phase. The result of the solvent depletion from the organic phase is polymer precipitation, leading to the formation of nanoparticles.

One of these is the solvent extraction-evaporation technique. In this method an organic solvent with poor water solubility, such as methylene chloride, ethyl acetate or chloroform is used. The solvent is nonetheless extracted from the organic phase into the water phase due to the large excess of water, a process which is further facilitated by subsequent evaporation of the solvent. The solvent extraction-evaporation technique can be essentially performed in two general ways to incorporate molecules into nanoparticles, depending on the hydrophobicity of the molecule to be incorporated. A hydrophobic molecule, or a water insoluble complex can be dissolved or suspended in the same organic solvent as the polymer, and then be emulsified in an external water phase containing a stabilizer, typically a surfactant such as poly (vinyl alcohol) (PVA), a poloxamer, or for example dextran, whereby the nanodroplets formed during the emulsion process form nanoparticles upon solvent extraction and evaporation. Preferably, the emulsion is prepared using high-speed or high-pressure homogenizers, microfluidization or sonication. Intensive stirring or vortexing may also be appropriate. This method is also referred to as the oil-in-water solvent extraction and evaporation technique.

More hydrophilic or amphiphilic compounds are incorporated as aqueous solutions into a larger volume of an organic solvent containing the polymer. Preferably, the aqueous solution is emulsified with the organic solvent, for example using high-speed or high-pressure homogenizers, microfluidization, sonication, vortexing or intensive stirring. The resulting water-in-oil emulsion or suspension is further emulsified in a larger volume of water, yielding a water-in-oil-in water emulsion, from which the nanoparticles form upon solvent extraction and evaporation. This method is also referred to as the water-in-oil-in-water emulsion solvent evaporation technique.

The process of solvent extraction and evaporation can be further accelerated for example by increasing the temperature, applying vacuum or adding an alcohol such as isopropanol (e.g. 2%) to the external water phase to increase the organic solvent solubility in that external water phase. For example, a rotavapor may be used to accelerate solvent extraction and evaporation.

Some components such as certain surfactants used in the production process and incompatible with parenteral injection into animals or humans may have to be eliminated, for example by washing steps with water. Purification techniques used are for example tangential-flow filtration, or centrifugation. Nanoparticles are then typically isolated by freeze-drying, whereby a cryoprotectant such as a sugar like trehalose or glucose is added to prevent aggregation of the nanoparticles.

Another polymer precipitation technique is the solvent displacement or nanoprecipitation method. It involves the use of an organic solvent that is completely soluble in the external water phase. The polymer is dissolved in acetone, ethanol or methanol, and precipitates upon incorporation under stirring into an aqueous solution of a surfactant, such as for example Poloxamer 188.

A further polymer precipitation method is the salting-out technique. In this method, the polymer is dissolved in, for example acetone, and a saturated aqueous solution of PVA is added under stirring to form an oil-in-water emulsion. Water is further added, and the polymer precipitates to form nanoparticles when acetone diffuses into the external water phase.

In a further embodiment of the invention, said nanoparticle is a PEG-polyester nanoparticle, such as for example, PEG-PLA or PEG-PLGA nanoparticles. PLA and PLGA particles absorb plasma proteins such as opsonin, and activate the complement system. To minimize plasma protein binding, core-shell nanoparticles have been produced, where a layer of a hydrophilic PEG, the shell, surrounds the polymer core of the particle, and prevents or reduces attachments of plasma proteins or opsonin to the hydrophobic polymer surface. Coating of nanoparticles and in particular of PLGA nanoparticles with poly(ethylene glycol) has been shown to strongly reduce complement activation and increase blood circulation time (Gref R et al. in Microparticulate systems for the delivery of proteins and vaccines, Eds. S. Cohen and Howard Bernstein, Marcel Dekker, New York 1996, p 279-305; Hawley A E et al. Pharm Res. 1997; 14:657-61). Enrichment in the lymph nodes upon subcutaneous injection was also enriched compared to naked PLGA nanoparticles (Hawley A E et al. Pharm Res. 1997; 14:657-61). When polystyrene or PLGA nanoparticles were coated with PLA-PEG copolymer, maximal lymph node enrichment was obtained with the shorter PEG chain (750 Da PEG, PLA:PEG 1.5:0.75; Hawley A E et al. Pharm Res. 1997; 14:657-61). Longer PEG chains led to increased drainage from the injection site and lower lymph node levels, suggesting less efficient capture by lymph node macrophages and hence increased systemic distribution as a result of the increased steric barrier of the longer PEG chains. When PLA-PEG (PLA:PEG 1.5:0.75) was incorporated in the PLGA nanoparticles during the precipitation process, the highest lymph node enrichment was obtained with nanoparticles having an intermediate percentage of PLA-PEG (35%), while particles with 45% PLA-PEG had increased systemic distribution, as reflected by higher blood and liver levels. Thus, variation of the PEG chain length and of the percentage of the PEG copolymer incorporated in the nanoparticles allows manipulation of the pharmacokinetic properties of the nanoparticles.

The methods for the preparation of PEG-PLA and PEG-PLGA nanoparticles are similar to the methods used for the preparation of PLA and PLGA nanoparticles, and have been reviewed by Avgoustakis K (Curr Drug Deliv. 2004; 1:321-33) and Gref R. et al. (in Microparticulate systems for the delivery of proteins and vaccines, Eds. S. Cohen and Howard Bernstein, Marcel Dekker, New York 1996, p 279-305). These methods include the emulsion-solvent evaporation method, the solvent displacement method and the salting-out method. Use of the salting-out method for the preparation of nanocapsules is also described therein. Methods for synthesizing block copolymers are know in the art. One method of preparing diblock copolymers (e.g. PEG-PLA) by ring-opening polymerization of monomers (lactide, glycolide, caprolactone or mixtures of them) on monomethoxy-PEG catalyzed by stannous octoate, as well as the preparation and use of multiblock copolymers for the preparation of nanoparticles is described and reviewed by Avgoustakis K (Curr Drug Deliv. 2004; 1:321-33) and references therein.

Variation of the PLA/PEG and PLGA/PEG allows to manipulate the structure of the nanoparticles produced. For example, a low ratio generates more dynamic type of particles, while higher ratios favour more solid-like structures. A shorter PLA or PLGA chain length ($x \leq 30$) can lead to nanoparticle formation via micelle formation process, while with longer chain length an agglomeration-precipitation process is taking place Avgoustakis K (Curr Drug Deliv. 2004; 1:321-33).

In a further embodiment of the invention, the nanoparticle is a polyalkylcyanoacrylate nanoparticle. Polyalkylcyanoacrylate nanoparticles may be prepared as described by Fattal E. et al. (J. Contr. Release 1998; 53:137-143), using an emulsion polymerization process. The nanoparticles are then coated with a cationic hydrophobic reagent, such as cetyltrimethylammonium bromide (CTAB), and the ISS-NA is adsorbed on the nanoparticle. In an alternative method, such as described by Zobel et al. (Antisense Nucleic Acid Drug Dev. 1997; 7:483-493), where nanoparticles are produced in an aqueous dispersion polymerization process. The surfactant used is DEAE-dextran, which allows subsequent adsorption of ISS-NA on the surface of the nanoparticle through electrostatic interactions. Particles of sizes ranging from about 170-1000 nm were obtained by Zobel et al.

In a further embodiment, the nanoparticle is a PEG-coated polycyanoacrylate nanoparticle, such as described by Li Y. et al. (Int J Pharm. 2003; 259:93-101), whereby the additional covalent attachment of transferrin to the nanoparticles is omitted. The nanoparticles are prepared by a water-in-oil-in-water emulsion solvent evaporation technique, using poly (aminopoly(ethylene glycol)-cyanoacrylate-co-hexadecyl cyanoacrylate) (poly($H_2$NPEGCA-co-HDCA)) as polymer. Briefly, the ISS-NA diluted in buffer (e.g. $NaHCO_3$, pH 8) is emulsified in dichloromethane/ethyl acetate (1:1) containing poly($H_2$NPEGCA-co-HDCA) by sonication. The resulting emulsion is poured into a 1% w/v PVA aqueous solution, and further emulsified. The percentage of PVA may be varied, and in particular a higher percentage (3% in 0.1 M $NaHCO_3$, pH 8) has been shown to limit damage to dsDNA (Li Y. et al. (Int J Pharm. 2003; 259:93-101). The resulting double emulsion is then diluted in a 0.3% w/v PVA aqueous solution, under magnetic stiffing. The organic solvents are then eliminated by evaporation under reduced pressure in a Rotavapor at 37° C., and the nanoparticles collected by centrifugation at 39000 g. Particle sizes obtained by Li et al. ranged from about 130 to 150 nm. In one embodiment, the ISS-NA is an unmethylated CpG-containing oligonucleotide.

Packaging of ISS-NA, and in particular unmethylated CpG-containing oligonucleotide in a particle produced by an emulsion-solvent evaporation technique or spray-dry technique, will be exemplified in the following for polyester nanoparticles. However, it is apparent for the artisan that similar procedures can be applied for PACA and PEG-PACA nanoparticles. Packaging of ISS-NA, such as for example unmethylated CpG-containing oligonucleotide, within polyester nanoparticles such as PLA, PLGA, PECL, PEG-PLA, PEG-PLGA or PEG-PECL nanoparticles, can be performed in several ways. In one method, ISS-NA is added to the initial water phase of the water-in-oil-in-water emulsion solvent evaporation technique, as has been reported by Aukunuru J. V. et al. (J. Pharm. Pharmacol. 2003; 55:1199-206). In another method, the ISS-NA is suspended in the organic solvent, e.g. dichloromethane, by sonication, and then spray dried to yield nanoparticles having packaged the ISS-NA. In certain embodiments, the capacity of a nanoparticle to package an ISS-NA, and in particular an ODN, is increased by adding a complexation agent, such as lysine rich oligopeptide (Emile C. et al. Drug Deliv 1996; 3:187-195), PLL, PEI, spermine or a salt such as Zinc acetate (Putney S D et al. Antisense Nucleic Acid Drug Dev. 1999; 9:451-8). An insoluble complex results from the mixing of the complexation agent and the ISS-NA in an aqueous solution, which can be incorporated into nanoparticles. As would be understood, the optimal ratio of complexation agent to ISS-NA, and when the complexation agent is PEI or PLL, the optimal length of the PLL or PEI, and when the complexation agent is PEI whether branched or linear PEI is chosen, have to be determined empirically. For example, a solution of the polymer, a complexation agent such as a lysine rich peptide, and of a ISS-NA such as an ODN, in acetone, is poured dropwise in an aqueous solution as reported by Emile C. et al. (Drug Deliv 1996; 3:187-195). The complex of the ISS-NA and the complexation agent precipitates with the polymer to form nanoparticles packaged with the ISS-NA. In one embodiment, the complex of the ISS-NA and the complexation agent is suspended in an organic solvent, e.g. methylene chloride, and incorporated and packaged in a PLGA nanoparticle using a spray-dry technique (Putney S D et al. Antisense Nucleic Acid Drug Dev. 1999; 9:451-8; Pamujula S et al. J Pharm Pharmacol 2004; 56:1119-25).

In a further embodiment said nanoparticle is a Block copolymer-coated calcium phosphate nanoparticle (CaP-PEG-PAA; Kakizawa et al. (2004) J. Contr. Release 97:345-56). These are core-shell particles suitable for packaging ISS-NA, preferably unmethylated CpG-containing oligonucleotides. They comprise a core of nanocrystals of CaP, surrounded by a hydrophilic tethered layer of PEG. Mixing of a calcium-, and a phosphate-containing solution in the presence of ISS-NA and PEG-block-poly(aspartic acid) (PEG-PAA) leads to the spontaneous formation of nanoparticles incorporating ISS-NA. In one embodiment the ISS-NA is an unmethylated CpG-containing oligonucleotide. The PAA-segment of PEG-PAA has high binding affinity for CaP, and the non-ionic and hydrophilic PEG has a steric stabilization function. Particle size can be adjusted by varying the PEG-PAA and phosphate concentration, as seen in FIG. 1 of Kakizawa et al. (2004) J. Contr. Release 97:345-56. Typical sizes obtained are between about 100 to about 300 nm. A critical minimal amount of PEG-PAA is required to prevent aggregation of the nanoparticles, while it higher levels, it starts to compete with ISS-NA for CaP binding, and optimal concentration and ratios of the components have to be determined empirically as taught by Kakizawa et al. Increasing phosphate concentration from 1.5 mM to 3 mM, for example, led to a higher ODN binding capacity (Kakizawa et al. (2004) J. Contr. Release 97:345-56).

Preparation of PEG-PAA and of the nanoparticles has been described in detail in (Kakizawa et al. (2004) J. Contr. Release 97:345-56). In essence, a solution containing $CaCl_2$, Tris, a low EDTA amount and ISS-NA is added quickly to an equal volume of a solution containing Hepes, Disodium Hydrogen phosphate and PEG-PAA. The resulting mixture is vigorously stirred by a vortex mixer and incubated at 37° C. for 24 hours. Kakizawa et al. envisage the use of Ca-P-PEG-PAA nanoparticles for delivery of siRNA to the cytoplasm, where they expect fast dissolution of the CaP core in the cytoplasm due to the lower $Ca^{2+}$ concentration and higher phosphate concentration. The ISS-NA of the present invention to be packaged into nanoparticles do not require delivery to the cytoplasm. For example, as for other ODN-cation interactions, ODN release can take place in low-pH compartments such as endosomes.

In another embodiment said nanoparticle is an alginate-PLL nanoparticle. Sodium alginate is a natural polysaccharide with mannuronic and guluronic acid as its constituents. Aynié et al. (Antisense Nucleic Acid Drug Dev. 1999; 9:301-12) have described alginate nanoparticles cross-linked by PLL to which ODN are bound. The preparation of the particles is a two-step process, where an initial alginate pre-gel is produced by the addition of calcium chloride under magnetic stiffing, and second PLL is added to form a polyelectrolyte complex with the remaining free charges of the pre-gel. ISS-NA is added either simultaneously with PLL to the pre-gel, or after nanoparticle formation. In a preferred embodiment said nanoparticle comprises or alternatively essentially consists of Polylysine polymers of MW 3900 and 7900, wherein preferably said ISS-NA is an unmethylated CpG-containing oligonucleotide. Aynié et al. report particle sizes of 200-600 nm, and ODN loading of approximately 10%. The loading capacity of the alginate nanoparticles however did not reach saturation under the conditions described by Aynié et al., while the encapsulation efficiency was 100%. Alginate-PLL nanoparticles have thus a high ODN loading capacity and are used in embodiments of the invention to package ODN or ISS-NA.

In a further preferred embodiment, the nanoparticle is a chitosan nanoparticle. Chitosan is a positively charged polysaccharide polymer prepared from chitin by deacetylation. The preparation of chitosan nanoparticles has been described for example by Roy K. et al. (Nat Med. 1999; 5:387-91) or Mao H Q et al. (J Control Release. 2001; 70:399-421), who obtained nanoparticles of 150-300 nm in size. These authors used a coacervation process, whereby a Chitosan solution in sodium acetate, is mixed to a solution of ISS-NA in sodium sulphate under vortexing at 55° C. Parameters such as temperature, pH, concentration of chitosan, of sodium sulphate, molecular weight of chitosan and DNA may be varied to obtain optimal nanoparticles. In some embodiments the chitosan nanoparticle are further reacted with an N-hydroxy-succinimide derivative of PEG (Leong K W. et al. J Control Release. 1998; 53:183-193). In other embodiments the chitosan nanoparticles are further concomitantly reacted with the homobifunctional cross-linking agent DSS (a bis-N-hydroxysuccinimide compound) (Leong K W. et al. J Control Release. 1998; 53:183-193). In one embodiment, the ISS-NA is an unmethylated CpG-containing oligonucleotide.

In a further preferred embodiment, said nanoparticle is a cationized-gelatin nanoparticle, wherein preferably said ISS-NA is an unmethylated CpG-containing oligonucleotide, preferably G10 (SEQ ID NO:27). The preparation of cationized-gelatin nanoparticle has been described by Zwiorek K. et al. (J Pharm Pharmaceut Sci 2004; 7:22-28) or Zillies J and Coester C (J Pharm Pharmaceut Sci 2004; 7:17-21), who report nanoparticles with sizes of 180-280 nm. A two-step desolvation technique is used to generate nanoparticles, which after resuspension in a buffer at pH 4.5, are further derivatized with cholamine in the presence of EDC. ISS-NA is subsequently packaged in the nanoparticles by resuspending the nanoparticles in a solution of ISS-NA and further incubating the resulting mixture. Zwiorek et al. obtained particles of sizes ranging from 180-290 nm. Further guidance in preparing gelatin nanoparticles is provided by Azarmi S. et al. (J. Pharm. Pharmaceut. Sci. 2006; 9:124-132), who uses glutaraldehyde instead of EDC for cross-linking the nanoparticles.

In a further preferred embodiment said nanoparticle is a gelatin nanosphere, wherein preferably said ISS-NA is an unmethylated CpG-containing oligonucleotide. Gelatine nanospheres are prepared as described by Truong-Le V L et al. Hum Gene Ther. 1998; 9:1709-1717), by a coacervation technique with $Na_2SO_4$ at low pH, and whereby the particles are cross-linked with EDC but omitting transferrin in the reaction mixture. Particle of sizes 300-600 nm were obtained by Truong-Le et al. In a preferred embodiment said nanoparticle is a gelatine-cholamin nanoparticle.

In a further preferred embodiment, said nanoparticle is an albumin nanoparticle, wherein preferably said ISS-NA is an unmethylated CpG-containing oligonucleotide. Preparation of albumin nanoparticles has been described, for example, by Irache J M et al. (Mini Rev Med Chem. 2005; 5:293-305), who report nanoparticles with a size of 250-300 nm. In very preferred embodiment, the albumin nanoparticles are made from human serum albumin. Albumin nanoparticles are prepared by a coacervation or desolvation process, and subsequently stabilized by cross-linking with glutaraldehyde. In one method, ISS-NA is incubated with an albumin aqueous solution (2% w/v), and the mixture is desolvated with ethanol, which induces formation of nanoparticles. These are then cross-linked with glutaraldehyde. As described by Wartlick et al. (J Control Release. 2004; 96:483-495), stability of the nanoparticles can be optimized by adjusting the concentration of glutaraldehyde during the cross-linking step. In one further embodiment, the albumin nanoparticle is a protamine-albumin-ISS-NA nanoparticle (Vogel V. et al. J control release. 2005; 103: 99-11).

In one further embodiment, the albumin nanoparticle is a protamine-albumin-ISS-NA nanoparticle (Weyermann et al. J control release. 2004; 100: 411-423; Vogel V. et al. J control release. 2005; 103: 99-11; Mayer G. et al. J control release 2005; 106:181-187). Nanoparticles useful in the practice of the invention also include the nanoparticles described by Kumar MNVR (J. Pharm. Pharmaceut. Sci. 2000; 3:234-258).

In a further preferred embodiment, said nanoparticle is a methacrylate-based hydrogel nanoparticle. Preparation of such nanoparticle as well as the adsorption of ISS-NA has been described by Jain S. et al. (Biomacromolecules. 2005; 6:2590-600), who obtained particles of about 500 nm in size. These nanoparticles are prepared by a two-phase miniemulsion polymerization process. The emulsion is formed in a near saturated salt solution of pluronic F-68 as described by Jain S. et al, except that no ovalbumin is included in the process. PEG-methacrylate, methacrylic acid and PEG-dimethacrylate are added to the pluronic salt solution under stirring. The resulting solution is heated to 40° C., causing phase separation and emulsion, and polymerization is initiated by addition of ammonium persulfate and sodium meta bisulfite. The nanoparticles are isolated by centrifugation, and poly(L-arginine) followed by ISS-NA are adsorbed onto the hydrophobic nanoparticles.

In a further preferred embodiment, said nanoparticle is a methyl methacrylate-based cationic nanoparticle. Preparation of such nanoparticles has been described by Tondelli L. et al. (J Biomater Sci Polymer Edn 2003; 14:1209-1227), who obtained nanoparticles of 500-1000 nm. Methylmethacrylate is mixed with a PEG-derivatized methyl methacrylate and a methacryl methacrylate derivative containing a quaternary ammonium ion in an emulsion polymerization reaction initiated with potassium persulfate. ISS-NA is then incubated with the cationic nanoparticle.

In a further preferred embodiment, said nanoparticle is a PLL-modified silica nanoparticle. Preparation of the nanoparticles is described by Zhu S G. et al. (Biotechnol Appl Biochem 2004; 39:179-187), who obtained nanoparticles of 20 nm in size. The nanoparticles are prepared using a water-in-oil microemulsion where hydrolysis and condensation reactions of tetraethoxysilane is initiated with ammoniumhydroxide. Silica nanoparticles are activated in carbonate buffer before addition of PLL, and ISS-NA is further incubated with washed PLL-silica nanoparticles.

Nanoparticles suitable in the practice of the invention can be tested for activation of bone marrow derived dendritic cells (BMDCs) as described in Example 11. Alternatively, in addition to interleukin-12 (IL-12) secretion, activity of the nanoparticle in this assay may be identified by detecting interleukin-6 (IL-6) or IFN-alpha in supernatants, or by quantifying CD-86 upregulation on BMDCs upon nanoparticle incubation by fluorescent associated cell-sorting. Importantly, these assays are reproducible when using an identical batch of BMDCs, which can be frozen. Comparison between active agents should therefore be performed with the same batch of BMDCs.

In a preferred embodiment, nanoparticles with unmethylated CpG-containing oligonucleotide induce activation of BMDCs in the cellular assay described in Example 11 in a similar way to Qβ packaged with G10 oligonucleotide and reach the lymph node upon subcutaneous injection in mice footpad with a kinetic similar to Qβ-VLP or a polystyrene bead of 20-500 nm size (see Examples 7 and 9). Activation of BMDCs in a way similar to Qβ packaged with G10 oligonucleotide is meant to express that an identical dose of G10 oligonucleotide package in nanoparticles give a half-maximal amount of IL-12 secretion within 80%, preferably 60%, more preferably 50%, 40% and 30% of the amount induced by the same dose of G10 oligonucleotide packaged in Qβ. In a further preferred embodiment, the nanoparticles are protective in the animal models of allergy described in the Examples.

In a preferred embodiment the nanoparticle of the invention is packaged with ISS-NA, preferably with unmethylated CpG-containing oligonucleotide, most preferably with QβG10, amounting to 0.5 to 80% (w/w) of said particle, preferably 0.5 to 40% (w/w), more preferably 2 to 40% (w/w), still more preferably 6 to 40% (w/w), even more preferably 10 to 40% (w/w), even more preferably 15 to 40% (w/w), most preferably 18 to 30% (w/w).

Processes for the preparation of nanoparticles have been reviewed in Microparticulate systems for the delivery of proteins and vaccines, Eds. S. Cohen and H. Bernstein, Marcel Dekker, New York 1996). The microparticles described therein include polyester microparticles, pegylated-polyester microparticles, polyphosphazene microparticles, lipospheres and gelatin microparticles. Additional microparticles include alginate microparticles (Aggarwal N. et al. Can J Vet Res. 1999; 63:148-52), chitosan microparticles (Aral C and Akbuga J. J Pharm Pharm Sci. 2003; 6:321-6; Xu W. Et al. Vaccine. 2004; 22:3603-12). Processes used for the preparation of nanoparticles where resulting particle size is determined by the size of the droplet within the emulsion used to prepare the nanoparticle, can be readily adapted for the preparation of microparticles, as is well-known in the art, whereby the mixing, vortexing, high-speed homogenization steps are modified such that microparticles are produced. The spra-drying method may also be adapted such that microparticles are generated. Microparticles useful in the practice of the invention also include the microparticles described in Kumar MNVR (J Pharm Pharmaceut Sci 2000; 3:234-258).

Processes for packaging of ISS-NA into nanoparticles described above can be adapted for packaging ISS-NA into microparticles, whereby the homogenization or mixing step is modified as would be known to those skilled in the art, such that the emulsion produced result in microparticle generation. The spray-drying method may also be adapted such that microparticles are generated.

The properties of polyester microsphere, and PLGA microsphere in particular, as well as methods to produce them have been reviewed and described for example by Kissel T and Koneberg R (in Microparticulate systems for the delivery of proteins and vaccines, Eds. S. Cohen and H. Bernstein, Marcel Dekker, New York 1996, p. 51-87). These methods include spray drying methods, water-in-oil-in-water emulsion solvent evaporation methods and phase separation methods. A favored molar ratio of the monomers constituting PLGA is 50% mol LA and 50% mol GA. Increasing the proportion of either of the monomer leads to slower degradation of the polymer. For example, a polymer with a ratio of LA to GA of 85:15 has a rate of degradation about two-and a half time slower than with a ratio of 50:50. Thus, the properties of PLGA polymer can be manipulated by changing the proportion of the monomers.

In one embodiment said synthetic particle is a liposome, wherein said liposome is a lipid vesicles consisting of a lipid bilayer. Liposomes can be packaged with ISS-NA using methods known in the art. The liposome of the invention may be selected from the group consisting of neutral liposome, anionic liposome, cationic liposome, stealth, or cationic stealth. In a preferred embodiment, the liposome is a cationic liposome. The liposome may have a diameter between 100 and 800 nm, preferably between 100 and 400 nm, more preferably between 100 and 300 nm, even more preferably between 100 and 200 nm, most preferably 200 nm.

In a preferred embodiment, the liposome exhibits positive charges in order to facilitate interaction of liposomes with target cells. In some embodiments, the liposome comprises a cationic lipid, a colipid, and a stabilizing additive. In another embodiment, the liposome comprises dimethylaminoethane-carbamol-cholisterol, and/or dioleoylphosphatidylethanolamine, and/or polyethylene glycol derivatized phosphatidylethanolamine. In a preferred embodiment, the liposome comprises phosphatidylcholine, and/or cholesterol, and/or DL-α-tocopherol, preferably phosphatidylcholine, cholesterol, and DL-α-tocopherol. Generation of such liposomes is well established e.g. in Bangham et al., (1965), J. Mol. Biol., 13, 238-252; Gursel et al., (2001), J Immunol 167: 3324; or Ludewig et al., (2000), Vaccine, 19, 23-32, the disclosure of which is incorporated herein by reference in its entirety.

Preferred liposomes and the packaging of ISS-NA in liposomes is described in WO2005/014110A1, which is incorporated herein by reference. ISS-NA may be mixed with preformed vesicles comprising or preferably essentially consisting of, most preferably consisting of cationic lipids, may be mixed directly with cationic lipid, resulting in lipoplexes, or in a preferred embodiment, encapsulated within the aqueous space enclosed by a lipid bilayer. In a further embodiment, said liposome is a lipopolyplex (Pelisek J. et al. J Gene Med 2006; 8:186-197). In one embodiment, the liposome is a microencapsulated liposome, in an alginate-PLL coat, as described by Cohen S. et al. Proc. Natl. Acad. Sci. USA 1991; 88:10440-10444). In a preferred embodiment, the ISS-NA, preferably an unmethylated CpG-containing oligonucleotide, is packaged within a "stabilized anti-sense-lipid particle" containing preferably PEG-ceramide-C14, as described by Semple S. C. et al. Methods Enzymol. 2000; 313:322-41. In the performance of this method for the practice of the invention, the antisense oligonucleotide is replaced by an ISS-NA, and in particular an unmethylated CpG-containing oligonucleotide. These liposomes are prepared with cationic lipids that are only charged at subphysiological pH. Hence the ISS-NA or unmethylated CpG-containing oligonucleotide bound to the outer surface of liposomes during the liposome preparation at low pH can be subsequently dissociated and eliminated by anion exchange chromatography once the preparation has been brought back to neutral pH. Suitable further liposomes, methods of preparation as well as methods for ISS-NA and in particular oligonucleotides, can be found in Semple S. C. et al. Methods Enzymol. 2000; 313:322-41 and references therein. Methods for preparing liposomes include the dry lipid hydration method, the reverse phase hydration method, the detergent dialysis method, the minimal volume entrapment method. In certain embodiments, packaging of the ISS-NA in particular an unmethylated CpG-containing oligonucleotide is facilitated by using an ISS-NA or unmethylated CpG-containing oligonucleotide substituted by a residue selected from the group consisting of C6-C30 alkyl chain, bile acids, cholic acid, taurocholic acid, desoxycholate, cholesterol, oleyl litocholic acid, oleoyl cholenic acid, glycolipids, phospholipids, sphingolipids, isoprenoids, steroids, vitamins, vitamin E, saturated fatty acids, unsaturated fatty acids, fatty acid esters, triglycerides.

In one aspect of the invention, the ISS-NA in liposomes are used to induce systemically increased levels of IFN-alpha. Such elevated levels of IFN-alpha are known to be therapeutically active in hypersensitivity, preferably allergy.

In a further embodiment, said synthetic particle is a virosome, wherein preferably said visosome is a reconstituted virus envelope of a influenza virus, wherein further preferably said influenza virus is a influenza A virus, wherein still further preferably said influenza A virus is influenza A/Singapore virus. Virosomes comprising cationic (positively charged) lipids are especially suited to deliver nucleic acids to a target cell. In a further embodiment, said synthetic particle is a virosome, wherein said virosome comprises a lipid membrane, wherein said lipid membrane comprises or preferably essentially consists of cationic lipids. In a very preferred embodiment, said synthetic particle is a virosome and said ISS-NA is a unmethylated CpG-containing oligonucleotide, wherein preferably said unmethylated CpG containing oligonucleotide is G10 (SEQ ID NO:27), and wherein further preferably said virosome comprises a lipid membrane, wherein said lipid membrane comprises or preferably essentially consists of cationic lipids. In a further preferred embodiment said virosome comprises a lipid membrane, wherein said lipid membrane comprises antibodies or fragments thereof, wherein preferably said antibodies specifically interact with a receptor of a target cell.

Synthetic particles of the invention, preferably microparticles and nanoparticles, most preferably nanoparticles may be injected subcutaneously, intravenously, intradermally, intraperitoneally, administered intranasally, orally, transdermally or inhaled.

In a very preferred embodiment said particle is a virus particle or a virus-like particle (VLP), preferably a VLP. Any virus known in the art may be selected as a VLP or a virus particle of the invention. Most commonly known viruses have been sequenced and are readily available to the public. The taxonomy of viruses is well known to the artisan and summarized, for example, in H. V. Van Regenmortel et al. (eds.), Virus Taxonomy: 7$^{th}$ Report of the International Committee on Taxonomy of Viruses (2000) (Academic Press/elsevier, Burlington Mass., USA), on the Virus Taxonomy web-page of the University of Leicester (UK) (http://www-micro.msb.le.ac.uk/3035/Virusgroups.html) and by the Taxonomy Browser of the National Center for Biotechnology Information (NCBI, Washington D.C., USA) (http://www.ncbi.nlm.nih.gov/ICTVdb/). The genes encoding viral coat proteins can be identified by a skilled artisan and their nucleotide and amino acid sequences may, for example, be obtained from Genbank (http://www.ncbi.nlm.nih.gov/). Viruses which are particularly useful in the context of the invention are generally disclosed in "Artificial DNA—Methods and Applications", Yury Khudyakov and Howard Fields, eds., CCR Press, 2003.

Virus particles or VLPs can be produced and purified from virus-infected cell cultures. For the purpose of the invention, said virus particles or VLPs are be preferably non-replicative or non-infectious, more preferably non-replicative and non-infectious. UV irradiation, chemical treatment, such as with formaldehyde, β-propione or chloroform, are the general methods known to skilled person to inactivate a virus. Alternatively, said non-replicative and non-infectious virus particle or said non-replicative and non-infectious VLP can be produced by purification and reassembly of core proteins of said virus.

In one embodiment said virus particle or VLP, preferably VLP, is a virus particle or VLP, preferably VLP, of a virus, wherein said virus may be a DNA virus, including DNA reverse transcribing viruses, or a RNA virus. In a preferred embodiment said virus is a DNA virus, wherein said DNA virus is a single stranded DNA virus, wherein said single stranded DNA virus is preferably selected from the group consisting of: (a) Parvovirus, preferably parvovirus B19, porcine parvovirus (PPV) or canine parvovirus (CPV), (b) Erythrovirus, (c) Dependovirus, (d) recombinant of CPV with feline panleucopenia virus (FPV) (Saliki. T. J. et al. (1992) J. Gen. Virol 73:369ff), (e) adeno-associated virus type 2 (AAV-2), (f) mink enteritis parvovirus (MEV), (g) muscovy duck parvovirus (DPV), (h) minute virus of mice (MVM), (i) aleutian mink disease parvovirus (ADV), and (j) *Galleria mellonella* densovirus (GMDNV).

In a further preferred embodiment said DNA virus is a double stranded DNA virus, including double stranded DNA reverse transcribing viruses, wherein said double stranded DNA virus is preferably selected from the group consisting of: (a) nucleopolyhedrovirus, preferably Autograpa californica nucleopolyhedrovirus (AcMNPV) or a chimera of AcMNPV polyhedrin and Trichoplusioa ni granulosis virus (TnGV) (Eason J. E. et al. (1998), J Virol 72:6237ff), (b) papillomavirus, preferably selected from (i) human papilloma virus (HPV, most preferably HPV6, HPV11, HPV16, HPV18, or HPV33), (ii) bovine papillomavirus (BPV, preferably BPV1), and (iii) cottontail rabbit papillomavirus (CRPV), (c) polyomavirus, preferably selected from (i) murine polyomavirus (preferably Py or SV40), (ii) budgerigar fledgling virus, (iii) human polyomavirus JC, (iv) hamster polyomavirus (HaPV), (v) monkey B-lympotropic papovirus (LPV), (vi) avian polyomavirus (APV) and (vii) recombinant human and non-human polyomaviruses (Sasnauskas K. et al (1999) Biol. Chem. 380, 381), (d) spleen necrosis virus (SNV, Jiang A. (1999) Hum. Gene Therapy 10(16):2627-2636), and, very preferably, (e) Hepatitis B virus.

In a further preferred embodiment said virus is a RNA virus, wherein said RNA virus may be a single stranded RNA virus or a double stranded RNA virus. In a further preferred embodiment said RNA virus is a single stranded RNA virus, wherein preferably said single stranded RNA virus is a single stranded positive sense RNA virus, wherein preferably said single stranded positive sense RNA virus is selected from: (a) bromoviridae, preferably selected from (i) alfamovirus (e.g. alfalfa mosaic virus (AlMV)), and (ii) ilarvirus (e.g. prunus necrotic ringspot ilarvirus (PNRSV, Pallas V. (1998) Arch. Virol. 144:797-803); prune dwarf virus (PDV, Abou-Jawdah Y. et al. (2004) J. Virological Methods 121:31-38)), (iii) bromovirus (e.g. cowpea chlorotic mottle virus (CCMV) or brome mosaic virus (BMV)), (iv) cucumovirus (e.g. cucumber mosaic virus, Natilla A. et al. Arch Virol 2004 149(1): 137-154), (b) tombusviridae, preferably (i) tombusvirus, preferably tomato bushy stunt virus (TBSV, Joelson T. et al. (1997) J. Gen. Virol. 78:1213-1217), (ii) carmovirus, turnic crinkle virus (TCV, Qu F. and Morris T. J. (1997) J. Virol. 71(2):1428-1435), (c) potyvirus, preferably Johnsongrass mosaic virus (JGMV) and plum pox potyvirus (PPV, Fernandez-Fernandes M. R. et al. (2002) J. Virol. 76(24):12646-12653), (d) tobacco mosaic virus (TMV), (e) comovirus, preferably cowpea mosaic virus (CPMV), (f) potato virus X (PVX, Marusic C. et al. (2001) J. Virol. 75(18):8434-8439, (g) calicivirus, preferably selected from (i) norwalk virus (NV), (ii) norwalk-like calcivirus, (iii) human calcivirus, (iv) Lorsdale calcivirus, (v) rabbit hemorrhagic disease virus (RHDV), (vi) European brown hare syndrome virus (EBHSV), (vii) Toronto virus, (viii) Hawaii virus, (ix) Sapporo-like virus, and (x) Grimsby feline calicivirus, (h) RNA bacteriophage, (i) luteovirus, preferably potato leaf roll virus (PLRV), (j) flock house virus, (k) retroid viruses, preferably selected from (i) oncoretrovirus, (ii) lentivirus, and (iii) yeast retrotransposon Ty1, (l) tick-borne encephalitis virus (TBEV, Leibl H. (1998) Vaccine 16(4):340-345) and (m) togaviridae, preferably alphavirus, most preferably Sindbis virus.

In a further preferred embodiment said RNA virus is a single stranded positive sense RNA virus selected from: (a) bromoviridae, preferably selected from (i) alfamovirus (e.g. alfalfa mosaic virus (AlMV)), and (ii) ilarvirus (e.g. prunus necrotic ringspot ilarvirus (PNRSV, Pallas V. (1998) Arch. Virol. 144:797-803); prune dwarf virus (PDV, Abou-Jawdah Y. et al. (2004) J. Virological Methods 121:31-38)), (iii) bromovirus (e.g. cowpea chlorotic mottle virus (CCMV) or brome mosaic virus (BMV)), (iv) cucumovirus (e.g. cucumber mosaic virus, Natilla A. et al. Arch Virol 2004 149(1): 137-154), (b) tombusviridae, preferably (i) tombusvirus, preferably tomato bushy stunt virus (TBSV, Joelson T. et al. (1997) J. Gen. Virol. 78:1213-1217), (ii) carmovirus, turnic crinkle virus (TCV, Qu F. and Morris T. J. (1997) J. Virol. 71(2):1428-1435), (c) potyvirus, preferably Johnsongrass mosaic virus (JGMV) and plum pox potyvirus (PPV, Fernandez-Fernandes M. R. et al. (2002) J. Virol. 76(24):12646-12653), (d) tobacco mosaic virus (TMV), (e) comovirus, preferably cowpea mosaic virus (CPMV), (f) potato virus X (PVX, Marusic C. et al. (2001) J. Virol. 75(18):8434-8439, (g) calicivirus, preferably selected from (i) norwalk virus (NV), (ii) norwalk-like calcivirus, (iii) human calcivirus, (iv)

Lorsdale calcivirus, (v) rabbit hemorrhagic disease virus (RHDV), (vi) European brown hare syndrome virus (EBHSV), (vii) Toronto virus, (viii) Hawaii virus, (ix) Sapporo-like virus, and (x) Grimsby feline calcivirus, (h) RNA bacteriophage, (i) luteovirus, preferably potato leaf roll virus (PLRV), (j) flock house virus, (k) retroid viruses, preferably selected from (i) oncoretrovirus, (ii) lentivirus, and (iii) yeast retrotransposon Ty1, (l) tick-borne encephalitis virus (TBEV, Leibl H. (1998) Vaccine 16(4):340-345), (m) togaviridae, preferably alphavirus, most preferably Sindbis virus, and (n) Nodaviridae, preferably Alphanodavirus, most preferably Pariacoto virus (Johnson K. N. et al. (2004) Journal of Virology 78:11371-11378).

In a further preferred embodiment said RNA virus is a double stranded RNA virus, wherein preferably said double stranded RNA virus is selected from: (a) birnavirus, (b) cypovirus, preferably *Bombyx mori* cytoplasmic polyhedrovirus (BmCPV), (c) orbivirus, preferably bluetoung virus (BTV) or African horse sickness virus (AHSV), (d) rotavirus and, very preferably, (e) double stranded RNA bacteriophages, preferably selected from (i) bacteriophage 8, (ii) bacteriophage phi6, (iii) bacteriophage phi12, and (iv) bacteriophage phi12.

In a further preferred embodiment said virus particle or VLP is a virus particle or VLP of a virus, wherein said virus is a bacteriophage, wherein said bacteriophage may be a DNA bacteriophage or an RNA bacteriophage.

In a preferred embodiment said bacteriophage is a DNA bacteriophage, wherein said DNA bacteriophage may be a single stranded DNA bacteriophage or a double stranded bacteriophage. In a preferred embodiment, said DNA bacteriophage is a single stranded DNA bacteriophage, wherein said single stranded DNA bacteriophage is preferably selected from (a) Microviridae, preferably Phi X 174 and (b) Inoviridae, preferably fd and M13. In a further preferred embodiment, said DNA bacteriophage is a double stranded DNA bacteriophage, wherein said double stranded DNA bacteriophage is preferably selected from the group consisting of: (a) Myoviridae, preferably T2, T4 or T6, (b) Siphoviridae, preferably bacteriophage Lambda, T1, T5 or HK97, (c) Podoviridae, preferably T2, T7 or P22, (d) Tectiviridae, preferably PRD1, (e) Corticoviridae, preferably PM2, (f) Plasmaviridae, preferably mycoplasma phages, (g) Lipothrixviridae, preferably Thermoproteus bacteriophage TTV1 and (h) Fuselloviridae, preferably sulfolobus bacteriophage 1.

In a more preferred embodiment said bacteriophage is an RNA bacteriophage, wherein said RNA bacteriophage may be a single stranded or a double stranded RNA bacteriophage. In one embodiment said RNA bacteriophage is a single stranded RNA bacteriophage, wherein preferably said single stranded RNA bacteriophage is an enterobacteriophage, wherein preferably said enterobacteriophage is a representative of the Leviviridae, wherein preferably said representative of the Leviviridae is selected from the group consisting of: (a) taxonomically not assigned family member *Acinetobacter* phage 205 (AP205), (b) levivirus, and, preferably (c) allolevivirus.

In a preferred embodiment said representative of the Leviviridae is a levivirus, wherein preferably said levivirus is selected from the group consisting of: (a) bacteriophage BZ13, (b) bacteriophage GA, (c) bacteriophage JP34, (d) bacteriophage KU1, (d) bacteriophage TH1, (e) bacteriophage MS2, (f) bacteriophage f2, (g) bacteriophage fr, (h) bacteriophage JP501, (i) bacteriophage M12, (j) bacteriophage R17, and (k) bacteriophage PP7.

In a more preferred embodiment said representative of the Leviviridae is an allolevivirus, wherein preferably said allolevivirus is selected from the group consisting of: (a) bacteriophage FI, (b) bacteriophage ID2, (c) bacteriophage NL95, (d) bacteriophage SP, (d) bacteriophage TW28, (e) bacteriophage Qβ, (f) bacteriophage M11, (g) bacteriophage MX1, (h) bacteriophage ST, (i) bacteriophage TW18, and (j) bacteriophage VK.

In a further preferred embodiment said RNA bacteriophage is selected from the group consisting of: (a) bacteriophage BZ13, (b) bacteriophage GA, (c) bacteriophage JP34, (d) bacteriophage KU1, (d) bacteriophage TH1, (e) bacteriophage MS2, (f) bacteriophage f2, (g) bacteriophage fr, (h) bacteriophage JP501, (i) bacteriophage M12, (j) bacteriophage R17, (k) bacteriophage PP7, (l) bacteriophage FI, (m) bacteriophage ID2, (n) bacteriophage NL95, (o) bacteriophage SP, (p) bacteriophage TW28, (q) bacteriophage Qβ, (r) bacteriophage M11, (s) bacteriophage MX1, (t) bacteriophage ST, (u) bacteriophage TW18, and (v) bacteriophage VK. In a further preferred embodiment said RNA bacteriophage is selected from the group consisting of: (a) bacteriophage Qβ, (b) bacteriophage R17, (c) bacteriophage fr, (d) bacteriophage GA, (e) bacteriophage SP, (f) bacteriophage MS2, (g) bacteriophage M11, (h) bacteriophage MX1, (i) bacteriophage NL95, (k) bacteriophage f2, (l) bacteriophage PP7, and (m) bacteriophage AP205.

In a further preferred embodiment said RNA bacteriophage is a double stranded RNA bacteriophage, wherein preferably said double stranded RNA bacteriophage is a representative of the Cystoviridae, more preferably said representative of the Cystoviridae is a Cystovirus, most preferably said Cystovirus is pseudomonas bacteriophage Phi 6.

In a preferred embodiment said particle is a virus particle of a bacteriophage, and wherein preferably said bacteriophage is a RNA bacteriophage, wherein further preferably said RNA bacteriophage is a single stranded positive sense RNA bacteriophage, and wherein still further preferably said single stranded positive sense RNA bacteriophage is a single stranded positive sense RNA bacteriophage selected from the group consisting of: (a) bacteriophage Qβ, (b) bacteriophage fr, (c) bacteriophage GA, and (d) bacteriophage AP205, most preferably said single stranded positive sense RNA bacteriophage is Qβ.

In a very preferred embodiment, said particle is a VLP, preferably a VLP of an RNA virus, more preferably a VLP of a single stranded positive sense RNA virus, most preferably a VLP of an RNA bacteriophage.

In a further preferred embodiment said particle is a VLP of a bacteriophage, more preferably a VLP of a enterobacteriophage, still more preferably a VLP of a representative of the Leviviridae, most preferably a VLP of a levivirus or an allolevivirus. I a very preferred embodiment said VLP is a VLP of an allolevivirus.

In a further embodiment said particle is a virus particle or a VLP, preferably a VLP, of a icosahedral virus, wherein said icosahedral virus is preferably a plant-infectious icosahedral virus. VLPs of plant-infectious icosahedral viruses are for example disclosed in WO2005/067478A2 which is incorporated herein by reference. In a preferred embodiment said icosahedral virus is selected from a representative of any one taxon selected from the group consisting of (a) Papillomaviridae, (b) Totiviridae, (c) Dcistroviridae, (d) Hepadnaviridae, (e) Togaviridae, (f) Polyomaviridae, (g) Nodaviridae, (h) Tectiviridae, (i) Leviviridae, (j) Microviridae, (k) Sipoviridae, (l) Picornoviridae, (m) Parvoviridae, (n) Calciviridae, (o) Tetraviridae, and (p) Satellite viruses. In a preferred embodiment, said icosahedral virus is a plant-infectious icosahedral virus, wherein said plant-infectious icosahedral virus is a representative of any one taxon selected from the group consisting of (a) Bunyaviridae, (b) Reoviridae, (c) Rhabdoviridae, (d) Luteoviridae, (e) Nanoviridae, (f) Partitiviridae, (g) Sequiviridae, (h) Tymoviridae, (i) Ourmiavirus, (j) Tobacco Necrosis Virus Satellite, (k) Caulimoviridae, (l) Geminiviridae, (m) Comoviridae, (n) Sobemovirus, (o) Tombusviridae, and (p) Bromoviridae. In a further preferred embodiment, said plant-infectious icosahedral virus is a representative of any one taxon selected from the group consisting of (a) Luteoviridae, (b) Nanoviridae, (c) Partitiviridae, (d) Sequiviridae, (e) Tymoviridae, (f) Ourmiavirus, (g) Tobacco Necrosis Virus Satellite, (h) Caulimoviridae, (i) Geminiviridae, (j) Comoviridae, (k) Sobemovirus, (l) Tombusviridae, and (m) Bromoviridae. In a further preferred embodiment, said plant-infectious icosahedral virus is a representative of any one taxon selected from the group consisting of (a) Caulimoviridae, (b) Geminiviridae, (c) Comoviridae, (d) Sobemovirus, (e) Tombusviridae, and (e) Bromoviridae. In a further preferred embodiment, said plant-infectious icosahedral virus is a representative of any one taxon selected from the group consisting of the (a) Comoviridae, (b) Sobemovirus, (c) Tombusviridae, and (d) Bromoviridae. In a further preferred embodiment, said plant-infectious icosahedral virus is a representative of any one taxon selected from Comoviridae and Bromoviridae. In a very preferred embodiment said plant-infectious icosahedral virus is a Cowpea Mosaic Virus or a Cowpea Chlorotic Mottle Virus. In a further preferred embodiment said plant-infectious icosahedral virus is a representative of the Bromoviridae, preferably Bromovirus, Cucumovirus, Ilarvirus or Alfamovirus. In a very preferred embodiment said plant-infectious icosahedral virus is selected from: brome mosaic virus, cowpea chlorotic mottle virus, cucumber mosaic virus, Tobacco streak virus and alfalfa mosaic virus (AMV, including AMV1 and AMV2).

In a further preferred embodiment said VLP is a synthetic VLP.

In a further preferred embodiment, the VLP is a recombinant VLP. The preparation of VLPs by recombinantly expressing the coat protein in a host is within the common knowledge of a skilled artisan. Illustrative DNA or RNA viruses, the coat or capsid protein of which can be used for the preparation of VLPs have been disclosed in WO 2004/009124 on page 25, line 10-21, on page 26, line 11-28, and on page 28, line 4 to page 31, line 4. These disclosures are incorporated herein by way of reference.

In one preferred embodiment, said VLP comprises, or alternatively consists of, recombinant proteins, mutants or fragments thereof, of a virus, wherein preferably said virus is selected from any virus listed above. In a very preferred embodiment said VLP comprises, or alternatively consists of, recombinant proteins, mutants or fragments thereof, of a virus, wherein said virus is selected form the group consisting of: (a) RNA bacteriophages, (b) bacteriophages, (c) Hepatitis B virus, preferably its capsid protein (Ulrich, et al., Virus Res. 50:141-182 (1998)) or its surface protein (WO 92/11291), (d) measles virus (Warnes, et al., Gene 160:173-178 (1995)), (e) Sindbis virus; (f) rotavirus (U.S. Pat. Nos. 5,071,651 and 5,374,426), (g) foot-and-mouth-disease virus (Twomey, et al., Vaccine 13:1603 1610, (1995)), (h) Norwalk virus (Jiang, X., et al., Science 250:1580 1583 (1990); Matsui, S. M., et al., J. Clin. Invest. 87:1456 1461 (1991)), (i) Alphavirus, (j) retrovirus, preferably its GAG protein (WO 96/30523), (k) retrotransposon Ty, preferably the protein p1; (l) human Papilloma virus (WO 98/15631), (m) Polyoma virus, (n) Tobacco mosaic virus, and (o) Flock House Virus. In a very preferred embodiment said VLP comprises, or alternatively consists of, recombinant proteins, mutants or fragments thereof, of a virus, wherein said virus is selected form the group consisting of: (a) Hepatitis B virus, and (b) Polyoma virus.

In a further preferred embodiment, said VLP comprises, or alternatively consists of, recombinant proteins, mutants or fragments thereof, of a virus, wherein said virus is a plant-infectious icosahedral virus, wherein preferably said plant-infectious icosahedral virus is selected from (a) Comoviridae, (b) Sobemovirus, (c) Tombusviridae, and (d) Bromoviridae.

In one preferred embodiment, the VLP comprises or consists of more than one amino acid sequences, preferably two amino acid sequences, of the recombinant proteins, mutants or fragments thereof. VLP comprises or consists of more than one amino acid sequence is referred, in this application, as mosaic VLP.

The term "fragment of a recombinant protein" or the term "fragment of a coat protein", as used herein, is defined as a polypeptide, which is of at least 70%, preferably at least 80%, more preferably at least 90%, even more preferably at least 95% the length of the wild-type recombinant protein, or coat protein, respectively and which preferably retains the capability of forming VLP. Preferably, the fragment is obtained by (i) at least one, preferably exactly one, internal deletion, (ii) at least one, preferably exactly one, truncation, or (iii) at least one, preferably exactly one, combination thereof. Further preferably, the fragment is obtained by at most 5, 4, 3 or 2 internal deletions, at most 2 truncations or exactly one combination thereof. Further preferably, the fragment is obtained by at most 5, 4, 3 or 2 internal deletions, wherein still further preferably each of said deletions comprises 1 to 5, preferably 1 to 4, more preferably 1 to 3, still more preferably 1 to 2, and most preferably exactly 1 amino acid.

The term "fragment of a recombinant protein" or "fragment of a coat protein" shall further encompass polypeptide, which has at least 80%, preferably 90%, even more preferably 95% amino acid sequence identity with the "fragment of a recombinant protein" or "fragment of a coat protein", respectively, as defined above and which is preferably capable of assembling into a virus-like particle.

The term "mutant coat protein" refers to a polypeptide having an amino acid sequence derived from the wild type recombinant protein, or coat protein, respectively, wherein the amino acid sequence is at least 80%, preferably at least 85%, 90%, 95%, 97%, or 99% identical to the wild type sequence and preferably retains the ability to assemble into a VLP.

In one preferred embodiment, the VLP of the invention is VLP of Hepatitis B virus. The preparation of Hepatitis B virus-like particles has been disclosed, inter alia, in WO00/32227, WO01/85208, WO01/056905 and WO2004/000351. All four documents are explicitly incorporated herein by way of reference. Other variants of HBcAg suitable for use in the practice of the present invention have been disclosed in page 34-39 of WO 01/056905. Specifically preferred Hepatitis B virus VLPs are described on page 43, line 12 to page 49, line 8 of WO2004/000351 and in SEQ IDs NO:19-68, 71 and 97 of WO2004/000351. In one further preferred embodiment of the invention, a lysine residue is introduced into the HBcAg polypeptide. In preferred embodiments, VLPs and compositions of the invention are prepared using a HBcAg comprising, or alternatively consisting of, amino acids 1-144, or 1-149, 1-185 of SEQ ID NO:1, which is modified so that the amino acids at positions 79 and 80 are replaced with a peptide having the amino acid sequence of Gly-Gly-Lys-Gly-Gly (SEQ ID NO:24). This modification changes the SEQ ID NO:1 to SEQ ID NO:2. In further preferred embodiments, the cysteine residues at positions 48 and 110 of SEQ ID NO:2, or its corresponding fragments, preferably 1-144 or 1-149, are mutated to serine. The invention further includes compositions comprising Hepatitis B core protein mutants having above noted corresponding amino acid alterations. The invention further includes compositions and pharmaceutical compositions respectively, comprising HBcAg polypeptides which comprise, or alternatively consist of, amino acid sequences which are at least 80%, 85%, 90%, 95%, 97% or 99% identical to SEQ ID NO:2.

In one preferred embodiment of the invention, the virus-like particle comprises, consists essentially of, or alternatively consists of, recombinant coat proteins, mutants or fragments thereof, of a RNA bacteriophage. Preferably, the RNA bacteriophage is selected from the group consisting of: (a) bacteriophage BZ13, (b) bacteriophage GA, (c) bacteriophage JP34, (d) bacteriophage KU1, (d) bacteriophage TH1, (e) bacteriophage MS2, (f) bacteriophage f2, (g) bacteriophage fr, (h) bacteriophage JP501, (i) bacteriophage M12, (j) bacteriophage R17, (k) bacteriophage PP7, (l) bacteriophage FI, (m) bacteriophage ID2, (n) bacteriophage NL95, (o) bacteriophage SP, (p) bacteriophage TW28, (q) bacteriophage Qβ, (r) bacteriophage M11, (s) bacteriophage MX1, (t) bacteriophage ST, (u) bacteriophage TW18, and (v) bacteriophage VK. Further preferably, the RNA bacteriophage is selected from the group consisting of: (a) bacteriophage Qβ, (b) bacteriophage R17, (c) bacteriophage fr, (d) bacteriophage GA, (e) bacteriophage SP, (f) bacteriophage MS2, (g) bacteriophage M11, (h) bacteriophage MX1, (i) bacteriophage NL95, (k) bacteriophage f2, (l) bacteriophage PP7, and (m) bacteriophage AP205.

In one preferred embodiment of the invention, the virus-like particle comprises at least one coat protein, mutant or fragment thereof, of an RNA bacteriophage, wherein the coat protein has an amino acid sequence selected from the group consisting of: (a) SEQ ID NO:3 referring to Qβ CP; (b) a mixture of SEQ ID NO:3 and SEQ ID NO:4 (Qβ A1 protein); (c) SEQ ID NO:5 (R17 capsid protein); (d) SEQ ID NO:6 (fr capsid protein); (e) SEQ ID NO:7 (GA capsid protein); (f) SEQ ID NO:8 (SP capsid protein); (g) a mixture of SEQ ID NO:8 and SEQ ID NO:9; (h) SEQ ID NO:10 (MS2 capsid protein); (i) SEQ ID NO:11 (M11 capsid protein); (j) SEQ ID NO:12 (MX1 capsid protein); (k) SEQ ID NO:13 (NL95 capsid protein); (l) SEQ ID NO:14 (f2 capsid protein); (m) SEQ ID NO:15 (PP7 capsid protein); and (n) SEQ ID NO:21 (AP205 capsid protein). In a further preferred embodiment of the present invention, the virus-like particle comprises coat proteins having an amino acid sequence selected from the group consisting of: (a) SEQ ID NO:3; (b) a mixture of SEQ ID NO:3 and SEQ ID NO:4; (c) SEQ ID NO:6; (d) SEQ ID NO:7; (e) SEQ ID NO:21. In a further very preferred embodiment of the present invention, the virus-like particle comprises coat proteins having an amino acid sequence selected from the group consisting of: (a) SEQ ID NO:3; and (b) a mixture of SEQ ID NO:3 and SEQ ID NO:4.

In a further very preferred embodiment of the present invention, the virus-like particle essentially consists of coat proteins having an amino acid sequence of SEQ ID NO:3, or essentially consists of a mixture of coat proteins having amino acid sequences of SEQ ID NO: 4, or mutants thereof, and of SEQ ID NO:3.

In one preferred embodiment of the invention, the VLP is a mosaic VLP comprising or alternatively consisting of more than one amino acid sequence, preferably two amino acid sequences, of coat proteins, mutants or fragments thereof, of a RNA bacteriophage.

In one embodiment, the virus particle or VLP is a VLP of bacteriophage fr or GA. Fr coat protein in the form of recombinant VLP may be obtained as described by Pushko P et al. ((1993) Prot Engin 6:883-891), while GA VLP may be obtained by cloning GA coat protein cDNA isolated by reverse transcription from GA phage into pQb185, which is described for example in WO2004/007538. Disassembly of Fr and GA VLPs can be readily done by incubating the VLPs in 7 M urea, optionally supplemented with acetic acid at a concentration of 0.1 M. The nucleic acid is further purified from the coat protein by ion exchange chromatography, either at a pH where a significant amount of the coat protein flows through while the nucleic acid is retained, or at a pH where the coat protein is also adsorbed on the column and subsequently eluted with a salt gradient. Reassembly of fr and GA coat protein with ISS-NA is effected essentially as described in WO2003/024481 by slow dialysis, wherein said ISS-NA preferably is an unmethylated CpG-containing oligonucleotide, more preferably G10 (SEQ ID NO:27), and even more preferably aggregated G10 (SEQ ID NO:27) having a retention time relative to Qβ capsid standard under HPLC conditions as set forth in Example 2 of 80 to 120%, most preferably of 80 to 95%. At the end of the reassembly reaction the reassembly mixture is concentrated for example by dialysis against a 50% (v/v) glycerol solution in NET buffer (WO2003/024481) and purified further by gel filtration, for example on a Sepharose CL-4B column. Additional purification methods include ultracentrifugation on a CsCl gradient or sucrose cushion. Further protocols for the disassembly and reassembly of Fr and GA VLPs are disclosed in Examples 5 and 6 of the present application.

In one very preferred embodiment, the VLP comprises or alternatively consists of two different coat proteins of a RNA bacteriophage, said two coat proteins have an amino acid sequence of CP Qβ (SEQ ID NO: 3) and CP Qβ A1 (SEQ ID NO:4), or of CP SP (SEQ ID NO:8) and CP SP A1 (SEQ ID NO:9).

In preferred embodiments of the present invention, the virus-like particle of the invention comprises, or alternatively consists essentially of, or alternatively consists of recombinant coat proteins, mutants or fragments thereof, of the RNA-bacteriophage Qβ, fr, AP205 or GA.

In one preferred embodiment, the VLP of the invention is a VLP of RNA bacteriophage Qβ. The capsid or virus-like particle of Qβ showed an icosahedral phage-like capsid structure with a diameter of 25 nm and T=3 quasi symmetry. The capsid contains 180 copies of the coat protein, which are linked in covalent pentamers and hexamers by disulfide bridges (Golmohammadi, R. et al., Structure 4:543-5554 (1996)), leading to a remarkable stability of the Qβ capsid. Capsids or VLPs made from recombinant Qβ coat protein may contain, however, subunits not linked via disulfide bonds to other subunits within the capsid, or incompletely linked.

Further preferred VLPs of RNA bacteriophages in accordance with this invention, in particular of Qβ and fr, are disclosed in WO 02/056905, the disclosure of which is herewith incorporated by reference in its entirety. In particular Example 18 of WO 02/056905 gave detailed description of preparation of VLP particles from Qβ.

In another preferred embodiment, the VLP of the invention is a VLP of RNA bacteriophage AP205. Assembly-competent mutant forms of AP205 VLPs, including AP205 coat protein with the substitution of proline at amino acid 5 to threonine, may also be used in the practice of the invention and leads to other preferred embodiments of the invention. WO 2004/007538 describes, in particular in Example 1 and Example 2, how to obtain VLP comprising AP205 coat proteins, and hereby in particular the expression and the purification thereto. WO 2004/007538 is incorporated herein by way of reference. In a further preferred embodiment said virus particle or VLP is a virus particle or VLP of RNA bacteriophage AP205, wherein said ISS-NA preferably is an unmethylated CpG-containing oligonucleotide, more preferably G10 (SEQ ID NO:27), and even more preferably aggregated G10 (SEQ ID NO:27) having a retention time relative to Qβ capsid standard under HPLC conditions as set forth in Example 2 of 80 to 120%, most preferably of 80 to 95%. The disassembly and reassembly of AP205 is demonstrated in Example 5.

Qβ mutants, of which exposed lysine residues are replaced by arginines can be used for the present invention. Thus, in another preferred embodiment of the present invention, the virus-like particle comprises, consists essentially of or alternatively consists of mutant Qβ coat proteins. Preferably these mutant coat proteins comprise or alternatively consist of an amino acid sequence selected from the group of a) Qβ-240 (SEQ ID NO:16, Lys13-Arg of SEQ ID NO: 3) b) Qβ-243 (SEQ ID NO:17, Asn10-Lys of SEQ ID NO:3); c) Qβ-250 (SEQ ID NO:18, Lys2-Arg of SEQ ID NO:3) d) Qβ-251 (SEQ ID NO:19, Lys16-Arg of SEQ ID NO:3); and e) Qβ-259 (SEQ ID NO:20, Lys2-Arg, Lys16-Arg of SEQ ID NO:3). The construction, expression and purification of the above indicated Qβ mutant coat proteins, mutant Qβ coat protein VLPs and capsids, respectively, are described in WO 02/056905. In particular is hereby referred to Example 18 of above mentioned application.

In a further preferred embodiment said virus particle or VLP is a virus particle or VLP of RNA bacteriophage Qβ, wherein said ISS-NA preferably is an unmethylated CpG-containing oligonucleotide, more preferably G10 (SEQ ID NO:27), and even more preferably aggregated G10 (SEQ ID NO:27) having a retention time relative to Qβ capsid standard under HPLC conditions as set forth in Example 2 of 80 to 120%, most preferably of 80 to 95%. The disassembly and reassembly of Qβ VLPs is demonstrated in Examples 1 and 3.

In another preferred embodiment of the present invention, the virus-like particle comprises, or alternatively consists essentially of, or alternatively consists of mutant coat protein of Qβ, or mutants or fragments thereof, and the corresponding A1 protein. In a further preferred embodiment, the virus-like particle comprises, or alternatively consists essentially of, or alternatively consists of mutant coat protein with amino acid sequence SEQ ID NO:16, 17, 18, 19, or 20 and the corresponding A1 protein.

Further RNA bacteriophage coat proteins have also been shown to self-assemble upon expression in a bacterial host (Kastelein, R A. et al., Gene 23:245-254 (1983), Kozlovskaya, T M. et al., Dokl. Akad. Nauk SSSR 287:452-455 (1986), Adhin, M R. et al., Virology 170:238-242 (1989), Priano, C. et al., J. Mol. Biol. 249:283-297 (1995)). In particular the biological and biochemical properties of GA (Ni, C Z., et al., Protein Sci. 5:2485-2493 (1996), Tars, K et al., J. Mol. Biol. 271:759-773 (1997)) and of fr (Pushko P. et al., Prot. Eng. 6:883-891 (1993), Liljas, L et al. J Mol. Biol. 244:279-290, (1994)) have been disclosed. The crystal structure of several RNA bacteriophages has been determined (Golmohammadi, R. et al., Structure 4:543-554 (1996)).

In one preferred embodiment, the virus particle or VLP is a VLP or virus particle of Cowpea cholortic mottle virus (CCMV). Assembly of CCMV virus from coat proteins expressed in *E. coli* and nucleic acids has been described (Zhao X. et al. (1995) Virology 207:486-494). In particular, the reassembly of CCMV with RNA was shown to be independent of RNA sequence (Johnson J M. et al. (2004) J Mol Biol 335:455-464). Furthermore, the virus may exist in a swollen form, susceptible to nuclease digestion, which can be disassembled by adding a high NaCl concentration (1 M; Johnson J E and Speir J A (1997) J Mol Biol 269:665-675). Methods for reassembly of CCMV in the presence of nucleic acids are also described therein. In one embodiment, the CCMV particle is thus reassembled with ISS-NA, preferably with an unmethylated CpG-containing oligonucleotide. In a very preferred embodiment, the unmethylated CpG-containing oligonucleotide is G10 (SEQ ID NO:27), more preferably aggregated G10, still more preferably aggregated G10 having a retention time relative to Qβ capsid standard under HPLC conditions as set forth in Example 2 of 80 to 120%, most preferably of 80 to 95%. In one further embodiment, native CCMV virus particle is swollen, treated with nucleases, and an ISS-NA, preferably an unmethylated CpG-containing oligonucleotide, and even more preferably G10 (SEQ ID NO:27) is added to the nuclease treated particle after nuclease removal. In one further embodiment, CCMV capsids are reassembled without nucleic acids, as has been described for example by Zlotnick et al. (2000) Virology 277:450-456, optionally swollen by bringing the solution to the appropriate pH and ionic strength as described by Zlotnick et al. ((2000) Virology 277:450-456) or Johnson J E and Speir J A ((1997) J Mol Biol 269:665-675) and ISS-NA, preferably an unmethylated CpG-containing oligonucleotide, and even more preferably G10 (SEQ ID NO:27) is added to the swollen empty particle.

In one further embodiment, the virus particle or VLP is a VLP or virus particle of Brome mosaic virus (BMV). Reassembly of BMV has been described previously (Choi Y G and Rao L N (2000) Virology 275: 249-257, and references therein). A tRNA-like structure (tls) at the 3' of each viral RNA has been shown to be required for packaging, and can be added in trans (Choi Y G et al. (2002) Proc. Natl. Acad. Sci. USA 99:655-660) as a nucleotide sequence of about 200 nucleotide in length. Tls from other viruses such as tobacco mosaic virus (TMV) or CMV, or even tRNAs such as wheat germ tRNAs may also be added in trans and facilitate reassembly, although Choi et al. did not detect packaging of tRNAs in the BMV capsid (Choi Y G et al. (2002) Proc. Natl. Acad. Sci. USA 99:655-660). Thus in one further embodiment, BMV is reassembled with an ISS-NA, preferably an unmethylated CpG-containing oligonucleotide, more preferably G10 and even more preferably aggregated G10 having a retention time relative to Qβ capsid standard under HPLC conditions as set forth in Example 2 of 80 to 120%, most preferably of 80 to 95%.

The compositions of the invention comprise an immunostimulatory nucleic acid (ISS-NA), wherein preferably said ISS-NA is capable of inducing the production of a cytokin, preferably of IFN-alpha, in a cell, preferably in a dendritic cell. In one embodiment, said ISS-NA is selected from the group consisting of: (a) ribonucleic acids; (b) desoxyribonucleic acids, (c) chimeric nucleic acids; and (d) any mixtures of at least one nucleic acid of (a), (b) and/or (c). In a preferred embodiment, said ISS-NA is a ribonucleic acid, wherein preferably said ribonucleic acid is a double stranded ribonucleic acid, preferably a double stranded ribonucleic acid selected from the group consisting of: (a) double stranded viral RNA, and (b) synthetic double stranded RNA, preferably poly-(A: U) or poly(I:C), most preferably poly(I:C).

The innate immune system has the capacity to recognize invariant molecular pattern shared by microbial pathogens. Recent studies have revealed that this recognition is a crucial step in inducing effective immune responses. The main mechanism by which microbial products augment immune responses is to stimulate APC, especially dendritic cells to produce proinflammatory cytokines and to express high levels co-stimulatory molecules for T cells. These activated dendritic cells subsequently initiate primary T cell responses and dictate the type of T cell-mediated effector function. Three classes of nucleic acids, namely (i) bacterial DNA that contains immunostimulatory sequences, in particular unmethylated CpG dinucleotides within specific flanking bases (referred to as CpG motifs), (ii) double-stranded RNA synthesized by various types of viruses represent important members of the microbial components that enhance immune responses, and (iii) single stranded RNA. Synthetic double stranded (ds) RNA such as polyinosinic-polycytidylic acid (poly I:C) are capable of inducing dendritic cells to produce proinflammatory cytokines and to express high levels of costimulatory molecules. A series of studies by Tokunaga and Yamamoto et al. has shown that bacterial DNA or synthetic oligodesoxynucleotides induce human PBMC and mouse spleen cells to produce type I interferon (IFN) (reviewed in Yamamoto et al., Springer Semin Immunopathol. 22:11-19). Poly (I:C) was originally synthesized as a potent inducer of type I IFN but also induces other cytokines such as IL-12. Preferred ribonucleic acid encompass polyinosinic-polycytidylic acid double-stranded RNA (poly I:C). Ribonucleic acids and modifications thereof as well as methods for their production have been described by Levy, H. B (Methods Enzymol. 1981, 78:242-251), DeClercq, E (Methods Enzymol. 1981, 78: 227-236) and Torrence, P. F. (Methods Enzymol 1981; 78:326-331) and references therein. Further preferred ribonucleic acids comprise polynucleotides of inosinic acid and cytidiylic acid such poly (I:C) of which two strands form double stranded RNA. Ribonucleic acids can be isolated from organisms. Ribonucleic acids also encompass further synthetic ribonucleic acids, in particular synthetic poly (I:C) oligonucleotides that have been rendered nuclease resistant by modification of the phosphodiester backbone, in particular by phosphorothioate modifications. In a further embodiment the ribose backbone of poly (I:C) is replaced by a desoxyribose. Those skilled in the art know procedures how to synthesize synthetic oligonucleotides.

In a further embodiment said ISS-NA is a single stranded ribonucleic acid, preferably polyuridylic acid (poly-U, Westwood A. (2006), Vaccine 24:1736-1743). In a preferred embodiment said ISS-NA is desoxyribonucleic acid, wherein preferably said desoxyribonucleic acid is a double stranded desoxyribonucleic acid. In very preferred embodiment said ISS-NA is desoxyribonucleic acid, wherein preferably said desoxyribonucleic acid is a single stranded desoxyribonucleic acid, most preferably a oligodesoxynucleotide (ODN).

In another embodiment, said ISS-NA is an oligonucleotide, wherein said oligonucleotide is preferably selected from the group consisting of (a) unmethylated CpG-containing oligonucleotide; and (b) oligonucleotide free of unmethylated CpG motifs. Preferably, said ISS-NA is an unmethylated CpG-containing oligonucleotide. Unmethylated CpG-dinucleotides within specific flanking bases (referred to as CpG motifs) represent important members of the microbial components that enhance immune responses. Toll-like receptor 9 (TLR9) is activated by bacterial DNA, in particular by unmethylated CpG-containing oligonucleotides. In general, the unmethylated CpG-containing oligonucleotide comprises the sequence: 5' $X_1X_2CGX_3X_4$ 3', wherein $X_1$, $X_2$, $X_3$ and $X_4$ are any nucleotide. Preferred unmethylated CpG-containing oligonucleotides further comprise about 6 to about 100,000 nucleotides, more preferably about 6 to about 2000 nucleotides, still more preferably about 20 to about 2000 nucleotides, and even more preferably comprises about 20 to about 300 nucleotides. Further preferred unmethylated CpG-containing oligonucleotides comprise 100 to about 2000 nucleotides, preferably 100 to about 1000 nucleotides, and more preferably 100 to about 500 nucleotides. Specifically preferred oligonucleotides, unmethylated CpG-containing oligonucleotide, in the context of the invention comprise 20 to 40, preferably 26, 27, 28, 29, 30, 31 or 32 nucleotides, most preferably 30 nucleotides.

The CpG-containing oligonucleotide can contain one or more phosphothioester modifications of the phosphate backbone to enhance the stability of the oligonucleotide. For example, a CpG-containing oligonucleotide having one or more phosphate backbone modifications or having all of the phosphate backbone modified and a CpG-containing oligonucleotide wherein one, some or all of the nucleotide phosphate backbone modifications are phosphorothioate modifications are included within the scope of the present invention. In a preferred embodiment said ISS-NA is a CpG-containing oligonucleotide, wherein preferably said CpG-containing oligonucleotide consisting exclusively of phosphodiester bound, preferably unmethylated nucleotides are preferred in the context of the invention.

The CpG-containing oligonucleotide can also be recombinant, genomic, synthetic, cDNA, plasmid-derived and single or double stranded. For use in the invention, the nucleic acids can be synthesized de novo using any of a number of procedures well known in the art. For example, the b-cyanoethyl phosphoramidite method (Beaucage, S. L., and Caruthers, M. H., *Tet. Let.* 22:1859 (1981); nucleoside H-phosphonate method (Garegg et al., *Tet. Let.* 27:4051-4054 (1986); Froehler et al., *Nucl. Acid. Res.* 14:5399-5407 (1986); Garegg et al., *Tet. Let.* 27:4055-4058 (1986), Gaffney et al., *Tet. Let.* 29:2619-2622 (1988)). These chemistries can be performed by a variety of automated oligonucleotide synthesizers available in the market. Alternatively, CpGs can be produced on a large scale in plasmids, (see Sambrook, T., et al., "Molecular Cloning: A Laboratory Manual," Cold Spring Harbor laboratory Press, New York, 1989) which after being administered to a subject are degraded into oligonucleotides. Oligonucleotides can be prepared from existing nucleic acid sequences (e.g., genomic or cDNA) using known techniques, such as those employing restriction enzymes, exonucleases or endonucleases.

The ISS-NA, preferably the unmethylated CpG-containing oligonucleotide, can be bound to the particle by any way known in the art provided the composition enhances an immune response in an animal. For example, the ISS-NA can be bound either covalently or non-covalently. Preferably, the particle, preferably the VLP, encloses, fully or partially, the ISS-NA, preferably the unmethylated CpG-containing oligonucleotide. In a very preferred embodiment said particle, preferably said VLP, is packaged with said ISS-NA, wherein further preferably said ISS-NA is a unmethylated CpG-containing oligonucleotide, most preferably G10 (SEQ ID NO:27).

In one embodiment the ISS-NA, preferably the unmethylated CpG-containing oligonucleotide, is bound to the particle, preferably to said VLP, at a binding site, preferably a binding site selected from (a) oligonucleotide binding site (either naturally or non-naturally occurring), (b) a DNA binding site, and (c) a RNA binding site. In another embodiment, the VLP binding site comprises an arginine-rich repeat or a lysine-rich repeat.

In another preferred embodiment of the present invention, the ISS-NA is an unmethylated CpG-containing oligonucleotide, wherein the CpG motif of said unmethylated CpG-containing oligonucleotide is part of a palindromic sequence, wherein preferably said palindromic sequence is selected from any one of SEQ ID NO:28 and SEQ ID NOs: 35 to 60. Preferably, said palindromic sequence is GACGATCGTC (SEQ ID NO:28).

In a preferred embodiment said ISS-NA is an A-type CpG or an C-type CpG. Preferably, said unmethylated CpG containing oligonucleotide is an A-type CpG, wherein preferably the nucleotides are exclusively linked by phosphodiester bonds. In a further preferred embodiment said ISS-NA is a A-type CpG comprising a palindromic sequence, wherein preferably said palindromic sequence is selected from the group consisting of: (a) GACGTC (SEQ ID NO:35), (b) AGCGCT (SEQ ID NO:36), (c) AACGTT (SEQ ID NO:37), (d) ATCGAT (SEQ ID NO:38); (e) CGATCG (SEQ ID NO:39); (f) CGTACG (SEQ ID NO:40); (g) CGCGCG (SEQ ID NO:41); (h) GCGCGC (SEQ ID NO:42); (i) TCGCGA (SEQ ID NO:43); (j) ACGATCGT (SEQ ID NO:44); (k) CGACGATCGTCG (SEQ ID NO:45); (l) CGACGAC-GATCGTCGTCG (SEQ ID NO:46); (m) GACGATCGTC (SEQ ID NO:28), (n) CGACGACGATCGTCGTCG (SEQ ID NO:47); (o) AACGTT (SEQ ID NO:48); (p) CAACGTTG (SEQ ID NO:49); (q) ACAACGTTGT (SEQ ID NO:50); (r) AACAACGTTGTT (SEQ ID NO:51); and (s) CAA-CAACGTTGTTG (SEQ ID NO:52). In a further preferred embodiment said ISS-NA is a A-type CpG comprising a palindromic sequence, wherein said palindromic sequence is GACGATCGTC (SEQ ID NO:28).

In a preferred embodiment, said palindromic sequence is flanked at its 3'-terminus and at its 5'-terminus by guanosine entities. In a further preferred embodiment said palindromic sequence is flanked at its 5'-terminus by at least 3 and at most 25 guanosine entities, wherein said palindromic sequence is flanked at its 3'-terminus by at least 3 and at most 25 guanosine entities. In a further preferred embodiment said palindromic sequence is flanked at its 5'-terminus by at least 3 and at most 15, preferably at most 10, guanosine entities, wherein said palindromic sequence is flanked at its 3'-terminus by at least 3 and at most 15, preferably at most 10 guanosine entities. In another preferred embodiment, the palindromic sequence is flanked at its 5'-terminus and at its 3'-terminus by at least 3 and at most 15, preferably at most 10, guanosine entities. In a further preferred embodiment, the palindromic sequence is flanked at its 5'-terminus by at least 3 and at most 15, preferably at most 10, guanosine entities, and wherein said palindromic sequence is flanked at its 3'-terminus by at least 6 and at most 15, preferably at most 10, guanosine entities. In a further preferred embodiment, the palindromic sequence is flanked at its 5'-terminus by at least 5 and at most 10 guanosine entities, and wherein said palindromic sequence is flanked at its 3'-terminus by at least 5 and at most 10 guanosine entities. In a further preferred embodiment, the palindromic sequence, preferably SEQ ID NO:28, is flanked at its 3'-terminus by at least 10, preferably exactly 10, guanosine entities and at its 5'-terminus by at least 10, preferably exactly 10, guanosine entities. In a very preferred embodiment said ISS-NA is a A-type CpG comprising a palindromic sequence, wherein said palindromic sequence is flanked at its 5'-terminus by 3 to 10 guanosine entities, and wherein said palindromic sequence is flanked at its 3'-terminus by 3 to 10 guanosine entities. In a even more preferred embodiment said ISS-NA is a A-type CpG comprising a palindromic sequence, wherein said palindromic is SEQ ID NO:28, and wherein said palindromic sequence is flanked at its 5'-terminus by 3 to 10 guanosine entities, and wherein said palindromic sequence is flanked at its 3'-terminus by 3 to 10 guanosine entities. These immunostimulatory substances can be efficiently packaged into VLPs, wherein the packaging efficiency is typically decreasing with increasing number of flanking guanosine entities at the 5' and/or 3' terminus.

In a very preferred embodiment of the present invention, the unmethylated CpG-containing oligonucleotide comprises, or alternatively consists essentially of, or alternatively consists of the a sequence selected from the group consisting of (a) "G8-8" GGGGGGGG GACGATCGTC GGGGGGGG (SEQ ID NO:25); (b) "G9-9" GGGGGGGGG GAC-GATCGTC GGGGGGGGG (SEQ ID NO:26); or (c) "G10" GGGGGGGGGG GACGATCGTC GGGGGGGGGG (SEQ ID NO:27). The latter was previously found to be able to stimulate blood cells in vitro (Kuramoto E. et al., Japanese Journal Cancer Research 83, 1128-1131 (1992)).

In a specifically preferred embodiment the unmethylated CpG-containing oligonucleotide comprises, or alternatively consists essentially of, or alternatively consists of "G10" (SEQ ID NO:27), wherein preferably said G10 consists exclusively of phosphodiester bound nucleotides, wherein further preferably said G10 is aggregated G10 having a retention time relative to Qβ capsid standard under HPLC conditions as set forth in Example 2 of 80 to 120%, most preferably of 80 to 95%.

In a further specifically preferred embodiment the unmethylated CpG-containing oligonucleotide comprises, or alternatively consists essentially of, or alternatively consists of "G9-9" (SEQ ID NO:26). In a further specifically preferred embodiment the unmethylated CpG-containing oligonucleotide comprises, or alternatively consists essentially of, or alternatively consists of "G8-8" (SEQ ID NO:25).

In a further preferred embodiment said ISS-NA is an unmethylated CpG-containing oligonucleotide, wherein the CpG motif of said unmethylated CpG-containing oligonucleotide is part of a palindromic sequence, wherein said unmethylated CpG-containing oligonucleotide has a nucleic acid sequence selected from (a) "G3-6" GGG GACGATCGTC GGGGGG (SEQ ID NO:29); (b) "G4-6" GGGG GACGATCGTC GGGGGG (SEQ ID NO:30); (c) "G5-6" GGGGG GAC-GATCGTC GGGGGG (SEQ ID NO:31); (d) "G6-6" GGGGGG GACGATCGTC GGGGGG (SEQ ID NO:32); and (e) "G7-7" GGGGGGG GACGATCGTC GGGGGGG (SEQ ID NO:33); (f) "G8-8" GGGGGGGG GACGATCGTC GGGGGGGG (SEQ ID NO:25); (g) "G9-9" GGGGGGGGG GACGATCGTC GGGGGGGGG (SEQ ID NO:26); and (h) "G6" GGGGGG CGACGACGATCGTCGTCG GGGGGG (SEQ ID NO:34).

In a further preferred embodiment of the present invention the ISS-NA is an unmethylated CpG-containing oligonucleotide, wherein the CpG motif of said unmethylated CpG-containing oligonucleotide is part of a palindromic sequence, wherein said palindromic sequence is GACGATCGTC (SEQ ID NO:28), and wherein said palindromic sequence is flanked at its 5'-terminus of at least 4 and at most 9 guanosine entities and wherein said palindromic sequence is flanked at its 3'-terminus of at least 6 and at most 9 guanosine entities.

In another preferred embodiment of the present invention the immunostimulatory substance is an unmethylated CpG-containing oligonucleotide, wherein the CpG motif of said unmethylated CpG-containing oligonucleotide is part of a palindromic sequence, wherein said unmethylated CpG-containing oligonucleotide has a nucleic acid sequence selected from (a) "G4-6" GGGG GACGATCGTC GGGGGG (SEQ ID NO:30); (b) "G5-6" GGGGG GACGATCGTC GGGGGG (SEQ ID NO:31); (c) "G6-6" GGGGGG GAC-GATCGTC GGGGGG (SEQ ID NO:32); (d) "G7-7" GGGGGGG GACGATCGTC GGGGGGG (SEQ ID NO:33); (e) "G8-8" GGGGGGGG GACGATCGTC GGGGGGGG (SEQ ID NO:25); and (f) "G9-9" GGGGGGGGG GACGATCGTC GGGGGGGGG (SEQ ID NO:26).

In another preferred embodiment of the present invention the ISS-NA is an unmethylated CpG-containing oligonucleotide, wherein the CpG motif of said unmethylated CpG-containing oligonucleotide is part of a palindromic sequence, wherein said unmethylated CpG-containing oligonucleotide has a nucleic acid sequence selected from (a) "G4-6" GGGG GACGATCGTC GGGGGG (SEQ ID NO:30); (b) "G5-6" GGGGG GACGATCGTC GGGGGG (SEQ ID NO:31); (c) "G6-6" GGGGGG GACGATCGTC GGGGGG (SEQ ID NO:32); (d) "G7-7" GGGGGGG GACGATCGTC GGGGGGG (SEQ ID NO:33); (e) "G8-8" GGGGGGGG GACGATCGTC GGGGGGGG (SEQ ID NO:25); and (f) "G9-9" GGGGGGGGG GACGATCGTC GGGGGGGGG (SEQ ID NO:26).

In a further preferred embodiment of the present invention the ISS-NA is an unmethylated CpG-containing oligonucleotide, wherein the CpG motif of said unmethylated CpG-containing oligonucleotide is part of a palindromic sequence, wherein said palindromic sequence is GACGATCGTC (SEQ ID NO:28), and wherein said palindromic sequence is flanked at its 5'-terminus of at least 5 and at most 8 guanosine entities and wherein said palindromic sequence is flanked at its 3'-terminus of at least 6 and at most 8 guanosine entities.

The experimental data show that the ease of packaging said ISS-NA, preferably the guanosine flanked, palindromic and unmethylated CpG-containing oligonucleotides, wherein the palindromic sequence is GACGATCGTC (SEQ ID NO:28), and wherein the palindromic sequence is flanked at its 3'-terminus and at its 5'-terminus by less than 10 guanosine entities, into particles, preferably VLPs, increases if the palindromic sequences are flanked by fewer guanosine entities. However, decreasing the number of guanosine entities flanking the palindromic sequences leads to a decrease of stimulating blood cells in vitro. Thus, packagability is paid by decreased biological activity of the indicated inventive immunostimulatory substances. The preferred embodiments represent, thus, a compromise between packagability and biological activity.

In another preferred embodiment of the present invention the ISS-NA is an unmethylated CpG-containing oligonucleotide, wherein the CpG motif of said unmethylated CpG-containing oligonucleotide is part of a palindromic sequence, wherein said unmethylated CpG-containing oligonucleotide has a nucleic acid sequence selected from (a) "G5-6" GGGGG GACGATCGTC GGGGGG (SEQ ID NO:31); (b) "G6-6" GGGGGG GACGATCGTC GGGGGG (SEQ ID NO:32); (c) "G7-7" GGGGGGG GACGATCGTC GGGGGGG (SEQ ID NO:33); and (d) "G8-8" GGGGGGGG GACGATCGTC GGGGGGGG (SEQ ID NO:25).

In a very preferred embodiment of the present invention the ISS-NA is an unmethylated CpG-containing oligonucleotide, wherein the CpG motif of said unmethylated CpG-containing oligonucleotide is part of a palindromic sequence, wherein said unmethylated CpG containing oligonucleotide has the nucleic acid sequence of SEQ ID NO:25 (G8-8).

As mentioned above, the optimal sequence used to package into VLPs is a compromise between packagability and biological activity. Taking this into consideration, the G8-8 immunostimulatory substance is a further very preferred embodiment of the present invention since it is biologically highly active while it is still reasonably well packaged.

In a further preferred embodiment said ISS-NA is a unmethylated CpC containing oligonucleotide, wherein said unmethylated CpC containing oligonucleotide is capable of inducing the production of IFN-alpha in a cell, preferably in PBMCs, spleenocytes or human pDCs, and wherein further preferably said unmethylated CpC containing oligonucleotide is selected from: (a) T*C*G* T*C*G*T*T*T*T*G*T*C*G*T*T*T*T*G*T*C*G*T (2006-PS, SEQ ID NO: 76); (b) GGGGGACGAT CGTCGGGGGG (2216-PO, SEQ ID NO:77); (c) G*G*GGGACGATCGTC*G*G*G*G*G*G (2216-PO core, SEQ ID NO:77); (d) GGTGCATCGATGCAGGGGGG (D19-PO, SEQ ID NO:78); (e) G*G*TGCATCGATGCAG*G*G*G*G*G (D19-PO core, SEQ ID NO:78); (f) GGGGACGATCGTCGGGGGG (G3-6, SEQ ID NO:29); (g) GGGGGACGATCGTCGGGGGG (G4-6, SEQ ID NO:30); (h) GGGGGGACGATCGTCGGGGGG (G5-6, SEQ ID NO:31); (i) GGGGGGGAC-GATCGTCGGGGGG (G6-6, SEQ ID NO:32); (j) GGGGGGGGAC GATCGTCGGGGGGG (G7-7, SEQ ID NO:33); (k) GGGGGGGGGA CGATCGTCGG GGGGGG (G8-8, SEQ ID NO:25); (l) GGGGGGGGGGAC-GATCGTCGGGGGGGGG (G9-9, SEQ ID NO:26); (m) GGGGGGGGGGGACGATCGTCGGGGGGGGGG (G10, SEQ ID NO:27); and (n) GGGGGGGGGG GACGATCGTC GGGGGGGGGG GGGGGGGGGG GACGATCGTC GGGGGGGGGG (G102x, SEQ ID NO:79), wherein * indicates a phosphorothioate modification, while all other nucleotides are phosphodiester bound. In a more preferred embodiment said unmethylated CpG containing oligonucleotide is capable of inducing the production of IFN-alpha in human pDCs, wherein preferably said unmethylated CpG containing oligonucleotide is T*C*G*T*C*G* T*T*T*T*G*T*C*G*T*T*T*T*G*T*C*G*T (2006-PS, SEQ ID NO: 76), wherein * indicates a phosphorothioate modification, while all other nucleotides are phosphodiester bound. In a still more preferred embodiment said unmethylated CpG containing oligonucleotide is capable of inducing the production of IFN-alpha in PBMCs or spleen cells, wherein preferably said unmethylated CpG containing oligonucleotide is selected from the group consisting of: (a) GGGGGACGAT CGTCGGGGGG (2216-PO, SEQ ID NO:77); (b) G*G*GGGACGATCGTC*G*G*G*G*G*G (2216-PO core, SEQ ID NO:77); (c) GGTGCATCGATG-CAGGGGGG (D19-PO, SEQ ID NO:78); (d) G*G*TGCATCGATGCAG*G*G*G*G*G (D19-PO core, SEQ ID NO:78); (e) GGGGACGATCGTCGGGGGG (G3-6, SEQ ID NO:29); (f) GGGGGACGATCGTCGGGGGG (G4-6, SEQ ID NO:30); (g) GGGGGGACGATCGTCGGGGGG (G5-6, SEQ ID NO:31); (h) GGGGGGGAC-GATCGTCGGGGGG (G6-6, SEQ ID NO:32); (i) GGGGGGGGAC GATCGTCGGGGGGG (G7-7, SEQ ID NO:33); (j) GGGGGGGGGA CGATCGTCGG GGGGGG (G8-8, SEQ ID NO:25); (k) GGGGGGGGGAC-GATCGTCGGGGGGGGG (G9-9, SEQ ID NO:26); (l) GGGGGGGGGGGACGATCGTCGGGGGGGGGG (G10, SEQ ID NO:27); and (m) GGGGGGGGGG GACGATCGTC GGGGGGGGGG GGGGGGGGGG GACGATCGTC GGGGGGGGGG (G102x, SEQ ID NO:79), wherein * indicates a phosphorothioate modification, while all other nucleotides are phosphodiester bound. In a very preferred embodiment said unmethylated CpG containing oligonucleotide is GGGGGGGGGG GACGATCGTC GGGGGGGGGG GGGGGGGGGG GACGATCGTC GGGGGGGGGG (G102x, SEQ ID NO:79), wherein preferably all nucleotides are phosphodiester bound.

In a further preferred embodiment said ISS-NA is a C-type CpG, wherein preferably said C-type CpG comprises a palindromic sequence, wherein further preferably said palindromic sequence is selected from any one of the sequences depicted in SEQ ID NOs:53 to 60. In a further preferred embodiment said C-type CpG is SEQ ID NO:64 or SEQ ID NO:65, wherein preferably all nucleic acids of said C-type CpG are phosphorothioate bound. Further preferred C-type CpGs are selected from the group consisting of (a) TCpGTCGTTTTACGGCGCCGTG CCG (SEQ ID NO:64); (b) TCGTCGTTTT ACpGGCpGCCpGTGCCG (SEQ ID NO:64); (c) TCGTCGTTT TACpGGCGCCpGTGCCG (SEQ ID NO:64); and (d) TCGTCpGTTTT ACpGGCGC-CpGTGCCG (SEQ ID NO:64); wherein p indicates phosphodiester bounds while all other nucleotides are phosphorothioate bound. C-type CpGs selected from the group consisting of (a) TCGTCGTTTTCGGCGCGCGCCG (SEQ ID NO:66); (b) TCGTCGTTTTCGACGGCCGTCG (SEQ ID NO:67); (c) TCGTCGTTTTCCGGCGCGCCGG (SEQ ID NO:68); (d) TCGTCGTTTTCGGCGCGCGTCG (SEQ ID NO:69); (e) TCGGCGCGCGCCGTCGTCGTTT (SEQ ID NO:70); (f) TTGGCGCGCGCCGTCGTCGTTT (SEQ ID NO:71); (g) TCGTCGTTTTCGTCGGCCGCCG (SEQ ID NO:72); (h) TCGTCGTTTTCGGCTTTTGCCG (SEQ ID NO:73); (i) TCGTCGTTTTCGGCGTTTTTTT (SEQ ID NO:74); and (j) TCGTCGTTTTCGGCGGCCGCCG (SEQ ID NO:75) are potent inducers of IFN-alpha production (Vollmer et al. 2004, Eur. J. Immunol. 43:351-262, p. 253, see Table 1 therein) and are thus specifically preferred ISS-NA in the context of the invention.

One embodiment of the invention is a composition for use in a method of treating or preventing hypersensitivity in an animal, preferably a mammal, most preferably a human, the composition comprising a particle and an immunostimulatory nucleic acid, wherein said particle is packaged with said immunostimulatory nucleic acid, and wherein preferably said hypersensitivity is an allergy or a non-allergic hypersensitivity. The compositions and pharmaceutical compositions of the invention can be used in a therapeutic as well as in a prophylactic treatment.

In a preferred embodiment said hypersensitivity is selected from the group consisting of: (a) asthma, (b) rhinitis, (c) conjunctivitis, (d) rhinoconjuctivitis, (e) dermatitis, (f) urticaria, and (g) anaphylaxis.

In a further preferred embodiment said hypersensitivity is an allergy, wherein said allergy is preferably selected from IgE-mediated allergy and non IgE-mediated allergy. In a preferred embodiment said hypersensitivity is asthma, preferably IgE-mediated asthma, wherein said asthma can be intermittent or persistent asthma. In a very preferred embodiment said hypersensitivity is atopic asthma.

In a further preferred embodiment said hypersensitivity is dermatitis, preferably eczema, most preferably atopic eczema.

In a very preferred embodiment said hypersensitivity is an IgE mediated allergy (type I allergy), wherein preferably said IgE-mediated allergy is an IgE-mediated allergy against a naturally occurring allergen, i.e. an allergen occurring in a natural source such as pollen, animal hair, house dust, dust mite etc.

In a preferred embodiment, said allergy, preferably said IgE-mediated allergy, is selected from the group consisting of: (a) pollen allergy (hay fever), (b) house dust allergy, (c) food allergy, (d) drug allergy, (e) insect venom allergy, preferably bee venom allergy, and (f) animal allergy, preferably cat allergy.

In a further preferred embodiment said allergy, preferably said IgE-mediated allergy, is an allergy against an allergen occurring in a source selected from the group consisting of (a) pollen; (b) dust, preferably house dust; (c) dust mite; (d) fungi, preferably aspergillus; (e) mammalian epideris, (f) bird feather; (g) insects, preferably bee venom; (h) food, preferably strawberry, kiwi, peanut, or wheat protein; (i) mammalian dander, preferably cat dander; (j) saliva; (k) serum; and (l) urine. In a further preferred embodiment said allergy, preferably said IgE-mediated allergy, is an allergy against an allergen occurring in a source selected from the group consisting of: (a) trees, (b) grasses, (c) animal products, and (d) plant products. In a further preferred embodiment said allergy, preferably said IgE-mediated allergy, is an allergy against an antigen selected from the group consisting of (a) bee venom phospholipase A2; (b) ragweed pollen Amb a 1; (c) birch pollen Bet v I; (d) white faced hornet venom 5 Dol m V; (e) house dust mite Der p 1; (f) house dust mite Der f 2; (g) house dust mite DerP 2; (h) dust mite Lep d; (i) fungus allergen Alt a 1; (j) fungus allergen Asp f 1; (k) fungus allergen Asp f 16; and (l) peanut allergens.

In a further preferred embodiment said allergy, preferably said IgE-mediated allergy, is an allergy against cat allergen, preferably an allergy against FelD1 antigen.

In a further preferred embodiment said allergy, preferably said IgE-mediated allergy, is an allergy against dust mite, wherein preferably said dust mite is selected from: (a) *Dermatophagoides pteronyssinus*, (b) *D. farinae*, (c) *D. microceras*, (d) *Euroglyphus maynei*, (e) *Glycyphagus* sp., (f) *Gohieria fusca*, (g) *Blomia tropicalis*.

In a further preferred embodiment said allergy, preferably said IgE-mediated allergy, is pollen allergy (hay fever). In further preferred embodiment said allergy, preferably said IgE-mediated allergy, is house dust allergy, preferably IgE-mediated allergy against house dust mite allergens contained in house dust, wherein said house dust mite allergens are preferably selected from the group consisting of (a) Der p 1; (b) Der f 2; and (c) DerP 2.

The present invention, inter alia, relates to the finding that particles, preferably VLPs, can be packaged with ISS-NA, preferably with single stranded DNA oligonucleotides rich in non-methylated C and G (CpGs).

A preferred embodiment of the invention is therefore a composition for use in a method of treating or preventing hypersensitivity in an animal, preferably a mammal, most preferably a human, the composition comprising a VLP and an unmethylated CpG containing oligonucleotide, wherein said VLP is packaged with said unmethylated CpG containing oligonucleotide.

A further preferred embodiment of the invention is a composition for use in a method of treating or preventing allergy in a human, the composition comprising a VLP of an RNA bacteriophage and an unmethylated CpG containing oligonucleotide, wherein said VLP of an RNA bacteriophage is packaged with said unmethylated CpG containing oligonucleotide, and wherein preferably said unmethylated CpG-containing oligonucleotide is G10 (SEQ ID NO:27).

A very preferred embodiment of the invention is a composition for use in a method of treating or preventing allergy in a human, the composition comprising a VLP of RNA bacteriophage Qβ and unmethylated CpG containing oligonucleotide G10 (SEQ ID NO:27), wherein said VLP of RNA bacteriophage Qβ is packaged with said unmethylated CpG containing oligonucleotide G10.

Further embodiments of the invention are processes for the production of the compositions of the invention and methods for treating hypersensitivity using said compositions, wherein preferably said hypersensitivity is atopic asthma, type I allergy or atopic eczema.

The invention provides a process of producing a composition for use in a method of treating hypersensitivity in an animal, said composition comprising a VLP and an unmethylated CpG containing oligonucleotide, wherein said VLP is packaged with said unmethylated CpG-containing oligonucleotide, said process comprising the steps of (i) incubating said VLP (a) with said unmethylated CpG-containing oligonucleotide (b); (ii) adding RNase; and (iii) purifying said composition. In a preferred embodiment, said VLP is produced in a bacterial expression system. In another preferred embodiment, said RNase is RNase A.

In a further preferred embodiment, said process comprises the steps of (i) incubating said VLP with RNase; (ii) adding said unmethylated CpG-containing oligonucleotide; and (iii) purifying the composition. In a preferred embodiment, said VLP is produced in a bacterial expression system. In another preferred embodiment, said RNase is RNase A.

In a further preferred embodiment, said process comprising the steps of (i) disassembling said VLP; (ii) adding said unmethylated CpG-containing oligonucleotide; and (iii) reassembling said VLP. In a further embodiment said process further comprises the step of removing nucleic acids from the disassembled VLP. Alternatively, said process further comprises the step of removing nucleic acids of the at least partially disassembled VLP and/or purifying the composition after reassembly. In a preferred embodiment, said VLP is produced in a bacterial expression system. In a further preferred embodiment said VLP referred to in step (i) of said process is a VLP of an RNA bacteriophage, more preferably a VLP of an RNA bacteriophage selected from the group consisting of (a) bacteriophage Qβ, (b) bacteriophage AP205, (c) bacteriophage GA, and (d) bacteriophage fr. In a very preferred embodiment said VLP referred to in step (i) of said process is a VLP of a RNA bacteriophage, more preferably a VLP of RNA bacteriophages AP205 or Qβ, most preferably of Qβ.

In a further preferred embodiment said unmethylated CpG-containing oligonucleotide referred to in step (ii) of said process consists of 5 to 60 nucleotides, preferably of 20 to 40 nucleotides most preferably of about 30 nucleotides. In a very preferred embodiment said unmethylated CpG-containing oligonucleotide is an A-type CpG, preferably an A-type CpG comprising poly G motifs at the 5' and/or 3' ends. In a still more preferred embodiment said unmethylated CpG-containing oligonucleotide is selected from the group consisting of: (a) "G8-8" GGGGGGGG GACGATCGTC GGGGGGGG (SEQ ID NO:25); (b) "G9-9" GGGGGGGGG GACGATCGTC GGGGGGGGG (SEQ ID NO:26); or (c) "G10" GGGGGGGGGG GACGATCGTC GGGGGGGGGG (SEQ ID NO:27), most preferably SEQ ID NO:27.

In a further preferred embodiment said process comprises the steps of (i) incubating said VLP in a solution comprising metal ions capable of hydrolyzing the nucleic acids of said VLP; (ii) adding said unmethylated CpG-containing oligonucleotide; and (iii) purifying said composition, wherein preferably said metal ions of step (i) are selected from the group consisting of (a) zinc (Zn) ions; (b) copper (Cu) ions; (c) iron (Fe) ions; (d) any mixtures of at least one ion of (a), (b) and/or (c). In a preferred embodiment, said VLP is produced in a bacterial expression system.

In a further preferred embodiment said process comprises the steps of (i) incubating said VLP with solutions comprising metal ions capable of hydrolyzing the nucleic acids of said VLP; (ii) adding said unmethylated CpG-containing oligonucleotide; and (iii) purifying said composition, wherein preferably said metal ions of step (i) are selected from the group consisting of (a) zinc (Zn) ions; (b) copper (Cu) ions; (c) iron (Fe) ions; (d) magnesium (Mg) ions, and any mixtures of at least one ion of (a), (b), (c) and/or (d). In a preferred embodiment, said VLP is produced in a bacterial expression system.

In a further preferred embodiment said process comprises the steps of (i) incubating said VLP with a solution capable of destabilizing said VLP; (ii) purifying the coat protein from said solution; and (iii) reassembling said VLP in the presence of unmethylated CpG-containing oligonucleotide, wherein preferably said solution capable of destabilizing said VLP comprises magnesium chloride, wherein further preferably the concentration of said magnesium chloride is 0.2 to 1.5 M, more preferably 0.4 to 1 M, most preferably about 0.7 M; and wherein still further preferably said VLP is a VLP of bacteriophage Qβ. In a very preferred embodiment said process comprises the steps of (i) incubating said VLP with a solution capable of destabilizing said VLP; (ii) purifying the coat protein from said solution; and (iii) reassembling said VLP in the presence of unmethylated CpG-containing oligonucleotide, wherein preferably said solution capable of destabilizing said VLP comprises magnesium chloride, wherein further preferably the concentration of said magnesium chloride is 0.2 to 1.5 M, more preferably 0.4 to 1 M, most preferably about 0.7 M; and wherein still further preferably said VLP is a VLP of bacteriophage Qβ; and wherein still further preferably said unmethylated CpG-containing oligonucleotide is G10 (SEQ ID NO:27), most preferably said unmethylated CpG-containing oligonucleotide is aggregated G10 having a retention time relative to Qβ capsid standard under HPLC conditions as set forth in Example 2 of 80 to 120%, most preferably of 80 to 95%.

In a further preferred embodiment said process comprises the steps of (i) incubating said VLP under alkaline conditions, preferably in the presence of NaOH, most preferably in the presence of about 25 mM NaOH; (ii) adding said unmethylated CpG-containing oligonucleotide; and (iii) purifying said composition.

It was found that the efficiency of said reassembling of said VLP can be improved and also that the stability of the reassembled VLP can be improved, by subjecting the unmethylated CpG-containing oligonucleotide to conditions supporting the formation of oligonucleotide aggregates prior to adding the oligonucleotide to the disassembled VLP. Conditions controlling the aggregation state of oligonucleotides have been described in Guschlbauer W., Journal of Biomolecular Structure & Dynamics, ISSN 0739-1102, Volume 8, Issue Number 3 (1990). Title: Four-Stranded Nucleic Acid Structures 25 Years. The aggregation of oligonucleotides is, for example, influenced by the ionic conditions, the concentration of the oligonucleotide, the pH, the temperature conditions and by the incubation time. Furthermore, it was found that aggregation of the oligonucleotide is particularly advantages for A-type oligonucleotides comprising poly G motifs at their 5' and/or 3' ends, most preferably for G10 (SEQ ID NO:27). Preferred conditions for the aggregation of unmethylated CpG-containing oligonucleotides are exemplified in Example 2. The optimal aggregation conditions may vary between different unmethylated CpG-containing oligonucleotides and even between different batches of the same unmethylated CpG-containing oligonucleotide. The actual aggregation state of an unmethylated CpG-containing oligonucleotide can be assessed by HPLC, preferably under conditions as set forth in Example 2.

Thus, in a further embodiment the invention provides a process comprising the steps of (i) disassembling said VLP; (ii) adding said unmethylated CpG-containing oligonucleotide; and (iii) reassembling said VLP, wherein prior to said adding of said unmethylated CpG-containing oligonucleotide said process comprises the additional step of incubating said unmethylated CpG-containing oligonucleotide under conditions supporting the formation of oligonucleotide aggregates. In a preferred embodiment said incubating is performed at a temperature of 70 to 100° C., preferably at about 85° C., preferably in the presence of sodium ions. In a still more preferred embodiment said incubating is performed at a concentration of said unmethylated CpG-containing oligonucleotide of 100 to 250 μm, preferably about 175 μm, in the presence of 200 to 500 mM sodium ions, preferably in the presence of about 250 mM sodium ions, preferably at 85° C. for about 10 min, wherein further preferably said unmethylated CpG-containing oligonucleotide comprises poly G motifs at their 5' and/or 3' ends. In a still more preferred embodiment said unmethylated CpG-containing oligonucleotide is selected from the group consisting of: (a) "G8-8" GGGGGGGG GACGATCGTC GGGGGGGG (SEQ ID NO:25); (b) "G9-9" GGGGGGGGG GACGATCGTC GGGGGGGGG (SEQ ID NO:26); or (c) "G10" GGGGGGGGGG GACGATCGTC GGGGGGGGGG (SEQ ID NO:27), most preferably said unmethylated CpG-containing oligonucleotide is G10 (SEQ ID NO:27). In a further preferred embodiment said conditions supporting the formation of oligonucleotide aggregates are chosen in such a way that aggregated unmethylated CpG containing oligonucleotide, preferably aggregated G10 (SEQ ID NO:27) is obtained, wherein said aggregated unmethylated CpG containing oligonucleotide, preferably said aggregated G10 (SEQ ID NO:27) shows a retention time relative to Qβ capsid standard under HPLC conditions as set forth in Example 2 of 80 to 120%, most preferably of 80 to 95%.

The invention further provides a process of producing a composition for use in a method of treating hypersensitivity in an animal, said composition comprising (a) a virus-like particle, a VLP of bacteriophage Qβ; and (b) an unmethylated CpG-containing oligonucleotide; wherein said virus-like particle (a) is packaged with said unmethylated CpG-containing oligonucleotide (b), said process comprising the steps of (i) incubating said VLP with a solution capable of destabilizing said VLP; (ii) purifying the coat protein from said solution; and (iii) reassembling said coat protein to a VLP in the presence of unmethylated CpG-containing oligonucleotide and an oxidizing agent. In a preferred embodiment, said solution capable of destabilizing said VLP comprises magnesium chloride and a reducing agent, wherein preferably the concentration of said magnesium chloride is 0.2 to 1.5 M, more preferably 0.4 to 1 M, most preferably about 0.7 M; and wherein further preferably said reducing agent is DTT, and wherein still further preferably the concentration of said DTT is 1 to 100 mM, preferably 2 to 15 mM, more preferably about 10 mM and most preferably about 10 mM. In a further preferred embodiment said oxidizing agent is $H_2O_2$, wherein further preferably the concentration of said $H_2O_2$ is 1 to 50 mM, preferably 1 to 10 mM, most preferably about 7 mM. In a further preferred embodiment said reassembling of said coat protein to a VLP is performed in the presence of salt, wherein preferably said salt is NaCl, and wherein further preferably the concentration of said salt, preferably of said NaCl is 100 mM to 1 M, most preferably 100 mM to 500 mM, most preferably about 250 mM. In a further preferred embodiment, prior to said reassembling said coat protein to a VLP, said purified coat protein is incubated in a solution comprising salt, reducing agent and unmethylated CpG-containing oligonucleotide, wherein preferably (i) said salt is NaCl, and wherein further preferably the concentration of said salt, preferably of said NaCl is 100 mM to 1 M, most preferably 100 mM to 500 mM, most preferably about 250 mM; (ii) the concentration of said urea is 100 mM to 7 M, more preferably 500 mM to 2 M, most more preferably about 1 M; and (iii) said reducing agent ist DTT, wherein preferably the concentration of said DTT is 1 to 10 mM, preferably 1 to 5 mM, most preferably 2.5 mM. In a further preferred embodiment said unmethylated CpG-containing oligonucleotide is G10 (SEQ ID NO:27), wherein most preferably said unmethylated CpG-containing oligonucleotide is aggregated G10 having a retention time relative to Qβ capsid standard under HPLC conditions as set forth in Example 2 of 80 to 120%, most preferably of 80 to 95%.

The invention further provides compositions for use in a method of treating hypersensitivity in an animal, wherein said compositions are obtainable by any one of the processes disclosed herein.

It is apparent for the artisan that the processes for the production of a composition of the invention as described above can also be performed using a virus particle instead of said VLP, wherein said virus particle preferably is a virus particle of a bacteriophage, preferably of a RNA bacteriophage.

In particular, the invention provides compositions for use in a method of treating hypersensitivity in an animal, wherein said compositions are obtainable by a process comprising the steps of (i) incubating a VLP with unmethylated CpG-containing oligonucleotides; (ii) adding RNase; and (iii) purifying said composition. In a preferred embodiment, said VLP is produced in a bacterial expression system. In another preferred embodiment, said RNase is RNase A.

The invention further provides compositions for use in a method of treating hypersensitivity in an animal, wherein said compositions are obtainable by a process comprising the steps of (i) incubating a VLP with RNase; (ii) adding unmethylated CpG-containing oligonucleotides; and (iii) purifying the composition. In a preferred embodiment, said VLP is produced in a bacterial expression system. In another preferred embodiment, said RNase is RNase A.

The invention further provides compositions for use in a method of treating hypersensitivity in an animal, wherein said compositions are obtainable by a process comprising the steps of (i) disassembling a VLP; (ii) adding unmethylated CpG-containing oligonucleotides; and (iii) reassembling said VLP. In a further embodiment said process further comprises the step of removing nucleic acids from the disassembled VLP. Alternatively, said process further comprises the step of removing nucleic acids of the at least partially disassembled VLP and/or purifying the composition after reassembly. In a preferred embodiment, said VLP is produced in a bacterial expression system.

The invention further provides compositions for use in a method of treating hypersensitivity in an animal, wherein said compositions are obtainable by a process comprising the steps of (i) incubating a VLP with solutions comprising metal ions capable of hydrolyzing the nucleic acids of said VLP; (ii) adding unmethylated CpG-containing oligonucleotides; and (iii) purifying said composition, wherein preferably said metal ions of step (i) are selected from the group consisting of (a) zinc (Zn) ions; (b) copper (Cu) ions; (c) iron (Fe) ions; (d) any mixtures of at least one ion of (a), (b) and/or (c). In a preferred embodiment, said VLP is produced in a bacterial expression system.

The invention further provides compositions for use in a method of treating hypersensitivity in an animal, wherein said compositions are obtainable by a process comprising the steps of (i) incubating a VLP with solutions comprising metal ions capable of hydrolyzing the nucleic acids of said VLP; (ii) adding unmethylated CpG-containing oligonucleotides; and (iii) purifying said composition, wherein preferably said metal ions of step (i) are selected from the group consisting of (a) zinc (Zn) ions; (b) copper (Cu) ions; (c) iron (Fe) ions; (d) magnesium (Mg) ions; and (e) any mixtures of at least one ion of (a), (b), (c) and/or (d). In a preferred embodiment, said VLP is produced in a bacterial expression system.

The invention further provides compositions for use in a method of treating hypersensitivity in an animal, wherein said compositions are obtainable by a process comprising the steps of (i) incubating said VLP with a solution capable of destabilizing said VLP, wherein preferably said VLP is a VLP of bacteriophage Qβ; (ii) purifying the coat protein from said solution; and (iii) reassembling said coat protein to a VLP in the presence of unmethylated CpG-containing oligonucleotide and an oxidizing agent. In a preferred embodiment, said solution capable of destabilizing said VLP comprises magnesium chloride and a reducing agent, wherein preferably the concentration of said magnesium chloride is 0.2 to 1.5 M, more preferably 0.4 to 1 M, most preferably about 0.7 M; and wherein further preferably said reducing agent is DTT, and wherein still further preferably the concentration of said DTT is 1 to 100 mM, preferably 2 to 15 mM, more preferably about 10 mM and most preferably about 10 mM. In a further preferred embodiment said oxidizing agent is $H_2O_2$, wherein further preferably the concentration of said $H_2O_2$ is 1 to 50 mM, preferably 1 to 10 mM, most preferably about 7 mM. In a further preferred embodiment said reassembling of said coat protein to a VLP is performed in the presence of salt, wherein preferably said salt is NaCl, and wherein further preferably the concentration of said salt, preferably of said NaCl is 100 mM to 1 M, most preferably 100 mM to 500 mM, most preferably about 250 mM. In a further preferred embodiment, prior to said reassembling said coat protein to a VLP, said purified coat protein is incubated in a solution comprising salt, reducing agent and unmethylated CpG-containing oligonucleotide, wherein preferably (i) said salt is NaCl, and wherein further preferably the concentration of said salt, preferably of said NaCl is 100 mM to 1 M, most preferably 100 mM to 500 mM, most preferably about 250 mM; (ii) the concentration of said urea is 100 mM to 7 M, more preferably 500 mM to 2 M, most more preferably about 1 M; and (iii) said reducing agent ist DTT, wherein preferably the concentration of said DTT is 1 to 10 mM, preferably 1 to 5 mM, most preferably 2.5 mM. In a further preferred embodiment said unmethylated CpG-containing oligonucleotide is G10 (SEQ ID NO:27), wherein most preferably said unmethylated CpG-containing oligonucleotide is aggregated G10 having a retention time relative to Qβ capsid standard under HPLC conditions as set forth in Example 2 of 80 to 120%, most preferably of 80 to 95%.

The invention further provides compositions for use in a method of treating hypersensitivity in an animal, wherein said compositions are obtainable by a process comprising the steps of (i) incubating said VLP under alkaline conditions, preferably in the presence of NaOH, most preferably in the presence of about 25 mM NaOH; (ii) adding said unmethylated CpG-containing oligonucleotide; and (iii) purifying said composition.

The invention further provides compositions for use as a medicament, wherein said compositions are obtainable by any one of the processes of the invention, said composition comprising a particle and an ISS-NA, wherein said particle is packaged with said unmethylated CpG-containing oligonucleotide, wherein said particle preferably is a VLP of a RNA bacteriophage, most preferably of RNA bacteriophage Qβ, and wherein preferably said ISS-NA is an unmethylated CpG-containing oligonucleotide, wherein said unmethylated CpG-containing oligonucleotide preferably exclusively consists of phosphodiester bound nucleotides, wherein further preferably said unmethylated CpG-containing oligonucleotide comprises the palindromic sequence of SEQ ID NO:28, wherein most preferably said unmethylated CpG-containing oligonucleotide is G10 (SEQ ID NO:27).

The invention further provides compositions for use in a method of treating hypersensitivity, preferably allergy, most preferably atopic asthma, atopic eczema, pollen allergy, house dust or dust mite allergy, in an animal, wherein said compositions are obtainable by any one of the processes of the invention, said composition comprising (a) a VLP; and (b) an unmethylated CpG-containing oligonucleotide; wherein said virus-like particle (a) is packaged with said unmethylated CpG-containing oligonucleotide (b), wherein said VLP preferably is a VLP of an RNA bacteriophage, most preferably of RNA bacteriophage Qβ, and wherein said unmethylated CpG-containing oligonucleotide preferably exclusively consists of phosphodiester bound nucleotides, wherein further preferably said unmethylated CpG-containing oligonucleotide comprises the palindromic sequence of SEQ ID NO:28, wherein most preferably said unmethylated CpG-containing oligonucleotide is G10 (SEQ ID NO:27).

The invention further provides compositions for use in a method of treating hypersensitivity, preferably allergy, most preferably atopic asthma, atopic eczema, pollen allergy, house dust or dust mite allergy, in an animal, wherein said compositions are obtainable by any one of the processes of the invention, said composition comprising a VLP and an unmethylated CpG-containing oligonucleotide, wherein said virus-like particle is packaged with said unmethylated CpG-containing oligonucleotide, wherein said VLP preferably is a VLP of a RNA bacteriophage, most preferably of RNA bacteriophage Qβ, and wherein said unmethylated CpG-containing oligonucleotide preferably exclusively consists of phosphodiester bound nucleotides, wherein further preferably said unmethylated CpG-containing oligonucleotide comprises the palindromic sequence of SEQ ID NO:28, wherein most preferably said unmethylated CpG-containing oligonucleotide is G10 (SEQ ID NO:27).

The invention also provides pharmaceutical compositions for use in a method of treating preventing and/or attenuating hypersensitivity in an animal. Pharmaceutical compositions of the invention comprise, or alternatively consist of, an immunologically effective amount of the inventive compositions together with a pharmaceutically acceptable diluent, carrier or excipient. The pharmaceutical composition may also optionally comprise an adjuvant.

In a further embodiment said pharmaceutical composition comprises a slow release formulation of the composition of the invention. Slow release formulations are well known in the art. Typical and preferred slow release formulations are compositions of the invention formulated in microparticles, emulsions, and gels.

In one embodiment, the invention provides pharmaceutical compositions for treating or preventing atopic eczema. In another embodiment, the invention provides pharmaceutical compositions for treating or preventing asthma. In another embodiment, the invention provides pharmaceutical compositions for treating or preventing IgE-mediates allergy (type I allergy), preferably pollen allergy, house dust or dust mite allergy.

As would be understood by one of ordinary skill in the art, when compositions of the invention are administered to an animal, they can be in a composition which contains salts, buffers, adjuvants or other substances which are desirable for improving the efficacy of the composition. Examples of materials suitable for use in preparing pharmaceutical compositions are provided in numerous sources including REMINGTON'S PHARMACEUTICAL SCIENCES (Osol, A, ed., Mack Publishing Co., (1990)).

Various adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts (Alum), MF-59, OM-174, OM-197, OM-294, isomatrix, and virosomal adjuvant technology. The adjuvants can also comprise a mixture of these substances.

Immunologically active saponin fractions having adjuvant activity derived from the bark of the South American tree Quillaja Saponaria Molina are known in the art. For example QS21, also known as QA21, is an Hplc purified fraction from the Quillaja Saponaria Molina tree and it's method of its production is disclosed (as QA21) in U.S. Pat. No. 5,057,540. Quillaja saponin has also been disclosed as an adjuvant by Scott et al, Int. Archs. Allergy Appl. Immun., 1985, 77, 409. Monophoryl lipid A and derivatives thereof are known in the art. A preferred derivative is 3 de-o-acylated monophosphoryl lipid A, and is known from British Patent No. 2220211. Further preferred adjuvants are described in WO00/00462, the disclosure of which is herein incorporated by reference.

Compositions of the invention are said to be "pharmacologically acceptable" if their administration can be tolerated by a recipient individual. Further, the compositions of the invention will be administered in a "therapeutically effective amount" (i.e., an amount that produces a desired physiological effect).

The compositions of the present invention can be administered by various methods known in the art. The particular mode selected will depend of course, upon the particular composition selected, the severity of the condition being treated and the dosage required for therapeutic efficacy. The methods of the invention, generally speaking, can be practiced using any mode of administration that is medically acceptable, meaning any mode that produces effective levels of the active compounds without causing clinically unacceptable adverse effects. Such modes of administration include oral, rectal, parenteral, intracisternal, intravaginal, intraperitoneal, topical (as by powders, ointments, drops or transdermal patch), bucal, or as an oral or nasal spray. The term "parenteral" as used herein refers to modes of administration which include intravenous, intramuscular, intraperitoneal, intrasternal, subcutaneous and intraarticular injection and infusion. The composition of the invention can also be injected directly in a lymph node. Compositions comprising microparticles are preferably injected subcutaneously, intravenously, intradermaly, intraperitoneally, administered intranasally, orally, transdermally or inhaled.

Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Dosage levels depend on the mode of administration, the nature of the subject, and the quality of the carrier/adjuvant formulation. Typical amounts are in the range of about 0.001 μg to about 20 mg per subject. Preferred amounts are 50 μg to 1000 μg, more preferably 100 μg to 600 μg, and most preferably about 300 μg of a composition of the invention per single administration. Further preferred amounts are at least about 50 μg to about 500 μg per subject, most preferably 300 μg per subject. Multiple administration to treat the subject is preferred, and protocols are those standard in the art adapted to the subject in question. The administration of said composition or said pharmaceutical composition is repeated several times, preferably at least three to 10 times, most preferably three to five times, in weekly, monthly or yearly intervals, preferably in intervals of about 1 week to about 1 month, more preferably in biweekly intervals, most preferably in weekly intervals. In a very preferred embodiment the administration of said composition or said pharmaceutical composition is repeated 6 times in weekly intervals, wherein preferably each time 50 μg to about 500 μg, most preferably about 300 μg are administered.

The compositions of the invention can conveniently be presented in unit dosage form and can be prepared by any of the methods well-known in the art of pharmacy. Methods include the step of bringing the compositions of the invention into association with a carrier which constitutes one or more accessory ingredients. In general, the compositions are prepared by uniformly and intimately bringing the compositions of the invention into association with a liquid carrier, a finely divided solid carrier, or both, and then, if necessary, shaping the product.

Compositions suitable for oral administration can be presented as discrete units, such as capsules, tablets or lozenges, each containing a predetermined amount of the compositions of the invention. Other compositions include suspensions in aqueous liquids or non-aqueous liquids such as a syrup, an elixir or an emulsion.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art.

A further aspect of the invention is a method of treating hypersensitivity, preferably atopic eczema, atopic asthma or IgE-mediated allergy (type I allergy), in an animal, preferably a mammal, most preferably a human, said method comprising introducing into said animal (i) a composition comprising a particle and an ISS-NA, wherein said particle is packaged with said ISS-NA or (ii) a pharmaceutical composition comprising an immunologically effective amount of the composition (i) together with a pharmaceutically acceptable diluent, wherein preferably said pharmaceutical composition (ii) further comprises an adjuvant. In a preferred embodiment said composition (i) or said pharmaceutical composition (ii) is introduced into said animal subcutaneously, intramuscularly, intravenously, intranasally or directly into the lymph node. In a further preferred embodiment said introducing into said animal of the composition (i) or the pharmaceutical composition (ii) is repeated at least twice, preferably at least three times, most preferably at least four times in intervals of 1 week to 3 months, preferably 1 week. In a still further preferred embodiment said introducing into said animal of the composition (i) or the pharmaceutical composition (ii) is repeated 6 times in intervals of about 1 week, wherein preferably each time about 300 μg of said composition (i) are introduced.

A preferred embodiment of the invention is a method of treating allergy in an animal, said method comprising introducing into said animal a composition comprising (a) a VLP; and (b) an unmethylated CpG-containing oligonucleotide; wherein said virus-like particle (a) is packaged with said unmethylated CpG-containing oligonucleotide (b), and wherein said allergy preferably is atopic eczema, asthma or type I allergy, preferably pollen allergy (hay fever), wherein further said VLP is a VLP of a RNA bacteriophage, preferably of RNA bacteriophage Qβ, and wherein preferably said unmethylated CpG-containing oligonucleotide (b) consists exclusively of phosphodiester bound nucleotides, most preferably of SEQ ID NO:27.

The effectiveness of a treatment of the invention with respect to a particular disease can be assessed by assessing the severity of the symptoms associated with said disease using standard methods known in the art. Generally symptoms are scored directly before the beginning of the treatment, i.e. before the first vaccination, in intervals during the treatment and 1 to 3 months after the last treatment. Symptoms of atopic dermatitis can, for example be scored as described in N. Engl. J. Med 1997, 337:816-21. Symptoms of asthma can be scored by various methods including questionnaires described in Juniper et al., Health Qual. Life Outcomes, 2005 Sep. 16, 3:58, and combinations of questionnaires and spirometric measurements of pulmonary functions as described in N. Engl. J. Med 2000, 343:1054-63. These references are incorporated herein by reference. Pollen allergy can, inter alia, be assessed using a nasal provocation test, other allergies, e.g. house dust or dust mite allergy, can be assessed using a conjunctival provocation procedure or a skin prick test. These testing methods are described in detail in the Example section.

A further aspect of the invention is the use of a composition of the invention or of a pharmaceutical composition of the invention for the manufacture of a pharmaceutical for the treatment of hypersensitivity in an animal, wherein said hypersensitivity preferably is an allergy, wherein further preferably said allergy is selected from the group consisting of: (a) atopic eczema; (b) atopic asthma; and (c) IgE-mediated allergy (type I allergy), preferably pollen allergy (hay fever) or house dust allergy.

A preferred embodiment of the invention is the use of a composition comprising a particle and an ISS-NA, wherein said particle is packaged with said ISS-NA, for the manufacture of a pharmaceutical for the treatment of hypersensitivity in an animal, wherein hypersensitivity is preferably selected from the group consisting of: (a) atopic eczema; (b) atopic asthma; and (c) IgE-mediated allergy (type I allergy), preferably pollen allergy (hay fever), and wherein further preferably said particle is a VLP of a RNA bacteriophage, preferably of RNA bacteriophage Qβ, and wherein preferably said ISS-NA is an unmethylated CpG-containing oligonucleotide, wherein preferably said unmethylated CpG-containing oligonucleotide consists exclusively of phosphodiester bound nucleotides, and wherein more preferably said unmethylated CpG-containing oligonucleotide comprises the palindromic sequence of SEQ ID NO:28, most preferably said unmethylated CpG-containing oligonucleotide is G10 (SEQ ID NO:27).

In all aspects and embodiments, in particular in all compositions, methods, processes and uses, of the invention wherein said particle is a VLP of bacteriophage Qβ, said VLP preferably essentially consists of coat proteins having the amino acid sequence of SEQ ID NO:3. In all aspects and embodiments, in particular in all compositions, methods, processes and uses, of the invention wherein said ISS-NA is the unmethylated CpG-containing oligonucleotide G10 (SEQ ID NO:27), said unmethylated CpG-containing oligonucleotide preferably consists exclusively of phosphodiester bound nucleotides.

In all aspects and embodiments, in particular in all compositions, methods, processes and uses, of the invention wherein said particle is a VLP of bacteriophage Qβ and wherein said ISS-NA is the unmethylated CpG-containing oligonucleotide G10 (SEQ ID NO:27), said VLP of bacteriophage Qβ preferably essentially consists of coat proteins having the amino acid sequence of SEQ ID NO:3, and, further preferably, said unmethylated CpG-containing oligonucleotide consists exclusively of phosphodiester bound nucleotides.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

If not indicated otherwise, the VLPs of bacteriophage Qβ used in the Examples are/were VLPs essentially consisting of coat proteins having the amino acid sequence of SEQ ID NO:3. Furthermore, if not indicated otherwise, the unmethylated CpG containing oligonucleotide G10 (SEQ ID NO:27) used in the Examples is/was unmethylated CpG containing oligonucleotide G10 (SEQ ID NO:27) consisting exclusively of phosphodiester bound nucleotides.

All patents, patent applications and publications referred to herein are expressly incorporated by reference in their entirety.

EXAMPLES

Example 1

Example for Packaging CpG-DNA 1668 into AP205 VLP and Qβ VLP

Bacterial produced VLPs contain high levels of single stranded RNA, randomly packaged into the VLP during self assembly, which can be visualized on a 1% agarose gel stained with ethidium bromide or Coomassie blue for the detection of RNA/DNA or protein. The RNA has to be removed from the VLP before packaging with CpG DNA by digestion with RNase A. Therefore 1 mg/ml VLP in 20 mM HEPES, pH 7.4 was incubated with 300 µg RNase A for 3 h at 37° C. For removal of RNAse A (and hydrolysed RNA) the VLP were dialysed for 2-3 days against 20 mM HEPES using a 100'000 or 300'000 MW cut off membrane. Emptied VLPs were then supplemented with CpG-oligonucleotide 1668-CpG (TCC ATG ACG TTC CTG AAT AAT, SEQ ID NO:80) which was protected by a phopshorothioate backbone (1 ml VLP (1 mg/ml in 20 mM HEPES, pH 7.4, 2 mM MgCl$_2$) with 100 nmol CpG) allowing free diffusion into the particle during incubation for 3 hrs at 37° C. The CpG-oligonucleotide containing VLPs were purified from unbound CpG-oligonucleotide via tangential flow filtration using a 300'000 MW cut off membrane. A 1% agarose gel stained with ethidium bromide or Coomassie blue visualized the removal of RNA followed by packaging of CpG into VLP and proves the removal of unbound CpG.

Example 2

Disaggregation and Aggregation of Oligonucleotide G10 (SEQ ID NO:27) and Analysis of Aggregation State Disaggregation (10.0 ml scale, 260 μM G10, 25 mM NaOH, 50° C., 70 min): 45.91 mg G10 were weighed into a 15 ml tube. The powder was dissolved in 11.0 ml purified water (c=325.3 μM; determined with the photometer). 8.0 ml of the oligonucleotide solution were mixed with 250 μl 1 M NaOH and 1.75 ml purified water in a 15 ml tube (260 μM G10, 25 mM NaOH). The mixture was disaggregated for 70 minutes at 50° C. in a water bath. After cooling the solution on ice, the pH was adjusted with 0.5 M HCl to pH 5.31; 540 μl 0.5 M HCl and 5 μl 1 M NaOH were added.

Aggregation (10.0 ml scale, 175 μM G10, 250 mM NaOH, 85° C., 9-24 min): 7.1 ml disaggregated G10 solution, 2.13 ml purified water and 770 μl 3 M NaCl were mixed in a 15 ml tube (175 μM oligo, 250 mM Na$^+$). The mixture was incubated for 9 minutes at 85° C. in a water bath. The solution was cooled down in an ice/water bath and stored on ice until use. Aggregated oligonucleotide solutions should be used within 3 hours after preparation.

Quantification of G10: G10 was quantified by UV absorption at 260 nm corrected by the absorption at 340 nm. 1 $A_{260-340}$=27.8 μg/ml.

Analysis of aggregation state: The aggregation state of G10 was analysed by HPLC using the following conditions using Qβ capsid as standard.

Column: TSKgel 5000 PWXL 7.8 mm*30.0 cm
(Lot: 5PWX06GNMH3304, Art: 08023, Tosoh Bioscience)
Eluent: PBS pH 7.2
Injection volume: 40.0 μl
Flow rate: 0.8 ml/min
Gradient: Isocratic
Run time: 20 min
Wavelength: 215, 260 and 280 nm, data evaluation at 260 nm
Column oven temp.: 25° C.
Autosampler temp.: 8° C.

The relative retention time X % of G10 was calculated as follows: X %=peak start time [min]/Retention time (Qβ capsid) [min]×100%. Disaggregated G10 showed a relative retention time of 138% (136.9-140.3%; n=5). G10 preparations which have not undergone the disaggregation/aggregation treatment described above show a relative retention time in the same range. After disaggregation and aggregation, the relative retention time of G10 was found to be 118%.

Example 3

Packaging of Qβ VLPs with G10 by Disassembly/Reassembly

Disassembly of Qβ VLPs: 45 mg Qβ VLP (2.5 mg/ml, as determined by Bradford analysis) in PBS (20 mM Phosphate, 150 mM NaCl, pH 7.5), was reduced with 10 mM DTT for 15 min at RT under stirring conditions. Then, magnesium chloride was added to 0.7 M final concentration and the incubation was continued for 15 min at RT under stirring conditions, leading to precipitation of the encapsulated host cell RNA and concomitant disintegration of the VLPs. The solution was centrifuged 10 min at 4000 rpm at 4° C. (Eppendorf 5810 R, in fixed angle rotor A-4-62 used in all following steps) in order to remove the precipitated RNA from the solution. The supernatant, containing the released, dimeric Qβ coat protein, was used for the chromatographic purification steps.

Purification of Qβ coat protein by cation exchange chromatography and size exclusion chromatography: The supernatant of the disassembly reaction, containing dimeric coat protein, host cell proteins and residual host cell RNA, was loaded onto a SP-Sepharose FF column (xk16/20, 6 ml, Amersham Bioscience). The column was equilibrated with 20 mM sodium phosphate buffer pH 7 and the sample was diluted 1:15 in water to adjust a conductivity below 10 mS/cm in order to achieve proper binding of the coat protein to the column. The elution of the bound coat protein was accomplished by a step gradient to 20 mM sodium phosphate/500 mM sodium chloride and the protein was collected in a fraction volume of approx. 25 ml. The chromatography was carried out at RT with a flow rate of 5 ml/min during all steps and the absorbance was monitored at 260 nm and 280° nm. In a second step, the isolated Qβ coat protein (the eluted fraction from the cation exchange column) was loaded onto a Sephacryl S-100 HR column (xk26/60, 320 ml, Amersham Bioscience) equilibrated with 20 mM sodium phosphate/250 mM sodium chloride; pH 7.2. The chromatography was carried out at RT with a flow rate of 2.5 ml/min and the absorbance was monitored at 260 nm and 280 nm. Fractions of 5 ml were collected.

Characterization of purified Qβ coat protein by analytical size exclusion chromatography: A sample of purified Qβ coat protein was analyzed by analytical size exclusion chromatography (FIG. 1C) and compared to i) intact Qβ VLP (FIG. 1A), which had been purified from *E. coli* lysate and which was used as source material for the purification procedure, and ii) to the supernatant of the disassembly reaction (FIG. 1B). Efficient separation of RNA molecules from the coat protein is indicated by the absence of any RNA-like peak (typical ratio of A280/A260=0.5) in FIG. 1C and the presence of a unique protein-like peak (typical ratio of A280/A260=1.7).

Assembly of QβG10 by diafiltration: Purified coat protein (in 20 mM sodium phosphate pH 7.2, 250 mM NaCl) was mixed with water and stock solutions of urea, NaCl, DTT and aggregated G10 oligonucleotide (prepared essentially as described in Example 2). The volume of the mixture was 50 ml and the final concentrations of the components were 1 mg/ml coat protein, 1.0 M urea, 250 mM NaCl, 2.5 mM DTT and 0.24 mg/ml G10. The solution was then diafiltrated at room temperature against 300 ml of 20 mM sodium phosphate 250 mM NaCl pH 7.2, using a 30 kDa cut off cartridge (Pellicon XL, Millipore) and a cross flow rate of 10 ml/min and a permeate flow rate of 2.5 ml/min. $H_2O_2$ was added to 7 mM final concentration and the solution incubated for 1 h at RT in order to induce the formation of disulfide bonds. The solution was then diafiltrated against 500 ml of 20 mM sodium phosphate 150 mM NaCl pH 7.2, using a 300 kDa cut off cartridge (Pellicon XL, Millipore) and a cross flow rate of 10 ml/min and a permeate flow rate of 2.5 ml/min, in order to remove excess of $H_2O_2$ and non-packaged G10 oligonucleotides from the assembled QβG10 product.

Example 4

Analysis of QβG10 Packaging Product and Determination of Yield of the Packaging Process Characterization of packaged QβG10 VLP by analytical size exclusion chromatography: A sample of packaged QβG10 VLP was analyzed by analytical size exclusion chromatography (FIG. 2) and compared to intact Qβ VLP, which had been purified from *E. coli* lysate. The presence of correctly assembled VLP in the product was confirmed by a peak migrating at identical retention time as the peak representing native Qβ VLP. The observed peak for QβG10 VLP (FIG. 2D)

is dominated by the nucleic acid content of the VLP, because the absorption coefficient nucleic acids at 260 nm is more than 100-fold higher than the absorption coefficient of the coat protein. The ratio A260/A280 of purified QβG10 VLP was found to be 1.70 (1.65-1.76; n=5), which is characteristic for G10 (A260/A280=1.74), wherein the A260/A280 ratio of Qβ VLP was found to be 1.87 (1.85-1.90; n=10) which is characteristic for RNA.

Characterization of packaged QβG10 VLP by SDS-PAGE analysis: A sample of packaged Qβ G10 was analyzed by non-reducing SDS-PAGE (FIG. 3) and compared to intact Qβ VLP, which had been purified from E. coli lysate. The presence of correctly assembled VLP in the product was confirmed by the formation of bands of disulfide-linked pentameric and hexameric forms of the coat protein, similar to the intact Qβ VLPs, indicating the correct structural arrangement of the coat protein units in the in vitro assembled QβG10 VLP.

Quantification of packaged oligonucleotide G10: Samples of QβG10 VLP (0.25 mg/ml in PBS) were treated by 0.1 mM TCEP (15 min at RT) in order to reduce the disulfide bonds. NaCl was added to the reduced samples (1 M final concentration) and the mixtures were incubated for 15 min at 60° C. in order to precipitate the protein component. After centrifugation, the resulting supernatants were incubated for 5 min at 95° C., cooled on ice for 1 min and then the A260 value was measured. The concentration of oligonucleotide G10 in the supernatants was calculated according to the formula:

$$c(G10)(mg/ml) = A_{260} \times 1.12 \times 9600/344580, \text{ where:}$$

1.12=correction factor for the salt content in the sample
9600=molecular mass of oligonucleotide G10
344580=specific molar absorption coefficient of oligonucleotide G10.

Typically, the amount of packaged oligonucleotide G10 was 0.2 mg per mg of Qβ coat protein.

G10 content of QβG10 VLP and yield calculation for the packaging reaction: Aggregated G10 was packaged into Qβ VLP by assembly/reassembly of the VLP as described in Example 3. 953 mg G10 oligonucleotide were introduced for reassembly with 4000 mg purified Qβ dimer. The reaction yielded QβG10 comprising 20 μg G10 oligonucleotide per 100 μg protein (protein content determined by Bradford analysis or HPLC). The G10 yield of the packaging reaction was 63% at a protein yield of 75%.

Example 5

Packaging of AP205 and GA355 VLPs with G10 by Disassembly/Reassembly

Disassembly: 50-100 mg of AP205 or GA355 VLPs (as determined by Bradford analysis) in buffer A (5 mM NaPO₄ pH 6.8, 100 mM NaCl, 2 mM MgCl₂) were incubated at 30° C. for 16 hours with RNAse A (Sigma) and Benzonase (Novagen) at 1 mg/ml and 5 U/ml, respectively. In the case of AP205 VLP deoxidation of the internal disulfide bridges was performed preceding the addition of RNAse A and Benzonase by addition of 20 mM DTT followed by a 30 min incubation at 37° C. After addition of 1 M NaCl precipitation of the viral coat proteins was induced by 15 min incubation at 70° C. Precipitated coat proteins were sedimented by centrifugation for 10 min, 27,000 g at 4° C. The supernatant containing RNAse A, Benzonase and degraded nucleic acids was discarded. Pellets were resuspended in buffer B (20 mM NaPO₄ pH 7.2, 6 M urea) and incubated for 10 min at room temperature.

Purification of coat proteins by cation exchange chromatography: The solutions were clarified by centrifugation for 10 min, 27,000 g at 4° C. A negligible pellet was discarded. And the supernatant containing the disassembled coat proteins were applied on a SP Sepharose™ FF column (16/20, Amersham Biosciences) equilibrated with buffer B. The flow through was discarded. After an extensive wash with buffer B (15 CV) the column was adjusted with a linear gradient from buffer B to buffer C (20 mM NaPO₄ pH 7.2, 1 M urea) with a gradient length of 37.5 CV. During the loading, wash and elution the absorbance at 254 nm and 280 nm was monitored. Coat proteins were eluted as one fraction with buffer D (20 mM NaPO₄ pH 6.5, 1 M urea, 300 mM NaCl) and analyzed by LDS-PAGE followed by Coomassie staining. Eluted protein fractions were stored at 4° C. as "disassembled coat protein". Protein concentrations were determined by Bradford analysis.

Reassembly: Purified AP205 or GA355 coat protein with were used in a five fold excess (w/w) to G10 oligonucleotide. The coat proteins were mixed with the G10 oligonucleotide in a reassembly buffer containing 1 M urea and 2.5 mM DTT and incubated for one hour at room temperature. After incubation the reassembly mix was dialyzed for 24 hours against 5 liter PBS. The resulting suspension was centrifuged for 10 min, 27,000 g at 4° C. A negligible sediment was discarded. The supernatant contained the reassembled and packaged VLPs. Protein concentration was determined by Bradford analysis and the reassembled and packaged VLPs were concentrated with centrifugal filter devices (Amicon Ultra 15, 10K MWCO).

Purification of reassembled and packaged VLPs: Up to 25 mg total protein was loaded onto a Sepharose™ CL-4B (26/60, Amersham Biosciences) equilibrated with PBS. Size exclusion chromatography was performed with equilibration buffer at room temperature with a flow rate of 1.25 ml/min. During the elution absorbance at 254 nm and 260 nm was monitored. Two peaks were isolated. A major high molecular weight peak preceded a small peak of lower apparent molecular weight. The major peak revealed a apparent molecular weight consistent to purified VLPs as shown by SE-HPLC. Analysis of AP205 or GA355 VLPs packaged with G10 oligonucleotide is performed essentially as shown in Example 16 of WO03/024481 (p. 131 ff).

Example 6

Packaging of FR VLPs with G10 by Disassembly/Reassembly

Disassembly: 50-100 mg of FR VLPs (as determined by Bradford analysis) in buffer A (5 mM NaPO₄ pH 6.8, 100 mM NaCl, 2 mM MgCl₂) are incubated at 30° C. for 16 hours with RNAse A (Sigma) and Benzonase (Novagen) at 1 mg/ml and 5 U/ml, respectively. After addition of 1 M NaCl precipitation of the FR coat proteins is induced by a 15 min incubation at 70° C. Precipitated coat proteins are sedimented by centrifugation for 10 min, 27,000 g at 4° C. The supernatant containing RNAse A. Benzonase and degraded nucleic acids are discarded. The pellet is resuspended in buffer B (20 mM NaPO₄ pH 7.2, 6 M urea) and incubated for 10 min at room temperature.

Purification of FR coat proteins by cation exchange chromatography: The solution is clarified by centrifugation for 10 min, 27,000 g at 4° C. A negligible pellet is discarded and the supernatant containing the disassembled coat proteins is applied on a SP Sepharose™ FF column (16/20, Amersham Biosciences) equilibrated with buffer B. The flow through is discarded. After an extensive wash with buffer B (15 CV) the column is adjusted with a linear gradient from buffer B to buffer C (20 mM $NaPO_4$ pH 7.2, 1 M urea) with a gradient length of 37.5 CV. During the loading, wash and elution the absorbance at 254 nm and 280 nm is monitored. FR coat proteins are eluted as one fraction with buffer D (20 mM $NaPO_4$ pH 6.5, 1 M urea, 300 mM NaCl) and analyzed by LDS-PAGE followed by Coomassie staining. The eluted protein fractions is stored at 4° C. as "disassembled coat protein". Protein concentration is determined by Bradford analysis.

Reassembly: Purified FR coat protein is used in a five fold excess (w/w) to G10 oligonucleotide. The FR coat proteins are mixed with the G10 oligonucleotide in a reassembly buffer containing 1 M urea and 2.5 mM DTT and incubated for one hour at room temperature. After incubation the reassembly mix is dialyzed for 24 hours against 5 liter PBS. The resulting suspension is centrifuged for 10 min, 27,000 g at 4° C. A negligible sediment is discarded. The supernatant contains the reassembled and packaged FR VLPs. Protein concentration is determined by Bradford analysis and the reassembled and packaged FR VLPs are concentrated with centrifugal filter devices (Amicon Ultra 15, 10K MWCO).

Purification of reassembled and packaged FR VLPs: Up to 25 mg total protein is loaded onto a Sepharose™ CL-4B (26/60, Amersham Biosciences) equilibrated with PBS. Size exclusion chromatography is performed with equilibration buffer at room temperature with a flow rate of 1.25 ml/min. During the elution absorbance at 254 nm and 260 nm is monitored. Two peaks are isolated. A major high molecular weight peak precedes a small peak of lower apparent molecular weight. The major peak reveals a apparent molecular weight consistent to purified FR VLPs as shown by SE-HPLC. Analysis of FR VLPs packaged with G10 oligonucleotide is performed essentially as shown in Example 16 of WO 03/024481 (p. 131 ff).

Example 7

Size Dependent Traffic of Nanoparticles to the Lymph Node

To study the mechanism of traffic of particulate antigens to the lymph node, yellow-green fluorescent polystyrene nanoparticles with sizes ranging from 20 nm to 2000 nm (Molecular probes) were injected in the footpads (25 µg/footpads) of C57BL/6 mice and tracked. VLPs of bacteriophage Qβ were coupled to Alexa488 using a protein labeling kit (Molecular probes) and included in the experiment as 30 nm fluorescent particles. Forty eight hours later the nanoparticles and VLPs were tracked in the popliteal draining lymph node (LN) by flow cytometry. Popliteal LN were isolated and digested with 1 mg/ml Collagenase D (Boehringer) and 0.04 mg/ml DNAse I (Roche) for 30 min at 37° C. In order to identify cell populations taking up nanoparticles, LN cells were stained with anti-CD11c-PE (BD). Flow cytometry analysis showed that 48 hours after injection, nanoparticles and VLPs have reached the popliteal LN and were associated to different level with LN cells, including dendritic cells (DC, Table 1). LN cells acquired more efficiently smaller particles (20-500), than larger ones (1000-2000 nm). VLP-Alexa488 (30 nm) showed efficiency of LN uptake between the efficiency of 20 and 100 nm polystyrene nanoparticles. These data suggest that nanoparticles and VLPs traffic from the injection site to the LN in a size-dependent manner, with significant trafficking taking place for particles of sizes between 20 and 500 nm.

TABLE 1

Flow cytometry analysis of the trafficking of nanoparticles or VLP to the popliteal LN: 48 h after injection.

| Size [nm] | % FL1 + DC | sd | % FL + LN cells | sd |
|---|---|---|---|---|
| 20 | 0.82 | 0.08 | 2.46 | 0.15 |
| 30 | 1.38 | 0.18 | 4.14 | 0.65 |
| 100 | 2.31 | 0.36 | 12.09 | 1.22 |

Anti - CD11c antibodies were used to identify DC.

Example 8

Kinetics of Trafficking of VLP to the LN

To study the kinetics of uptake of nanoparticles in LN cells, VLP-Alexa488 (prepared as described in Example 7) were injected in C57BL/6 mice (as described in Example 7) and tracked after 2 to 96 h. LN cells were stained with combinations of the following antibodies: anti-CD11c-PE, anti-CD11b-APC, anti-CD11c-biotin, anti-CD19-APC, anti-B220-PE, antiCD8-CyChr, anti-CD40-APC and streptavidin-CyChr (all from BD). Flow cytometry analysis showed that 2 h after injection in the footpad, VLP-Alexa488 have associated with antigen presenting cells (APC) from the popliteal LN (Table 2). It is quite unlikely that dendritic cells from the skin had taken up and had trafficked VLP-Alexa488 to the draining LN for the short period of 2 h. These results rather suggest that VLP-Alexa488 had drained in a cell-free manner through the lymphatic system into the draining lymph node. Macrophages and DC were the most prominent populations taking up VLP-Alexa488. Most importantly, 2 h after injection, 1.9% of LN-resident plasmacytoid DC also acquired VLP-Alexa488. pDC in humans are mostly found in secondary lymphoid tissues and are the only DC population expressing TLR9. Therefore, the ability of VLP-Alexa488 to drain free to the LN makes them a very appropriate vehicle to target pDC with the possibility to simultaneously deliver ISS (such as CpG), packaged in VLP.

The uptake of VLP-Alexa488 peaked at 24 h after injection (Table 2), remained quite stable by 48 h and declined after 96 h. It is likely, that at that later time point also skin derived DC contribute to the traffic of VLP-Alexa488 to the draining LN. Indeed, the ratio between the uptake of VLP-Alexa488 at 2 h (draining) and 24 h (DC-mediated transport) is lower for myeloid (including skin-derived, CD11c+CD40hiCD8−) compared to lymphoid (CD11c+CD40loCD8+) DC, which acquire VLP while in the LN (FIG. 4).

TABLE 2

Flow cytometry analysis of the kinetics of trafficking of Qβ-VLP to the popliteal LN.

| | % VLP-Alexa488+ cells | | | |
|---|---|---|---|---|
| time [h] | DCs | Macrophages | pDC | B-cells |
| 2 | 2.82 | 13.04 | 1.9 | 0.9 |
| 24 | 26.83 | 38.32 | 3.66 | 2 |
| 48 | 18.28 | 24.9 | 1.5 | 0.96 |
| 96 | 4.31 | 18.35 | 0.24 | 0.21 |

Anti - CD11c, CD11b, B220 and CD19 antibodies were used to identify DC, Macrophages, pDC and B-cells. The percentage of green cells in the gate of the indicated LN cell populations is shown.

Example 9

Kinetics of Trafficking of Nanoparticles by In Vivo Imaging

The traffic of 20 and 500 nm fluorescent polystyrene nanoparticles, as well as VLP-Alexa488 was investigated in vivo using an UV light tool (LT-99D2-220, Lightools Research, CA) equipped with 470/40 nm excitation filter and high resolution camera (KM_Dynax_5D). Mice were injected with the fluorescent nanoparticles in the footpad as described in Example 7 and pictures were taken at 2, 24 and 192 h after injection. In agreement with flow cytometry data (Table 2), 2 h after injection VLP-Alexa488 have reached the popliteal LN as detected by fluorescence microscopy. Similarly to VLP (30 nm), 20 nm nanoparticles (Table 3) were also detected, suggesting that small nanoparticles are able to drain in a cell-free manner to the LN. On the contrary, at this early time point 500 nm nanoparticles were not detected in the popliteal LN (Table 3), demonstrating a slower kinetics of traffic of larger particles to the LN. Flow cytometry analysis were performed 2 h after injection of 20 or 500 nm nanoparticles. These results confirmed the findings with the light tool imaging (Table 3). One possibility for the slower trafficking kinetics of 500 nm particles is that it takes place in part via DC uptake at the injection site and transport to the LN.

Twenty four hours after injection, 500 nm particles have reached the draining LN as detected by fluorescence microscopy, although the associated fluorescence was quantitatively less than in LN of mice injected with 20 nm and VLP-Alexa488 nanoparticles. At later time points (192 h) VLP-Alexa488, 20 and 500 nm particles were still present at the injection site and in the popliteal LN, suggesting a depot formation and continuous delivery of antigen.

Taken together, these data suggest a size dependent mechanism of traffic of nanoparticles to the LN. Small particles, such as 20 nm and VLP-Alexa488 drain in a cell-free manner to LN at early time points whereas large particles (500 nm) show slower kinetics due to requirement for DC-mediated transport.

TABLE 3

Flow cytometry analysis of the trafficking of nanoparticles to the popliteal LN 2 h after injection.

| Particle Size [nm] | FL1 + LN cells |
|---|---|
| 20 | 1.59 |
| 500 | 0.05* |

The percentage of green cells in the total LN cell gate is shown.
*the value is in the range of the background observed in naïve animals Example 10

DC-Dependence of the Delivery of Nanoparticles to the LN

Macrophages are thought to be non-migratory cells, therefore particle bearing macrophages are supposed to be LN-resident cells that had acquired particles while in the LN. On the contrary, DC have the capacity to engulf particles at the injection site and to migrate to the draining LN. To investigate the relationship between the size of a nanoparticle and the mechanism of trafficking to the LN, the fluorescent nanoparticles ranging in size from 20 to 2000 nm were injected in the footpads of mice as described in Example 7, and the ratio between the nanoparticle-containing DC and macrophages was calculated (FIG. 5). The larger the injected particle (500-2000 nm), the more DCs are involved in its uptake in LN. Smaller particles (20-200 nm) were detected in comparable percentage of DC and macrophages, suggesting cell-free draining and association with LN-resident APC.

In vivo imaging kinetic studies in wild type mice and in mice conditionally depleted of DCs (CD11c-DTR-GFP mice, Jung S. et al., 2002) showed that large particles (500 nm) reached the draining LN only in the presence of DCs, whereas small (20 nm) nanoparticles trafficked efficiently also in DC-depleted animals. These data suggest that small nanoparticles can target lymph node resident DC populations. Indeed, as shown in Table 4, 20 nm particles and VLP (30 nm) associated with the lymph node-resident plasmacytoid DCs (PDCA-1$^+$ B220$^+$), B cells (PDCA-1$^-$B220$^+$) and lymphoid DCs (CD11c$^+$CD8$^+$). Therefore, small particles are useful to target LN-resident APC, whereas large particles exclusively target DC at the injection site.

TABLE 4

Flow cytometry analysis of the trafficking of nanoparticles to the popliteal LN 48 h after injection.

| Particle size [nm] | % FL1$^+$ Lymphoid DCs | % FL1$^+$ plasmacytoid DCs | % FL1$^+$ B cells |
|---|---|---|---|
| 20 | 12 | 8 | 4 |
| 30 (VLP) | 13 | 16 | 2 |
| 1000 | 3 | 0 | 0 |

The percentage of green cells in the gate of the indicated LN cell populations is shown.

Example 11

Generation of Bone Marrow-Derived Dendritic Cells (BMDC) and Treatment with QβG10 Batches 11 week old mice from the LPS-resistant (C3H/HeJ) and LPS-responding (C3H/HeN) strains were sacrificed and the femurs and tibias isolated and kept in PBS. After removing the flesh, bones were cut from both sides and the bone marrow flushed out using a syringe filled with 10% FCS RPMI. Released cells were collected and passed through a 70 μm cell strainer. Cells were washed and re-suspended at 20×10$^4$ cells/ml in 10% FSC RPMI containing 10 ng/ml mouse GM-CSF (R&D). 2×10$^6$ cells were plated in bacterial grade Petri dishes in 10 ml medium for 6 days. The differentiation status of BMDC was ascertained on day 6 by analyzing cells for the expression of CD11c and CD11b by flow cytometry. At day 6 of differentiation, BMDC were harvested from the Petri dishes, washed once and plated in 96-well U-bottom plate (BD) at 5×10$^4$/well. 6 dilutions (4-fold) of QβG10 were prepared in a separate plate and added to BMDC for 20 h.

ELISA for determination of IL-12: Microtiters plates (Maxisorp, Nunc) were coated overnight with 2 μg/ml rat anti-mouse IL-12 (p40/p70) monoclonal antibody (mAb, Pharmingen) in coating buffer (0.1 M NaHCO$_3$, pH 9.6). After washing (0.05% Tween 20/PBS) and blocking (2% BSA/0.05% Tween 20/PBS), 70 μl of supernatants from BMDC or two-fold dilutions of recombinant IL-12 (starting from 20 μg/ml) were added and incubated for 2 h at room temperature (RT). After washing the plates, biotin-labeled rat anti-mouse IL-12 mAb (p40/p70, Pharmingen) was added at 1 μg/ml for 1 h at RT. Plates were washed and incubated with 1 μg/ml streptavidin-HRPO (Jackson laboratories) for 1 h at RT. After washing, o-phenylene diamine (OPD, Fluka) in citric acid buffer (pH 5) was added for 5 min and the reaction was stopped with 5% H$_2$SO$_4$. Optical density at 490 nm was measured in an ELISA reader (Molecular Devices) and data were analyzed using the software Soft max Pro.

Results: Activation of BMDCs by Qβ packaged with G10 oligo is shown on FIG. 6. BMDCs were activated by QβG10 and hence secreted IL-12 in a dose dependent way (dose is given as equivalent of G10 oligonucleotide packaged in the Qβ VLPs) while untreated control cells did not secrete any IL-12. Therefore G10 oligonucleotide packaged in Qβ VLPs is able to activate BMDCs, demonstrating that the particles are taken up by the cells and oligonucleotide is made subsequently available for stimulation of the BMDCs.

Example 12

BMDC Release IL-12 upon AP205G10 Treatment

BMDC from C3H/HeJ mice were in vitro generated as described in Example 11. Cells were plated in a 96-well plate and stimulated either mock or with the indicated concentrations of AP205 reassembled with G10 (AP205G10). Eighteen hours later the supernatants were collected and IL-12 was measured by a sandwich ELISA, as described in Example 11. AP205G10 induced a dose-dependent secretion of IL-12, while untreated cells released IL-12 only to basal levels (Table 5). These results demonstrate that AP205G10 is taken up by BMDC and activates them to release IL-12.

TABLE 5

Dose response of AP205G10 induced IL-12 secretion by BMDCs.

| AP205G10 µg/ml | IL-12 [pg/ml] |
| --- | --- |
| 300 | 4699.7 |
| 150 | 4831.3 |
| 75 | 4535.9 |
| 37.5 | 3644.7 |
| 18.75 | 2760.3 |
| 9.375 | 1407.0 |
| 0 | 471.1 |

Example 13

Preparation and Characterization of Gelatin Nanoparticles as Delivery System for G10 Oligodesoxynucleotide (G10-DN)

Preparation of Plain Gelatin Nanoparticles (Gnp) by Two Step Desolvation: the Procedure used was the original one described by (Coester et al. 2000) as follows. 1.25 g of gelatin type A (Bloom175) was dissolved in 25 ml highly purified water (HPW) to 5% (w/w) under gentle heating to 50° C. A first desolvation step was initiated by the addition of 25 ml acetone. After sedimentation of the precipitated gelatin fractions for 60 seconds, the supernatant consisting of dispersed gelatin as well as dissolved gelatin was discarded. The sediment was dissolved again by the addition of 25 ml water under heating to 50° C. and the pH was adjusted to 2.5. In situ gelatin nanoparticles were formed during a second desolvation step by drop wise addition of 50 ml acetone under constant stiffing (500 rpm). After 10 min, 175 µl of glutaraldehyde (25%) were added to the reaction vessel to crosslink the nanoparticles. Finally, after stiffing for 12 hours in an extractor hood, the particles were purified by three-fold centrifugation (20000 g for 20 min) and redispersion in acetone/water (30/70), the last step in HPW alone. The purified nanoparticles were stored as dispersion in HPW (conductivity<0.04 µs/cm) at 4-8° C. The following standard process parameters are critical for nanoparticle preparation: (a) Temperature before the first and second desolvation step: 50° C.; (b) stiffing speed: 500-700 rpm; (c) precipitation time after the first desolvation step: 60 sec; (d) speed of acetone addition (second desolvation step): 3-5 ml/min.

Determination of nanoparticle size: Particle sizes were determined employing dynamic light scattering (DLS) technology. DLS experiments were performed with a Zetasizer ZS (Malvern Instruments, Worcestershire, England) using NIBST™-technology (Non Invasive Back Scattering) at a static detection angle of 173°. The nanoparticles were diluted in sterile filtered, highly purified water and measured in concentrations between 30 and 100 µg/ml. Due to these low concentrations, the nanoparticles did not influence the viscosity of the dispersion, so that the viscosity of pure water which is of 0.8872 cP at 25° C. was used. The experiments were performed at 25° C.

Cationisation of plain Gelatin Nanoparticles: A new, modified version of the original method described by Coester (2003) using cholaminechloride hydrochloride was used (Ahlers et al. 2005; Coester 2003; Zwiorek et al. 2004). An aqueous dispersion of plain nanoparticles was adjusted to pH 4.5 and a molar excess of the cationization agent cholamine chloride hydrochloride (e.g. 50 mg per 500 mg nanoparticles) was added under constant stirring. After 5 minutes of incubation, 50 mg of 1-ethyl-3-(3-dimethyl-aminopropyl) carbodiimide hydrochloride (EDC) was added to activate the free carboxyl groups on the particles to react with cholaminechloride hydrochloride. During the cationization reaction the primary amino groups of the cholaminechloride hydrochloride can react with two possible functional groups on the nanoparticle's surface. The first interaction sites are residual aldehyde groups derived from the only mono-functionally bound cross linking reagent glutaraldehyde. Furthermore, the primary amino groups can react with activated carboxyl groups on the nanoparticles surface. The reaction was stopped after 1 h and the nanoparticles were purified by 3-fold centrifugation and redispersion, analogous to the purification of plain nanoparticles. The final particles were characterized by size determination using dynamic light scattering, and measurement of the Zeta potential. Each assigned size and corresponding polydispersity index was the mean of 10 subruns. The Zeta potential was determined using the same instrument and calculated as the mean of 10 individual measurements in PBS. Particles showing a positive charge of 5 mV or higher in PBS were used for loadings.

G10-DN loading on cationized gelatin nanoparticles: G10-ODN was employed either in an aggregated or non-aggregated form (omitting the aggregation step in the protocol for ODN G10 preparation, Example 2) in purified water and in PBS. For the cellular assays described below the contents were 1% for GNP and 0.1% for G10-ODN leading to a targeted loading of 10% (w/w) in PBS. For the mouse model study described below, a G10-ODN content of 0.25% and GNP of 2.5% were prepared as well providing a 10% (w/w) loading in PBS. The loading experiment is exemplary described for a targeted (aspired) 10% (w/w) G10-ODN loading on GNP in PBS, and the same procedure was adapted for the other targeted loading percentages using aggregated or non-aggregated G10-ODN. 43.3 µl of an aqueous GNP dispersion containing 1.2 mg GNP were transferred to an Eppendorf™ 1.5 ml cap under aseptic conditions. Then 1086 µl of PBS were added and mixed at the same time with the pipette. In the next step, 71.4 µl of G10 stock solution containing 120 µg of aggregated G10, were added into the dispersion by quick but gentle up and down pipetting for at least 20 seconds. The prepared sample was subsequently incubated for 1 h 15 min at 22° C. and 750 rpm on a Thermomixer™ device.

Determination of G10-ODN loading efficiency (Zillies and Coester 2004): After incubation, the G10-ODN loaded GNP samples to be tested for successful loading were centrifuged for 1 h at 15000 g. After centrifugation the supernatant was carefully separated from the remaining pellet and analyzed spectrophotometrically at a wavelength of 260 nm. A reference of unloaded GNP of the same concentration (1 mg/ml) and a reference of G10-ODN of the same concentration (100 µg/ml) were prepared and centrifuged along. G10-ODN loading in percent was calculated from the percentage free G10-ODN, which was obtained by subtracting the measured absorption of the particle reference from the sample result and then dividing this result by the measured absorption of the G10-ODN reference, and multiplying by hundred. Finally, the loading efficiency was calculated by subtracting the percentage free G10-ODN from 100%.

Results of G10-ODN loading determination: Results of loading efficiency were obtained by various GNP batches. However, the preparation process and especially cationization was the same in each case. Hence, loadings can be compared as well as among batches with different particle sizes. All results given in percent are mass percentage (w/w) calculated on the employed masses of G10-ODN and GNP. As shown in Tables I-III for non-aggregated G10-ODN and Tables IV-V for aggregated G10-ODN, G10-GNPs with loading percentage from 3-15% (non-aggregated G10-ODN) or 5-10% (aggregated G10-ODN) were successfully obtained. Optimal loading medium was PBS, where no flocculation was detected in the preparations. Results of not aggregated G10-ODN show sufficient bindings over all with a tendency to decreased efficiency from 5 to 10% loading in water and without this tendency in PBS. The loading of 15% G10-ODN onto GNP shows only a slightly lower efficiency.

TABLES I and II

| loading efficiency [%] of not aggregated G10 on GNP (314 nm) in water (left) and GNP (218 nm) in PBS (right). The single numbers on top of each sub table give the targeted G10 - ODN loading onto GNP in percent. | | | |
| --- | --- | --- | --- |
| 3 | | 3 | |
| particle reference | 0.132 (n = 3, S.D. = 0.0021) | particle reference | 0.103 (n = 3, S.D. = 0.006) |
| ODN reference 3% | 0.404 (n = 3, S.D. = 0.0029) | ODN reference 3% | 0.964 |
| sample G10 3% (water) | 0.117 (n = 3, S.D. = 0.0006) | sample G10 3% (PBS) | 0.127 (n = 3, S.D. = 0.001) |
| loading [%] | 100.000 | loading [%] | 97.476 |
| 5 | | 5 | |
| particle reference | 0.132 (n = 3, S.D. = 0.0021) | particle reference | 0.103 (n = 3, S.D. = 0.006) |
| ODN reference 5% | 0.652 (n = 3, S.D. = 0.0021) | ODN reference 5% | 1.647 |
| sample G10 5% (water) | 0.132 (n = 3, S.D. = 0.0021) | sample G10 5% (PBS) | 0.106 (n = 3, S.D. = 0.0056) |
| loading [%] | 100.000 | loading [%] | 99.798 |
| 8 | | 8 | |
| particle reference | 0.132 (n = 3, S.D. = 0.0021) | particle reference | 0.103 (n = 3, S.D. = 0.006) |
| ODN reference 8% | 1.079 (n = 3, S.D. = 0.0026) | ODN reference 8% | 2.673 |
| sample G10 8% (water) | 0.149 (n = 3, S.D. = 0.0000) | sample G10 8% (PBS) | 0.100 (n = 3, S.D. = 0.0107) |
| loading [%] | 97.898 | loading [%] | 100.000 |
| 10 | | 10 | |
| particle reference | 0.132 (n = 3, S.D. = 0.0021) | particle reference | 0.103 (n = 3, S.D. = 0.006) |
| ODN reference 10% | 1.344 | ODN reference 10% | 3.356 |
| sample G10 10% (water) | 0.186 (n = 3, S.D. = 0.0010) | sample G10 10% (PBS) | 0.166 (n = 3, S.D. = 0.0079) |
| loading [%] | 95.700 | loading [%] | 98.113 |

TABLE III

| loading efficiency [%] of not aggregated G10 onto GNP (218 nm) in PBS | |
| --- | --- |
| particle reference | 0.105 (n = 3, S.D. = 0.0006) |
| ODN reference 15% | 2.557 |

TABLE III-continued

| loading efficiency [%] of not aggregated G10 onto GNP (218 nm) in PBS | |
| --- | --- |
| sample G10 15% (PBS) | 0.238 (n = 3, S.D. = 0.0154) |
| loading [%] | 94.798 |

TABLE IV

| loading efficiency [%] of aggregated G10 onto GNP (218 nm) in PBS | |
| --- | --- |
| ODN-reference | 0.827 (n = 5, S.D. = 0.002) |
| particle reference | 0.145 (n = 5, S.D. = 0.004) |
| sample G10 5% aggl | 0.176 (n = 5, S.D. = 0.005) |
| loading [%] | 96.251 (n = 5, S.D. = 1.089) |
| ODN-reference | 0.827 (n = 4, S.D. = 0.002) |
| particle reference | 0.145 (n = 4, S.D. = 0.004) |
| sample G10 10% aggl | 0.159 (n = 4, S.D. = 0.001) |
| loading [%] | 98.277 (n = 4, S.D. = 0.425) |

TABLE V

| Loading efficiency [%] of aggregated G10 onto GNP (218 nm) in HPW | |
| --- | --- |
| particle reference | 0.106 (n = 3, S.D. = 0.0005) |
| ODN reference | 1.870 (n = 3, S.D. = 0.0037) |
| sample G10 10% (water) | 0.285 (n = 3, S.D. = 0.0034) |
| loading [%] | 90.426 |

G10-loaded gelatin nanoparticles (GNP-G10) induce IL-12 secretion from BMDC: GNP-G10 were prepared as described above. To evaluate the effect of unbound G10, an aliquot of GNP-G10 preparation was centrifuged at 16000 g for 1 h at 4° C. and the supernatant was collected (supGNP-G10). BMDC from C3H/HeJ mice were generated in vitro, as described in Example 11. Cells were plated in a 96-well plate and stimulated either mock or with the indicated concentrations of GNP-G10 or supGNP-G10 (given as their molar concentration of G10). Eighteen hours later the cell supernatants were collected and IL-12 was measured by a sandwich ELISA, as described in Example 11. GNP-G10 induced secretion of IL-12 from BMDC at all tested concentrations (Table VI). In contrast, BMDC did not release significant amounts of IL-12 upon treatment with supGNP-G10. These results suggest that GNP-G10 are taken up by BMDC and trigger release of IL-12. In addition, these data show that G10 is efficiently loaded on GNP, as supGNP-G10 did not induce IL-12 secretion from BMDC. GNPs without G10 do not induce IL-12 secretion in mouse dendritic cells.

TABLE VI

GNP-G10 induced secretion of IL-12 from BMDC.

| | IL-12 [pg/ml] | | | |
|---|---|---|---|---|
| G10 [nM] | GNP-G10 | std | supGNP-G10 | std |
| 5200 | 7841.0 | 846.5 | 382.7 | 42.4 |
| 2600 | 7444.4 | 365.8 | 232.9 | 10.8 |
| 1300 | 7382.9 | 379.3 | 83.3 | 1.4 |
| 650 | 6968.6 | 271.9 | 58.2 | 13.7 |
| 325 | 7701.7 | 210.6 | 371.2 | 456.2 |
| 162.5 | 7007.7 | 348.7 | 52.0 | 3.7 |
| 0 | 41.3 | 21.5 | 41.3 | 21.5 |

G10-loaded gelatin nanoparticles (GNP-G10) are protective in an mouse model of asthma: An experimental asthma model of allergic airway (Hessel E M et al., J. Exp. Med. 2005, 202, 1563) is used to assess the effects of GNP-G10 on total IgE level. For sensitization, four groups of mice (groups B-E, five mice per group) are injected intraperitonealy (i.p.) with 150 μg ragweed (*Ambrosia artemisiifolia*) pollen extract (RW, Greer) mixed with 450 μg of Alum (Alhydrogel 2.0% Brenntag Biosector, Denmark) on day 0 and 3. Mice from one group (group A) are treated i.p. with PBS only. On day 10, mice from group C are injected subcutaneously with 300 μg QbG10 (equivalent to 60 μg G10), mice from group D with 600 μg GNP-G10 (equivalent to 60 μg G10), mice from group E with 600 μg GNP-G10aggregated (equivalent to 60 μg G10) mice from groups A and B with PBS. Blood is sampled from all animals prior to injection. On day 17, all animals are bled, and total IgE titer is determined. The total IgE level in blood is measured by ELISA. Briefly, an ELISA plates (96 well MAXIsorp, NUNC immuno plate #442-404) is coated with anti-IgE (BD Pharmingen, #553413) at a concentration of 5 μg/ml in coating buffer (0.1 M NaHCO$_3$, pH 9.6) over night at 4° C. The plates are then washed with wash buffer (PBS/ 0.05% Tween) and blocked for 2 h at 37° C. with 2% BSA in wash buffer. The plate is then extensively washed and then incubated with 1 to 20 diluted mouse sera or serially diluted mouse IgE standard (BD Pharmingen, #557079). The plate is incubated at RT for 2 h and then extensively washed with wash buffer. Bound specific mouse antibodies are then detected by one hour incubation with a HRPO-labelled, epsilon chain specific, rat anti-mouse IgE antibody (Southern Biotech #H021-NBB4C). After extensive washing with wash buffer, plates are developed with OPD solution (1 OPD tablet, 25 ml OPD buffer and 8 μl H$_2$O$_2$) for 6 minutes and the reaction is stopped with 5% H$_2$SO$_4$ solution. Plates are then read at OD 450 nm on an ELISA reader (Biorad Benchmark). The concentrations of IgE in sera is calculated with GraphPad Prism4 using the mouse IgE standard as reference.

References For Example 13

Ahlers, Michael, et al. Biodegradable gelatin nanoparticles and procedure for their production. (Deutsche Gelatine-Fabriken Stoess A.-G., Germany, assignee. Patent 102004041340. 20060223. (2005).

Coester, C. J., et al. "Gelatin nanoparticles by two step desolvation-a new preparation method, surface modifications and cell uptake." Journal of Microencapsulation 17.2 (2000): 187-93.

Coester, Conrad. Development of a new carrier system for oligonucleotides and plasmids based on gelatin nanoparticles. New Drugs [1], 14-17. 2003.

Zillies, Jan and Coester, Conrad. Evaluating gelatin based nanoparticles as a carrier system for double stranded oligonucleotides. Journal of Pharmacy & Pharmaceutical Sciences 7[4], 17-21. 2004.

Zwiorek, Klaus, Kloeckner, Julia, Wagner, Ernst, and Coester, Conrad. Gelatin nanoparticles as a new and simple gene delivery system. Journal of Pharmacy & Pharmaceutical Sciences 7 [4], 22-28. 2004.

Example 14

Detection of IFN-Alpha Production in Cells by ELISA

Human peripheral blood mononuclear cells (PBMC) were isolated from buffy coats and treated with immunostimulatory nucleic acids in RPMI medium containing 10% fetal calf serum (FCS) for 18 h. IFN-alpha in the supernatants was measured by sandwich ELISA, using an antibody set provided by PBL Biomedical Laboratories. Briefly, ELISA plates were coated with 5 μg/ml of the capture anti-IFN-alpha antibody. After washing, plates were blocked with 0.5% BSA for 1 h at room temperature (RT). Supernatants from treated and control PBMC, as well as recombinant IFN-alpha were added to the plate and incubated for 2 h at 37° C. Rabbit polyclonal anti-IFN-alpha serum was used as detection antibody and incubated for 1 h at RT. Peroxidase-conjugated goat anti-rabbit serum was subsequently added to the plates for 1 h at RT. Washing step was performed after each incubation. The color reaction was developed using the enzyme substrate o-phenylendiamine and read at 490 nm in an ELISA reader device. The data are expressed as pg/ml secreted IFN-alpha according to a standard curve of recombinant IFN-alpha.

Example 15

Flow Cytometry Analysis Using Fluorochrom-Conjugated Antibodies

PBMC are stimulated for 3-6 h with immunostimulatory nucleic acids followed by incubation with brefeldin A for additional 4 h. Cells are then stained with DC-specific surface markers, permeabilized and intracellularly stained for IFN-alpha.

Example 16

Effects of QβG10 on Eosinophilia after Sensitization with Ragweed Pollen and One Challenge on Day 11

An experimental asthma model of allergic airway (Hessel E M et al., J. Exp. Med. 2005, 202, 1563) was used to assess the effects of QβG10 on eosinophilia, a pathologic maker of asthma. For sensitization, three groups of mice (five mice per group) were injected intraperitonealy (i.p.) with 150 μg ragweed (*Ambrosia artemisiifolia*) pollen extract (RW, Greer) mixed with 450 μg of Alum (Alhydrogel 2.0% Brenntag Biosector, Denmark) on day 0 and 3. On day 9, mice from group B received 375 μg of QβG10 subcutaneously (s.c.). On day 10, mice from group C received 375 μg of QβG10 subcutaneously. Mice from of group A received PBS as control. On day 11, all mice were challenged with 200 μg of RW in PBS intranasally (i.n.). 48 hours after the challenge mice were sacrificed and the lungs were washed with PBS (Table 6). The cells contained in the broncho alveolar lavage (BAL) were analysed by FACS. Eosinophils were identified by high CCR3 (Mouse CCR3Phycoerythrin MAb, R & D) expression. As shown in Table 7, the total amount of cells in BAL was strongly reduced in QβG10 treated compared to PBS control mice. The reduction was more pronounced when QβG10 was given 48 hours (61%, p<0.05) before the challenge than 24 hours (52%) before the challenge. As shown in Table 8, the amount of eosinophils was strongly reduced in QβG10 treated compared to PBS control mice. Again, the reduction was more pronounced when QβG10 was given 48 hours (70%, P<0.05) than 24 hours (60%, p<0.05) before the challenge. Thus, QβG10 treatment prevents the development of asthma in a murine model for asthma.

two groups of mice (five mice per group) were injected intraperitonealy with 150 μg RW pollen extract in 450 μg of alum on day 0 and 3. On day 9 and 13, mice from group B were subcutaneously injected with 375 μg of QβG10. Mice from of group A received PBS as control. On day 11 and 15, mice were challenged with 200 μg of RW in PBS intranasally. 48 hours after the challenge mice were sacrificed and the lungs were washed with PBS (Table 9). The cells contained in the BAL were analyzed by FACS as described in Example 16. As shown in Table 10 and 11, the total amount of cells (51%, p<0.01) and the amount of eosinophils (62%, p<0.001) were strongly reduced in QβG10 treated compared to PBS control mice. Thus, QβG10 prevents the development of asthma in a stronger murine model for asthma.

TABLE 6

Experimental Protocol.

| | Day 0 | Day 3 | Day 9 | Day 10 | Day 11 | Day 13 |
|---|---|---|---|---|---|---|
| A | RW alum i.p. | RW alum i.p. | | PBS s.c. | RW | Analysis |
| B | RW alum i.p. | RW alum i.p. | QβG10 s.c. | | RW | Analysis |
| C | RW alum i.p. | RW alum i.p. | | QβG10 s.c. | RW | Analysis |

TABLE 7

Total Cell Counts in BAL.

| | Group A | Group B | Goup C |
|---|---|---|---|
| mouse 1 | 210'000 | 60'000 | 180'000 |
| mouse 2 | 636'000 | 66'000 | 312'000 |
| mouse 3 | 330'000 | 60'000 | 120'000 |
| mouse 4 | 246'000 | 366'000 | 102'000 |
| mouse 5 | 480'000 | 360'000 | 36'000 |
| average | 380'400 | 182'400 | 150'000 |
| reduction | | 52% | 61% |

TABLE 8

Eosinophil counts in BAL.

| | Group A | Group B | Goup C |
|---|---|---|---|
| mouse 1 | 61'696 | 11'208 | 19'855 |
| mouse 2 | 90'166 | 15'913 | 32'487 |
| mouse 3 | 106'682 | 9'811 | 12'786 |
| mouse 4 | 36'300 | 64'255 | 13'276 |
| mouse 5 | 82'757 | 58'752 | 4'222 |
| average | 75'520 | 31'988 | 16'525 |
| reduction | | 63% | 70% |

The total IgE level in blood was measured by ELISA. Briefly, an ELISA plates (96 well MAXIsorp, NUNC immuno plate #442-404) were coated with anti-IgE (BD Pharmingen, #553413) at a concentration of 5 μg/ml in coating buffer (0.1 M $NaHCO_3$, pH 9.6) over night at 4° C. The plates were then washed with wash buffer (PBS/0.05% Tween) and blocked for 2 h at 37° C. with 2% BSA in wash buffer. The plate was then extensively washed and then incubated with 1 to 20 diluted mouse sera or serially diluted mouse IgE standard (BD Pharmingen, #557079). The plate was incubated at RT for 2 h and then extensively washed with wash buffer. Bound specific mouse antibodies were then detected by one hour incubation with a HRPO-labelled, epsilon chain specific, rat anti-mouse IgE antibody (Southern Biotech #H021-NBB4C). After extensive washing with wash buffer, plates were developed with OPD solution (1 OPD tablet, 25 ml OPD buffer and 8 μl $H_2O_2$) for 6 minutes and the reaction was stopped with 5% $H_2SO_4$ solution. Plates were then read at OD 450 nm on an ELISA reader (Biorad Benchmark). The concentrations of IgE in sera were calculated with GraphPad Prism4 according to the standard. As shown in Table 12, the total IgE level in mice treated with QβG10 are significantly (P<0.05) reduced comparing to untreated mice.

TABLE 9

Experimental Protocol.

| | Day 0 | Day 3 | Day 9 | Day 11 | Day 13 | Day 15 | D17 |
|---|---|---|---|---|---|---|---|
| A | RW alum i.p. | RW alum i.p. | PBS | RW | PBS | RW | Analysis |
| B | RW alum i.p. | RW alum i.p. | QβG10 s.c. | RW | QβG10 s.c. | RW | Analysis |

Example 17

Effects of QβG10 on Eosinophilia after Sensitization with Ragweed Pollen and Two Challenges (Day 11 and 15)

A stronger experimental asthma model of allergic airway (modified from Hessel E M et al., J. Exp. Med. 2005, 202, 1563) was also used to assess the effects of QβG10 on eosinophilia and IgE concentration in blood. For sensitization,

TABLE 10

Total Cell Counts in BAL.

| | Group A | Group B |
|---|---|---|
| mouse 1 | 877'250 | 437'250 |
| mouse 2 | ND | 805'750 |

TABLE 10-continued

Total Cell Counts in BAL.

|  | Group A | Group B |
|---|---|---|
| mouse 3 | 1'057'375 | 534'875 |
| mouse 4 | 1'199'000 | 460'625 |
| mouse 5 | 1'287'000 | 496'375 |
| average | 1'105'156 | 546'975 |
| reduction |  | 51% |

TABLE 11

Eosinophil Counts in BAL.

|  | Group A | Group B |
|---|---|---|
| mouse 1 | 611132 | 208045 |
| mouse 2 | ND | 492788 |

TABLE 11-continued

Eosinophil Counts in BAL.

|  | Group A | Group B |
|---|---|---|
| mouse 3 | 802727 | 337733 |
| mouse 4 | 901931 | 244154 |
| mouse 5 | 949650 | 276519 |
| average | 816360 | 311848 |
| reduction |  | 62% |

ND: not determined

TABLE 12

IgE Concentration in sera (µg/ml).

|  | Group A | Group B |
|---|---|---|
| mouse 1 | 4.6 | 0.7 |
| mouse 2 | 0.7 | 0.4 |
| mouse 3 | 3.5 | 0.4 |
| mouse 4 | 4.6 | 0.6 |
| mouse 5 | 1.7 | 0.3 |
| average | 3.0 | 0.5 |
| reduction |  | 84.5% |

Example 18

Duration of the Effect of QβG10 and Interaction of QβG10 with RW Antigen

Mice were sensitized with RW mixed with alum as in Example 16 on day 0 and 3. On day 10 and day 12, mice received QβG10, QβG10 mixed with RW (20 µg) or PBS subcutaneously. 6 and 14 days after the treatment, mice were challenged with RW. 48 hours after the challenge, IgE level in sera was analyzed (Table 13). The data clearly show that IgE level in QβG10 or QβG10 mixed with RW treated mice is significantly reduced comparing to PBS treated controls (Table 14) and no clear difference has been seen between QβG10 and QβG10 mixed with RW.

TABLE 13

Experimental Protocol.

|  | Day 0 | Day 3 | Day 10 | Day 12 | Day 19 | Day 21 | Day 26 | Day 29 | Day 40 | Day 42 |
|---|---|---|---|---|---|---|---|---|---|---|
| A | RW alum i.p. | RW alum i.p. | PBS s.c. | PBS s.c. | RW i.n. | Analysis |  |  |  |  |
| B | RW alum i.p. | RW alum i.p. | QβG10 s.c. | QβG10 s.c. | RW i.n. | Analysis |  |  |  |  |
| C | RW alum i.p. | RW alum i.p. | QβG10 RW s.c. | QβG10 RW s.c. | RW i.n. | Analysis |  |  |  |  |
| D | RW alum i.p. | RW alum i.p. | PBS s.c. | PBS s.c. |  |  | RW i.n. | Analysis |  |  |
| E | RW alum i.p. | RW alum i.p. | QβG10 s.c. | QβG10 s.c. |  |  | RW i.n. | Analysis |  |  |
| F | RW alum i.p. | RW alum i.p. | QβG10 RW s.c. | QβG10 RW s.c. |  |  | RW i.n. | Analysis |  |  |

TABLE 14

IgE Concentration in sera (µg/ml).

|  | A | B | C | D | E | F |
|---|---|---|---|---|---|---|
| mouse 1 | 1.62 | 0.13 | 0.30 | 1.70 | 0.47 | 0.30 |
| mouse 2 | 0.78 | 0.16 | 0.37 | 0.62 | 0.05 | 0.33 |
| mouse 3 | 0.56 | 0.10 | 0.21 | 0.70 | 0.16 | 0.31 |
| mouse 4 | 1.98 | 0.22 | 0.12 | 1.47 | 0.42 | 0.29 |
| mouse 5 | 0.54 | 0.24 | 0.22 | 0.60 | 0.35 | 0.29 |
| average | 1.10 | 0.17 | 0.24 | 1.02 | 0.29 | 0.30 |
| reduction |  | 84.5% | 77.8% |  | 71.5% | 70.2% |

Example 19

Specificity of QβG10

Mice are sensitized with RW and Fel d1 (Cytos, Switzerland) on day 0 and 3. On day 10, mice are treated with either PBS (group A and B), or QβG10 (group C and D), or QβG10 mixed with RW (group E and F) or QβG10 mixed with Fel d1. On day 12, mice from group A, C, E and G are challenged with RW mixed with alum. On the other hand, mice from group B, D, F and H are challenged with Fel d1. On day 14, all mice receive the same treatment as on day 10. On day 16 all the mice are challenged as on day 12. 48 hours after the last challenge, RW and Fel d1 specific IgE in the BAL and blood are measured and infiltrating cells in BAL are analyzed (Table 15).

TABLE 15

Experimental Protocol.

| | Day 0 | Day 3 | Day 10 | Day 12 | Day 14 | Day 16 | Day 18 |
|---|---|---|---|---|---|---|---|
| A | RW Feld1 alum i.p. | RW Feld1 alum i.p. | PBS s.c. | RW i.n. | PBS s.c. | RW i.n. | Analysis |
| B | RW Feld1 alum i.p. | RW Feld1 alum i.p. | PBS s.c. | Feld1 i.n. | PBS s.c. | Feld1 i.n. | Analysis |
| C | RW Feld1 alum i.p. | RW Feld1 alum i.p. | QβG10 s.c. | RW i.n. | QβG10 s.c. | RW i.n. | Analysis |
| D | RW Feld1 alum i.p. | RW Feld1 alum i.p. | QβG10 s.c. | Feld1 i.n. | QβG10 s.c. | Feld1 i.n. | Analysis |
| E | RW Feld1 alum i.p. | RW Feld1 alum i.p. | QβG10 RW s.c. | RW i.n. | QβG10 RW s.c. | RW i.n. | Analysis |
| F | RW Feld1 alum i.p. | RW Feld1 alum i.p. | QβG10 RW s.c. | Feld1 i.n. | QβG10 RW s.c. | Feld1 i.n. | Analysis |
| G | RW Feld1 alum i.p. | RW Feld1 alum i.p. | QβG10 Feld1 s.c. | RW i.n. | QβG10 Feld1 s.c. | RW i.n. | Analysis |
| H | RW Feld1 alum i.p. | RW Feld1 alum i.p. | QβG10 Feld1 s.c. | Feld1 i.n. | QβG10 Feld1 s.c. | Feld1 i.n. | Analysis |

Example 20

Comparison G10 and QβG10

The effects of G10 and QβG10 were compared in the ragweed allergic model. Three groups of mice were sensitized with ragweed on day 0 and day 3 by i.p. injection of ragweed mixed with alum. On day 10 and 12, mice from group B and C were treated with G10 or QβG10 respectively. Mice from group A received PBS as control. All mice were challenged with 200 μg of RW by i.n. administration and two days after the challenge mice were sacrificed. Infiltrating cells and IL-4 concentration in BAL and IgE level in blood were analysed (Table 16).

As shown in Table 17, whereas the total amount of cells in BAL was not significantly changed in G10 treated mice, it was strongly reduced in QβG10 treated mice compared to PBS control mice (32%, p<0.05). Similarly, the amount of eosinophils was strongly reduced (64.1%, p<0.01) in QβG10 treated compared to PBS control mice and the changes in G10 treated mice were not significant (Table 18). Thus, whereas non-packaged G10 had not significant effects on infiltrating cells in BAL, G10 packaged in Qβ prevented cells infiltrating to the lung. As shown in Table 19, whereas the changes of IgE level in mice treated with G10 were not significant, the QβG10 treated mice had significantly (p<0.001) reduced blood IgE levels in comparison with PBS treated mice. As shown in Table 20, whereas the changes of IL4 level in BAL from mice treated with G10 were not significant, the QβG10 treated mice had significantly (p<0.001) reduced BAL IL-4 levels in comparison with PBS treated mice. Therefore, when G10 was packaged in Qβ, it reduced the pathological markers of asthma and allergy.

TABLE 16

Experimental design.

| | Day 0 | Day 3 | Day 10 | Day 12 | Day 14 | Day 16 |
|---|---|---|---|---|---|---|
| A | RW alum i.p. | RW alum i.p. | PBS s.c. | PBS s.c. | RW i.n. | Analysis |
| B | RW alum i.p. | RW alum i.p. | G10 s.c. | G10 s.c. | RW i.n. | Analysis |
| C | RW alum i.p. | RW alum i.p. | QβG10 s.c. | QβG10 s.c. | RW i.n. | Analysis |

TABLE 17

Total Cell Counts in BAL and changes relative to group A.

| | Group A | Group B | Group C |
|---|---|---|---|
| mouse 1 | 402000 | 439500 | 274500 |
| mouse 2 | 358500 | 325500 | 319500 |
| mouse 3 | 309000 | 357000 | 112500 |
| mouse 4 | 306000 | 196500 | 274500 |
| mouse 5 | 337500 | 279000 | 177000 |
| average | 342600 | 319500 | 231600 |
| % reduction | | 7 | 32 |

TABLE 18

Eosinophils in BAL and changes relative to group A.

| | Goup A | Group B | Group C |
|---|---|---|---|
| mouse 1 | 158020 | 146095 | 37134 |
| mouse 2 | 109612 | 76898 | 65099 |
| mouse 3 | 85261 | 95275 | 20344 |
| mouse 4 | 72211 | 43605 | 33118 |
| mouse 5 | 97900 | 53716 | 31945 |
| average | 104601 | 83118 | 37528 |
| % reduction | | 20.5 | 64.1 |

TABLE 19

IgE Concentration (μg/ml) and changes relative to group A.

|  | Goup A | Group B | Group C |
|---|---|---|---|
| mouse 1 | 0.93 | 0.49 | 0.16 |
| mouse 2 | 0.86 | 0.30 | 0.11 |
| mouse 3 | 0.82 | 0.66 | 0.17 |
| mouse 4 | 0.44 | 0.52 | 0.18 |
| mouse 5 | 0.54 | 0.49 | 0.19 |
| average | 0.72 | 0.49 | 0.16 |
| % reduction |  | 31.6 | 77.6 |

TABLE 20

IL-4 Concentration (pg/ml) in BAL and changes relative to group A.

|  | Goup A | Group B | Group C |
|---|---|---|---|
| mouse 1 | 17.7 | 24.9 | 1.4 |
| mouse 2 | 26.2 | 25.0 | 1.6 |
| mouse 3 | 51.2 | 35.9 | 1.5 |
| mouse 4 | 37.6 | 6.5 | 4.3 |
| mouse 5 | 49.1 | 4.9 | 2.4 |
| Average | 36.4 | 19.4 | 2.2 |
| % reduction |  | 46.5 | 93.8 |

Example 21

Treatment of Cat Allergy with QβG10

Mice are sensitized by intraperitoneal injection with 5 μg of Fel d1 on day 1 and 14, and then boosted intranasally with 1 μg of Fel d1 on days 28, 29, 30 and 33. Mice are injected subcutaneously with 375 μg of QβG10 or PBS on days 37, 39 and 41. On day 43, mice are challenged intranasally with 1 μg of Fel d1 and the core temperature of the mice is measured rectally using a rectal probe digital thermometer. Mast cell degranulation is monitored in the cat allergy model. Mice are injected subcutaneously with 375 μg of QβG10 on day 0 and day 3. On day 5, mice are injected intradermally with 50 μl of 1:5 diluted cat allergic sera or purified IgE from that serum or control serum. 4 or 24 h later, mice are injected intravenously with 10 μg of Fel d1 plus Evans blue dye. The mice are sacrificed 30 min after the intravenous challenge and the blue staining reaction is analyzed. QβG10 treated mice have reduced blue staining as compared to untreated mice.

Example 22

Treatment of Bee Venom Allergy with QβG10

Female 6 to 8 week-old CBA/J mice are obtained from Harlan (Zeist, The Netherlands). Animals are sensitized every other week by s.c. injection in the ventral region and at the base of the tail of 0.1 μg PLA2 adsorbed to 1 mg alum. Two protocols are applied for QβG10 therapy. First, presensitized mice receive daily s.c. injections of 375 μg of QβG10 for 6 consecutive days. IgE levels are measured 48 hours after the last QβG10 injection. Second, naive mice are injected s.c. with 375 μg of QβG10 on day 0 and day 3. Two weeks after the last QβG10 injection, mice are sensitized with PLA2 in alum. IgE levels are measured 7 days after PLA2 sensitization. Control groups receive either PBS or 30 μg native PLA2. For the induction of anaphylactic responses, animals are injected i.p. with 30 μg native PLA2 in PBS, and rectal temperature is monitored with a calibrated digital thermometer. In comparison to untreated mice, the temperature drop in QβG10 treated mice is less pronounced.

Example 23

Treatment of House Dust Mite Allergy with QβG10

Male CBA/CaH mice are sensitized with an intraperitoneal injection of 5 μg of Der P1+1 mg of alhydrogel. For intranasal instillations, 25 μl aliquots containing 5 μg of Der P1 or sterile saline are applied to the noses of anesthetized mice. Two protocols are applied QβG10 therapy. First, presensitized mice receive daily s.c. injections of 375 μg of QβG10 for 6 consecutive days in. IgE levels are measured 48 hours after the last QβG10 injection. Second, naive mice are injected s.c. with 375 μg of QβG10 on day 0 and day 3. Two weeks after the last QβG10 injection, mice are sensitized with Der P1 in alum. IgE levels are measured 7 days after Der P1 sensitization. QβG10 treated mice exhibit lower IgE concentrations than the untreated control.

Example 24

Treatment of a Patient Suffering from Atopic Dermatitis with QβG10 and Assessment of Efficacy 24.1 Assessment of Symptoms of Atopic dermatitis: Total body involvement is estimated with the use of shapes of 100 to 1000 cm$^2$ or by the rule of nine which assigns standard measurements to body parts on the basis of the size of the body part. The total body score is the sum of the individual scores, on a scale of 0 to 3, for erythema, edema, pruritus, oozing crusting, excoriation, and lichenification of all involved skin, dryness of noninvolved skin, and sleep loss. The investigator grades affected skin areas of the test persons on a scale of 0 to 3 for the severity of erythema, edema, oozing or crustating, excoriation, and lichenification of involved skin and dryness of noninvolved skin. The test persons grade the pruritus of the selected areas on a 10-cm visual analogue scale, with severe at the bottom and absent at the top; this grade is converted to a score of 0 to 3 for analysis. To ensure consistency in the assessment of efficacy, all the investigators receive a manual and participate in a on-day, centralized training course, as well as on-site training.

24.2 Treatment with QβG10: A group of test persons suffering from Atopic dermatitis is treated at least three times in intervals of 1 week with 300 μg QβG10 (Qβ VLP packaged with G10 (SEQ ID NO:27)), a control group with comparable symptoms is treated with placebo. Dependent on the average symptom score of the test group the treatment of the test group can be repeated up to a total of 6 to 10 vaccinations with 300 μg QβG10 each; the control group is always treated with placebo in parallel.

24.3 Assessment of Efficacy: Total body involvement is assessed before the first treatment and at the end of the study. The symptoms on selected skin areas individually chosen for each patient are assessed directly before each treatment and in intervals up to 3 months after the last treatment. The changes in the symptom scores of the test group at the beginning and at the end of the study are compared to that of the control group.

Example 25

Efficacy Parameters Atopic Dermatitis

The Physician's Global Assessment (PGA) of Atopic Dermatitis (AD): The investigator will rate the overall disease severity using the scale described in Table 21. The rating is to be assigned in consideration of the patient's current condition, without reference to previous assessments.

Eczema Area and Severity Index (EASI): The extent and severity of dermatitis over 4 body surface areas will be calculated using the Eczema Area and Severity Index (EASI) (Hanifin J. M. et al. (2001), Exp. Dermatol. 10:11-18). The four body regions are assigned proportionate body surface areas (BSA) such that the head and neck together comprise 10% BSA, the front and back of the trunk each comprise 15% BSA, each arm comprises 10% BSA, and each leg comprises 20% BSA. The percentage of area involved for each of the body regions is given a score, ranging from 0 to 6, where 0=no eruption, 1=<10%, 2=10% to 29%, 3=30% to 49%, 4=50% to 69%, 5=70% to 89%, and 6=90% to 100%. The four key symptoms of atopic dermatitis to be assessed are: Erythema, Induration/papulation, Excoriation (linear abrasions of the skin due to scratching), and Lichenification. Each of these symptoms will be scored at each of the four body regions using a scale of 0 to 3, with half-steps allowed, where 0=none, 1=mild, 2=moderate, and 3=severe. The definitions outlined in Table 22 will be used.

The score for each body region is obtained by multiplying the sum of the severity scores of the four key symptoms by the percentage of area involved on the body region, then multiplying the result by the constant weighted value assigned to the particular body region (see Table 23). The EASI score is the sum of the four body region scores.

Patient's Assessment of Pruritus Score: At each study visit, the patient will be asked to assess the severity of pruritus since the last visit using the scale shown in Table 24.

TABLE 21

Physician's Global Assessment (PGA) of Atopic Dermatitis.

| Score | Grade | Definition |
|---|---|---|
| 0 | Clear | No inflammatory signs of atopic dermatitis |
| 1 | Almost clear | Just perceptible erythema, and just perceptible papulation/induration |
| 2 | Mild disease | Mild erythema, and mild papulation/induration |
| 3 | Moderate disease | Moderate erythema, and moderate papulation/induration |
| 4 | Severe disease | Severe erythema, and severe papulation/induration |
| 5 | Very severe disease | Severe erythema, and severe papulation/induration with oozing or crusting |

TABLE 22

Severity scoring of key symptoms.

| | Erythema | Induration/Papulation | Excoriation | Lichenification |
|---|---|---|---|---|
| None (0) | No evidence of erythema | No perceptible elevation | No evidence of excoriations | No evidence of skin thickening |
| Mild (1) | Very light pink, faintly detectable erythema | Barely perceptible elevation | Scant evidence of excoriations with no sign of deeper skin damage (ie, erosion, crust) | Slight thickening of the skin, discernible only by touch and with markings minimally exaggerated |
| Moderate (2) | Dull red, clearly distinguishable erythema | Clearly perceptible, but not extensive, elevation | Several linear marks of skin, with some showing evidence of deeper skin injury (ie, erosion, crust) | Definite thickening of the skin, with skin markings exaggerated so that they form a visible criss-cross pattern |
| Severe (3) | Deep, dark red | Marked and extensive elevation | Many erosive or crusty lesions | Thickening indurated skin with skin markings visibly portraying an exaggerated criss-cross pattern |

TABLE 23

Eczema Area and Severity (EASI) Calculation (patients of 8 years and older).

| Body region | EASI Score[a,b] |
|---|---|
| Head/neck | (E + IP + Ex + L) × Area × 0.1 |
| Upper limbs | (E + IP + Ex + L) × Area × 0.2 |
| Trunk | (E + IP + Ex + L) × Area × 0.3 |
| Lower limbs | (E + IP + Ex + L) × Area × 0.4 |
| EASI = | Sum of the above 4 body region scores |

[a]Symptoms: E = erythema, IP = induration/papulation, Ex = excoriation, L = lichenification.
[b]Area: 0 = no eruption, 1 = <10%, 2 = 10%-29%, 3 = 30%-49%, 4 = 50%-69%, 5 = 70%-89%, and 6 = 90%-100%.

TABLE 24

Patient Assessment of Pruritus Score.

| Score | Grade | Definition |
|---|---|---|
| 0 | None | No pruritus |
| 1 | Mild | Clearly present but minimal awareness; occasional, slight itch |
| 2 | Moderate | Definite awareness that is bothersome but tolerable; does not disturb sleep |
| 3 | Severe | Hard to tolerate; interferes with sleep |

Example 26

Treatment of Test Persons Suffering from Atopic Dermatitis with QβG10 and Assessment of Efficacy Treatment with QβG10: A double-blind parallel-group clinical trial is performed with 36 patients with atopic dermatitis. Patients are allocated randomly to two groups of 18 patients each. The first group is treated with 300 μg QβG10 (Qβ VLP filled with G10 (SEQ ID NO:27)) six times in intervals of 1 week. The second group is treated with placebo.

Assessment of Efficacy: Physician Global Assessment (PGA), EASI Scores, and Patient's assessment of pruritus (see Example 25) are performed prior to the first treatment, bi-weekly during the treatment period, and several times after treatment until the end of the study at 24 weeks after the first treatment. The changes in the symptom scores from before the treatment are compared between the groups at the various assessment points after the treatment.

Example 27

Treatment of Test Persons Suffering from Asthma with QβG10 or Ap205G10 and Assessment of Efficacy Using a Standardized Asthma Quality of Life Questionnaire 27.1 Assessment of Asthma Symptoms: Asthma symptoms are assessed using the standardized Asthma Quality of Life Questionnaire (AQLQ(S) or AQLQ12+, Juniper et al., Health Qual. Life Outcomes September 2005 3:58).

27.2 Treatment with QβG10 or AP205G10: Two test groups and one control group of persons suffering from asthma and showing comparable symptom score with AQLQ(S) or AQLQ12+ are treated with VLPs of bacteriophage Qβ packaged with G10 (SEQ ID NO:27), VLPs of bacteriophage AP205 packaged with G10 (SEQ ID NO:27) or placebo, respectively. QβG10 and AP205G10 are produced according to Examples 16 and 17 of WO03/024481 or preferably according to the Examples herein. The test persons are treated at least three times with 300 μg QβG10 or 300 μg AP205G10 in intervals of 1 week. Dependent on the average symptom score of the test group the treatment of the test group can be repeated up to a total of 6 to 10 vaccinations with 300 μg VLP-G10 each; the control group is always treated with placebo in parallel.

27.3 Assessment of Efficacy: All test persons are scored using the AQLQ(S) or AQLQ12+ method directly before each treatment and 1 and 3 months after the last treatment. The development of the average score in the two groups treated with CpG packaged VLPs and the control group are compared.

Example 28

Assessment of Asthma Symptoms

The severity of asthma symptoms can be assessed by spirometric measurements before and after administration of methacholine according to the following protocol.

Step 1: Preparation of Test Solution
Remove the test solution (methacholine) from the refrigerator 20 minutes before testing and bring it to room temperature;
Check the expiry date of the test solution;

Step 2: Preparation of Test Patient
Let patient adapt to room climate for 10 min;
Perform the respiratory spirometer test (see Appendix 11.4 Respiratory Spirometry);
Exclude contraindications for methacholine testing (relevant airway obstruction, acute infection, pregnancy, β-blocker or anti-cholinergic medication) (cholinergic or anticholinergic);

Step 3: Preparation of "Dosimeter Mefar MB3"
Switch on machine by pressing the two yellow buttons ("unit", "compressor") on the right and wait till the pressure reaches 25 kg/cm$^2$;
define inhalation time by pressing the grey numbered buttons 05, then define the time of pause 050 and inhalation time (N. inhale) 02, press "Reset"
Prepare the inhalation set by filling in lower plastic piece of the inhalation set 1.5 ml of NaCl 0.9%, screw on upper part with the same number, then put on linking and mouth piece and hose that connects the inhalation instrument with the machine
Press the button for "Air Tank Release"

Step 4: Negative Control and Instruction of the Patient
Perform negative control with NaCl 0.9% by asking the patient to enclose the mouth piece with his lips and take a deep breath. While taking a deep breath press button; "Emergency Manual Thermistor";
Repeat once (see dose protocol below), then press "End" and "Reset 02";
Wait for 2 minutes, then repeat the respiratory spirometer test;

Step 5: Provocation with Methacholine
Fill in lower piece of inhalation set 1.5 ml of methacholine concentration 10 mg/ml and screw set back together and press "Air Tank Release";
Ask the patient to enclose the mouth piece with his lips and to take a deep breath. While taking a deep breath press button "Emergency Manual Thermistor";
Repeat once (see dose protocol below, Table 25), then press "End" and "Reset 02";
Wait for 2 minutes, then repeat the respiratory spirometer test;

TABLE 25

Dosage protocol for methacholine challenge.

| Methacholine concentration | Number of inhalations | Dose per inhalation | Total dose | Cumulative dose |
|---|---|---|---|---|
| NaCl 0.9% | 2 | — | — | — |
| 10 mg/ml | 2 | 50 μg | 100 μg | 100 μg |
| 10 mg/ml | 3 | 50 μg | 150 μg | 250 μg |
| 50 mg/ml | 1 | 250 μg | 250 μg | 500 μg |
| 50 mg/ml | 2 | 250 μg | 500 μg | 1000 μg |
| 50 mg/ml | 4 | 250 μg | 1000 μg | 2000 μg |

Flowchart for the Respiratory Spirometry (RS)
Step 1: Preparation
Calibrate the spirometer daily before use
Step 2: Test
Ask the subject to sit in an upright position, breathing normally;
Instruct the subject to inhale as much as possible, and then to exhale into the spirometer as rapidly and completely as possible, until all air is exhaled;
Repeat two more times (total 3 times);
Step 3: Result
Define the best effort (defined as the greatest $FEV_1/FVC$ ratio). If the greatest $FEV_1/FVC$ ratio is seen in more than one effort, the best effort will be the one with the highest $FEV_1$;
If the greatest $FEV_1/FVC$ ratio is LESS than 70% of normal categorize as "relevant airway obstruction" and prove exclusion criteria. Otherwise continue;
Subtract 20% off of measured $FEV_1$ and define it as $FEV_1$-20%;
Transcribe the measured $FEV_1$, the "$FEV_1$-normal" and the calculated $FEV_1$-20% onto prepared sheets ("Methacholine-(Broncho) Provocation Test");

Example 29

Treatment of Test Persons Suffering from Asthma with QβG10 or Ap205G10 and Assessment of Efficacy Using Spirometry after Methacholine Challenge 29.1 Assessment of Asthma Symptoms: Asthma symptoms are assessed by Spirometry with measurements obtained before and after the administration of methacholine according to Example 28. Determined are the parameters FEV1 and the ratio of FEV1 to the forced vital capacity FVC expressed as a percentage of the predicted value. Additionally, the test persons (or their parents or guardians) complete a diary card each day throughout the study recording night awakenings due to asthma, morning and evening peak flows as measured by peak-flow meters, use of medication, use of rescue medicine (albuterol) for symptoms and to prevent exercise-induced bronchospasm, use of prednisone, absence from school/work due to asthma, visits to a physician's office or hospital because of asthma and severity of symptoms. Test persons use their usual medication throughout the study.

29.2 Treatment with QβG10 or AP205G10: see Example 27.2.

29.3 Assessment of Efficacy: Spirometry data of all test persons are obtained directly before each treatment, diary data are obtained 1 month before the first treatment until 3 month after the last treatment on a daily basis. Analyzed are, for example, the number of asthma related night awakenings per month, the number of episode-free days and the morning peak flow. Average data of the two groups treated with CpG packaged VLPs are compared to the placebo group.

Example 30

Skin Prick Test

A skin prick test (SPT) is performed to verify that a subject shows hypersensitization to a certain allergen. The test is useful to test the reaction of a patient to a wide range of allergens, including pollen allergen and allergen mix that is routinely used to screen for atopy. The test is useful to test the reaction towards dust mite allergens (Der p and Der f). At Screening this test must be performed prior to CPT (Example 31). Skin prick tests and intradermal skin tests allow a visualisation of sensitisation. The basic principle of skin testing is the introduction of a small amount of allergen into the dermis. The released mediators cause vasodilatation and increase vascular permeability, which in turn leads to tissue edema and the development of a weal. Histamine triggers the release of the neuromediator substance P by an axon reflex, which causes the surrounding skin to flush.

A small drop of about 30 μl of serial dilutions of the allergen is placed on the volar surface of the forearm. The test sites must be at least 2 cm apart to avoid false-positive reactions. Using a so called prick needle, i.e. a needle that can be perpendicularly inserted into the skin, the allergen solution is "pricked" into the dermis, giving highly reproducible results. For a negative control, the diluent of the allergen solution is used. Histamine is used as a positive control to detect suppression of cutaneous reactivity by medications (mainly anti-histaminic drugs). A histamine solution at 1 mg/ml induces a weal ranging from 2-7 mm in diameter.

Areas of weal and flare reactions will be recorded after 15 min. To obtain a permanent record, the size of the wheal as well as the flare is outlined on the skin with a pen, then blotted onto a cellophane tape and stored on paper. Both the area of the wheal and the flare will be assessed by planimetry. Therefore the reactions are scanned by a computer and the surface areas are measured using commercial software. A weal size of 7 mm2 or greater is regarded as positive.

Knowing that inter-individual variation in the skin response to histamine is considerable, the reaction will then be scored as a percentage of the positive control. The evaluation of the end-point titrations will be based on parallel line bioassay and on median slope.

Flowchart for Skin Prick Test (SPT)
Step 1: Preparation
  Ask Patient about recently taken medication (corticosteroids, anti-allergic therapy, neuroleptical and antidepressant therapy) and exclude contraindications for SPT;
  Check test solutions (expiry date, control temperature, body temperature required);
  Clean test site (volar side of arm) with alcohol. Use a pen to mark those areas of the arm where allergens are to be pricked. These prick sites should be at least 2 cm apart.;
  The concentrations to be used for dust mites will be 1:1000, 1:100, 1:10 and 1:1;
Step 2: Test
  A drop of the allergen solution is placed onto each of the marked areas of the skin. A sterile prick lancet with 1 mm point is used to prick the drop into the skin. This should not cause any bleeding. The lanced is wiped with an alcohol swab between pricks, in order to prevent carry-over of allergens;
  The house dust mite allergen tests will be performed with allergen concentrations of 1:1000, 1:100, 1:10 and 1:1;
  A positive (histamine) and negative control (diluent) must be included;
  After 1 minute the solutions must be blotted, not wiped, off the test site;
  Wait for 30 minutes;
Step 3: Result
  Wipe test site with alcohol, then with wound benzine, draw a line around the erythema and edema with a marker pen;
  Stick clear scotch tape over test site, then rip it off and stick it onto a paper sheet;
  Determine the diameter and/or the area of the erythema and edema. Record the measurements in the source document and transcribe onto the case report form;
  Itching test sites can be treated topically with anti-histamine gel;
  The allergic reaction is always assessed with respect to the control reaction (diluent only). Typically, subjects are considered allergic if they exhibit at least one edema or erythema of at least 6 mm diameter or at least one edema or erythema with an area of at least 7 mm$^2$.

Example 31

Conjunctival Provocation Test

The response of a subject to an allergen can be assessed using the so called conjunctival provocation test which is performed according to the following procedure. The test is useful to test the reaction of a patient to a wide range of allergens, including pollen allergen. The test is useful to test the reaction towards dust mite allergens (Der p and Der f).
Flowchart for the Conjuctival Provocation Test (CPT):
Step 1: Preparation
  Let patient adapt to room climate for 10 min;
  Check test solutions (expiry date, control temperature, body temperature required);
  Confirm that the eye is without irritation at the beginning of the provocation;
  Exclude contraindications for CPT (any eye disease except for anomalies of refraction or allergic conjunctivitis, contact lenses, anti-allergic therapy);
Step 2: Control
  Administer 50 μl of control solution identical to the allergen solution except for allergen content in the lower conjunctival sac of left eye (control eye);

Step 3: Provocation with Allergen Concentration 1
  Immediately after application of control solution, administer 50 µl of allergen solution concentration 1 in the lower conjunctival sac of the right/opposite eye (provocation eye);
  Inform the patient not to rub his/her eye;
  Wait for 10 min, then fill out the two symptom scores for CPT;
Step 4: Response to Provocation with Allergen
  If positive, administer topical antihistamine and stop CPT;
  If negative, repeat provocation with the next higher allergen concentration in provocation eye until concentration 4 (see step 5);
  If negative after provocation with concentration 4, categorize as negative and stop;
Step 5: Provocation with Next Higher Allergen Concentration
  administer 50 µl of allergen solution with next higher concentration/number in the lower conjunctival sac of the opposite eye (provocation eye);
  Inform the patient not to rub his/her eye;
  Wait for 10 min, then fill out the two symptom scores for CPT (see step 4);
Categorization of the Response to Allergen in the CPT (Stage Criteria)
0: no subjective or visible reaction;
I: itching, reddening, foreign body sensation;
II: stage I and in addition tearing, vasodilatation of conjunctiva bulbi;
III: stage II and in addition vasodilation and erythema of conjunctiva tarsi, blepharospasm;
IV: stage III and in addition chemosis, lid swelling;

The stages are determined for the following solutions (dilution factor of the standard allergen solution): Negative Solution; Concentration I: 1:1000, Concentration II: 1:100; Concentration III: 1:10; and Concentration IV: 1; The CPT is positive if the response is stage II or higher.

Symptoms are scored using the Score Sheet for CPT (Table26) which provides for scores from 0 to 3 for 5 different parameters. Thus, the maximum score is 15 per challenge. The CPT is positive if the total response is >10.

TABLE 26

CPT Score Sheet - Challenge Symptom Questionnaire.

| Symptom | None | Mild (1) | Moderate (2) | Severe (3) | 10' Score |
|---|---|---|---|---|---|
| Conjunctival hyperemia | none | Slight redness | Definite redness | severe redness | |
| Tearing | none | Slight sensation | Definite sensation | need to whipe off | |
| Itching | none | Slight sensation | Definite sensation | need to rub eyes | |
| Burning | none | Slight sensation | Definite sensation | severe sensation | |
| Swelling of eyelids | none | Slight sensation | Definite sensation | unable to open eyes | |

Example 32

Nasal Provocation Test

Nasal provocation test is useful to test the reaction of a patient to a wide range of allergens, especially pollen allergens. The nose provides an ideal site for allergen provocation. Allergen can be applied to the mucosa with a high degree of accuracy. The challenge procedure should reflect natural exposure. Quantitative measurements with high reproducibility are important (Andersson M, L. Greiff, C. Svensson and C. Persson. Acta Otolaryngol. 115 (1995), pp. 705-713). Recently, Bousquet (Bousquet J, P. van Cauwenberge and N. Khaltaev. Aria Workshop Group; WHO, J. Allergy Clin. Immunol. 108 (2001), pp. S147-334.) and the ARIA Workshop Group have presented a document on allergic rhinitis and its impact on asthma (Bousquet et al., 2001), presenting guidelines from a subcommittee of the "International Committee on Objective Assessment of the Nasal Airways" for nasal provocation tests concerning indications, techniques, and evaluation of the tests (Malm L, R. Gerth van Wijk and C. Bachert. Rhinology 38 (2000), pp. 1-6.). Also, the German Society for Allergology and Clinical Immunology worked out a position paper together with the Working Group for Clinical Immunology, Allergology and Environemental Medicine of the German Society for Ear, Nose and Throat (Reichelmann et al. Position statement. Allergo J (2002) 11:29-36.).

Deposition of the allergen and allergen dosing: The solutions of allergen will be delivered from a meter-dose pump spray, as the nasal pump spray delivers the solution over a large area of the nasal mucosa. The allergen solution will be an isotonic, buffered aqueous solution with a neutral pH. Serial 1:3 dilutions with saline will be freshly prepared prior to testing. The exact allergen concentrations are to be determined in a previous study. The allergen solution will be applied at a volume of 100 µl.

Contraindications for NPT: Episode of rhinitis in last 4 weeks; Exacerbation of allergic disease; Use of allergen known to have caused anaphylactic reaction; Pregnancy; Nasal surgery in last 8 weeks; Coexisting severe general disease, especially cardiopulmonary diseases; Treatment with medications that may interfere with the treatment of systemic allergic reactions (e.g. β-blockers or ACE inhibitors); Vaccinations within one week prior to testing.

Withdrawal period for medications known to interfere with nasal provocation testing: Antihistamines, systemic: 48 hours to 1 week depending on their half life; Antihistamines, nasal: 1 week; Ketotifen: 2 weeks; DNCG, Nedocromil: 3 days; Corticosteroids, nasal: 1 week; Corticosteroids, systemic 1 week; Topical β-adrenergic agonists: 1 day; Nonsteroidal antiinflammatory drugs (NSAIDs): 1 week; Antihypertensives (e.g. reserpine, clonidine): 3 weeks; Antidepressants (e.g., imipramines, tricyclics): 3 days.

Technique and Practical Protocol of Nasal Provocation Testing

Rhinoscopic examination including anterior or posterior rhinoscopy, preferably anterior rhinoscopy, will be performed preceding NPT in order to evaluate the baseline condition. Patients should be well adapted to room temperature for at least 15 minutes before a baseline evaluation by rhinoscopy and a clinical symptom score, as well as rhinomanometry. The wider side of the nose is used for the challenge. Before administration of the actual allergen solution, the nasal mucosa of the wider side of the nose is challenged for unspecific hyperresponsiveness by 100 µl of the allergens diluent. Evaluation of the scores and rhinomanometry is repeated after 10 minutes to check on clinical symptoms or significant changes in objective measurements of nasal patency. If no significant changes occur, the actual allergen provocation is performed on the wider side of the nose. The applicator of the delivery device is inserted into the nasal vestibulum and pointed upward and laterally towards the medial canthus of the eye to deposit allergen on the inferior and the middle turbinate mucosa when spraying 100 µL of allergen test solution into the nose. During allergen application, the patient must hold his or her breath to avoid inhaling the allergen into the lower airways. Patients are told to inhale before and to exhale right after the application.

Measurements of Response

Nasal symptom recording will be performed in parallel according to three common methods (Bachert C: Nasal provocation test: critical evaluation. In Ring J, Behrendt H D, editors: New trends in allergy, IV, Berlin, 1997, Vieluf Springer-Verlag, p 277).

Score 1: Severity of each nasal symptom is recorded on a 10-cm linear visual analog scale. The severity is then evaluated based on the score (mild 1-3 cm; moderate 4-7 cm; severe 8-10 cm) obtained with diluent (negative control) and each provocation dose.

Score 2: A practical scoring system for a standardized quantification of these clinical parameters, which has been proposed by the ENT section of the German Society for Allergology and Clinical Immunology is summarized in Table27 (Reichelmann et al. Position statement. Allergo J (2002) 11:29-36.).

TABLE 27

Scoring system for evaluation of clinical symptoms after nasal provocation ("Score 2").

| Symptom | Severity | Score (points) |
| --- | --- | --- |
| Secretion | No secretion | 0 |
|  | Little secretion | 1 |
|  | Heavy secretion | 2 |
| Irritation | 0-2 sneezes | 0 |
|  | 3-6 sneezes | 1 |
|  | >5 sneezes | 2 |
| Extranasal symptoms | None | 0 |
|  | Tearing/itching | 1 |
|  | Conjunctivitis/chemosis +− | 2 |
|  | Urticaria +− |  |
|  | Coughing/dyspnoea |  |

Score 3: This score is often used in both clinical and scientific research studies (Linder, 1988). The end point is considered the amount of stimulant that produces a total symptom score of 5 from a maximum score of 13 points (Table 28).

TABLE 28

Scoring system for evaluation of clinical symptoms after nasal provocation ("Score 3").

| Nasal symptom | Point score |
| --- | --- |
| Sneezing |  |
| 0 to 2 sneezes | 0 |
| 3 or 4 sneezes | 1 |
| 5 or more sneezes | 3 |
| Pruritus |  |
| Nose | 1 |
| Palate | 1 |
| Ear | 1 |
| Rhinorrhea | 0 to 3 |
| Nasal Blockage | 0 to 3 |
| Ocular Symptoms | 1 |

Rhinorrhea: 0 = mild, 1 = moderate, 3 = severe; sneezing: 0 = ≤2 sneezes; 1 point = 3-5 sneezes; 2 points = >5 sneezes). Other symptoms include itching or tearing (1 point) and conjunctivitis, cough, urticaria, or dyspnea (2 points).

Rhinorrhea: 0=mild, 1=moderate, 3=severe; sneezing: 0=0-2 sneezes; 1 point=3-5 sneezes; 2 points=>5 sneezes). Other symptoms include itching or tearing (1 point) and conjunctivitis, cough, urticaria, or dyspnea (2 points).

End Point: After the allergen challenge the end point is reached when the patient has more than 3 points in score 2, or if the reduction in nasal flow rate is >40% at 150 Pa. The end point shall also be reached, if the reduction in nasal flow rate is >20% at 150 Pa in conjunction with >2 points in score 2.

Objective measurement of nasal patency: Nasal air-space volume and patency will be assessed by anterior rhinomanometry. It is designed to analyze the transnasal airflow in one nostril at a time depending on transnasal pressure, which is assessed contralaterally during tidal breathing. For complete and state of the art evaluation of nasal patency, this method is combined with acoustic rhinometry, which documents nasal geometry as cross-sectional area within the nasal cavity.

Results of both methods, anterior rhinomanometry and acoustic rhinometry, are visualized graphically to facilitate analysis and documentation. Measurements before and after NPT can be easily compared and accurately assessed using these graphs in combination with the exact numbers for nasal airflow (cm3/s) and cross-sectional area (cm2), which are computed by the respective analyzers.

Example 33

Treatment of a Test Person Suffering from Pollen Allergy and Atopic Eczema with QβG10 and Assessment of Efficacy Using a Nasal Provocation Test An individual suffering from pollen allergy and atopic eczema was treated four times by subcutaneous injection of 300 μg QβG10 in 1 week intervals. A skin prick test according to Example 30 and nasal provocation test according to Example 32 were performed on the day before the first treated to determine a baseline. The nasal provocation test was performed with a commercial challenging agent containing pollen allergen in dilutions of 1:1000, 1:100, 1:10 and 1:1 and repeated 1 week after the second treatment (directly before the third treatment) and 1 week after the fourth treatment. The reaction of the test person was scored using score 2 and score 3 as described in Example 32. Additionally, the number of sneezes was recorded (Table 31). As shown in Tables 29-31 all three parameters indicate a significant reduction of the test person's reaction to allergen challenge. Additionally, the test person who is typically suffering from atopic eczema, with symptoms developing in early winter, reported to be totally free of symptoms of atopic eczema after the study, which was performed in late autumn. The latter observation is an indication for a prophylactic effect of the treatment with respect to atopic eczema.

TABLE 29

Scoring result after nasal provocation test (Score 2).

|  | 1:1000 | 1:100 | 1:10 | 1:1 |
| --- | --- | --- | --- | --- |
| baseline | 1 | 2 | 6 | 4 |
| 1 week after 2nd treatment | 0 | 0 | 1 | 6 |
| 1 week after 3rd treatment | 0 | 0 | 0 | 1 |

TABLE 30

Scoring result after nasal provocation test (Score 3).

|  | 1:1000 | 1:100 | 1:10 | 1:1 |
| --- | --- | --- | --- | --- |
| baseline | 2 | 7 | 9 | 9 |
| 1 week after 2nd treatment | 0 | 1 | 4 | 9 |
| 1 week after 3rd treatment | 0 | 0 | 0 | 2 |

TABLE 31

Number of sneezes after nasal provocation test.

|  | 1:1000 | 1:100 | 1:10 | 1:1 |
|---|---|---|---|---|
| baseline | 1 | 2 | 6 | 1 |
| 1 week after 2nd treatment | 0 | 0 | 1 | 7 |
| 1 week after 3rd treatment | 0 | 0 | 0 | 0 |

Example 34

Treatment of Test Persons Suffering from Pollen Allergy with QβG10 and QβG8-8 and Assessment of Efficacy Using a Nasal Provocation Test 34.1 Treatment with QβG10 QβG8-8: After determination of a base line with skin prick and nasal provocation test (see Examples 30 and 32) three groups of test persons suffering from pollen allergy are formed, wherein all groups show a similar test score in average. The first group is treated at least three times in intervals of 1 week with 300 μg QβG10 (Qβ VLP packaged with G10 (SEQ ID NO:27)). The second group is treated in parallel with 300 μg Qβ packaged with G8-8 (SEQ ID NO 25). The third group is treated with placebo. Dependent on the average symptom score of the test group during the study the treatment of the test group can be repeated up to a total of 6 to 10 vaccinations with 300 μg of QβG10 or QβG8-8, respectively; the control group is always treated with placebo in parallel.

34.2 Assessment of Efficacy: Nasal provocation test is performed before each treatment and in intervals up to 3 months after the last treatment. The changes in the symptom scores of the test group at the beginning and at the end of the study are compared to that of the control group.

Example 35

Treatment of Test Persons Suffering from House Dust Allergy with QβG10 and QβG8-8 and Assessment of Efficacy Using the Conjunctival Provocation Test 35.1 Treatment with QβG10 QβG8-8: After determination of a base line with skin prick and conjunctival provication test (see Examples 30 and 31) three groups of test persons suffering from house dust allergy are formed, wherein all groups show a similar test score in average. The first group is treated at least three times in intervals of 1 week with 300 μg QβG10 (Qβ VLP packaged with G10 (SEQ ID NO:27)). The second group is treated in parallel with 300 μg Qβ packaged with G8-8 (SEQ ID NO 25). The third group is treated with placebo. Dependent on the average symptom score of the test group during the study the treatment of the test group can be repeated up to a total of 6 to 10 vaccinations with 300 μg of QβG10 or QβG8-8, respectively; the control group is always treated with placebo in parallel.

35.2 Assessment of Efficacy: Conjunctival provocation test is performed before each treatment and in intervals up to 3 months after the last treatment. The changes in the symptom scores of the test group at the beginning and at the end of the study are compared to that of the control group.

Example 36

Treatment of Test Persons Suffering from House Dust Allergy with HBc and HBcG8-8 and Assessment of Efficacy Using the Conjunctival Provocation Test 36.1 Treatment with HBcG10 HBcG8-8: After determination of a base line with skin prick and conjunctival provication test (see Examples 30 and 31) three groups of test persons suffering from house dust allergy are formed, wherein all groups show a similar test score in average. The first group is treated at least three times in intervals of 1 week with 300 μg HBcG10 (HBc VLP packaged with G10 (SEQ ID NO:27)). The second group is treated in parallel with 300 μg HBc packaged with G8-8 (SEQ ID NO 25). The third group is treated with placebo. Dependent on the average symptom score of the test group during the study the treatment of the test group can be repeated up to a total of 6 to 10 vaccinations with 300 μg of HBcG10 or HBcG8-8, respectively; the control group is always treated with placebo in parallel.

36.2 Assessment of Efficacy: Conjunctival provocation test is performed before each treatment and in intervals up to 3 months after the last treatment. The changes in the symptom scores of the test group at the beginning and at the end of the study are compared to that of the control group.

Example 37

Treatment of Test Persons Suffering from Pollen Allergy with QβG10 and Assessment of Efficacy Using a Nasal Provocation Test, Skin Prick Test, and Patient Diary Treatment with QβG10: An open-label clinical trial was performed with patients with allergy to grass pollen. Patients were treated with 300 μg QβG10 (Qβ VLP filled with G10 (SEQ ID NO:27)) six times in intervals of 1 week.

Assessment of Efficacy: Nasal provocation test with a standardized grass pollen extract (see Example 32) was performed prior to the first treatment and 2 weeks after the last treatment. Nasal provocation testing is also performed at months 6 and 12 following the first treatment. The changes in the symptom scores from before the treatment are assessed at the various assessment points after the treatment. Efficacy is also measured with the skin prick test (see Example 30) using solutions containing various amounts of grass pollen allergens. Efficacy of the treatment in daily life is measured using a validated patient diary to record symptoms and medication use during the first pollen season following the treatment. The validated patient diary is also used to record symptoms and medication use during the second pollen season following the treatment.

Results of the nasal provocation test: 5 patients with grass pollen allergy treated with 6 weekly injections of 300 μg QβG10 were subjected to nasal provocation (Example 32) before treatment and 2 weeks after the treatment. As shown in Table 32 these patients showed reduced symptom score as compared to their reaction before the treatment.

TABLE 32

Symptoms due to nasal provocation were assessed using score system 2 (Example 32).

| | Before Treatment Allergen solution (dilution) | | | | | After Treatment Allergen solution (dilution) | | | | |
|---|---|---|---|---|---|---|---|---|---|---|
| Patient | Control | 1/1000 | 1/100 | 1/10 | 1/1 | Control | 1/1000 | 1/100 | 1/10 | 1/1 |
| A | 0 | 0 | 0 | 0 | 4 | 0 | 0 | 0 | 0 | 1 |
| B | 0 | 0 | 3 | 2 | 5 | 0 | 0 | 0 | 0 | 1 |
| C | 0 | 0 | 1 | 0 | 4 | 0 | 0 | 0 | 0 | 2 |
| D | 0 | 0 | 1 | 2 | 3 | 0 | 0 | 0 | 0 | 1 |

TABLE 32-continued

Symptoms due to nasal provocation were assessed using score system 2 (Example 32).

| Patient | Before Treatment Allergen solution (dilution) | | | | | After Treatment Allergen solution (dilution) | | | | |
|---|---|---|---|---|---|---|---|---|---|---|
| | Control | 1/1000 | 1/100 | 1/10 | 1/1 | Control | 1/1000 | 1/100 | 1/10 | 1/1 |
| E | 0 | nd | nd | nd | 5 | 0 | 0 | 0 | 2 | 5 |
| F | 1 | 1 | 1 | 1 | 4 | 0 | 0 | 0 | 0 | 1 |
| G | 0 | 1 | 1 | 2 | 4 | 0 | 0 | 1 | 1 | 4 |
| H | 0 | 0 | 1 | 1 | 3 | 0 | 0 | 0 | 0 | 1 |
| I | 0 | 0 | 0 | 0 | 3 | 0 | 0 | 0 | 0 | 1 |
| J | 1 | 1 | 2 | 5 | nd | 0 | 0 | 0 | 0 | 2 | nd = not determined

Example 38

Treatment of Test Persons Suffering from Pollen Allergy with QβG10 and Assessment of Efficacy Using a Conjunctival Provocation Test, Skin Prick Test, and Patient Diary Treatment with QβG10: A double-blind parallel-group clinical trial is performed with 30 patients with allergy to grass pollen. Patients are allocated randomly to three groups of 10 patients each. The first group is treated with 300 µg QβG10 (Qβ VLP packaged with G10 (SEQ ID NO:27)) six times in intervals of 1 week. The second group is treated with 300 µg QβG10 in combination with the adjuvant aluminum hydroxide six times in intervals of 1 week. The third group is treated with placebo.

Assessment of Efficacy: Conjunctival provocation test with a standardized grass pollen extract (see Example 31) is performed prior to the first treatment, 2 weeks after the last treatment, and 6 and 12 months after the first treatment. The changes in the symptom scores from before the treatment are compared between the groups at the various assessment points after the treatment. Efficacy is also measured with the skin prick test (see Example 30) using solutions containing various amounts of grass pollen allergens. Efficacy of the treatment in daily life is measured using a validated patient diary to record symptoms and medication use during the first pollen season following the treatment. The validated patient diary is also used to record symptoms and medication use during the second pollen season following the treatment.

Example 39

Treatment of Test Persons Suffering from House Dust Mite Allergy with QβG10 and Assessment of Efficacy Using Conjunctival Provocation Test, Skin Prick Test, and Patient Diary Treatment with QβG10: A double-blind parallel-group clinical trial is performed with 20 patients with allergy to house dust mites. Patients are allocated randomly to two groups of 10 patients each. The first group is treated with 300 µg QβG10 (Qβ VLP packaged with G10 (SEQ ID NO:27)) in combination with the adjuvant aluminum hydroxide six times in intervals of 1 week. The second group is treated with placebo.

Assessment of Efficacy: Conjunctival provocation test with a standardized house dust mite extract (see Example 31) is performed prior to the first treatment, 2 weeks after the last treatment, and 6 and 12 months after the first treatment. The changes in the symptom scores from before the treatment are compared between the groups at the various assessment points after the treatment. Efficacy is also measured with the skin prick test (see Example 30) using solutions containing various amounts of house dust mite allergens. Efficacy of the treatment in daily life is measured using a validated patient diary to record symptoms and medication use during 14 consecutive days prior to treatment, two weeks after treatment, and 6 and 12 months after the first treatment.

The invention claimed is:

1. A method of treating a hypersensitivity in an animal, wherein said hypersensitivity is allergy or asthma, wherein said method comprises introducing a composition into said animal, and wherein said composition comprises:
   (a) virus-like particle of an RNA bacteriophage Qβ; and
   (b) an unmethylated CpG-containing oligonucleotide consisting essentially of the sequence GGGGGGGGGG GACGATCGTC GGGGGGGGGG (SEQ ID NO:27); wherein said virus-like particle of an RNA bacteriophage Qβ is packaged with said unmethylated CpG-containing oligonucleotide, wherein said composition does not comprise an allergen, and wherein introduction of said composition treats said hypersensitivity in said animal.

2. The method of claim 1, wherein said unmethylated CpG-containing oligonucleotide consists exclusively of phosphodiester bound nucleotides.

3. The method of claim 1, wherein said hypersensitivity is asthma.

4. The method of claim 3, wherein said asthma is IgE-mediated asthma.

5. The method of claim 1, wherein said hypersensitivity is an IgE-mediated allergy (type I allergy).

6. The method of claim 5, wherein said IgE-mediated allergy is pollen allergy or house dust allergy.

7. The method of claim 1, wherein said animal is a human.

8. The method of claim 1, wherein said method does not comprise introducing an allergen to said animal.

9. The method of claim 1, wherein an allergen is not introduced in said animal for at least eight weeks before and at least eight weeks after said introduction of said composition in said animal.

10. The method of claim 1, wherein said virus-like particle of an RNA bacteriophage Qβ consists of coat proteins having the amino acid sequence of SEQ ID NO:3.

11. A method of treating a hypersensitivity in an animal, wherein said hypersensitivity is allergy or asthma, wherein said method comprises introducing a composition into said animal, and wherein said composition comprises:
   (a) virus-like particle of an RNA bacteriophage Qβ; and
   (b) an unmethylated CpG-containing oligonucleotide consisting essentially of the sequence GGGGGGGGGG GACGATCGTC GGGGGGGGGG (SEQ ID NO:27); wherein said virus-like particle of an RNA bacteriophage Qβ is packaged with said unmethylated CpG-containing oligonucleotide, and wherein said method does not comprise co-administering an allergen to said animal, and wherein introduction of said composition treats said hypersensitivity in said animal.

12. The method of claim 11, wherein said animal is a human.

13. The method of claim 12, wherein said virus-like particle of an kNA bacteriophage Qβ consists of coat proteins having the amino acid sequence of SEQ ID NO:3.

14. The method of claim 13, wherein said unmethylated CpG-containing oligonucleotide consists exclusively of phosphodiester bound nucleotides.

15. The method of claim 14, wherein said hypersensitivity is asthma.

16. The method of claim 15, wherein said asthma is IgE-mediated asthma.

17. The method of claim 16, wherein said method does not comprise introducing an allergen to said animal.

18. The method of claim 16, wherein an allergen is not introduced in said animal for at least one week before and at least one week after said introduction of said composition in said animal.

19. The method of claim 16, wherein an allergen is not introduced in said animal for at least four weeks before and at least four weeks after said introduction of said composition in said animal.

20. The method of claim 16, wherein an allergen is not introduced in said animal for at least eight weeks before and at least eight weeks after said introduction of said composition in said animal.

* * * * *

UNITED STATES PATENT AND TRADEMARK OFFICE
CERTIFICATE OF CORRECTION

Page 1 of 1

PATENT NO.       : 8,574,564 B2
APPLICATION NO.  : 12/576086
DATED            : November 5, 2013
INVENTOR(S)      : Wolfgang A. Renner et al.

It is certified that error appears in the above-identified patent and that said Letters Patent is hereby corrected as shown below:

In the Claims

In column 142, line 16, delete "kNA" and insert --RNA-- therefore.

Signed and Sealed this
Twenty-eighth Day of January, 2014

Michelle K. Lee
*Deputy Director of the United States Patent and Trademark Office*